(12) United States Patent
Shulman et al.

(10) Patent No.: US 11,484,608 B2
(45) Date of Patent: Nov. 1, 2022

(54) NON-INVASIVE ASSESSMENT OF HEPATIC MITOCHONDRIAL METABOLISM BY POSITIONAL ISOTOPOMER NMR TRACER ANALYSIS (PINTA)

(71) Applicant: YALE UNIVERSITY, New Haven, CT (US)

(72) Inventors: Gerald I. Shulman, East Haven, CT (US); Rachel Jamison Perry, Hamden, CT (US); Gary Cline, New Haven, CT (US); Douglas Rothman, Branford, CT (US); Kitt Petersen, East Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 16/652,892

(22) PCT Filed: Oct. 5, 2018

(86) PCT No.: PCT/US2018/054616
§ 371 (c)(1),
(2) Date: Apr. 1, 2020

(87) PCT Pub. No.: WO2019/071130
PCT Pub. Date: Apr. 11, 2019

(65) Prior Publication Data
US 2020/0246490 A1    Aug. 6, 2020

Related U.S. Application Data

(60) Provisional application No. 62/613,254, filed on Jan. 3, 2018, provisional application No. 62/568,680, filed on Oct. 5, 2017.

(51) Int. Cl.
| | | |
|---|---|---|
| *A61K 49/10* | (2006.01) |
| *A61K 49/00* | (2006.01) |
| *G01N 33/58* | (2006.01) |
| *A61K 9/00* | (2006.01) |
| *G01N 33/66* | (2006.01) |

(52) U.S. Cl.
CPC ............ *A61K 49/10* (2013.01); *A61K 9/0019* (2013.01); *A61K 49/0004* (2013.01); *G01N 33/58* (2013.01); *G01N 33/66* (2013.01); *G01N 2400/00* (2013.01); *G01N 2458/15* (2013.01)

(58) Field of Classification Search
CPC .......... A61K 49/00; A61K 49/10; A61K 9/00; G01N 33/58
See application file for complete search history.

(56) References Cited

PUBLICATIONS

Rachel J. Perrt et al. Propionate Increases Hepatic Pyruvate Cycling and Anaplerosis and Alters mitochondrial Metabolism, JBC, 291(23), 12161-12170. (Year: 2016).*
Nishanth E. Sunny et al. Progressive adaptation of hepatic ketogenesis in mice fed a high-fat diet, Am. J. Physiol Endocrinol Metab, 298, E1226-E1235. (Year: 2010).*
Sunny, et al. "Excessive hepatic mitochondrial TCA cycle and gluconeogenesis in humans with nonalcoholic fatty liver disease." Cell metabolism 14.6 (2011): 804-810.
Jin, et al. "Glucose production, gluconeogenesis, and hepatic tricarboxylic acid cycle fluxes measured by nuclear magnetic resonance analysis of a single glucose derivative." Analytical biochemistry 327.2 (2004): 149-155.
Burgess, et al. "Noninvasive evaluation of liver metabolism by 2H and 13C NMR isotopomer analysis of human urine." Analytical biochemistry 312.2 (2003): 228-234.
Jones, et al. "13C NMR measurements of human gluconeogenic fluxes after ingestion of [U-13C] propionate, phenylacetate, and acetaminophen." American Journal of Physiology-Endocrinology And Metabolism 275.5 (1998): E843-E852.

* cited by examiner

*Primary Examiner* — Jake M Vu
*Assistant Examiner* — Jagadishwar R Samala
(74) *Attorney, Agent, or Firm* — Saul Ewing Arnstein & Lehr LLP; Kathryn Doyle; Domingos J. Silva

(57) ABSTRACT

The present provides a Positional Isotopomer NMR Tracer Analysis (PINTA) method that can be used to noninvasively assess rates of hepatic mitochondrial oxidation ($V_{CS}$) and/or pyruvate carboxylase ($V_{PC}$) flux in a subject. In certain embodiments, the methods utilize a combined NMR/gas chromatography-mass spectrometry analysis of plasma following infusion of [3-$^{13}$C]lactate and glucose tracer. The method of the invention provides investigators with a tool to non-invasively examine the role of altered hepatic mitochondrial metabolism and study the effects of therapeutic interventions for the treatment of non-alcoholic fatty liver disease (NAFLD), non-alcoholic steatohepatitis (NASH), and type 2 diabetes (T2D).

7 Claims, 164 Drawing Sheets
Specification includes a Sequence Listing.

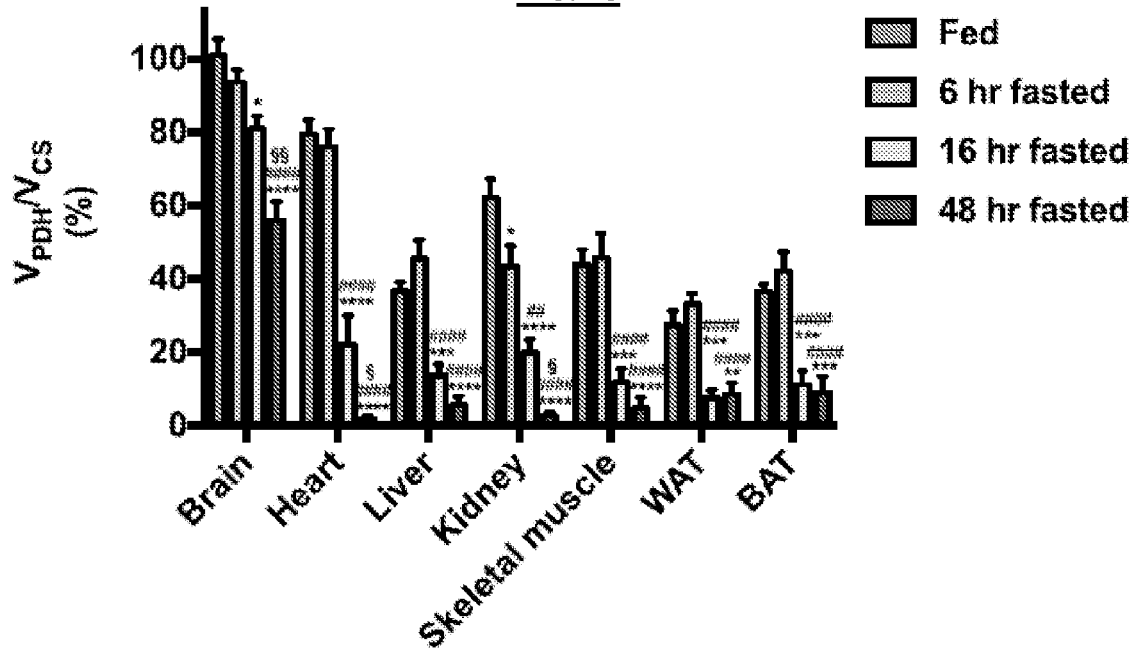
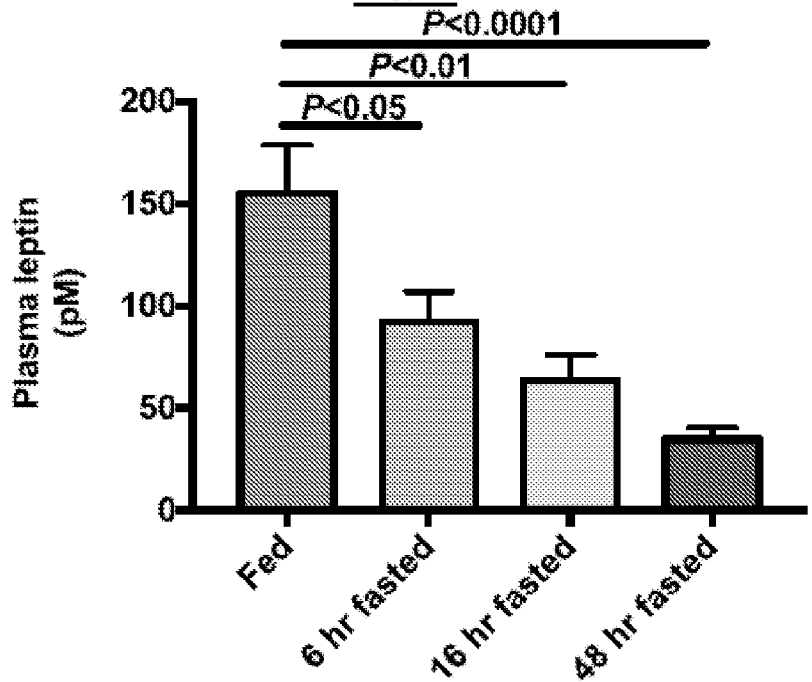

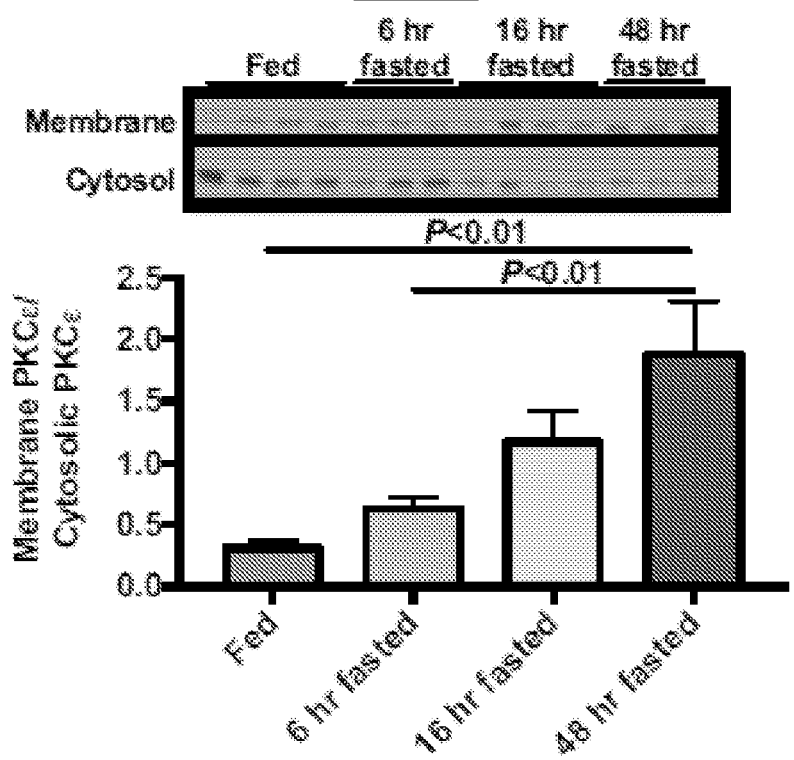
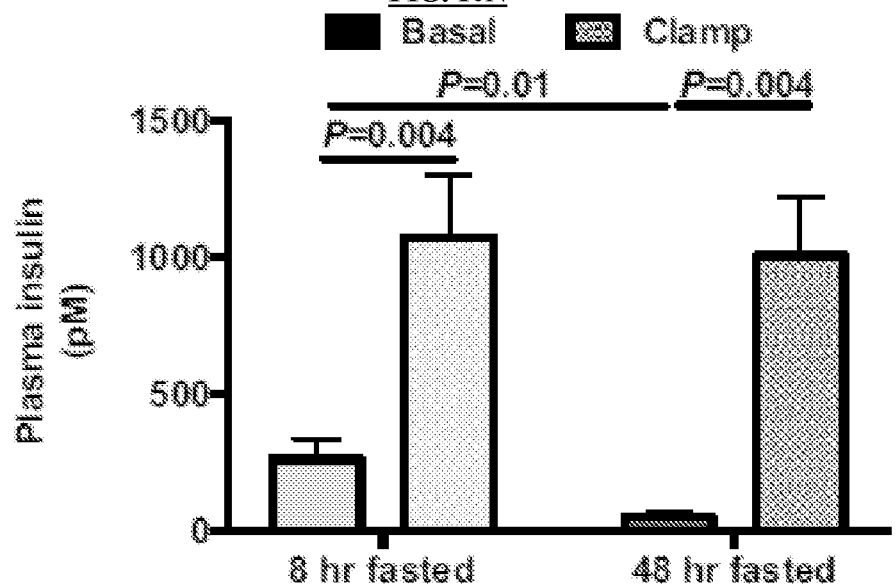

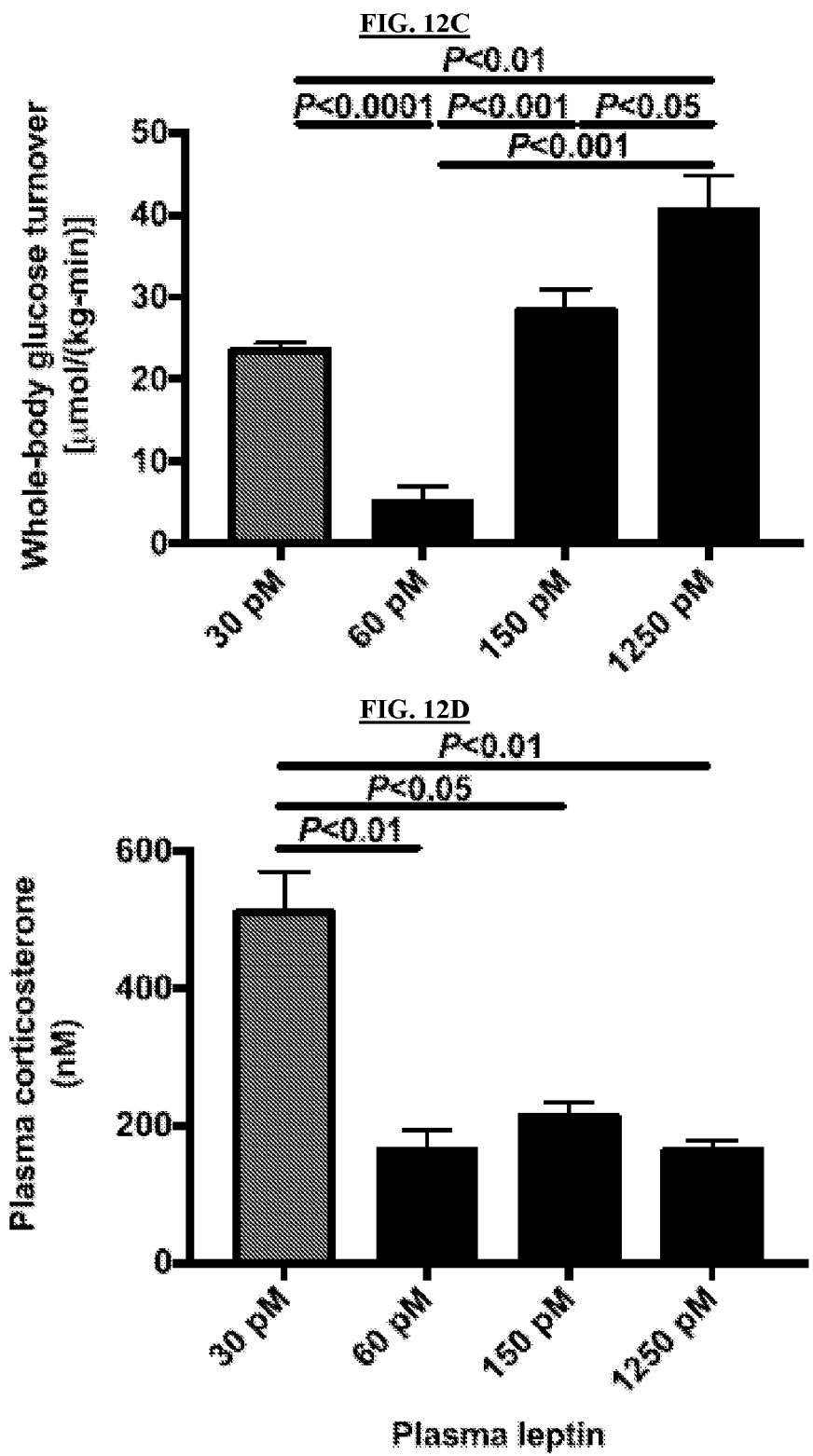

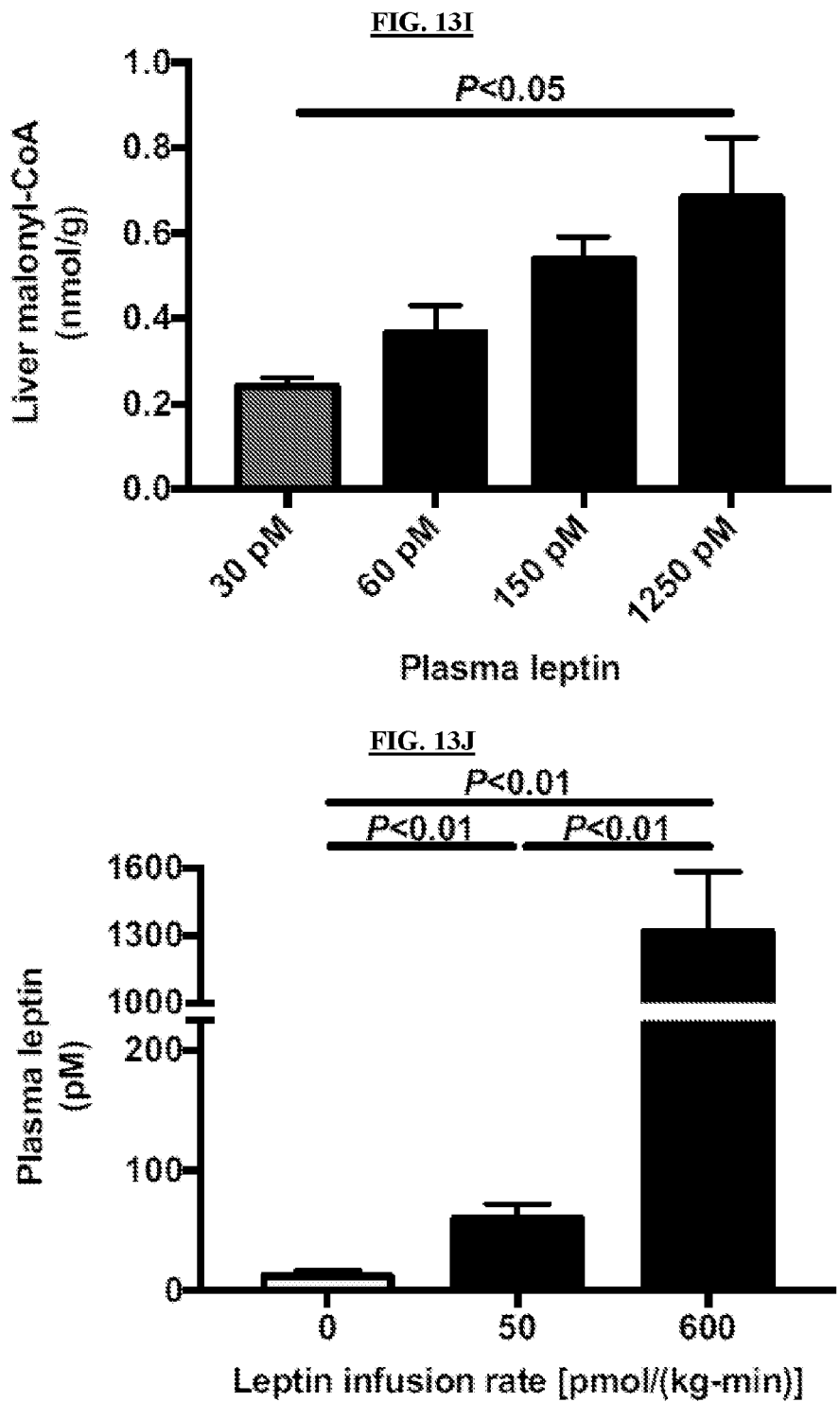

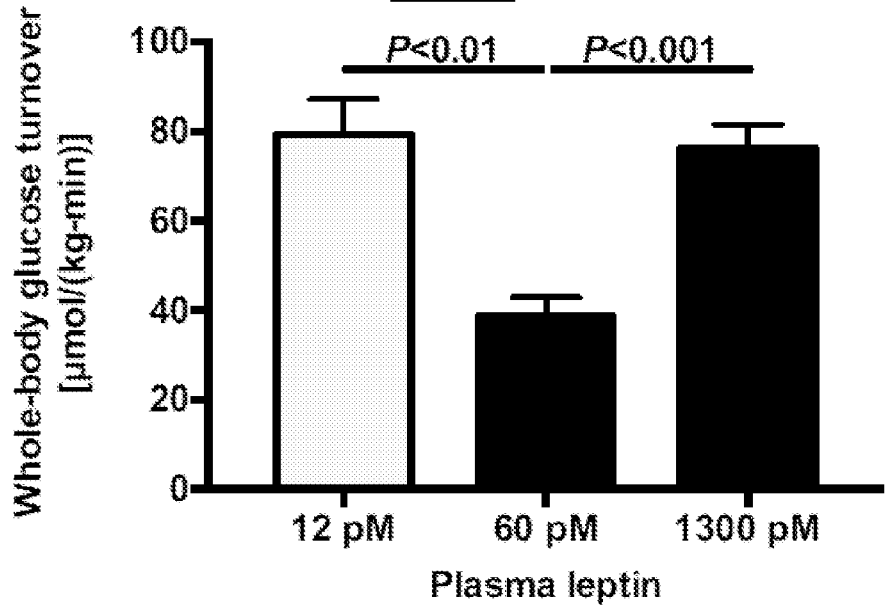
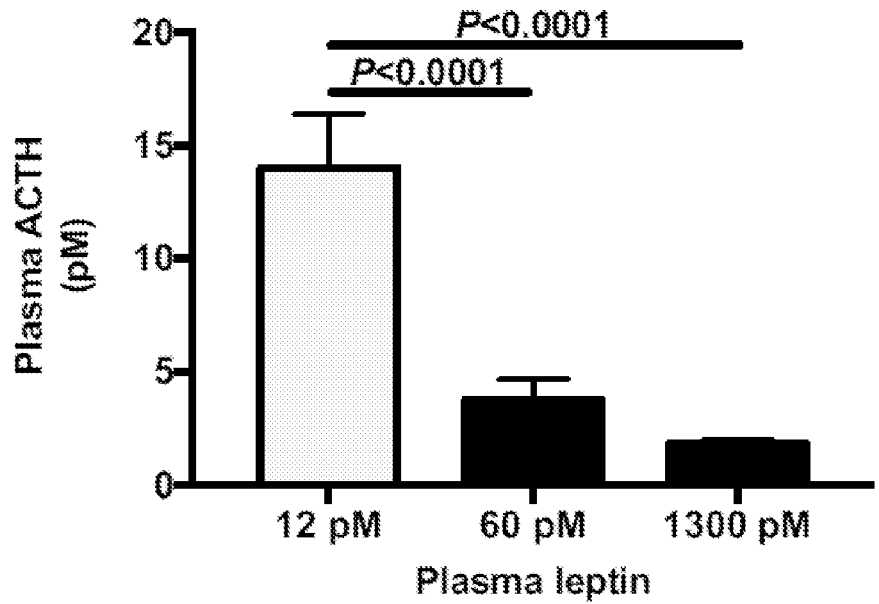

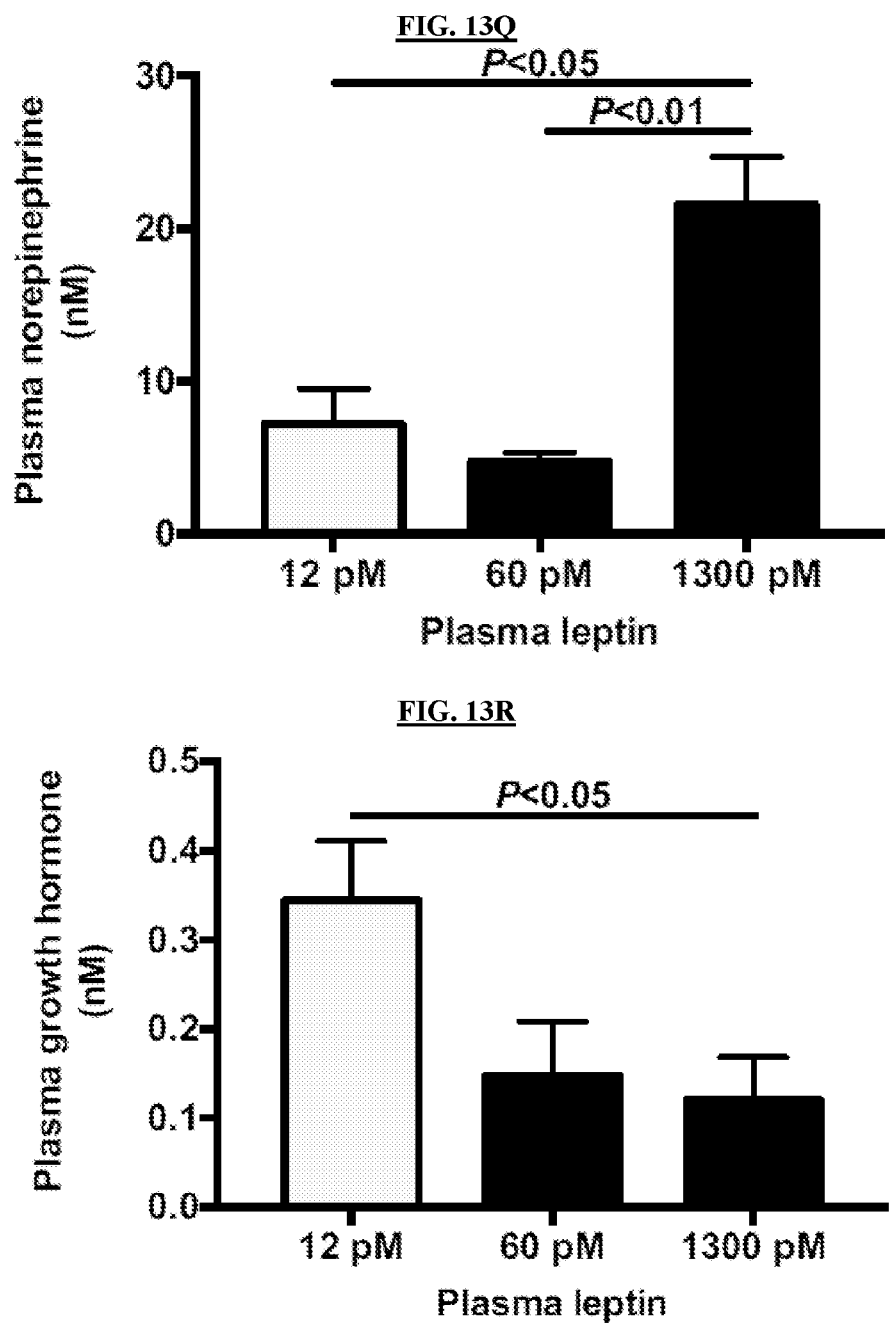

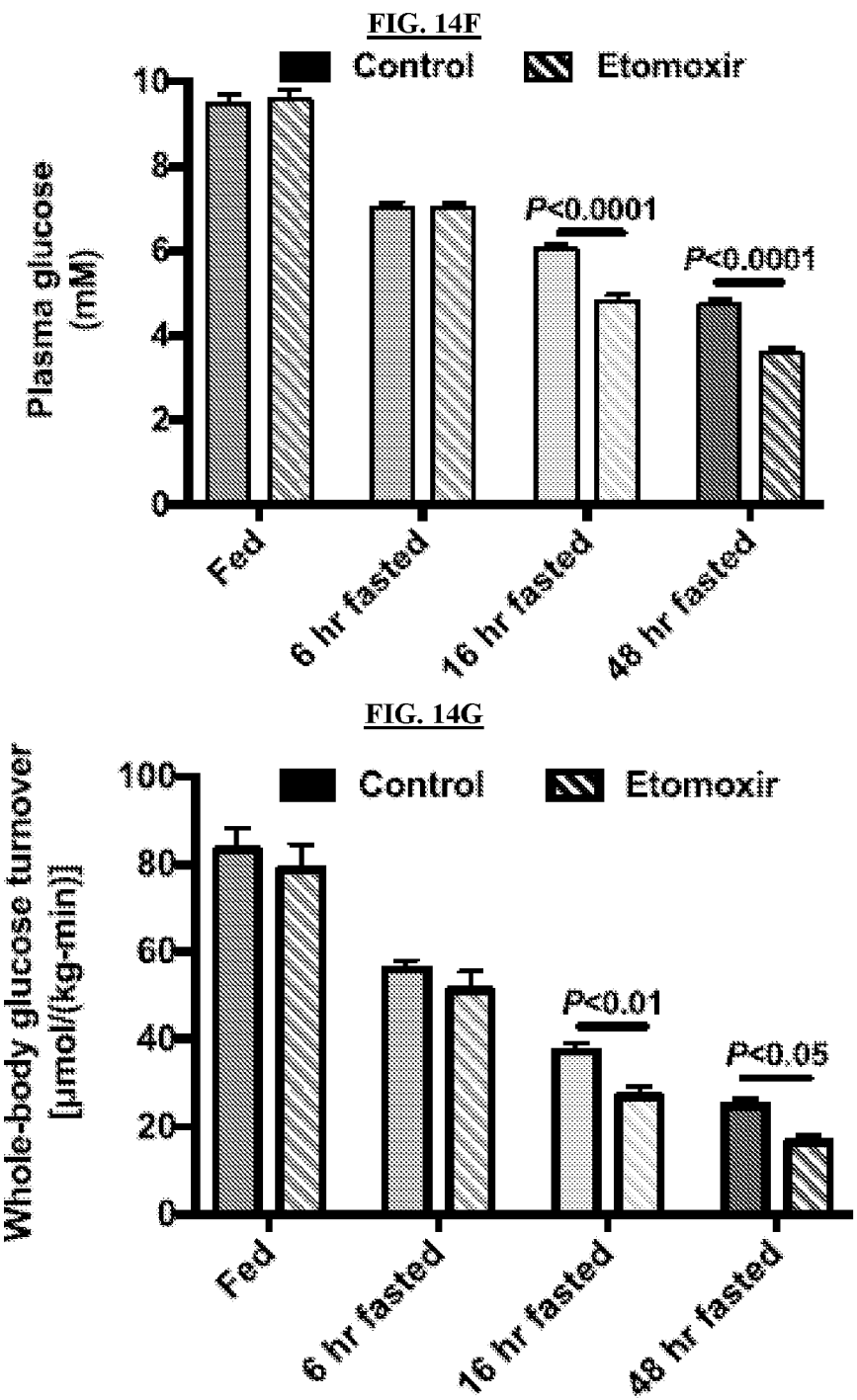

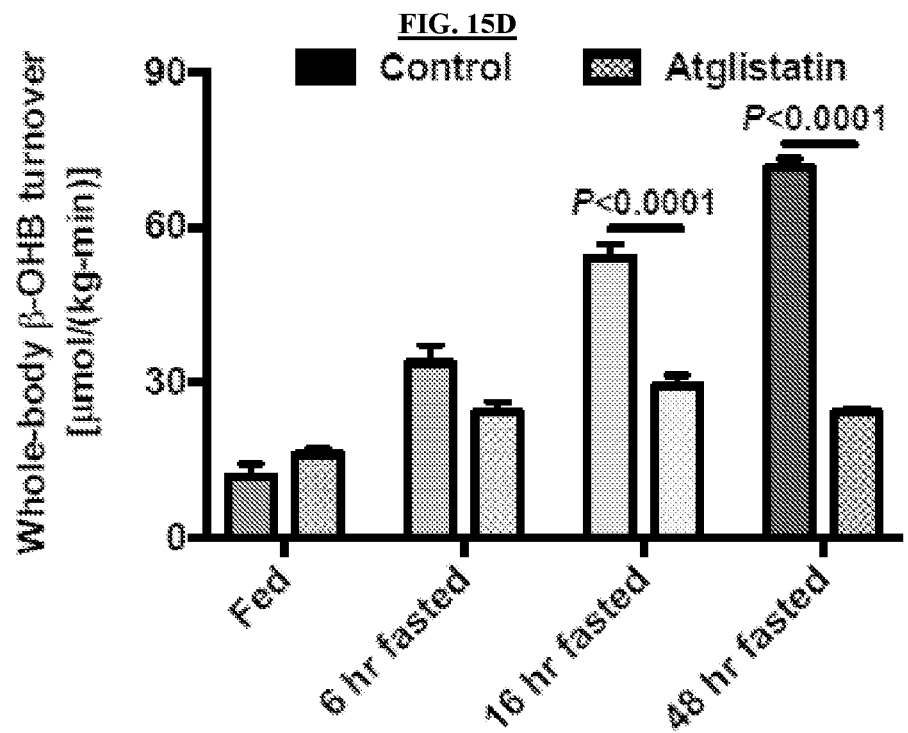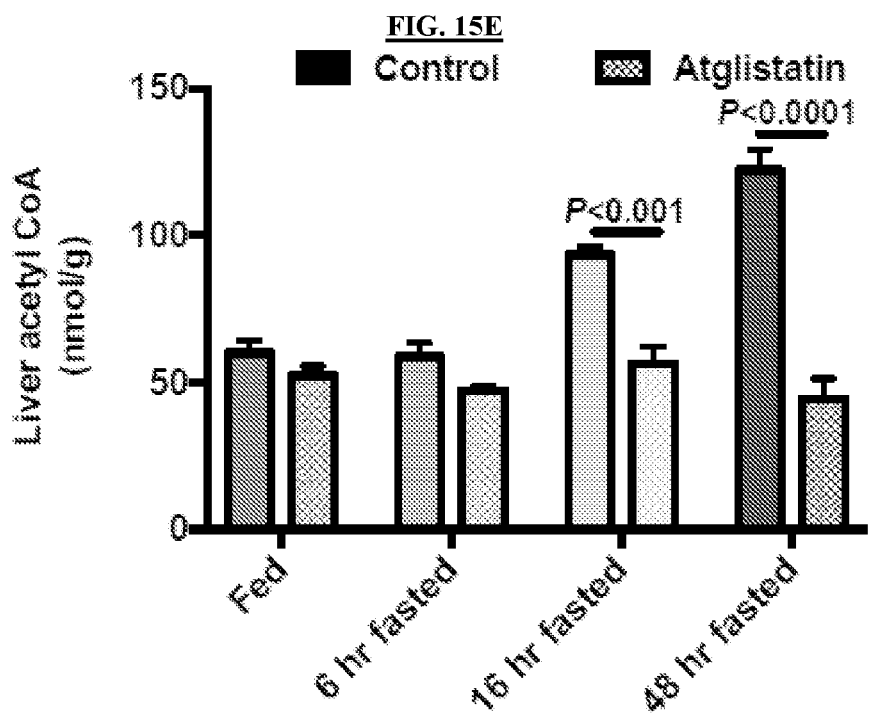

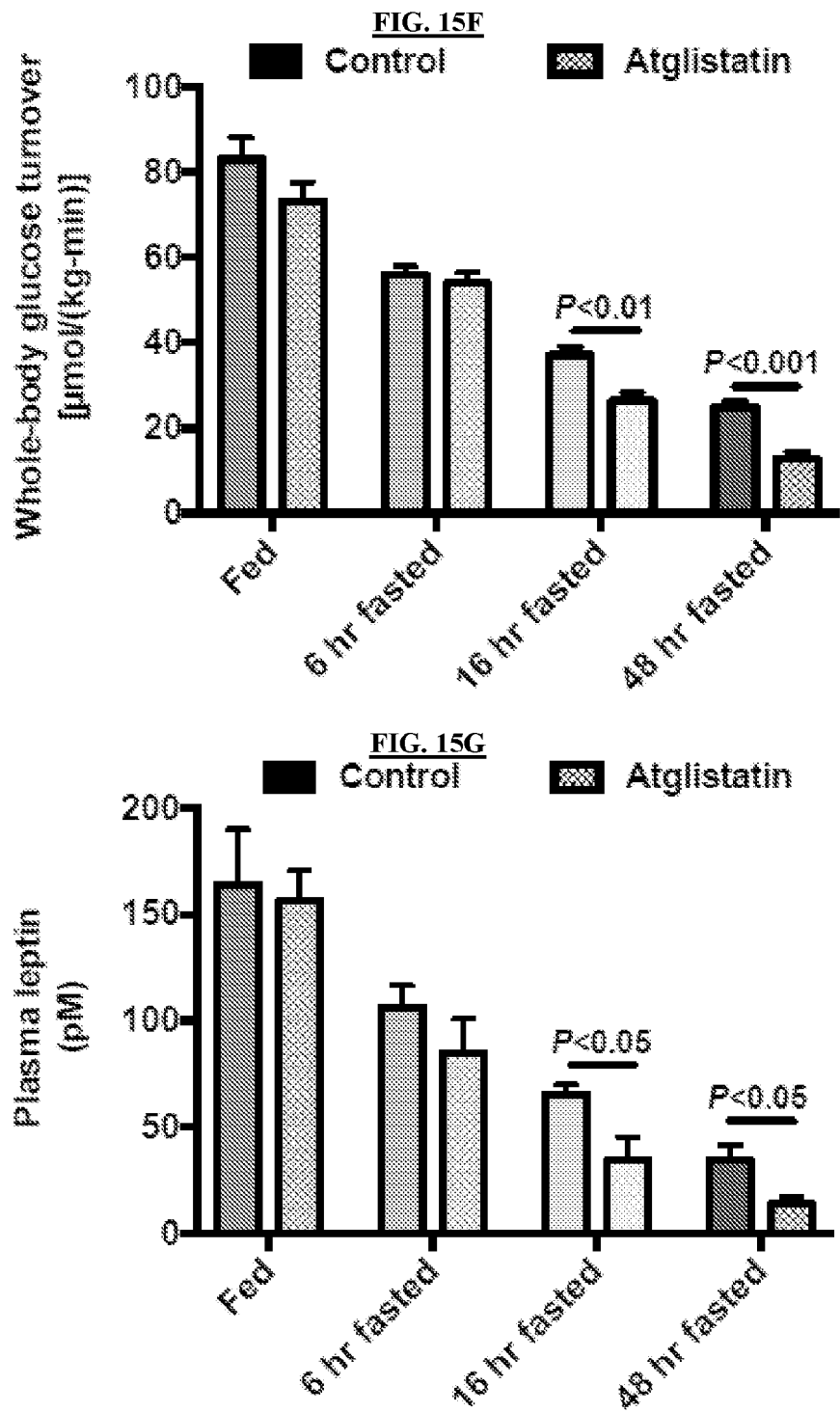

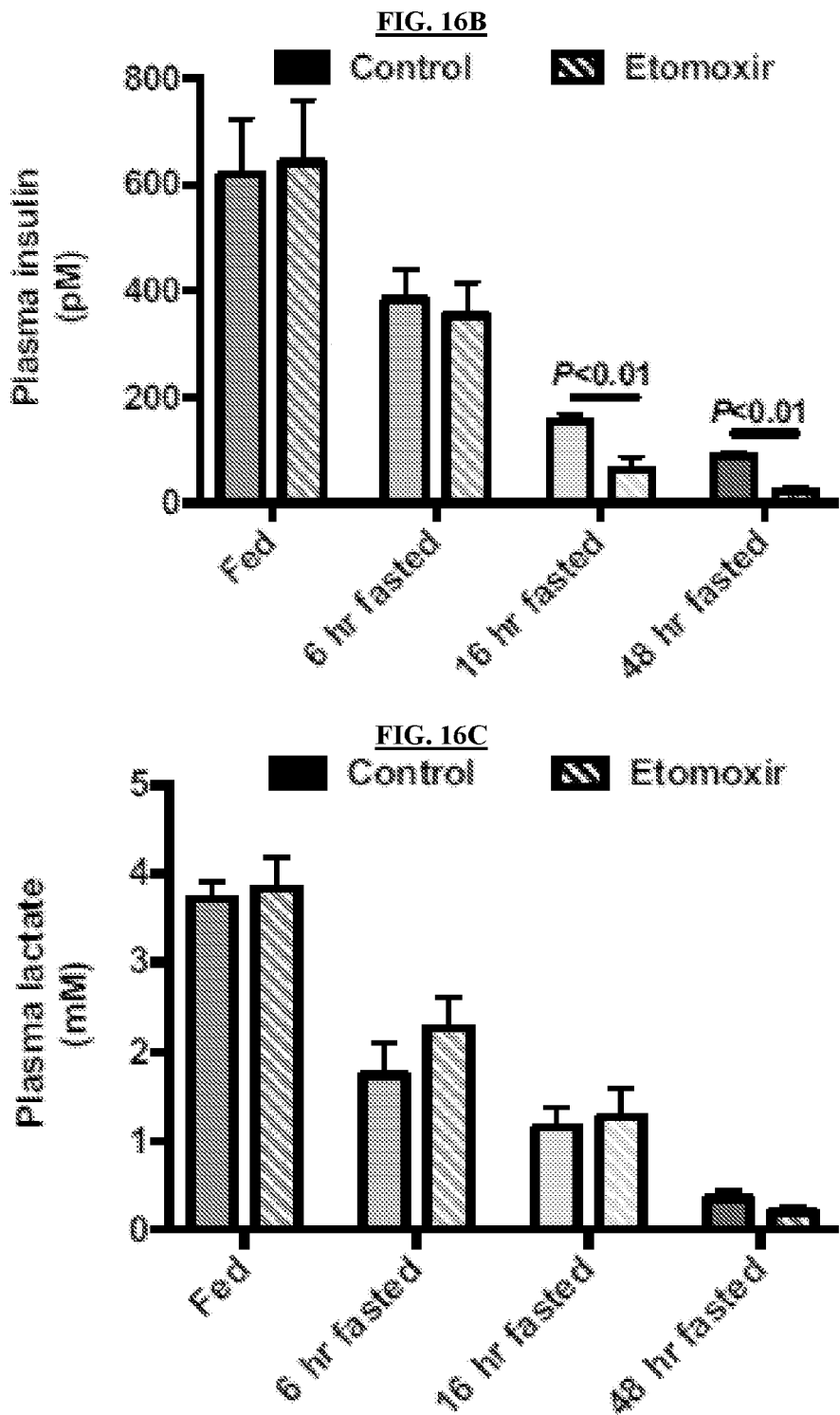

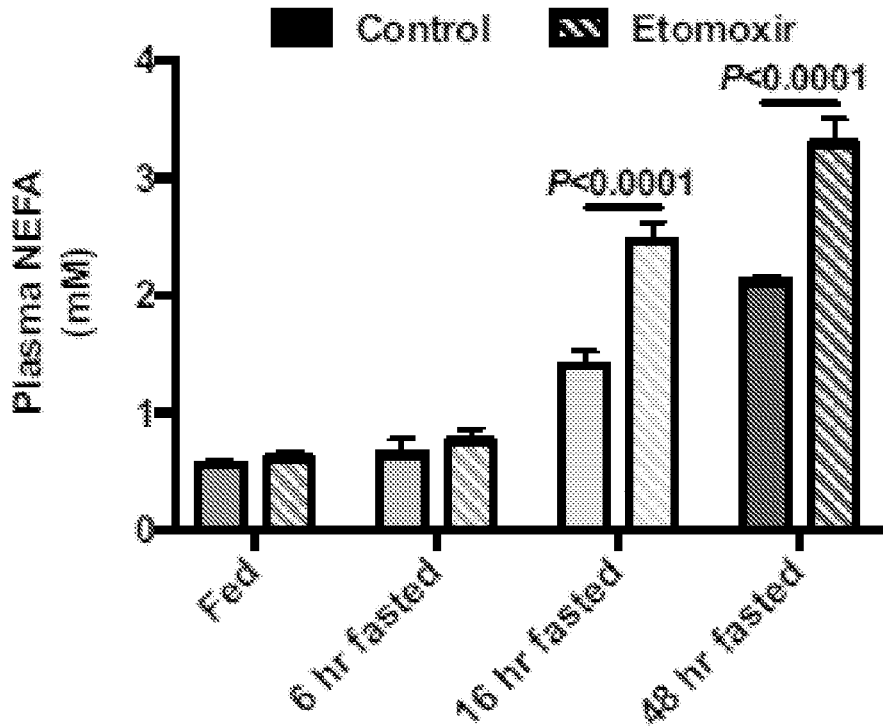
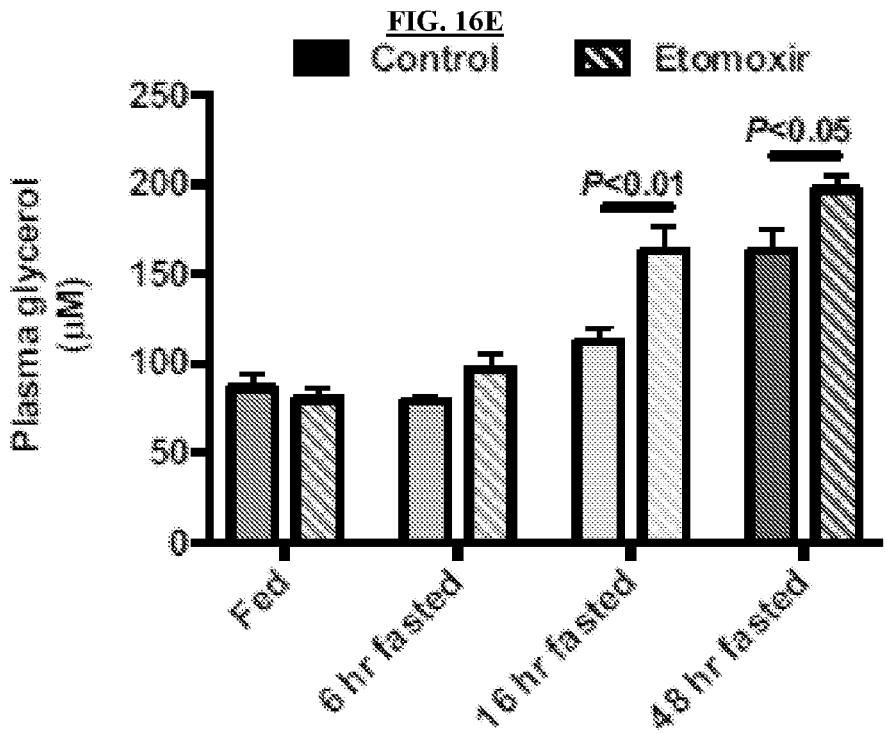

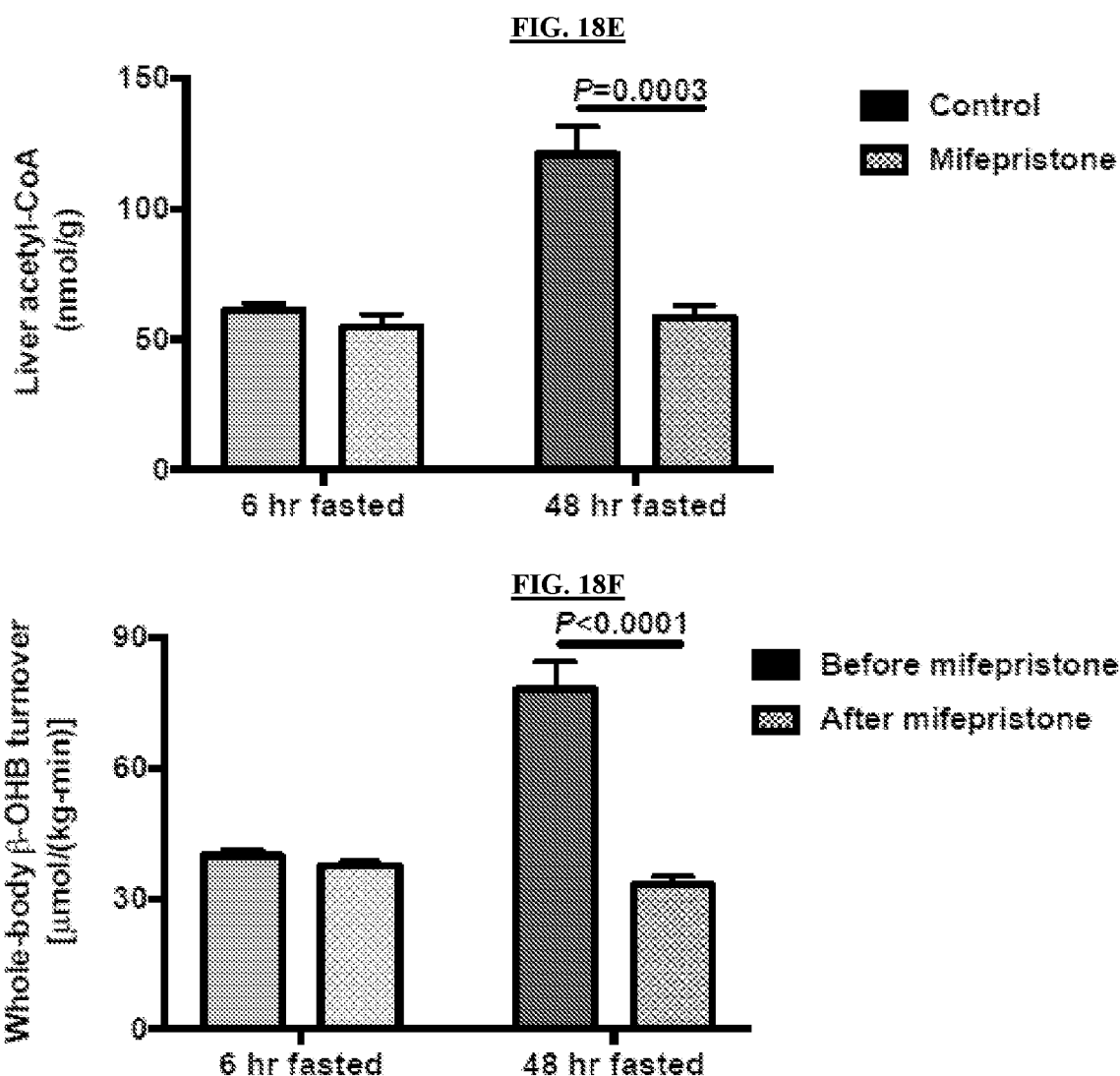

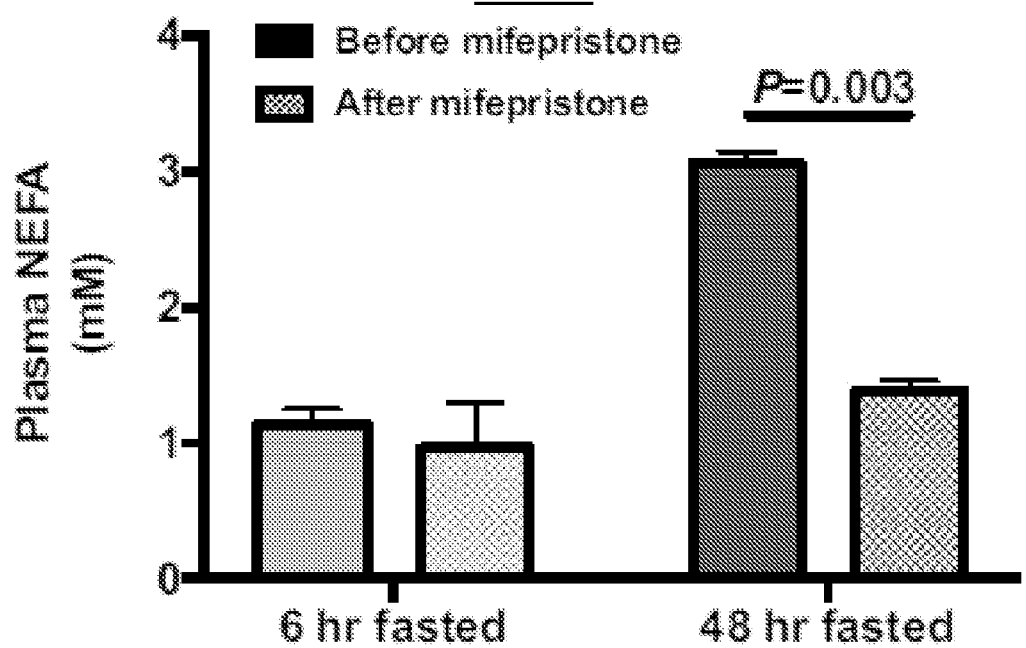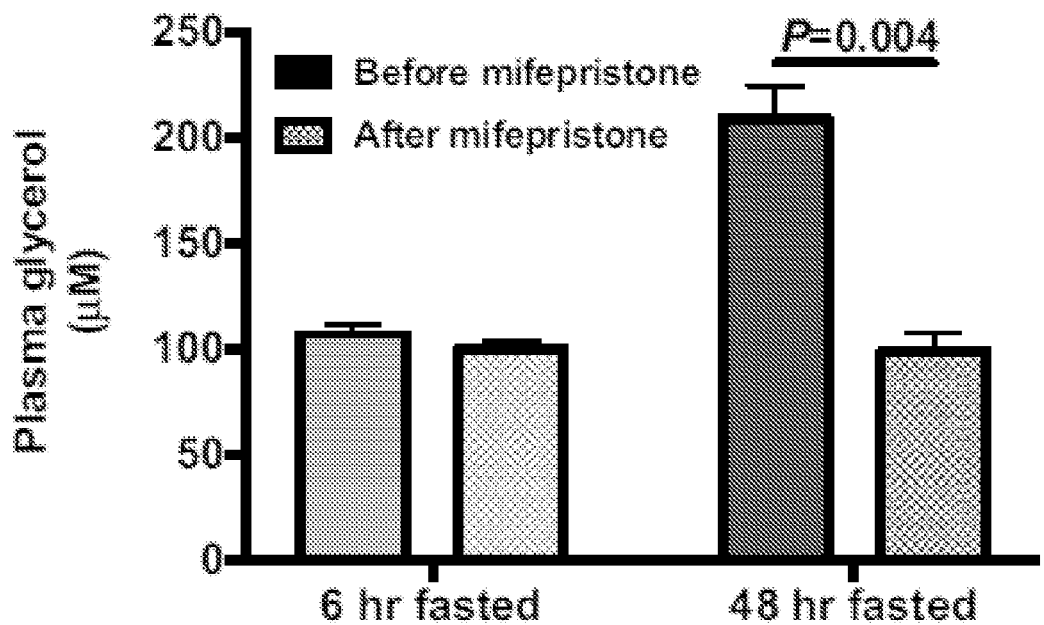

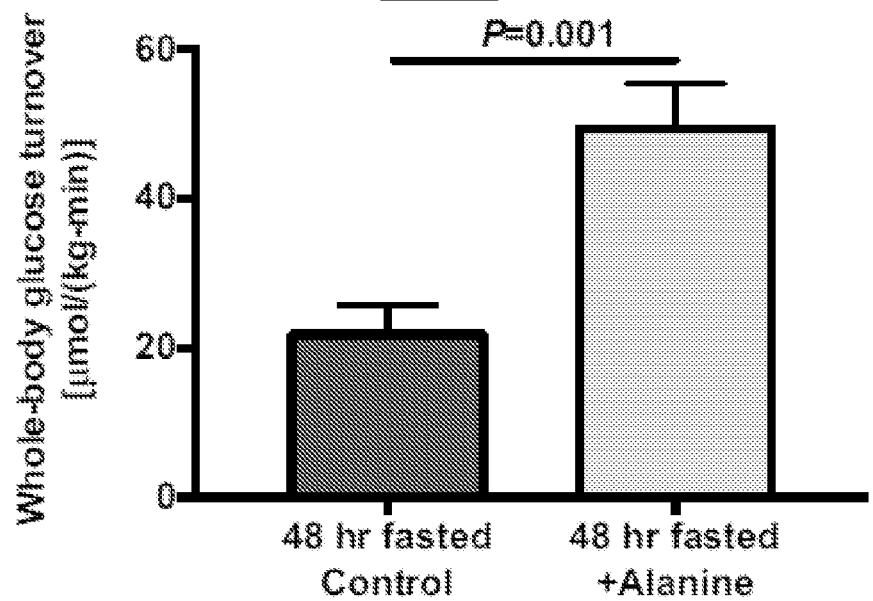
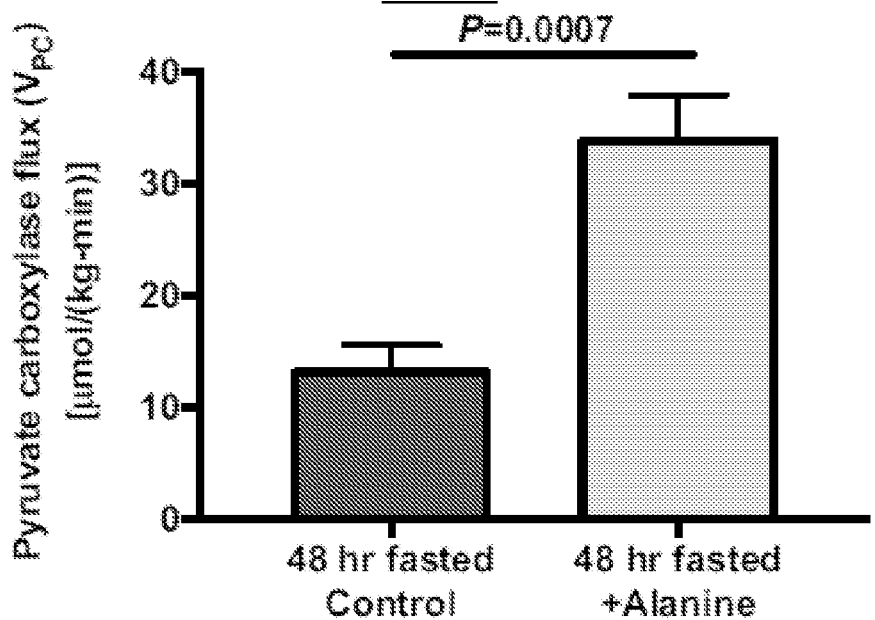

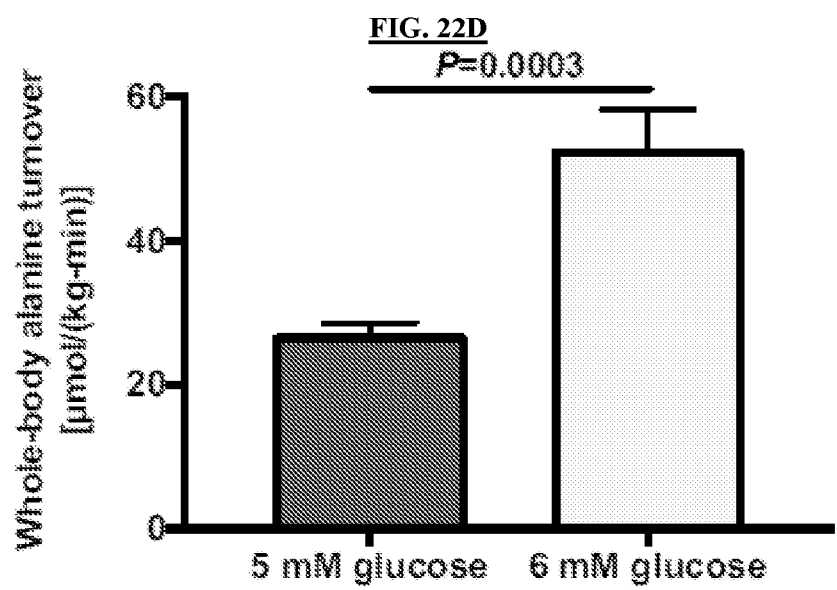
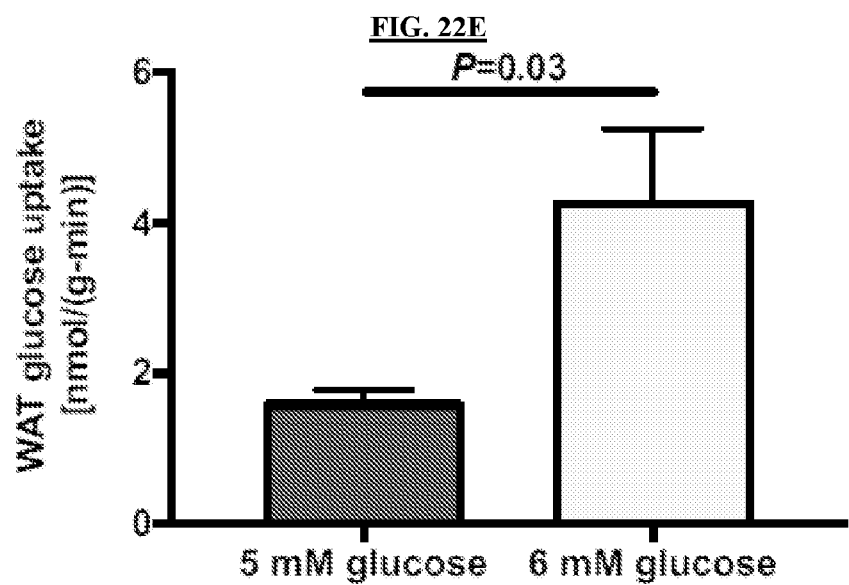

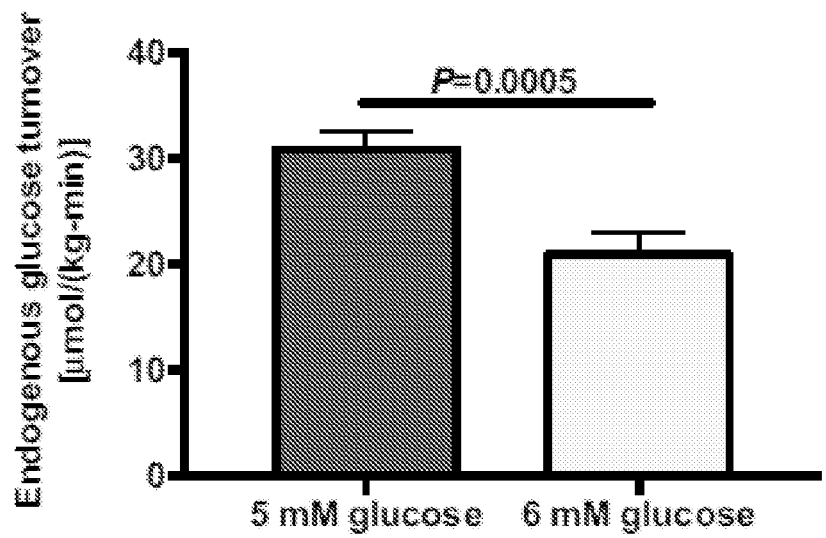
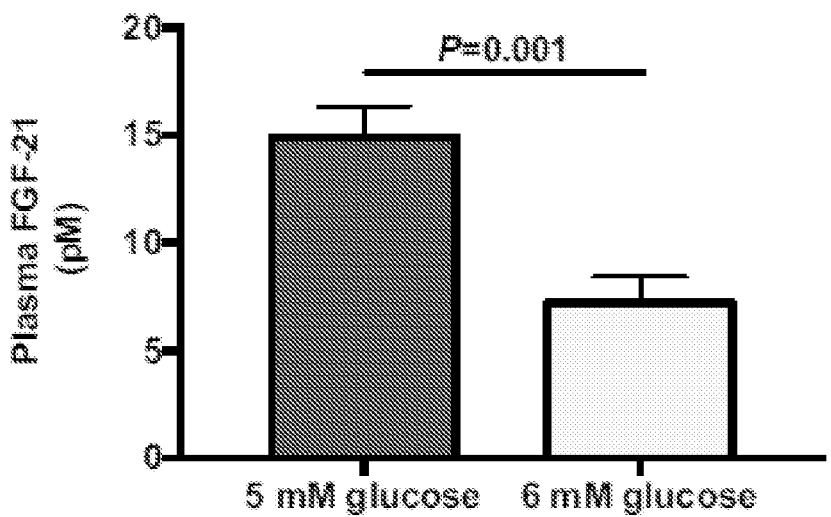

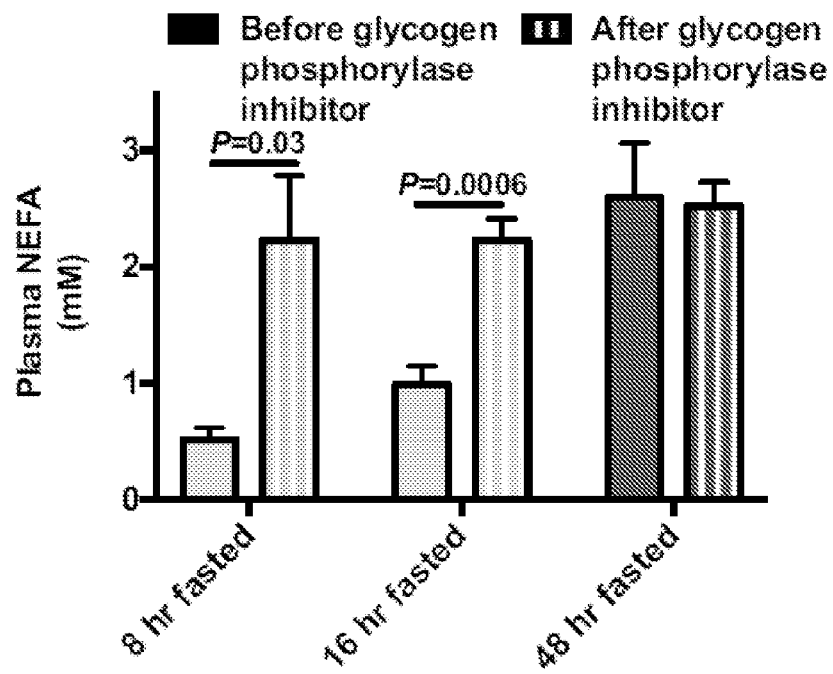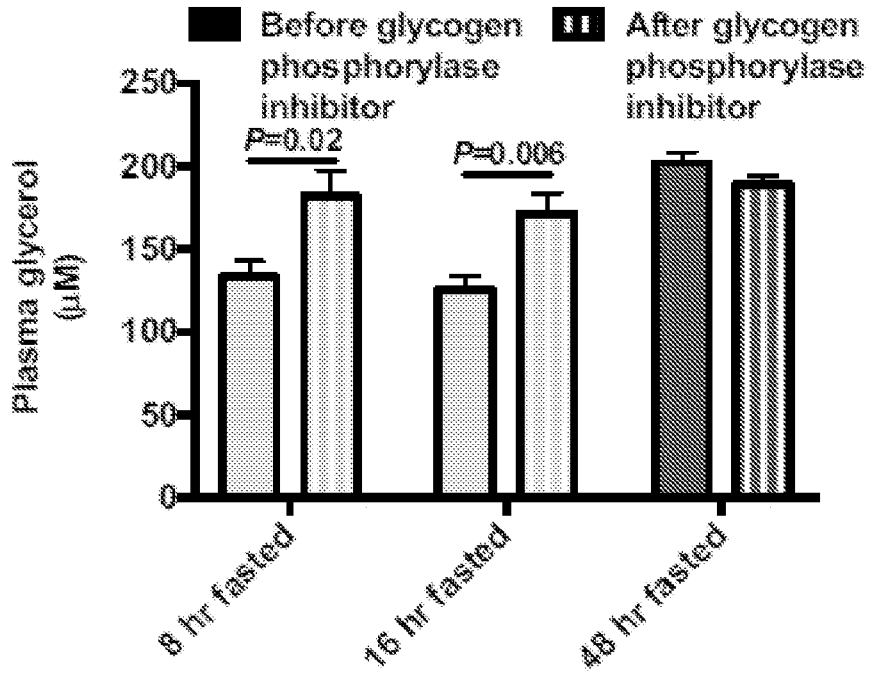

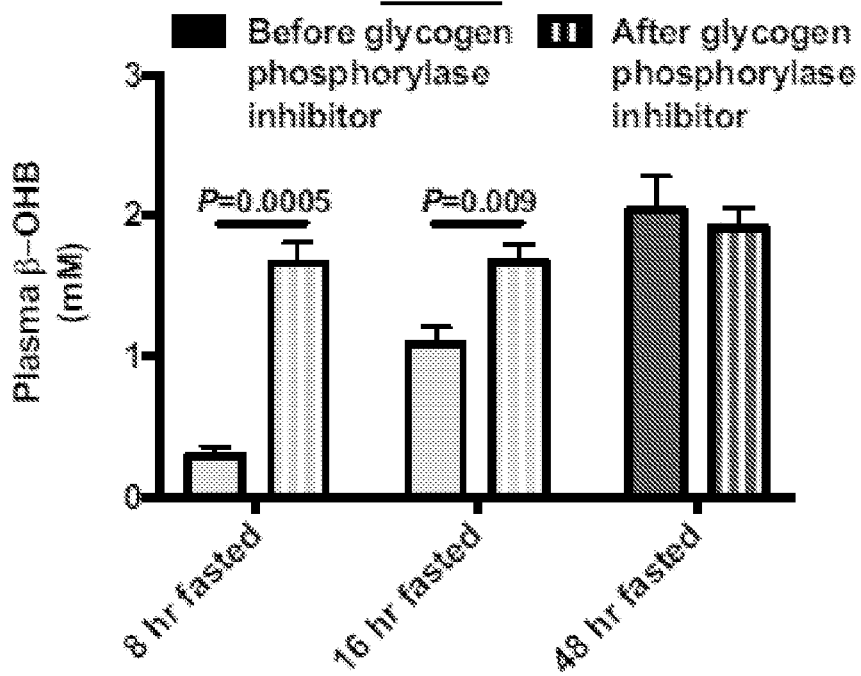
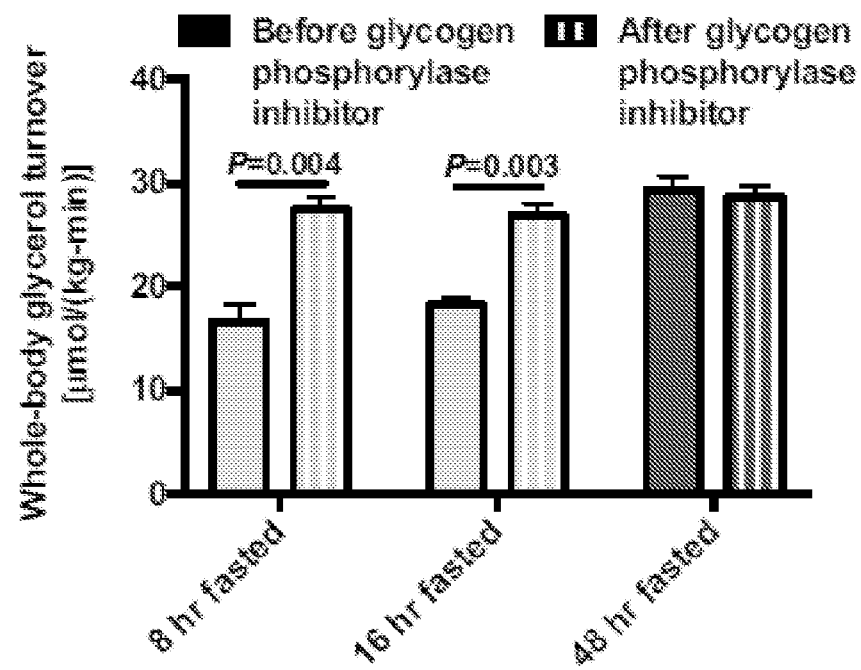

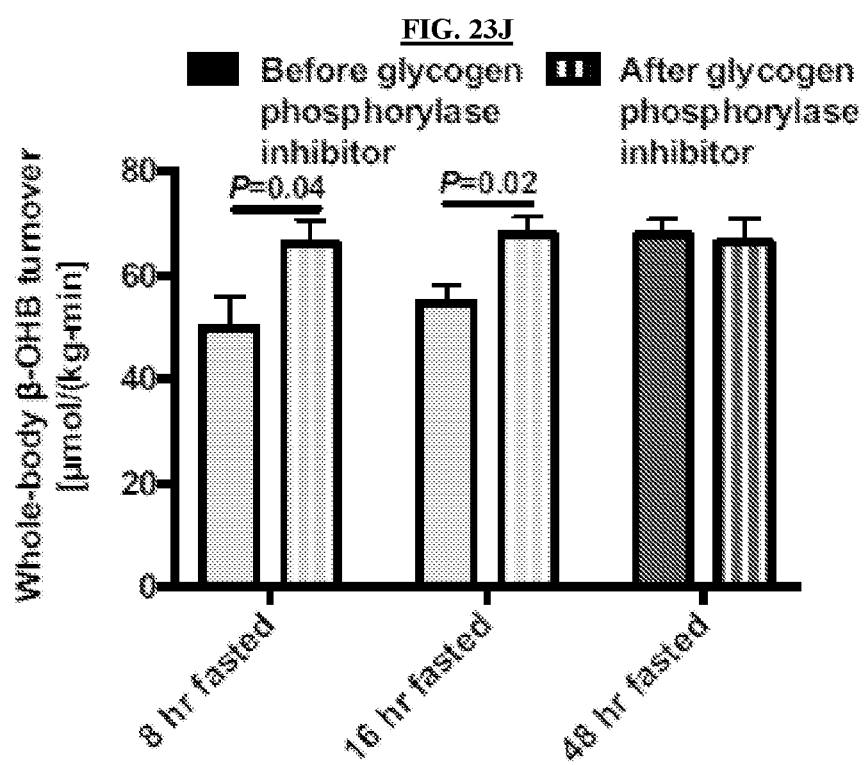

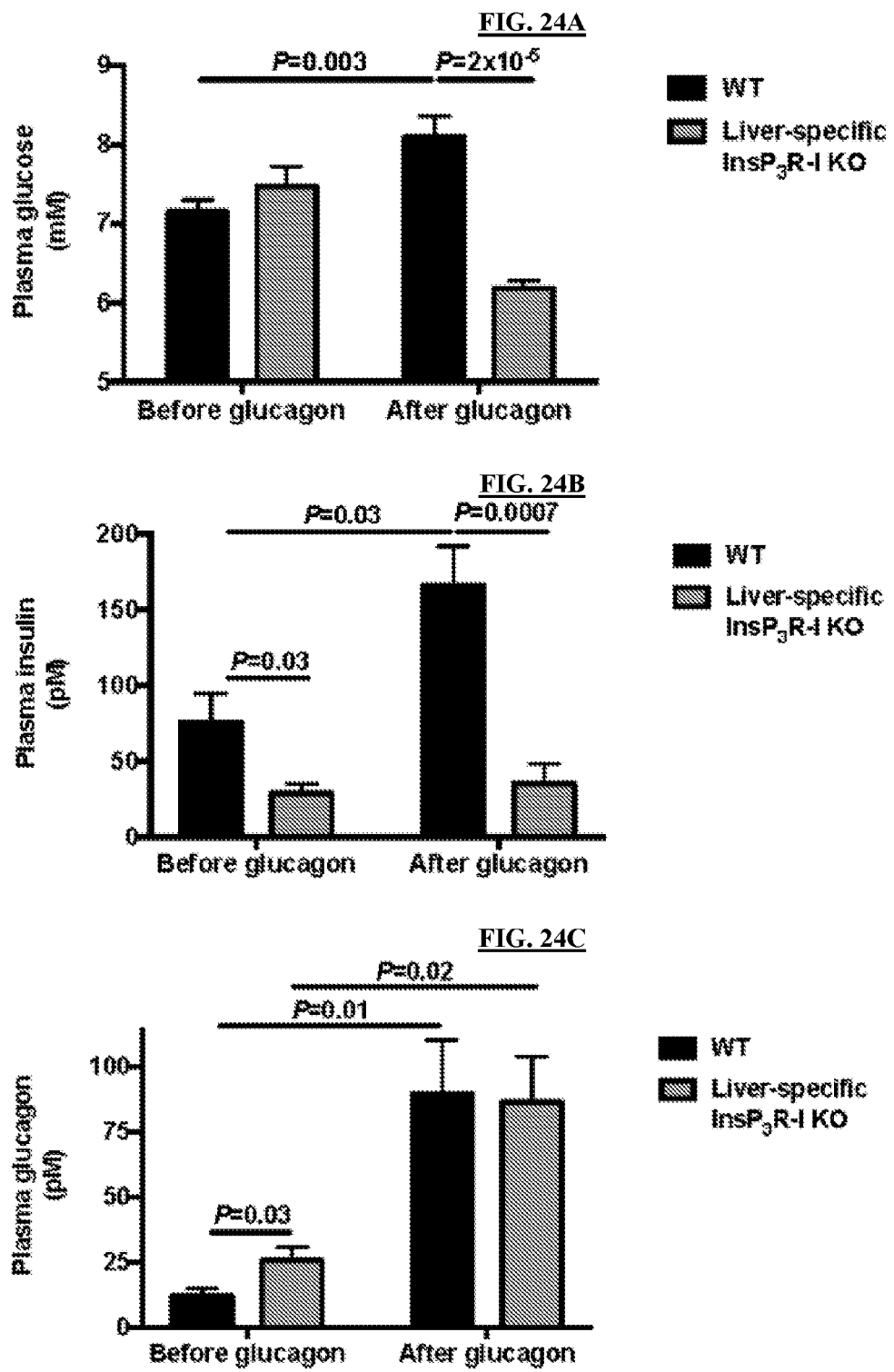

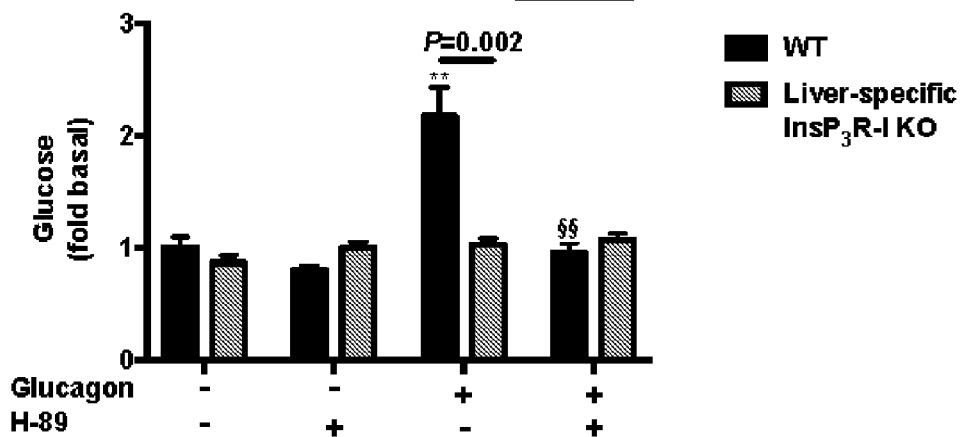
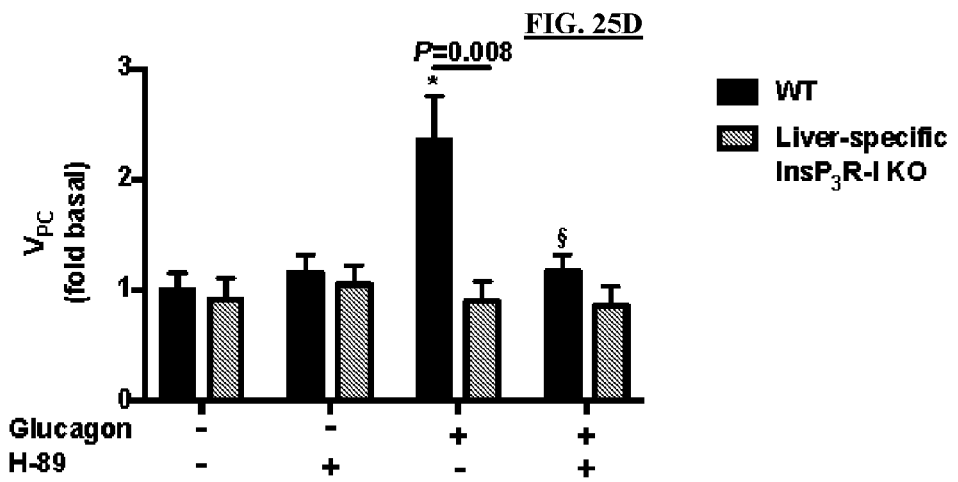
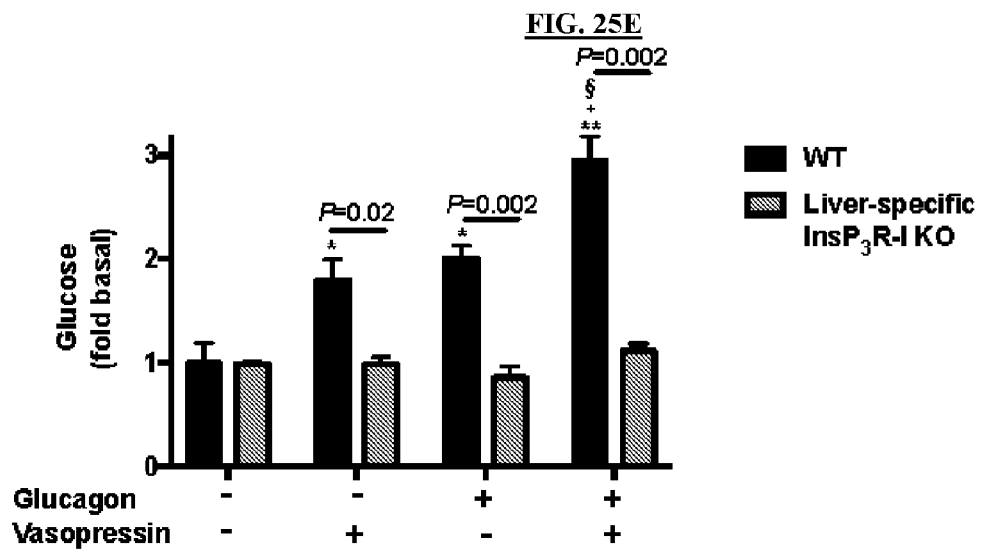

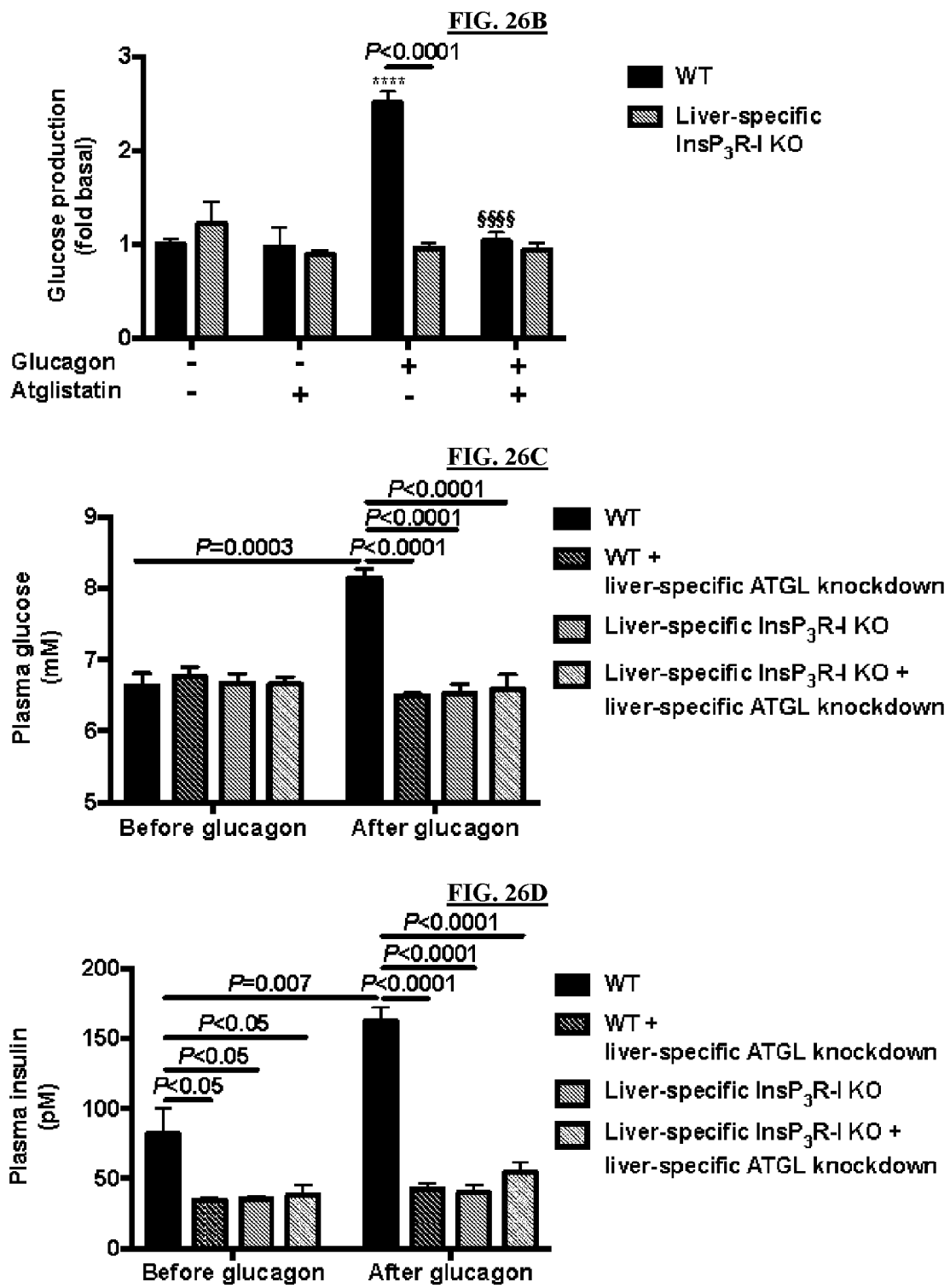

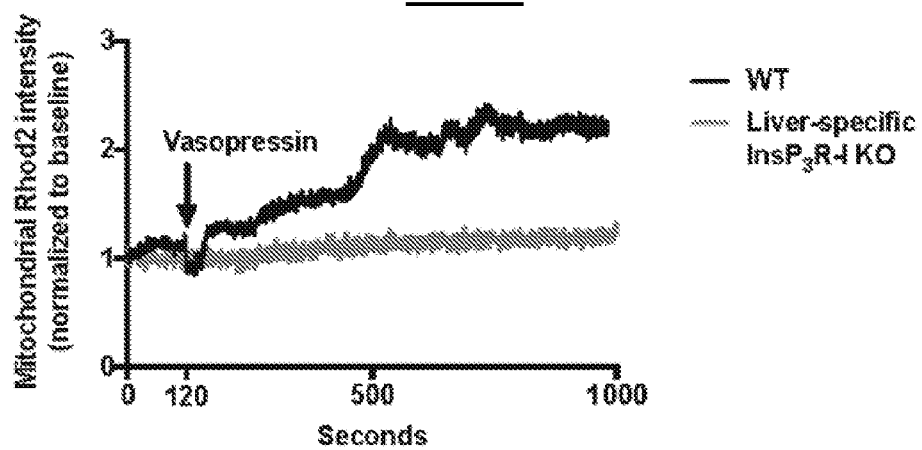
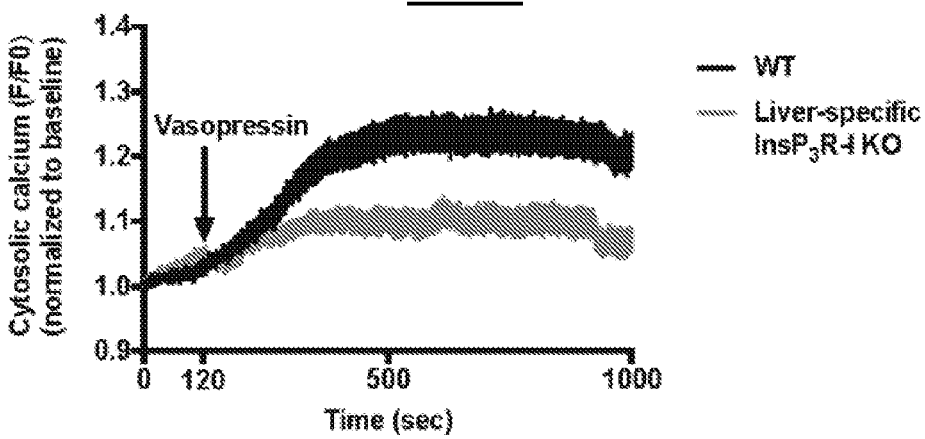
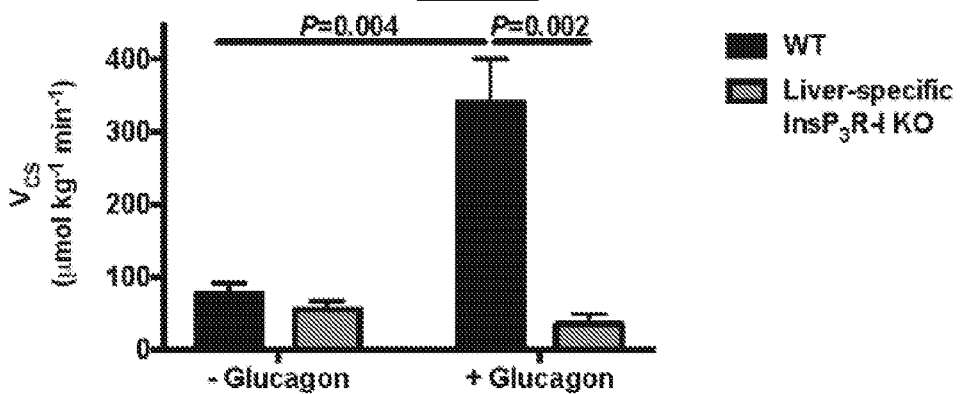

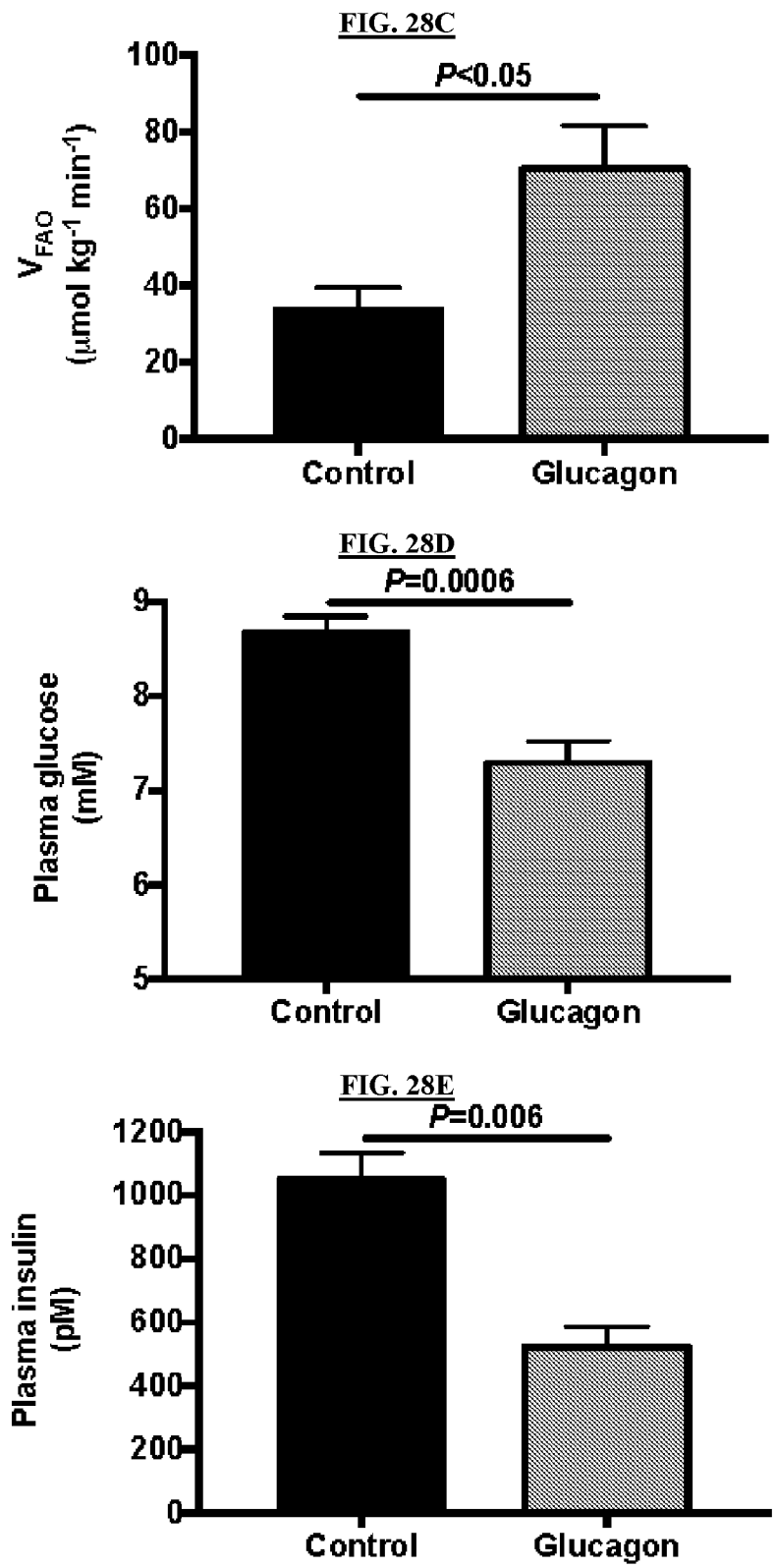

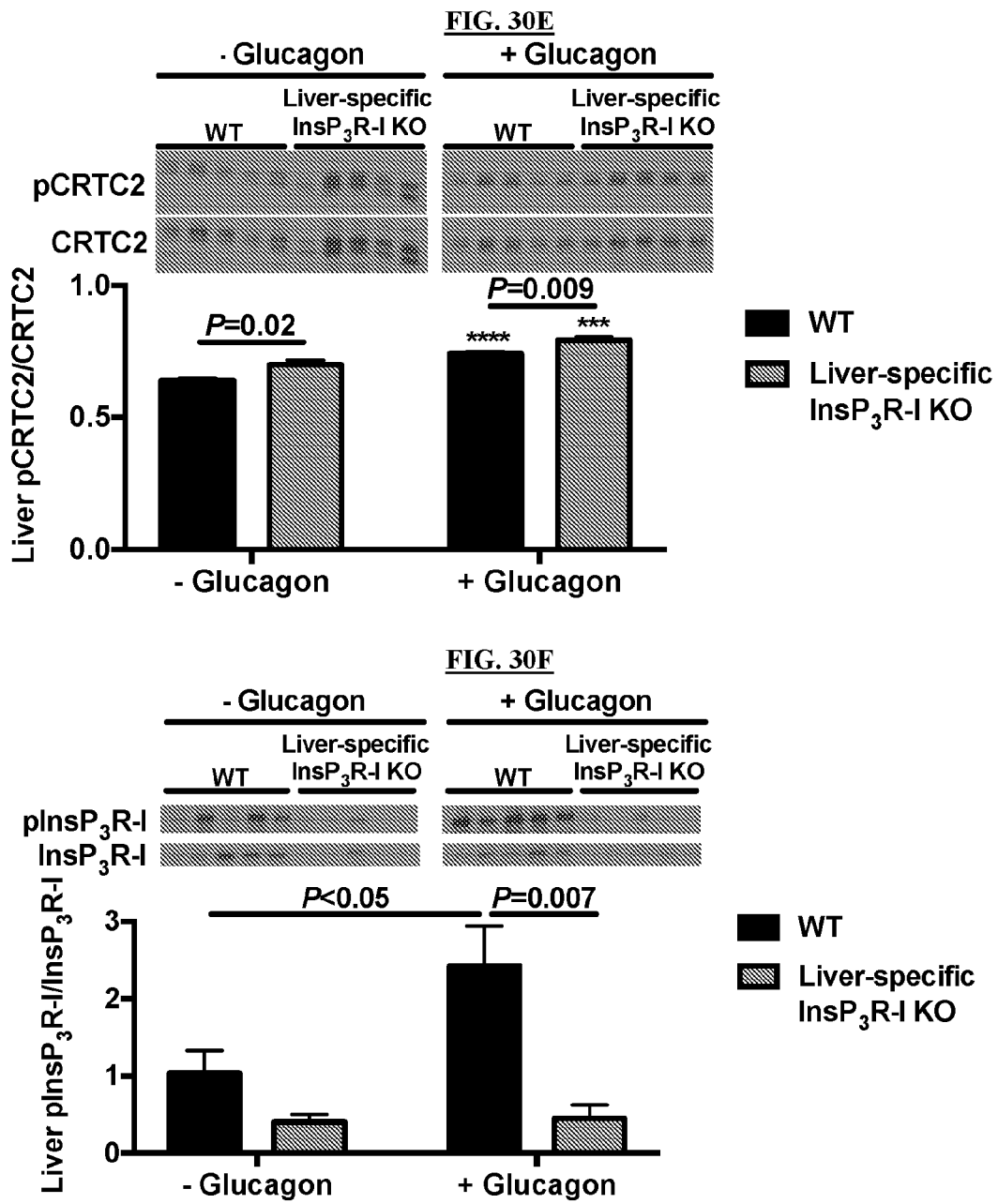

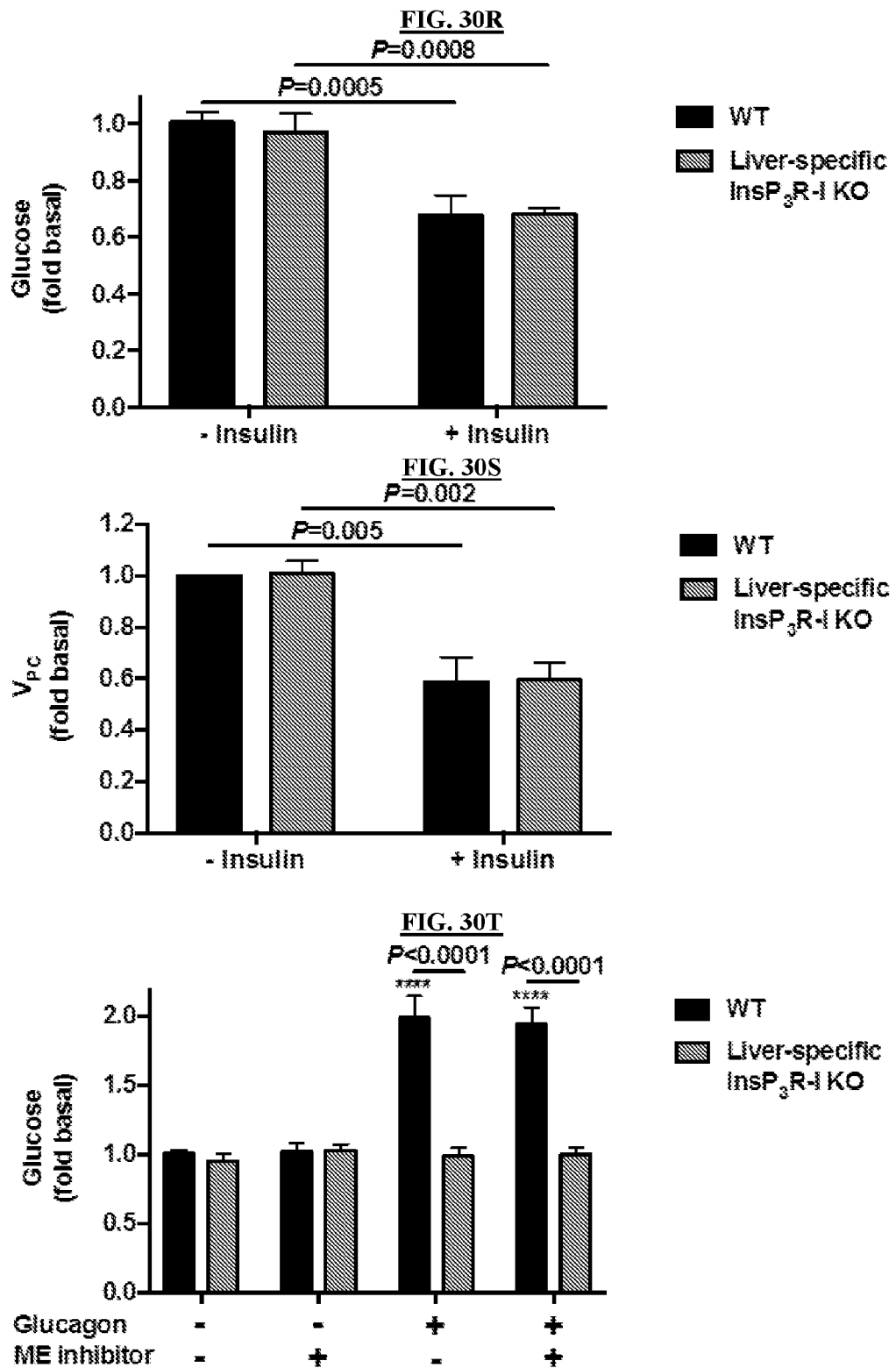

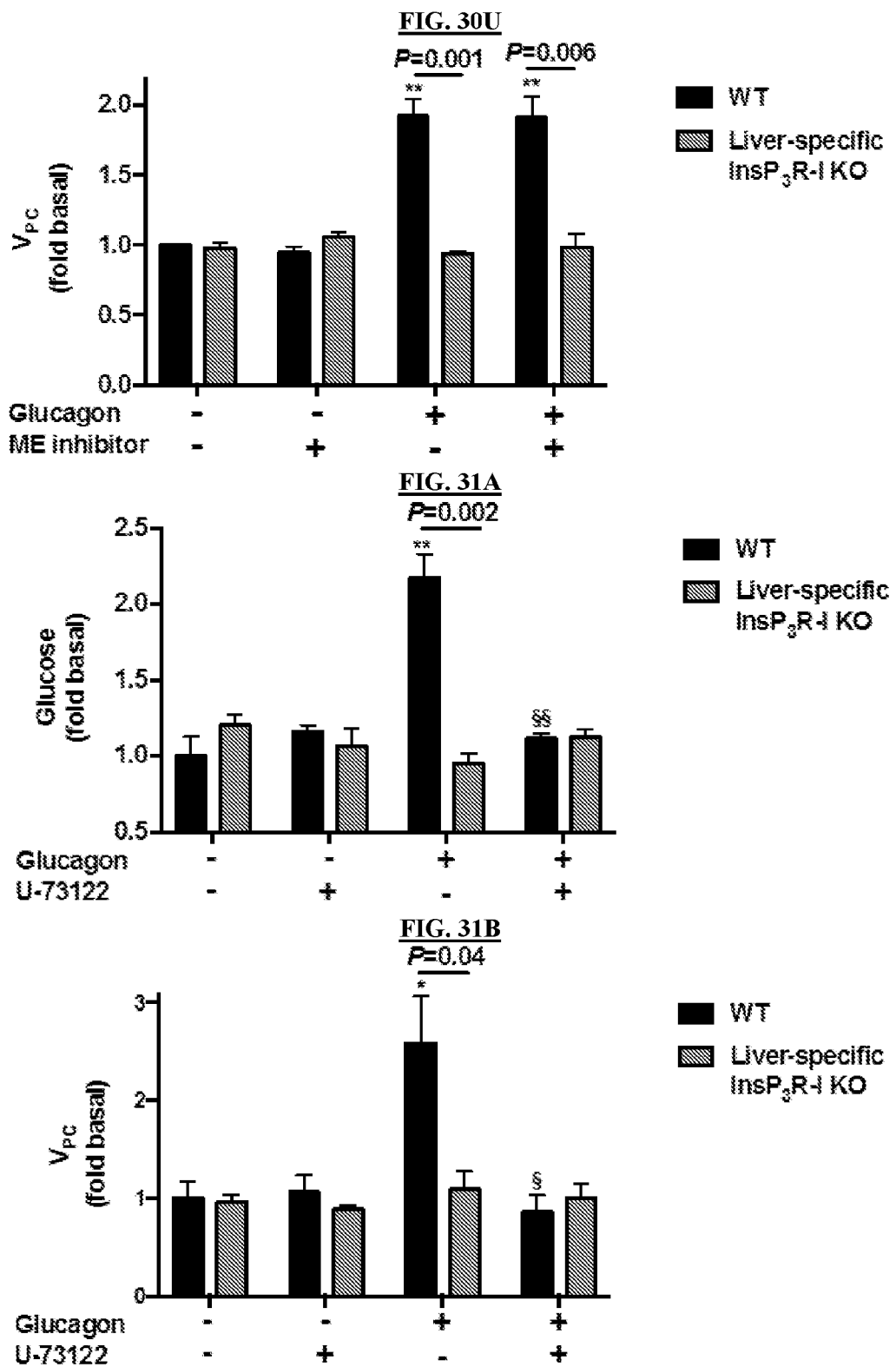

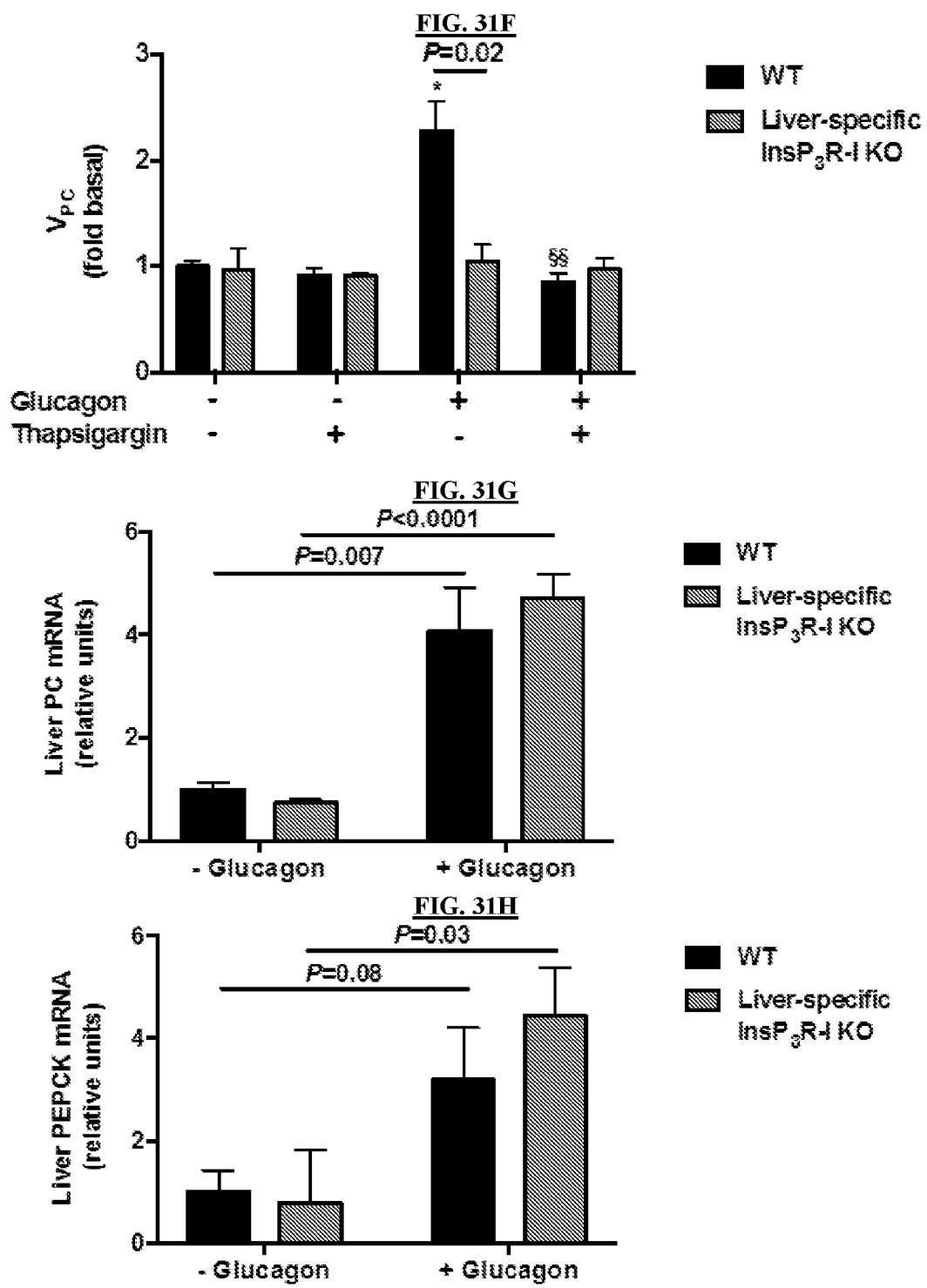

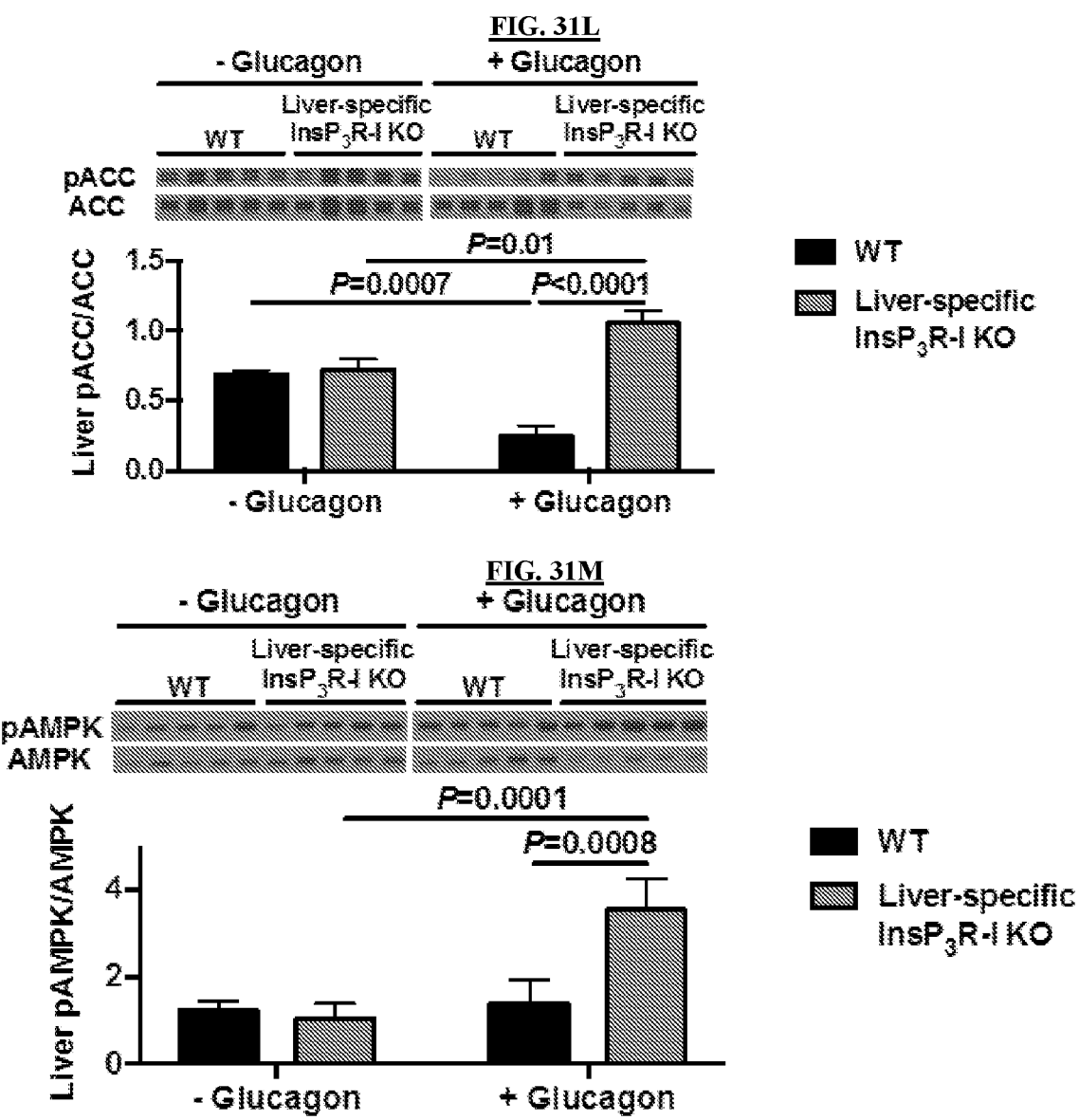

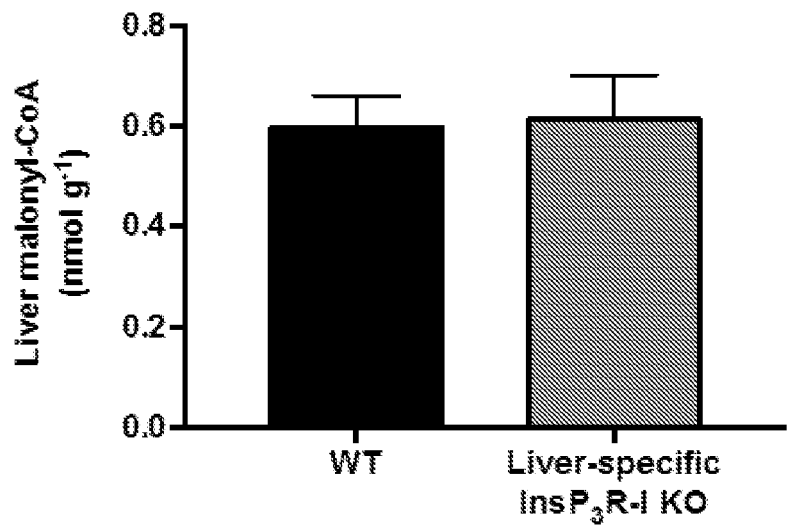
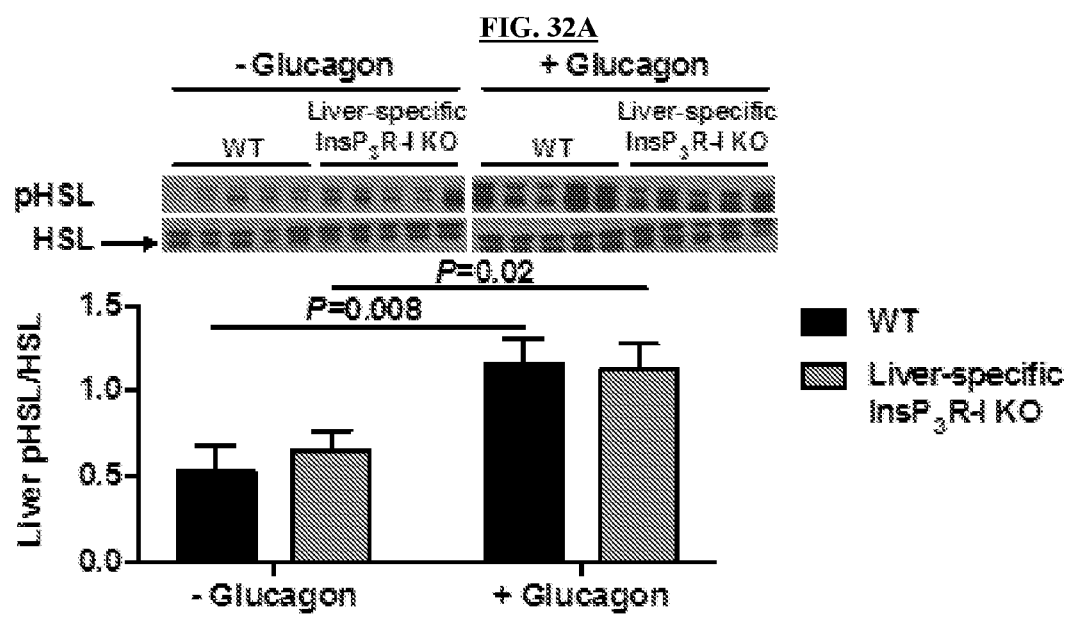

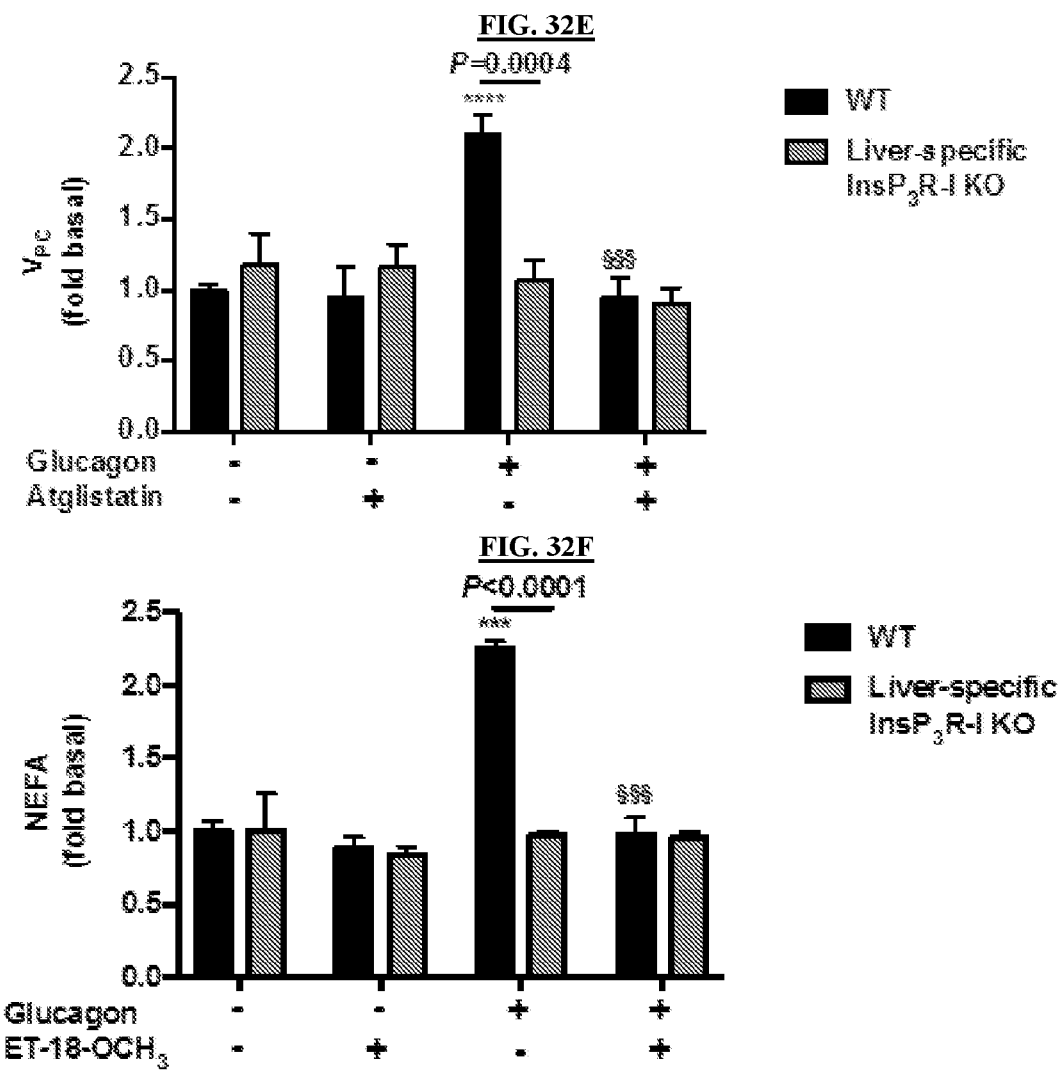

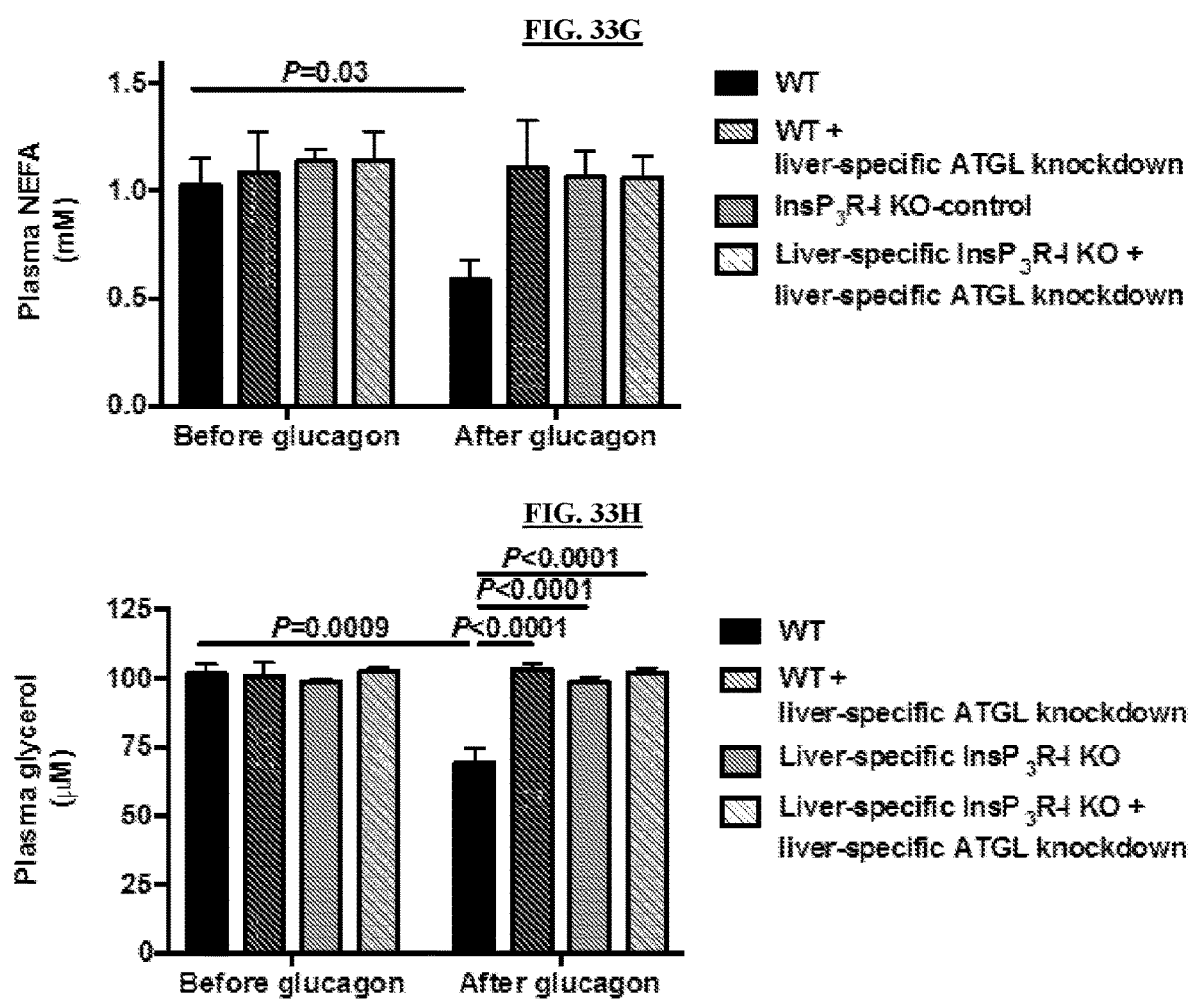

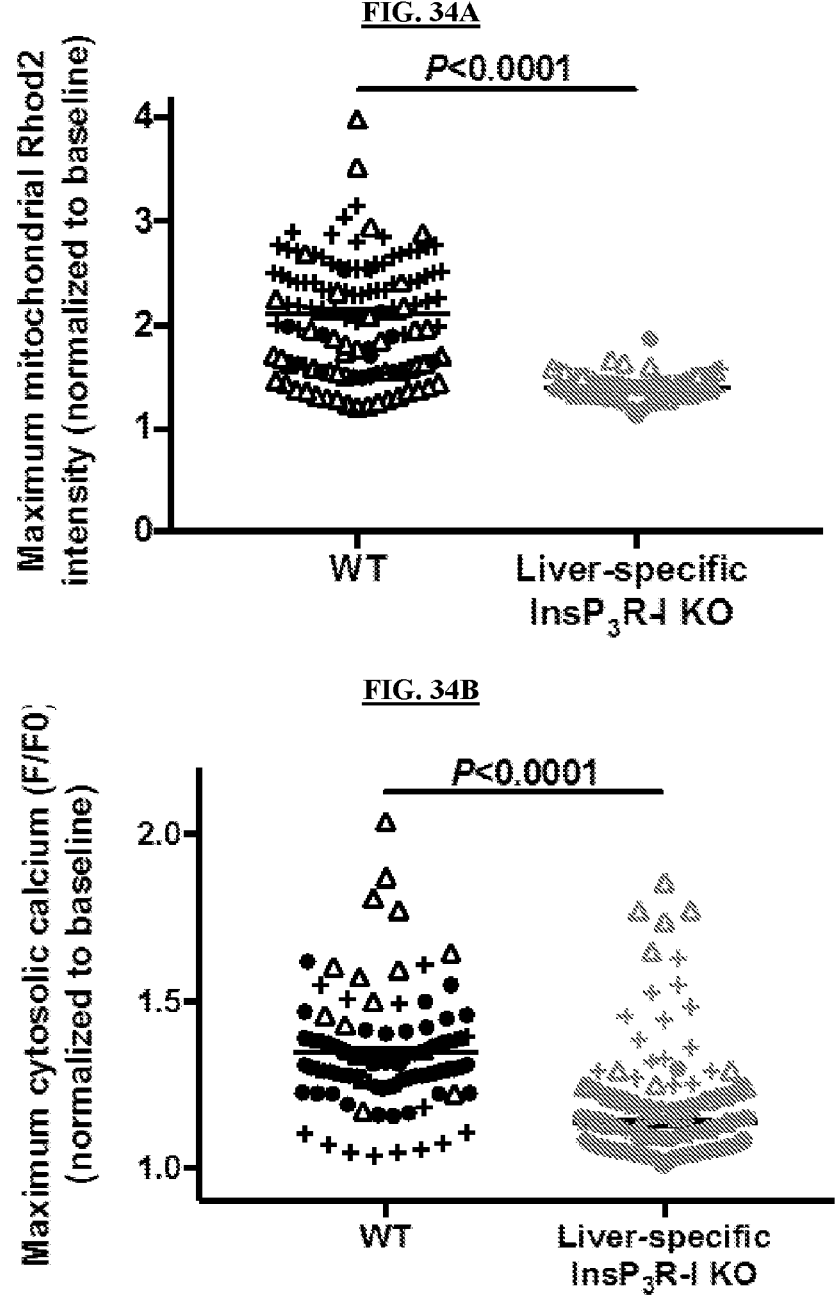

![](US 11,484,608 B2)

NON-INVASIVE ASSESSMENT OF HEPATIC MITOCHONDRIAL METABOLISM BY POSITIONAL ISOTOPOMER NMR TRACER ANALYSIS (PINTA)

CROSS-REFERENCE TO RELATED APPLICATIONS

The present application is a 35 U.S.C. § 371 national phase application from, and claims priority to, International Application No. PCT/US2018/054616, filed Oct. 5, 2018, and published under PCT Article 21(2) in English, which claims priority under 35 U.S.C. § 119(e) to U.S. Provisional Patent Application No. 62/568,680, filed Oct. 5, 2017 and U.S. Provisional Patent Application No. 62/613,254, filed Jan. 3, 2018, all of which applications are hereby incorporated by reference in their entireties.

STATEMENT REGARDING FEDERALLY SPONSORED RESEARCH OR DEVELOPMENT

This invention was made with government support under DK113984, DK116774, DK040936 and CA215315 awarded by National Institutes of Health. The government has certain rights in the invention.

BACKGROUND OF THE INVENTION

Hepatic mitochondrial function plays a critical role in the regulation of liver and whole-body glucose and fat metabolism. There is great interest in understanding the potential role for alterations in hepatic mitochondrial activity in the pathogenesis of non-alcoholic fatty liver disease (NAFLD), non-alcoholic steatohepatitis (NASH), and type 2 diabetes (T2D), as well for the evaluation of potential novel therapies targeting hepatic mitochondrial fat oxidation to treat these diseases.

While recent studies have demonstrated the utility of in vivo $^{13}C$ magnetic resonance spectroscopy (MRS) to directly assess rates of hepatic mitochondrial oxidation flux ($V_{CS}$) and pyruvate carboxylase flux ($V_{PC}$) in humans, application of this method is expensive, time- and labor-intensive, and requires an in vivo wide-bore (>0.8 m), high field (≥4-Tesla) magnetic resonance imaging (MRI) system modified to do $^{13}C$ MRS, which is available at only a few academic medical centers worldwide. To date the only non-invasive tracer method described to assess hepatic mitochondrial fluxes in vivo utilizes [$^{13}C_3$]propionate. A disadvantage of the propionate method is that it can alter hepatic mitochondrial metabolism in part through generation of high concentrations of propionyl-CoA. An alternative non-invasive tracer method to model hepatic metabolism in vivo with minimal perturbation of hepatic mitochondrial metabolism is unfortunately not available at this time.

There remains a need in the art for non-invasive methods of tracking and measuring hepatic mitochondrial metabolism. In certain embodiments, these methods can be used to assess and evaluate the efficacy of novel therapies targeting hepatic mitochondrial activity. The present invention meets these needs.

BRIEF SUMMARY OF THE INVENTION

In one aspect, the invention provides a composition comprising at least one isotopically labelled $C_3$ compound selected from the group consisting of $^{13}C$-labelled L-lactic acid, $^{13}C$-labelled pyruvic acid, and $^{13}C$-labelled alanine, or any salt or solvate thereof, and at least one isotopically labelled glucose selected from the group consisting of $^2H$-labelled glucose and $^3H$-labelled glucose, or any solvate thereof.

In certain embodiments, the isotopically labelled glucose comprises at least one selected from the group consisting of [1,2,3,4,5,6,6-$^2H_7$] glucose, [1,2,3,4,5,6,6-$^3H_7$] glucose, and [3-$^3H$]glucose.

In certain embodiments, the at least one isotopically labelled $C_3$ compound comprises at least one selected from the group consisting of [3-$^{13}C$] L-lactic acid, [2-$^{13}C$] L-lactic acid, [2-$^{13}C$]pyruvate, [3-$^{13}C$] pyruvate, [2-$^{13}C$] alanine, and [3-$^{13}C$] alanine.

In certain embodiments, the at least one isotopically labelled $C_3$ compound is at a concentration of about 50 to about 500 mg/mL.

In certain embodiments, the isotopically labelled glucose is at a concentration of about 10 to about 50 mg/mL.

In certain embodiments, the composition is a pharmaceutically acceptable composition. In other embodiments, the composition is formulated for intravenous infusion in a subject.

In certain embodiments, the composition further comprises $^{13}C$-labelled beta-hydroxybutyric acid, or any salt or solvate thereof. In other embodiments, the $^{13}C$-labelled beta-hydroxybutyric acid comprises [1,2,3,4-$^{13}C_4$] beta-hydroxybutyric acid. In yet other embodiments, the $^{13}C$-labelled beta-hydroxybutyric acid is at a concentration of about 0.5 to about 5 mg/mL.

In another aspect, the invention provides a method of measuring at least one metabolic rate in a subject selected from the group consisting of hepatic mitochondrial oxidation and pyruvate carboxylase flux. In certain embodiments, the method comprises administering to the subject isotopically labelled glucose, and at least one isotopically labelled $C_3$ compound selected from the group consisting of lactate, pyruvate, and alanine. In other embodiments, the subject is further administered isotopically labelled beta-hydroxybutyric acid, or any salts or solvates thereof. In yet other embodiments, the method comprises collecting a biological sample from the subject through a non-invasive procedure. In yet other embodiments, the method comprises analyzing the collected biological sample to assess the rate of endogenous glucose production in the subject.

In certain embodiments, the isotopically labelled glucose comprises at least one selected from the group consisting of [1,2,3,4,5,6,6-$^2H_7$] glucose, [1,2,3,4,5,6,6-$^3H_7$] glucose, and [3-$^3H$]glucose. In other embodiments, the isotopically labelled glucose is administered to the subject at a rate of about 0.21 mg/(m²-min) to about 21 mg/(m²-min).

In certain embodiments, the $^{13}C$-labelled $C_3$ compound comprises [3-$^{13}C$] L-lactic acid. In other embodiments, the $^{13}C$-labelled L-lactic acid is administered to the subject at a rate of about 0.5 µmol/(kg-min) to about 150 µmol/(kg-min).

In certain embodiments, the $^{13}C$-labelled beta-hydroxybutyric acid comprises [1,2,3,4-$^{13}C_4$] beta-hydroxybutyric acid. In other embodiments, the $^{13}C$-labelled beta-hydroxybutyric acid is administered to the subject at a rate of about 0.1 mg/(kg-min) to about 1 mg/(kg-min).

In certain embodiments, the isotopically labelled glucose and the isotopically labelled $C_3$ compound, and optionally the isotopically labelled beta-hydroxybutyric acid, are administered to the subject separately. In other embodiments, the isotopically labelled glucose and the isotopically labelled $C_3$ compound, and optionally the isotopically labelled beta-hydroxybutyric acid, are co-formulated. In yet other embodiments, the isotopically labelled glucose and the isotopically labelled $C_3$ compound, and optionally the isotopically labelled beta-hydroxybutyric acid, are administered to the subject intravenously.

In certain embodiments, the biological sample from the subject comprises at least one material selected from the group consisting of plasma, blood, and serum. In other embodiments, the biological sample is collected from the subject intravenously.

In certain embodiments, the biological sample is analyzed through one or more methods selected from the group consisting of nuclear magnetic resonance spectroscopy (NMR), gas chromatography/mass spectrometry (GC/MS), liquid chromatography/mass spectrometry/mass spectrometry (LC/MS-MS), scintillation counting and any combinations thereof.

In certain embodiments, the subject is a mammal. In other embodiments, the subject is a human.

In certain embodiments, the pyruvate carboxylase flux ($V_{PC}$) is determined by measuring the $V_{PC}/V_{HGP}$ ratio using the equation $$\frac{V_{PC}}{V_{HGP}} = \frac{G2}{XFE^2},$$

wherein:

XFE represents the fractional triose enrichment:

$$XFE = \frac{1}{1 + \frac{G1}{2*G2}};$$

G1 represents the measured [m+1] glucose; and
G2 represents the [m+2] glucose enrichment corrected for any [m+2] glucose synthesized from $^{13}C_2$-labeled trioses: Corrected m+2 glucose=G2=Measured [m+2] glucose–2*C4C5C6 [m+2]glucose; and wherein absolute $V_{PC}$ flux equals measured endogenous glucose production multiplied by $V_{PC}/V_{HGP}$.

In certain embodiments, the [m+1], [m+2], and C4C5C6 [m+2] glucose are measured by GC/MS.

In certain embodiments, the hepatic mitochondrial oxidation flux ($V_{CS}$) is determined by measuring the positional enrichment of glucose and calculating the ratio of hepatic $V_{PC}/V_{CS}$ flux as $$\frac{V_{PC}}{V_{CS}} = \frac{[5-^{13}C]\text{glucose}}{2*[4-^{13}C]\text{glucose}} - 1.$$

In other embodiments, the positional enrichment of glucose is measured by $^{13}C$ NMR. In certain embodiments, the $V_{PC}/V_{CS}$ flux is corrected for the contribution of $^{13}C$ bicarbonate enrichment.

BRIEF DESCRIPTION OF THE DRAWINGS

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

FIG. 6A is a graph showing plasma lactate concentrations before and after a 120 min infusion of [3-$^{13}C$]lactate. FIG. 6B is a graph showing plasma $^{13}C$ lactate enrichment and $^3H$ glucose specific activity at steady-state. Data in FIGS. 6A-6B are the mean±S.E.M. of n=16 per time point. FIGS. 6C-6D are graphs showing m+1 (FIG. 6C) and m+2 (FIG. 6D) glucose enrichment.

FIGS. 9A-9H are graphs showing that a decreased rate of hepatic glycogenolysis was the primary determinant of the switch from glucose to fat oxidation during starvation. FIG. 9A is a graph showing plasma glucose concentration over 48 hours of fasting. FIG. 9B is a graph showing hepatic glucose production from net hepatic glycogenolysis, gluconeogenesis from oxaloacetate (i.e., $V_{PC}$), and gluconeogenesis from glycerol. *p<0.05 versus 8-hr fasted rats and §§§§ p<0.0001 versus 16-hr fasted rats, in both cases comparing gluconeogenesis from oxaloacetate. FIG. 9C is a graph showing percent glucose oxidation in the TCA cycle (pyruvate dehydrogenase flux [VPDH]/citrate synthase flux [$V_{CS}$]). *p<0.05, p<0.01, *p<0.001, and ****p<0.0001 versus fed rats; ####p<0.0001 versus 6-hr fasted rats; and § p<0.05 and §§ p<0.01 versus 16-hr fasted rats. FIGS. 9D-9E are graphs of plasma leptin (FIG. 9D) and corticosterone (FIG. 9E) concentrations. FIG. 9F is a graph of endogenous glucose production before and 2 hr after treatment with a glycogen phosphorylase inhibitor. FIGS. 9G-9H are graphs of plasma leptin (FIG. 9G) and corticosterone (FIG. 9H) concentrations in glycogen phosphorylase inhibitor-treated rats. In FIGS. 9F-9H, data from the same rats before and after treatment with the inhibitor were compared by the paired Student's t test. In FIGS. 9A-9E, ANOVA with Bonferroni's multiple comparisons test was used. Data are the mean±SEM of n=6-8 per group.

FIG. 10A is a graph showing body weight during 48 hours of fasting. FIG. 10M is a graph showing hepatic membrane/cytosolic PKC epsilon content. FIG. 10N is a graph showing plasma insulin concentrations before (basal) and after a 150-min hyperinsulinemic-euglycemic clamp. FIGS. 10U-10W are graphs showing liver PC (FIG. 10U), PEPCK (FIG. 10V), and G6Pase (FIG. 10W) protein expression. In FIGS. 10A, 10C, 10E, 10G-10M and 10Q-10W, data were compared by ANOVA with Bonferroni's multiple comparisons test. In FIGS. 10N-10O basal and clamp data within the same group were compared by the 2-tailed paired Student's t test. In FIG. 10P, 6 and 48 hr fasted rats were compared with the 2-tailed unpaired Student's t-test. In all panels, data are the mean±SEM of n=6-8 per group.

FIGS. 11A-11B are graphs showing plasma insulin (FIG. 11A) and glucagon (FIG. 11B) concentrations. FIG. 11P-11W are graphs showing plasma glucose (FIG. 11P), insulin (FIG. 11Q), lactate (FIG. 11R), ACTH (FIG. 11S), glucagon (FIG. 11T), epinephrine (FIG. 11U), norepinephrine (FIG. 11V), and FGF-21 (FIG. 11W) concentrations. In FIGS. 11A-11N, all time points were compared by ANOVA with Bonferroni's multiple comparisons test. In FIGS. 11P-11W, data were compared before and after phosphorylase inhibitor treatment by the 2-tailed paired Student's t test. In all panels, data are the mean±SEM of n=6-8 per group.

FIGS. 12A-12J are graphs showing that physiologic leptin replacement reduced WAT lipolysis and hepatic gluconeogenesis in 48-hr fasted rats, and that supraphysiologic leptin reversed this effect by stimulation of catecholamine secretion. FIGS. 12A-12B are graphs showing plasma leptin (FIG. 12A) and glucose (FIG. 12B) concentrations during a 6 hr infusion of stepwise increasing doses of leptin in 48-hr fasted rats. FIG. 12C is a graph showing whole-body glucose turnover. FIGS. 12D-12F are graphs showing plasma corticosterone (FIG. 12D), epinephrine (FIG. 12E), and norepinephrine (FIG. 12F) concentrations. FIGS. 12G-12H are graphs showing whole-body fatty acid (FIG. 12G) and glycerol (FIG. 12H) turnover. FIG. 12I is a graph showing liver acetyl-CoA content. FIG. 12J is a graph showing whole-body β-hydroxybutyrate turnover. In FIGS. 12A-12J, n=8. Paired comparisons (ANOVA with Bonferroni's multiple comparisons test) were performed, except in FIG. 12I, where groups were compared by unpaired ANOVA with Bonferroni's multiple comparisons test. Data are the mean±SEM.

FIGS. 13A-13I show the results of experiments conducted on 48-hr fasted normal chow-fed rats. FIGS. 13J-13U show the results of experiments conducted on Type 1 diabetic rats. FIG. 13A is a graph showing glucose infusion rate during a stepwise leptin infusion study. FIGS. 13B-13E are graphs showing plasma non-esterified fatty acid (FIG. 13B), glycerol (FIG. 13C), β-hydroxybutyrate (FIG. 13D), and lactate (FIG. 13E) concentrations. FIGS. 13F-13H are graphs of plasma insulin (FIG. 13F), growth hormone (FIG. 13G), and FGF-21 (FIG. 13H) concentrations. FIG. 13I is a graph of liver malonyl-CoA content. FIGS. 13J-13L are graphs showing plasma leptin (FIG. 13J), glucose (FIG. 13K), and insulin (FIG. 13L) concentrations. FIG. 13M is a graph showing whole-body glucose turnover. FIGS. 13N-13R are graphs showing plasma lipolytic hormone concentrations: plasma ACTH (FIG. 13N), corticosterone (FIG. 13O), epinephrine (FIG. 13P), norepinephrine (FIG. 13Q), and growth hormone (FIG. 13R). FIGS. 13S-13U are graphs showing whole-body fatty acid (FIG. 13S), glycerol (FIG. 13T), and β-hydroxybutyrate (FIG. 13U) turnover. In all panels, data were compared by paired ANOVA with Bonferroni's multiple comparisons test, except in FIG. 13I, where unpaired ANOVA was used. The mean±SEM of n=8 per dose are shown. Each rat was studied stepwise with increasing leptin infusion rates.

FIGS. 14A-14J are graphs showing that increased hepatic acetyl-CoA content maintained euglycemia during starvation. FIGS. 14A-14C are graphs showing whole-body fatty acid (FIG. 14A), glycerol (FIG. 14B), and β-hydroxybutyrate (FIG. 14C) turnover. FIGS. 14D-14E are graphs showing hepatic acetyl-CoA (FIG. 14D) and malonyl-CoA (FIG. 14E) content. FIGS. 14F-14G are graphs showing plasma glucose (FIG. 14F) and whole-body glucose turnover (FIG. 14G) 2 hr after treatment with etomoxir. FIG. 14H is a graph showing liver acetyl-CoA content. FIGS. 14I-14J are graphs showing plasma leptin (FIG. 14I) and corticosterone (FIG. 14J) concentrations. In FIGS. 14A-14E, n=7 per time point, and data were compared by ANOVA with Bonferroni's multiple comparisons test. In FIGS. 14F-14J, data are the mean±SEM of n=6 per group. Data were compared by ANOVA with Bonferroni's multiple comparisons test (control versus etomoxir versus atglistatin, with these groups compared separately at each time point; control data are duplicated in and FIGS. 14A-14J and 15A-15H).

FIGS. 15A-15H are graphs showing that increased WAT lipolysis was necessary to increase hepatic acetyl-CoA content and maintain euglycemia in the starved state. FIG. 15A is a graph showing plasma glucose concentrations in control and atglistatin-treated rats. FIGS. 15B-15D are graphs showing whole-body fatty acid (FIG. 15B), glycerol (FIG. 15C), and β-hydroxybutyrate (FIG. 15D) turnover. FIG. 15E is a graph showing hepatic acetyl-CoA content. FIG. 15F is a graph showing whole-body glucose turnover. FIGS. 15G-15H are graphs showing plasma leptin (FIG. 15G) and corticosterone (FIG. 15H) concentrations. In FIGS. 15A-15H, data are the mean±SEM of 5-6 rats per group, and control data are duplicated from FIGS. 14A-14J. Data were compared by ANOVA with Bonferroni's multiple comparisons test (control versus etomoxir versus atglistatin, with these groups compared separately at each time point.

FIGS. 16A-16L are graphs showing that increased hepatic acetyl-CoA content maintained euglycemia in an extended fast. FIG. 16A is a graph showing whole-body palmitate turnover during a fast. FIGS. 16B-16F are graphs showing plasma insulin (FIG. 16B), lactate (FIG. 16C), NEFA (FIG. 16D), glycerol (FIG. 16E), and β-hydroxybutyrate (FIG. 16F) concentrations in rats treated with the CPT-1 inhibitor etomoxir. FIGS. 16G-16I are graphs showing whole-body fatty acid (FIG. 16G), glycerol (FIG. 16H), and (β-hydroxybutyrate (FIG. 16I) turnover. FIG. 16J is a graph showing liver malonyl-CoA. FIGS. 16K-16L are graphs showing plasma epinephrine (FIG. 16K) and norepinephrine (FIG. 16L) concentrations. Data are the mean±SEM of n=6 per group. In FIGS. 16B-16L, data were compared by ANOVA with Bonferroni's multiple comparisons test (control versus etomoxir versus atglistatin, with these three groups compared separately at each time point; control data are duplicated between FIGS. 16A-16L and FIGS. 17A-17I).

FIG. 17A is a graph showing that the glucose infusion rate required to maintain euglycemia in 48 hr fasted rats treated with ATGL inhibitor atglistatin (rats fasted for 0, 6, and 16 hr) did not require glucose to avoid symptomatic hypoglycemia. FIGS. 17B-17E are graphs showing plasma NEFA (FIG. 17B), glycerol (FIG. 17C), lactate (FIG. 17D), and β-hydroxybutyrate (FIG. 17E) concentrations. FIGS. 17F-17H are graphs showing plasma insulin (FIG. 17F), epinephrine (FIG. 17G), and norepinephrine (FIG. 17H) concentrations. FIG. 17I is a graph showing liver malonyl-CoA content. In all panels, data are the mean±SEM of n=5-6 per group. In FIGS. 17B-17I, data were compared by ANOVA with Bonferroni's multiple comparisons test (control versus etomoxir versus atglistatin, with these three groups compared separately at each time point; control data are duplicated between FIGS. 16A-16L and FIGS. 17A-17I).

FIGS. 18A-18H are graphs showing that glucocorticoid activity was required to maintain WAT lipolysis and euglycemia in starvation. FIGS. 18A-18B are graphs showing plasma glucose (FIG. 18A) and lactate (FIG. 18B) concentrations. FIGS. 18C-18D are graphs showing whole-body fatty acid (FIG. 18C) and glycerol (FIG. 18D) turnover. FIG. 18E is a graph showing hepatic acetyl-CoA content. FIGS. 18F-18G are graphs showing whole-body β-hydroxybutyrate (FIG. 18F) and glucose (FIG. 18G) turnover. FIG. 18H is a graph showing plasma leptin concentrations. In FIGS. 18A-18H, data are the mean±SEM of n=6, with data from before and after mifepristone treatment compared by the two-tailed paired Student's t test.

FIGS. 19A-19F are graphs showing that glucocorticoid activity was required to maintain WAT lipolysis and euglycemia in the starved state. FIG. 19A is a graph showing the glucose infusion rate required to avoid symptomatic hypoglycemia. p<0.01, *p<0.001, ****p<0.0001 by the 2-tailed unpaired Student's t test. FIGS. 19B-19E are graphs showing plasma insulin (FIG. 19B), NEFA (FIG. 19C), glycerol (FIG. 19D), and (β-hydroxybutyrate (FIG. 19E) concentrations. FIG. 19F is a graph showing hepatic malonyl-CoA concentration. In FIGS. 19A-19F, data are the mean±SEM of n=6 per group, with the 2-tailed paired Student's t test used to compare before versus after mifepristone treatment at each time point separately in FIGS. 19B-19F.

FIGS. 20A-20H are graphs showing that reductions in glucose-alanine cycling with prolonged starvation led to suppression of hepatic gluconeogenesis and hepatic mitochondrial oxidation. FIG. 20A is a graph showing whole-body alanine turnover during the fed-fasted transition. FIG. 20B is a graph showing hepatic citrate concentrations during the fed to fasted transition. FIG. 20C is a graph showing rates of hepatic citrate synthase flux (hepatic mitochondrial oxidation) during the fed-to-fasted transition. FIG. 20D is a graph showing Plasma glucose concentrations in 48-hr fasted rats before and after a 2-hr infusion of alanine (45 mmol/[kg, min]). FIGS. 20E-20F are graphs showing whole-body glucose turnover (FIG. 20E) and hepatic pyruvate carboxylase flux (FIG. 20F) in 48-hr fasted rats before and after alanine infusion. FIG. 20G is a graph showing liver citrate content in 48-hr fasted rats before and after alanine infusion. FIG. 20H is a graph showing rates of hepatic citrate synthase flux (mitochondrial oxidation) in 48-hr fasted rats before and after alanine infusion. In FIGS. 20A-20H, data are the mean±SEM of n=6-8 per group, with data compared by ANOVA (FIGS. 20A-20C) or by the two-tailed unpaired Student's t test (FIGS. 20D-20H).

FIGS. 21A-21B are graphs showing plasma (FIG. 21A) and liver (FIG. 21B) alanine concentrations. FIG. 21Y is a graph comparing plasma T3 concentrations between control rats and alanine infused rats. Data are the mean±SEM of n=6-8 per group. In FIGS.

21A-21O, comparisons were performed using ANOVA with Bonferroni's multiple comparisons test. In FIGS. 21P-21Y, data were compared by the 2-tailed unpaired Student's t test, with the exception of FIG. 21S, in which the 0 and 120 min time points were compared by the 2-tailed paired Student's t test.

FIGS. 22A-22J are graphs showing that reductions in plasma glucose concentrations from ~6 to ~5 mm during prolonged starvation led to reduced glucose-alanine cycling, hypoleptinemia, and HPA axis activation. FIGS. 22A-22B are graphs showing plasma insulin (FIG. 22A) and NEFA (FIG. 22B) concentrations. FIG. 22C is a graph showing muscle glucose uptake in 48-hr fasted rats with and without an infusion of glucose to increase plasma glucose concentrations from 5 to 6 mM. FIG. 22D is a graph showing whole-body alanine turnover. FIG. 22E is a graph showing white adipose tissue glucose uptake. FIGS. 22F-22H are graphs showing plasma leptin (FIG. 22F), ACTH (FIG. 22G), and corticosterone (FIG. 22H) concentrations. FIGS. 22I-22J are whole-body alanine (FIG. 22I) and fatty acid (FIG. 22J) turnover in rats treated with an inhibitor of glycogen phosphorylase. In FIGS. 22C and 22E, data were compared by the two-tailed unpaired Student's t test; otherwise, the paired t test was used. Data are the mean±SEM of n=6-7 per group.

FIGS. 23A-23J are graphs showing that reductions in plasma glucose concentrations from 6 to 5 mm in the starved state leads to reduced muscle glucose-alanine cycling and hypoleptinemia. FIGS. 23A-23B are graphs showing plasma glucose (FIG. 23A) and glucose (FIG. 23B) infusion rate during a clamp to increase plasma glucose concentrations in 48 hr fasted rats to 6 mM. FIG. 23C is a graph showing plasma lactate concentrations. FIGS. 23D-23E are graphs showing endogenous glucose turnover (FIG. 23D) and plasma FGF-21 (FIG. 23E) concentrations. FIGS. 23F-23H are graphs showing plasma NEFA (FIG. 23F), glycerol (FIG. 23G), and β-hydroxybutyrate (FIG. 23H) concentrations in rats treated with a glycogen phosphorylase inhibitor. FIGS. 23I-23J are graphs showing whole-body glycerol (FIG. 23I) and β-hydroxybutyrate (FIG. 23J) turnover. In FIGS. 23C-23E, rats with 5 mM (time zero of the clamp) and 6 mM (120 min of the clamp) plasma glucose were compared by the 2-tailed paired Student's t test. In FIGS. 23F-23J, data at each time point were compared by the 2-tailed paired Student's t test. In all panels, data are the mean±SEM of n=6 per group.

FIGS. 24A-24J are graphs showing that glucagon acutely stimulates hepatic gluconeogenesis by increasing hepatic acetyl-CoA content and PC flux. FIGS. 24A-24C are graphs showing plasma glucose (FIG. 24A), insulin (FIG. 24B), and glucagon (FIG. 24C) concentrations before and at the end of a 2 hr intravenous infusion of glucagon. FIGS. 24D-24F are graphs showing hepatic cAMP concentrations (FIG. 24D), protein kinase A activity (FIG. 24E), and CAMKII phosphorylation (FIG. 24F). FIGS. 24G-24H are graphs showing hepatic glucose production and $V_{PC}$. FIGS. 24I-24J are graph showing hepatic long-chain and acetyl-CoA content. In FIGS. 24A-24J, data are the mean±S.E.M. of n=5-6 per group. Genotypes were compared by the 2-tailed unpaired Student's t-test, while mice were compared before and after glucagon treatment using the 2-tailed paired Student's t-test.

FIGS. 25A-25J are graphs showing that glucagon-stimulated hepatic glucose production required InsP$_3$R-I signaling as well as PKA and PLC activity. FIGS. 25A-25B are graphs showing glucose production and $V_{PC}$ in hepatocytes incubated in the PLC inhibitor ET-18-OCH$_3$. FIGS. 25C-25D are graphs showing glucose production and $V_{PC}$ in hepatocytes incubated in the PKA inhibitor H-89. FIGS. 25E-25F are graphs showing glucose production and $V_{PC}$ in hepatocytes incubated in the InsP$_3$R agonist vasopressin. FIGS. 25G-25H are graphs showing glucose production and $V_{PC}$ in hepatocytes incubated in the InsP$_3$R antagonist 2-APB. FIGS. 25I-25J are graphs showing glucose production and $V_{PC}$ in hepatocytes incubated in the CAMKII/IV inhibitor KN-93. In FIGS. 25A-25J, data are the mean±S.E.M. of n=3 mice, with groups compared using the 2-tailed unpaired Student's t-test.

FIGS. 26A-26H are graphs showing that glucagon required InsP$_3$-mediated intrahepatic lipolysis to promote $V_{PC}$ and hepatic gluconeogenesis. FIG. 26A is a graph and blot showing ATGL S406 phosphorylation. FIG. 26B is a graph showing glucose production in hepatocytes (n=3 mice per group) incubated in the ATGL inhibitor atglistatin and/or glucagon. FIG. 26C-26D are graphs showing plasma glucose (FIG. 26C) and insulin (FIG. 26D) concentrations in mice treated with an adeno-associated virus to knock down ATGL in a liver-specific manner. FIGS. 26E-26F are graphs showing liver long-chain and acetyl-CoA concentrations following a 2 hr glucagon infusion. FIGS. 26G-26H are graphs showing rates of hepatic glucose production and hepatic $V_{PC}$. Unless otherwise specified, data are the mean±S.E.M. of n=5-6 per group, with ANOVA with Bonferroni's multiple comparisons test used to compare the four groups, and the 2-tailed unpaired Student's t-test used to compare the same mice before and after glucagon treatment.

FIGS. 27A-27H are graphs showing that glucagon stimulates mitochondrial oxidation through hepatocellular calcium signaling. FIGS. 27A-27D are graphs showing calcium response to glucagon in isolated hepatocytes from WT and liver specific InsP$_3$R-I knockout mice. In FIGS. 27A-27F, data are replicates from three independent experiments, with different symbols used in FIGS. 27B and 27D to represent each experiment, and the mean±S.E.M. of all data points plotted in FIGS. 27A, 27C, 27E, and 27F. FIGS. 27E-27F are graphs showing calcium response to the InsP$_3$R agonist vasopressin. n=81 WT and 23 InsP$_3$R-I KO (mitochondrial) and n=20 WT and 40 InsP$_3$R-I KO (cytosolic). FIGS. 27G-27H are graphs showing in vivo mitochondrial citrate synthase flux and fatty acid oxidation. In FIGS. 27G-27H, data are the mean±S.E.M. of n=5-6 per group. In FIGS. 27A-27H, comparisons were performed using the 2-tailed unpaired Student's t-test.

FIGS. 28A-28J are graphs showing that chronic increases in mitochondrial oxidative metabolism with a 10-day glucagon infusion led to reversal of NAFLD and improvements in glucose tolerance in diet-induced obese rats. FIGS. 28A-28C are graphs showing that plasma glucagon, hepatic mitochondrial oxidation ($V_{CS}$), and hepatic fatty acid oxidation ($V_{FAO}$) measured on day 10 during the glucagon infusion. FIGS. 28D-28E are graphs showing 6 hr fasted plasma glucose and insulin concentrations measured two hours after cessation of the glucagon infusion. FIGS. 28F-28G are graphs showing liver TAG and DAG concentrations. FIG. 28H is a graph showing hepatic PKCε translocation. FIGS. 28I-28J are graphs showing plasma glucose and insulin concentrations during an intraperitoneal glucose tolerance test. In all panels, data are the mean±S.E.M. of n=6 per group, with comparisons by the 2-tailed unpaired Student's t-test.

FIGS. 29A-29C are graphs showing liver TAG, ceramide, and DAG concentrations in HFD mice chronically infused with glucagon. FIG. 29D is a graph showing PKCε translocation. FIGS. 29E-29F are graphs showing plasma glucose and insulin concentrations during a glucose tolerance test. All data are the mean±S.E.M. of n=5-11 per group. Genotypes were compared using the 2-tailed unpaired Student's t-test.

FIGS. 30A-30U are graphs showing that glucagon acutely stimulated hepatic gluconeogenesis by increasing hepatic acetyl-CoA content and pyruvate carboxylase flux. FIG. 30A is a graph showing body weight of the rat test subjects. FIGS. 30E-30G are graphs showing liver CRTC2, InsP$_3$R-I, and CAMKIV phosphorylation±a 2 hr acute infusion of glucagon. In FIGS. 30A-30O, data are the mean±S.E.M. of n=5-6 per group. FIGS. 30R-30S are graphs showing in vitro glucose production (n=9) and V$_{PC}$ flux (n=4) in isolated hepatocytes with and without 150 pM insulin. Basal data (no insulin) are duplicated from FIGS. 30P-30Q. FIGS. 30T-30U are graphs showing in vitro glucose production (n=8) and V$_{PC}$ flux (n=3) in isolated hepatocytes with and without a malic enzyme inhibitor. In all panels, data are the mean±S.E.M.

FIGS. 31A-31U are graphs showing that glucagon-stimulated glucose production required activation of the PLC and PKA pathways, converging to activate InsP$_3$ signaling. FIGS. 31A-31F are graphs showing in vitro glucose production and V$_{PC}$ flux in isolated hepatocytes with and without U-73122 (n=2 KO-glucagon-U-73122), caffeine and thapsigargin. In FIGS. 31A-31F, n=3 unless otherwise stated, with *P<0.05, P<0.01, *P<0.001 vs. WT-glucagon-drug; § P<0.05, § § P<0.01, § § § P<0.001 vs. WT+glucagon-drug by the 2-tailed unpaired Student's t-test. FIGS. 31G-31I are graphs showing liver PC, PEPCK, and G6Pase mRNA expression. FIGS. 31L-31M are graphs showing liver ACC and AMPK phosphorylation. FIGS. 31S-31U are graphs showing liver long-chain-, acetyl-, and malonyl-CoA content. In FIGS. 31G-31U, 5-6 per group, with comparisons by the 2-tailed unpaired Student's t-test. In all panels, data are the mean±S.E.M.

FIGS. 32A-32M are graphs showing that glucagon acutely stimulated hepatic gluconeogenesis by increasing hepatic acetyl-CoA content and pyruvate carboxylase flux. FIG. 32A is a graph showing liver HSL phosphorylation (n=5 per group). FIGS. 32B-32C are graphs showing in vitro NEFA and glycerol production from isolated hepatocytes (n=14-15 per group). FIGS. 32D-32E are graphs showing NEFA production and V$_{PC}$ in isolated hepatocytes incubated in the ATGL inhibitor atglistatin. FIGS. 32F-32M are graphs showing NEFA production from isolated hepatocytes treated with calcium-modulating agents. Unless otherwise stated, data are presented as the mean±S.E.M. of n=3 per group, with groups compared by the 2-tailed unpaired Student's t-test.

FIGS. 33A-33J are graphs showing that glucagon required InsP$_3$-mediated intrahepatic lipolysis to promote V$_{PC}$ and hepatic gluconeogenesis. FIG. 33A is a graph showing the body weight in mice treated with an adeno-associated virus to knock down liver ATGL. FIGS. 33B-33C are graphs showing WAT and liver ATGL protein expression. FIGS. 33D-33E are graphs showing hepatic PC and PEPCK protein expression. FIGS. 33F-33H are graphs showing plasma glucagon, NEFA and glycerol concentrations. Mice were compared before and after glucagon treatment using the 2-tailed unpaired Student's t-test. FIGS. 33I-33J are graphs showing liver glycogen and malonyl-CoA content. In all panels, data are the mean±S.E.M. of n=5-6 per group, with groups compared by the 2-tailed unpaired Student's t-test, unless otherwise specified.

FIGS. 34A-34J are graphs showing that glucagon stimulated mitochondrial oxidation through hepatocellular calcium signaling. FIGS. 34A-34B are graphs showing maximum mitochondrial and cytosolic response to the InsP$_3$R agonist vasopressin (50 nM). FIGS. 34C-34F are graphs showing calcium response to glucagon in WT hepatocytes±the PKA inhibitor H-89 (25 μM). WT data are duplicated from FIGS. 27A-27D. In FIG. 34C, n=17 WT, n=11 WT+H-89; in FIG. 34E, n=14 WT, n=60 WT+H-89. FIGS. 34G-34H are graphs showing hepatic PDH and PK flux in vivo. FIG. 34I is a graph showing in vitro oxygen consumption in isolated hepatocytes incubated in media±100 nM glucagon. Data shown are the mean±S.E.M. of n=122-210 data points. FIG. 34J is a graph showing liver triglyceride content (without glucagon infusion). In FIGS. 34G-34J, data are the mean-S.E.M. of n=5-6 per group. In all panels, groups were compared by the 2-tailed unpaired Student's t-test (WT vs. KO, and –vs. +glucagon).

FIG. 35A is a graph showing body weight after 10 days of glucagon or saline infusion. FIGS. 35B-35C are graphs showing that hepatic V$_{PC}$/V$_{EGP}$ and V$_{PC}$/V$_{CS}$ flux ratios are identical whether measured with PINTA or ex vivo NMR analysis. In FIGS. 35B-35J, measurements were performed while the glucagon infusion continued. FIGS. 35D-34E are graphs showing liver V$_{PDH}$ and V$_{PK}$. FIG. 35F is a graph showing food intake during the glucagon infusion, determined twice during the 10 day infusion (days 4 and 9) by weighing the food in the cage. FIGS. 35G-35J are graphs showing liver glycogen, acetyl-CoA, malonyl-CoA, and ceramide content. FIGS. 35K-35L are graphs showing plasma glucose and insulin area under the curve during an intraperitoneal glucose tolerance test which began 2 hrs after completing a 10 day continuous infusion of glucagon or saline vehicle. In all panels, data are the mean±S.E.M. of n=6 per group, with comparisons by the 2-tailed unpaired Student's t-test.

FIG. 36A is a graph tracking body weight of mice test subjects. FIGS. 36B-36C are graphs showing food and water intake. FIG. 36D is a graph showing energy expenditure. FIGS. 36E-36F are graphs showing oxygen consumption and carbon dioxide production. FIG. 36G is a graph showing test subject activity. FIGS. 36H-36I are graphs showing glucose and insulin area under the curve during an intraperitoneal glucose tolerance test. In all panels, groups were compared by the 2-tailed unpaired Student's t-test (WT vs. KO, and –vs. +glucagon). Data are presented as the mean±S.E.M. of n=7-11 per group.

DETAILED DESCRIPTION OF THE INVENTION

Figure 5A:
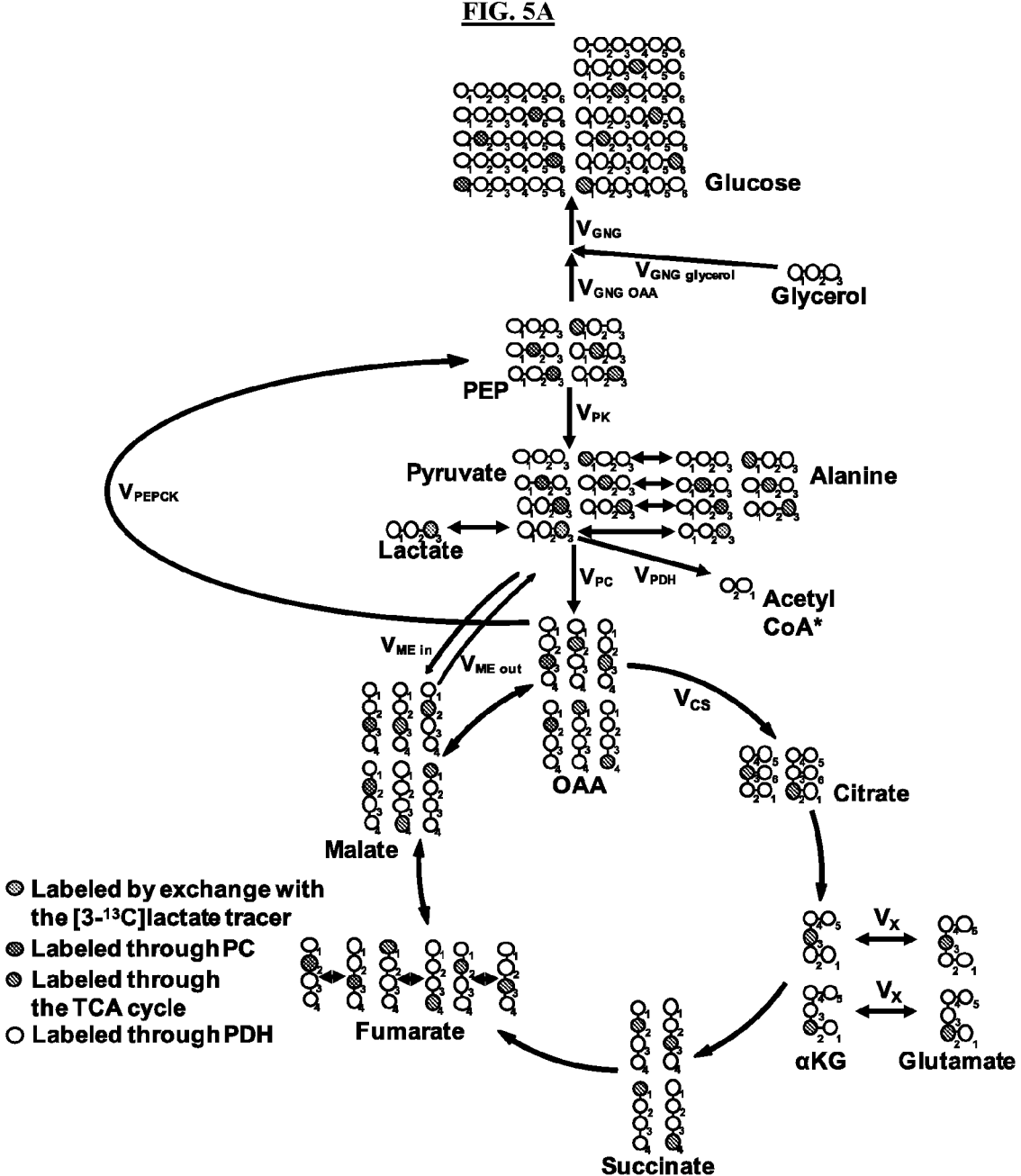
FIG. 5A is a scheme showing [3-$^{13}C$]lactate tracer labeling. αKG,α-ketoglutarate; CS, citrate synthase; GNG, gluconeogenesis; ME, malic enzyme; OAA, oxaloacetate; PEPCK, phosphoenolpyruvate carboxykinase.
Figure 5B:
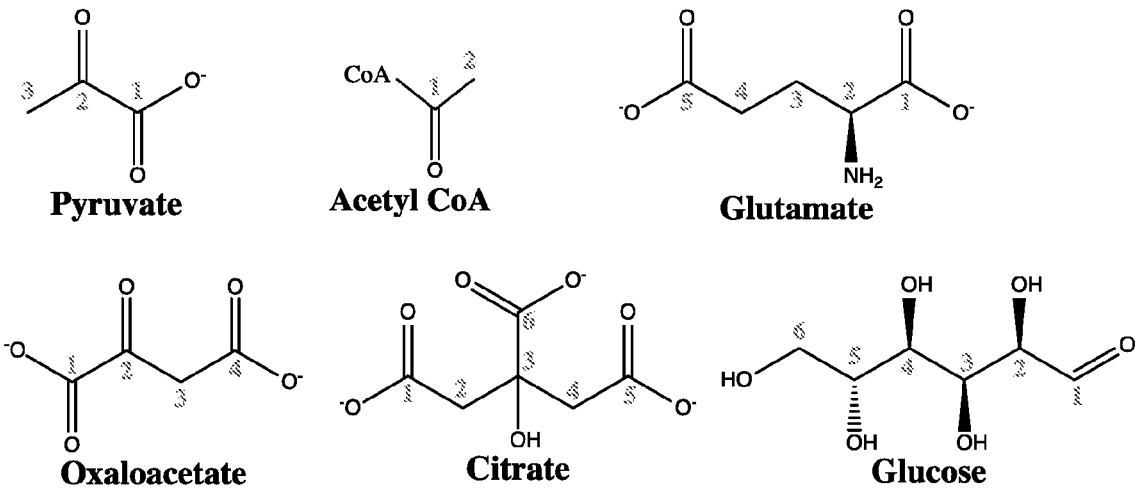
FIG. 5B is a set of chemical structures of key metabolites with the labeling conventions used to describe the embodiments of the invention.

The present invention provides a Positional Isotopomer NMR Tracer Analysis (PINTA) method by which hepatic glucose production, anaplerosis, and citrate synthase flux can be non-invasively assessed based on NMR and gas chromatography/mass spectrometry analysis of plasma following an infusion of [3-$^{13}$C]lactate (FIGS. 5A-5B). To validate this method independent cross-validation studies were performed, with an excellent correlation ($P<10^{-15}$, $R^2=0.99$) between $V_{PC}/V_{CS}$ calculated using the PINTA method of the invention and previous ex vivo NMR tracer technique in rats, and similar $V_{PC}/V_{CS}$ ratios measured in healthy human subjects using two independent tracer methods (infusion of [3-$^{13}$C]lactate or [1-$^{13}$C]acetate).

Validation studies demonstrated the ability of the PINTA method to measure an increase in $V_{CS}$ flux following treatment with a Controlled Release Mitochondrial Protonophore (CRMP), which promoted liver-targeted mitochondrial uncoupling and an increase in the $V_{PC}/V_{EGP}$ ratio after an extended fast. Taken together, these data demonstrated that the PINTA method is sensitive to differences in hepatic mitochondrial flux rates in various physiologic and pathophysiologic states in both humans and rodent models of diabetes, non-alcoholic fatty liver disease (NAFLD), non-alcoholic steatohepatitis (NASH), and other metabolic diseases. Furthermore, this method is useful for assessing target engagement for novel therapies that are currently being developed to promote increased hepatic mitochondrial fatty acid oxidation for the treatment of NAFLD/NASH and type-2 diabetes (T2D).

Compositions

In one aspect, the invention provides a composition comprising isotopically labelled glucose and at least one isotopically labelled $C_3$ compound selected from the group consisting of lactate, pyruvate, and alanine, or any salts or solvates thereof. As used herein, the term "$C_3$ compound" refer to certain organic compounds containing 3 carbons atoms, such as lactic acid, pyruvic acid, alanine, or any salt or solvate thereof. In certain embodiments, the composition further comprises isotopically labelled beta-hydroxybutyric acid, or any salts or solvates thereof.

In certain embodiments, the isotopically labelled glucose is $^2$H-labelled glucose. In other embodiments, the isotopically labelled glucose is $^3$H-labelled glucose. In yet other embodiments, the isotopically labelled glucose comprises at least one selected from the group consisting of [1,2,3,4,5,6,6-$^2$H$_7$] glucose, [1,2,3,4,5,6,6-$^3$H$_7$] glucose, [3-$^3$H]glucose, or any solvate thereof.

In certain embodiments, the at least one isotopically labelled $C_3$ compound is selected from the group consisting of $^{13}$C-labelled lactate, $^{13}$C-labelled pyruvate, and $^{13}$C-labelled alanine. In other embodiments, the at least one isotopically labelled $C_3$ compound is isotopically labelled L-lactate. In yet other embodiments, the isotopically labelled lactate is at least one selected from the group consisting of [3-$^{13}$C] L-lactic acid, [2-$^{13}$C] L-lactic acid, [2-$^{13}$C] pyruvate, [3-$^{13}$C]pyruvate, [2-$^{13}$C] alanine, and [3-$^{13}$C] alanine, or any salt or solvate thereof.

In certain embodiments, the isotopically labelled beta-hydroxybutyric acid is a $^{13}$C-labelled beta-hydroxybutyric acid. In other embodiments, the $^{13}$C-labelled beta-hydroxybutyric acid comprises [1,2,3,4-$^{13}$C4] beta-hydroxybutyric acid, or any salt or solvate thereof.

In certain embodiments, the composition is a pharmaceutically acceptable composition further comprising at least one pharmaceutically acceptable carrier. In other embodiments, the composition further comprises saline. In other embodiments, the saline is 0.9% NaCl saline. In yet other embodiments, the pharmaceutically acceptable composition is formulated for continuous intravenous infusion in a subject.

In certain embodiments, the pharmaceutically acceptable composition comprises isotopically labelled glucose at a concentration of about 10 to about 50 mg/mL. In other embodiments, the pharmaceutically acceptable composition comprises isotopically labelled glucose at a concentration of about 25 mg/mL. In yet other embodiments, the pharmaceutically acceptable composition comprises the at least one isotopically labelled $C_3$ compound at a concentration of about 50 to about 500 mg/mL. In yet other embodiments, the pharmaceutically acceptable composition comprises the at least one isotopically labelled $C_3$ compound at a concentration of about 200 mg/mL. In yet other embodiments, the pharmaceutically acceptable composition comprises isotopically labelled beta-hydroxybutyric acid at a concentration of about 0.5 to about 5 mg/mL. In yet other embodiments, the pharmaceutically acceptable composition comprises isotopically labelled beta-hydroxybutyric acid at a concentration of about 2 mg/mL.

In certain embodiments, the molar ratio between the isotopically labelled glucose and the at least one isotopically labelled $C_3$ compound in the composition ranges from about 0.013 to about 0.63. In yet other embodiments, the molar ratio between the isotopically labelled glucose and the isotopically labelled beta-hydroxybutyric acid in the composition ranges from about 1.47 to about 73.2. In yet other embodiments, the molar ratio between the at least one isotopically labelled $C_3$ compound and the isotopically labelled beta-hydroxybutyric acid in the composition ranges from about 11.68 to about 1168.

Methods

In another aspect, the invention provides a method of non-invasively measuring hepatic mitochondrial oxidation flux ($V_{CS}$) and/or pyruvate carboxylase flux ($V_{PC}$) in a subject.

In certain embodiments, the method comprises administering to a subject isotopically labelled glucose, at least one isotopically labelled $C_3$ compound and, optionally isotopically labelled beta-hydroxybutyric acid or any salts or solvates thereof. In other embodiments, the method comprises collecting a biological sample from the subject through a non-invasive procedure. In yet other embodiments, the method comprises analyzing the biological sample to assess the rate of endogenous glucose production in the subject.

In certain embodiments, the isotopically labelled glucose, isotopically labelled $C_3$ compound, and isotopically labelled beta-hydroxybutyric acid are co-formulated in a single composition. In other embodiments, the isotopically labelled glucose, the isotopically labelled $C_3$ compound, and isotopically labelled beta-hydroxybutyric acid are administered separately as part of separate compositions.

In certain embodiments, the isotopically labelled glucose is $^2$H-labelled glucose. In other embodiments, the isotopically labelled glucose is $^3$H-labelled glucose. In yet other embodiments, the isotopically labelled glucose comprises at least one selected from the group consisting of [1,2,3,4,5,6,6-$^2$H$_7$] glucose, [1,2,3,4,5,6,6-$^3$H$_7$] glucose, [3-$^3$H]glucose, or any solvate thereof.

In certain embodiments, the at least one isotopically labelled C$_3$ compound is selected from the group consisting of $^{13}$C-labelled lactate, $^{13}$C-labelled pyruvate and $^{13}$C-labelled alanine. In other embodiments, the at least one isotopically labelled C$_3$ compound is isotopically labelled L-lactate. In yet other embodiments, the isotopically labelled C$_3$ compound is at least one selected from the group consisting of [3-$^{13}$C] L-lactic acid, [2-$^{13}$C] L-lactic acid, [2-$^{13}$C] pyruvate, [3-$^{13}$C] pyruvate, [2-$^{13}$C] alanine, and [3-$^{13}$C] alanine or any salt or solvate thereof.

In certain embodiments, the isotopically labelled beta-hydroxybutyric acid is a $^{13}$C-labelled beta-hydroxybutyric acid. In other embodiments, the $^{13}$C-labelled beta-hydroxybutyric acid comprises [1,2,3,4-$^{13}$C4] beta-hydroxybutyric acid, or any salt or solvate thereof.

In certain embodiments, the one or more compositions are pharmaceutically acceptable compositions further comprising at least one pharmaceutically acceptable carrier. In other embodiments, the compositions further comprises saline. In yet other embodiments, the pharmaceutically acceptable compositions are formulated for intravenous administration. In yet other embodiments, the pharmaceutically acceptable compositions are formulated for continuous intravenous infusion in a subject.

In certain embodiments, the pharmaceutically acceptable composition comprises isotopically labelled glucose at a concentration of about 10 to about 50 mg/mL. In other embodiments, the pharmaceutically acceptable composition comprises isotopically labelled glucose at a concentration of about 25 mg/mL. In yet other embodiments, the pharmaceutically acceptable composition comprises isotopically labelled lactate at a concentration of about 50 to about 500 mg/mL. In yet other embodiments, the pharmaceutically acceptable composition comprises isotopically labelled lactate at a concentration of about 200 mg/mL. In yet other embodiments, the pharmaceutically acceptable composition comprises isotopically labelled beta-hydroxybutyric acid at a concentration of about 0.5 to about 5 mg/mL. In yet other embodiments, the pharmaceutically acceptable composition comprises isotopically labelled beta-hydroxybutyric acid at a concentration of about 2 mg/mL.

In certain embodiments, the molar ratio between the isotopically labelled glucose and the isotopically labelled lactate in the composition ranges from about 0.013 to about 0.63. In yet other embodiments, the molar ratio between the isotopically labelled glucose and the isotopically labelled beta-hydroxybutyric acid in the composition ranges from about 1.47 to about 73.2. In yet other embodiments, the molar ratio between the isotopically labelled lactate and the isotopically labelled beta-hydroxybutyric acid in the composition ranges from about about 11.68 to about 1168.

In certain embodiments, the pharmaceutically acceptable compositions are administered to the subject intravenously. In other embodiments, the pharmaceutically acceptable compositions are administered to the subject via continuous intravenous infusion. In certain embodiments, the pharmaceutically acceptable compositions are administered to the subject through continuous intravenous infusion for a period of about 5 minutes to about 200 minutes. In other embodiments, the pharmaceutically acceptable compositions are administered to the subject through continuous intravenous infusion for a period of 120 minutes. In yet other embodiments, the pharmaceutically acceptable compositions are administered to the subject through continuous intravenous infusion at an initial high "priming" rate for a priming period of time and then a low continual rate for the remainder of the infusion. In yet other embodiments, the priming rate is about 3 to about 5 times higher than the low continual rate.

In certain embodiments, the isotopically labelled glucose is administered to the subject at a low continual rate of about 0.21 to about 21 mg/(m$^2$·min). In other embodiments the isotopically labelled glucose is administered to the subject at a rate of about 0.15 µCi/(kg·min) to about 0.45 µCi/(kg·min).

In certain embodiments, the isotopically labelled C$_3$ compound is administered to the subject at a rate of about 0.5 µmol/(kg·min) to about 150 µmol/(kg·min). In other embodiments the isotopically labelled C$_3$ compound is administered to the subject at a rate of about 30 mol/(kg·min) to about 120 µmol/(kg·min).

In certain embodiments, the isotopically labelled beta-hydroxybutyric acid is administered to the subject at a rate of about 0.001 mg/(kg·min) to about 1 mg/(kg·min). In other embodiments the isotopically labelled beta-hydroxybutyric acid is administered to the subject at a rate of about 0.001 mg/(kg·min) to about 1 mg/(kg·min). In other embodiments the isotopically labelled beta-hydroxybutyric acid is administered to the subject at a rate of about 0.1 mg/(kg·min) to about 0.1 mg/(kg·min).

In certain embodiments, the biological sample comprises at least one material from the subject selected from the group consisting of blood, plasma and any combinations thereof.

In certain embodiments, the biological sample is collected from the subject intravenously.

In certain embodiments, the biological sample is analyzed by at least one method selected from the group consisting of nuclear magnetic resonance (NMR) spectroscopy, gas chromatography/mass spectrometry (GC/MS), liquid chromatography/mass spectrometry-mass spectrometry (LC/MS-MS), and scintillation counting.

In certain embodiments, the rate of endogenous glucose production is determined by measuring the isotopic enrichment of at least one isotope in the glucose contained within the biological sample. In other embodiments, the at least one isotope is selected from the group consisting of $^2$H, $^3$H, and $^{13}$C.

In certain embodiments, pyruvate carboxylase flux ($V_{PC}$) can be determined by measuring the $V_{PC}/V_{HGP}$ ratio using the equation $$\frac{V_{PC}}{V_{HGP}} = \frac{G2}{XFE^2},$$

where G2 represents the [m+2]glucose enrichment corrected for any [m+2] glucose synthesized from $^{13}$C2-labeled trioses: Corrected m+2 glucose=G2=Measured [m+2] glucose− 2*C4C5C6 [m+2]glucose, and XFE represents the fractional triose enrichment:

$$XFE = \frac{1}{1 + \frac{G1}{2*G2}},$$

where G1 represents the measured [m+1] glucose and G2 as described above. [m+1], [m+2], and C4C5C6 [m+2] glucose are measured by GC/MS. To calculate absolute $V_{PC}$ flux, the measured endogenous glucose production is multiplied by the ratio $V_{PC}/V_{EGP}$.

In certain embodiments, hepatic mitochondrial oxidation flux ($V_{CS}$) can be determined by measuring the positional enrichment of glucose by $^{13}C$ NMR and calculating the ratio of hepatic $V_{PC}/C_{CS}$ flux as $$\frac{V_{PC}}{V_{CS}} = \frac{[5-^{13}C] \text{ glucose}}{2*[4-^{13}C] \text{ glucose}} - 1$$

This ratio can then be corrected for the contribution of $^{13}C$ bicarbonate enrichment in certain embodiments. In other embodiments, liver [$^{13}C$] bicarbonate enrichment is measured by GC/MS. Without intending to be limited to any particular theory, the fractional enrichment of glucose from $^{13}CO_2$ can be increased from PC synthesis of [4-$^{13}C$]OAA from $^{13}CO_2$ and pyruvate. The labeling of glucose from 13-bicarbonate is dependent upon the relative flux of pyruvate to OAA with equilibration with fumarate and formation of PEP vs. flux of pyruvate to OAA to citrate (i.e. $V_{PC}/V_{CS}$). Only [1-$^{13}C$]OAA (from the equilibration of [4-$^{13}C$]OAA with fumarate) converted directly to PEP will label glucose (C3 and C4), since all $^{13}CO_2$ of [4-$^{13}C$]OAA is lost with flux through the TCA cycle. Hence, the correction for $^{13}CO_2$ follows from:
1. $^{13}CO_2$ will label C4 of OAA to give [4-$^{13}C$]OAA.
2. [4-$^{13}C$]OAA randomizes to [1-$^{13}C$]OAA and [4-$^{13}C$] OAA. Enrichment in each position is ½ of the original [$^{13}CO_2$] enrichment.
3. [1-$^{13}C$]OAA→[1-$^{13}C$]PEP: Label of [4-$^{13}C$]OAA is lost in OAA→PEP.
4. [1-$^{13}C$]PEP→[3-$^{13}C$] glucose and [4-$^{13}C$] glucose
5. $^{13}C$ of [4-$^{13}C$]OAA and [1-$^{13}C$]OAA is lost as $^{13}CO_2$ with CS flux to $^{13}C$-citrate and first turn of the TCA cycle.
5. Therefore, the correction for [$^{13}CO_2$] is 2*[4-$^{13}C$] glucose-$^{13}CO_2 \times \frac{1}{2} \times$ CF, where [$^{13}CO_2$] is the liver $^{13}C$-bicarbonate enrichment, and CF=($V_{PC}$+$V_{CS}$)/$V_{PC}$
6. $V_{PC}/V_{CS}$ corrected for [$^{13}CO_2$] is determined iteratively.

The absolute $V_{CS}$ can be calculated by dividing $V_{PC}$ by $V_{PC}/V_{CS}$ corrected for the contribution of $^{13}C$ bicarbonate.

In certain embodiments, the method further comprises administering to the subject $^2H$-labelled glycerol and $^{13}C$-labelled palmitate and, optionally $^{13}C$-labelled beta-hydroxybutyric acid or any salts or solvates thereof in order to assess the rate of lipolysis in the subject. In certain embodiments, the $^2H$-labelled glycerol, $^{13}C$-labelled palmitate, and optionally $^{13}C$-labelled beta-hydroxybutyric acid, are administered separately from one another or as a single pharmaceutical composition. In yet other embodiments, the $^2H$-labelled glycerol, $^{13}C$-labelled palmitate, and optionally $^{13}C$-labelled beta-hydroxybutyric acid, are administered at a period of time sufficient for the $^2H$-labelled glucose and $^{13}C$-labelled L-lactic acid to have been metabolized and excreted from the subject.

In certain embodiments, the methods of the invention are useful for evaluating roles of hepatic mitochondrial function in the regulation of liver and whole-body glucose and fat metabolism. In other embodiments, the methods of the invention can be used to evaluate the efficacy of novel therapies targeting hepatic mitochondrial fat oxidation. In yet other embodiments, the methods of the invention can be used to evaluate the efficacy of novel therapies for the treatment of non-alcoholic fatty liver disease (NAFLD), non-alcoholic steatohepatitis (NASH), hyperglycemia, hypoglycemia, hypertriglyceridemia, hepatic insulin resistance, and type 2 diabetes (T2D).

Kits

In another aspect, the invention provides a kit comprising a composition comprising isotopically labelled glucose and at least one isotopically labelled $C_3$ compound, or any salts or solvates thereof. In certain embodiments, the composition further comprises isotopically labelled beta-hydroxybutyric acid, or any salts or solvates thereof.

In another aspect, the invention provides a kit comprising a first composition comprising isotopically labelled glucose or any solvates thereof and a second composition comprising at least one isotopically labelled $C_3$ compound or any salts or solvates thereof. In certain embodiments, the kit further comprises a third composition comprising isotopically labelled beta-hydroxybutyric acid, or any salts or solvates thereof.

In certain embodiments, the isotopically labelled glucose is $^2H$-labelled glucose. In other embodiments, the isotopically labelled glucose is $^3H$-labelled glucose. In yet other embodiments, the isotopically labelled glucose comprises at least one of [1,2,3,4,5,6,6-$^2H_7$] glucose, [1,2,3,4,5,6,6-$^3H_7$] glucose, [3-$^3H$]glucose, or any solvate thereof.

In certain embodiments, the at least one isotopically labelled $C_3$ compound is selected from the group consisting of $^{13}C$-labelled lactate, $^{13}C$-labelled pyruvate and $^{13}C$-labelled alanine.

In other embodiments, the isotopically labelled lactate is isotopically labelled L-lactate. In yet other embodiments, the isotopically labelled lactate is at least one selected from the group consisting of [3-$^{13}C$] L-lactic acid, [2-$^{13}C$] L-lactic acid, [2-$^{13}C$] pyruvate, [3-$^{13}C$] pyruvate, [2-$^{13}C$] alanine, and [3-$^{13}C$] alanine, or any salt or solvate thereof.

In certain embodiments, the isotopically labelled beta-hydroxybutyric acid is a $^{13}C$-labelled beta-hydroxybutyric acid. In other embodiments, the $^{13}C$-labelled beta-hydroxybutyric acid comprises [1,2,3,4-$^{13}C_4$] beta-hydroxybutyric acid, or any salt or solvate thereof.

In certain embodiments, the kit further comprises an additional composition comprising at least one selected from $^2H$-labelled glycerol, $^{13}C$-labelled palmitate and both $^2H$-labelled glycerol and $^{13}C$-labelled palmitate. In certain embodiments the additional composition further comprises $^{13}C$-labelled beta-hydroxybutyric acid or any salt or solvate thereof.

In certain embodiments, the one or more compositions are pharmaceutically acceptable compositions further comprising at least one pharmaceutically acceptable carrier. In other embodiments, the compositions further comprises saline.

In another aspect, the invention further provides a kit comprising at least one pharmaceutical composition of the invention, at least one applicator, and instructional material for use thereof. The instructional material included in the kit comprises instructions for carrying out the method of the invention.

In certain embodiments, the at least one applicator comprises an intravenous infusion pump.

Dosing and Administration

In one embodiment, the present invention is directed to a packaged pharmaceutical composition comprising a container holding an amount of a compound of the invention, alone or in combination with a second pharmaceutical agent; and instructions for using the compounds and compositions as contemplated in the invention.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents.

Administration of the compositions of the present invention to a patient, preferably a mammal, more preferably a human, may be carried out using known procedures, at dosages and for periods of time contemplated in the invention. An effective amount of the compound necessary to accurately measure the desired parameters may vary according to factors such as the state of the patient; the age, sex, and weight of the patient. Dosage regimens may be adjusted to provide the optimum effect desired. One of ordinary skill in the art would be able to study the relevant factors and make the determination regarding the effective amount of the compound without undue experimentation.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, separation science and organic chemistry are those well-known and commonly employed in the art. It should be understood that the order of steps or order for performing certain actions is immaterial, so long as the present teachings remain operable. Moreover, two or more steps or actions can be conducted simultaneously or not.

As used herein, the articles "a" and "an" refer to one or to more than one (i.e., to at least one) of the grammatical object of the article. By way of example, "an element" means one element or more than one element.

The term "abnormal," when used herein in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type might be abnormal for a different cell or tissue type.

As used herein, the term "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

In one aspect, the terms "co-administered" and "co-administration" as relating to a subject refer to administering to the subject a compound and/or composition of the invention along with a compound and/or composition that may also treat or prevent a disease or disorder contemplated herein. In certain embodiments, the co-administered compounds and/or compositions are administered separately, or in any kind of combination as part of a single therapeutic approach. The co-administered compound and/or composition may be formulated in any kind of combinations as mixtures of solids and liquids under a variety of solid, gel, and liquid formulations, and as a solution.

As used herein, the term "composition" or "pharmaceutical composition" refers to a mixture of at least one compound useful within the invention with a pharmaceutically acceptable carrier. The pharmaceutical composition facilitates administration of the compound to a patient. Multiple techniques of administering a compound exist in the art including, but not limited to, intravenous, oral, aerosol, inhalational, rectal, vaginal, transdermal, intranasal, buccal, sublingual, parenteral, intrathecal, intragastrical, ophthalmic, pulmonary and topical administration.

A used herein, the term "CRMP" refers to controlled-release oral formulation of a mitochondrial protonophore.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the terms "DNP" and "2,4-DNP" refer to 2,4-dinitrophenol, or a salt or solvate thereof, or any combinations thereof.

An "effective amount" of a delivery vehicle is that amount sufficient to effectively bind or deliver a compound.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "efficacy" refers to the maximal effect ($E_{max}$) achieved within an assay.

"Instructional material," as that term is used herein, includes a publication, a recording, a diagram, or any other medium of expression which can be used to communicate the usefulness of the composition and/or compound of the invention in a kit.

As used herein, the term "LC/MS/MS" refers to liquid chromatography/mass spectrometry/mass spectrometry.

As used herein, the term "NAFLD" refers to non-alcoholic fatty liver disease.

As used herein, the term "NMR" refers to nuclear magnetic resonance.

"Parenteral" administration of a composition includes, e.g., subcutaneous (s.c.), intravenous (i.v.), intramuscular (i.m.), or intrasternal injection, or infusion techniques.

As used herein, the term "non-invasive" when referring to a medical procedure that causes little to no trauma to the subject. "Non-invasive" procedures of the invention generally refer to methods and procedures that do not significantly harm the subject and carry little to no risk of long-term injury. As used herein, procedures such as extraction of a blood, serum or plasma sample via syringe are considered "non-invasive". In contrast, procedures such as biopsies or sample collection methods requiring incisions to be made in the body of the subject are considered to be invasive.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, individual or subject is human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof. Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable pharmaceutically acceptable base addition salts of compounds of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the term "potency" refers to the dose needed to produce half the maximal response ($ED_{50}$).

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound useful within the invention (alone or in combination with another pharmaceutical agent), to a patient, or application or administration of a therapeutic agent to an isolated tissue or cell line from a patient (e.g., for diagnosis or ex vivo applications), who has a disease or disorder, a symptom of a disease or disorder or the potential to develop a disease or disorder, with the purpose to cure, heal, alleviate, relieve, alter, remedy, ameliorate, improve or affect the disease or disorder, the symptoms of the disease or disorder, or the potential to develop the disease or disorder. Such treatments may be specifically tailored or modified, based on knowledge obtained from the field of pharmacogenomics.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. Although the description herein contains many embodiments, these should not be construed as limiting the scope of the invention but as merely providing illustrations of some of the presently preferred embodiments of the invention.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction or administration conditions, with art-recognized alternatives and using no more than routine experimentation, are within the scope of the present application. In general the terms and phrases used herein have their art-recognized meaning, which can be found by reference to standard texts, journal references and contexts known to those skilled in the art. Any preceding definitions are provided to clarify their specific use in the context of the invention.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1: Non-Invasive Assessment of Hepatic Mitochondrial Metabolism by Positional Isotopomer NMR Tracer Analysis Materials and Methods
Animal Studies Male Sprague-Dawley rats (~10 weeks of age) were ordered from Charles River (Wilmington, Mass.) at ~300 g and fed regular chow unless otherwise specified. High fat-fed rats ordered at the same age and weight were given ad lib access to a safflower oil-based high fat diet (Dyets, Bethlehem, Pa., #112245) for four weeks, the latter two weeks of which they were treated with either a controlled-release mitochondrial protonophore (1 mg/kg in a small amount (~200 mg) of peanut butter) or a similar amount of peanut butter vehicle each day. Prior to studies, rats underwent surgery under general isoflurane anesthesia to place polyethylene catheters in the jugular vein and common carotid artery (PE90 and PE50 tubing, respectively; Instech, Plymouth Meeting, Pa.). After 1 week, recovery was verified by confirming that the rats had regained their surgical weight. Unless otherwise specified, all experiments were performed following an overnight fast (16 hrs food withdrawal prior to sacrifice). In both the rodent and human studies, data are represented as the mean of two technical replicates for each subject (i.e. two technical replicates per biological replicate). Sample sizes were selected to give power to detect moderate to large differences between groups (n=5-6 per group), and all animals were included in the final analysis.

Human Studies

Three healthy, normal weight men (<4% hepatic triglyceride) were studied; this sample size was chosen to give sufficient power to detect large differences between groups and to demonstrate the practical feasibility of this tracer method.

Tracer Studies

All rats were infused with [3-$^{13}$C]lactate (Sigma, St. Louis, Mo.; 120 μmol (kg-min)$^{-1}$ prime for 5 min, 40 μmol (kg-min)$^{-1}$ continuous infusion) and [3-$^{3}$H]glucose (PerkinElmer, Waltham, Mass.; 0.45 μCi (kg-min)$^{-1}$ prime for 5 min, 0.15 μCi (kg-min)$^{-1}$ for 120 min. Certain rats were treated with interventions [ME inhibitor, hydroxymalonate, Sigma, 200 mg/kg by IP injection at time zero of the tracer infusion; glucagon, Sigma, 5 ng/(kg-min) by continuous intra-arterial infusion throughout the tracer infusion; epinephrine, Sigma, 2 μg/(kg-min) by continuous intra-arterial infusion throughout the tracer infusion; and hyperinsulinemic-euglycemic clamp: insulin prime 200 mU/kg at time zero of the clamp and 4 mU/(kg-min) infusion throughout the tracer infusion, with a variable glucose infusion rate infused to maintain euglycemia ~100-110 mg/dl] following randomization to groups using a random number generator. The investigator performing the animal studies was not blinded for practical reasons, but the investigators analyzing fluxes were blinded as to the group allocation.

TABLE 1

Raw data from all groups of rats studied in Example 1.
Data are presented as the mean ± S.E.M. of n = 16 (controls),
n = 5 (HFD-CRMP), or n = 6 (all other groups) rats per group.

|  | [1-$^{13}$C] Glucose | [2-$^{13}$C] Glucose | [3-$^{13}$C] Glucose | [4-$^{13}$C] Glucose | [5-$^{13}$C] Glucose |
|---|---|---|---|---|---|
| Control | 6.0 ± 0.3 | 4.6 ± 0.2 | 0.9 ± 0.1 | 0.9 ± 0.1 | 5.7 ± 0.3 |
| ME inhibitor | 3.6 ± 0.5 | 2.7 ± 0.3 | 0.6 ± 0.1 | 0.6 ± 0.1 | 3.3 ± 0.4 |

TABLE 1-continued

Raw data from all groups of rats studied in Example 1.
Data are presented as the mean ± S.E.M. of n = 16 (controls),
n = 5 (HFD-CRMP), or n = 6 (all other groups) rats per group.

| | | | | | |
|---|---|---|---|---|---|
| Glucagon | 4.9 ± 0.4 | 3.5 ± 0.2 | 1.3 ± 0.2 | 1.2 ± 0.1 | 4.0 ± 0.3 |
| Epinephrine | 5.0 ± 0.3 | 3.9 ± 0.2 | 0.4 ± 0.1 | 0.5 ± 0.1 | 5.1 ± 0.4 |
| Hyperinsulinemic-euglycemic clamp | 3.8 ± 0.4 | 2.9 ± 0.3 | 0.6 ± 0.2 | 0.8 ± 0.1 | 3.7 ± 0.4 |
| HFD | 4.1 ± 0.3 | 3.0 ± 0.3 | 0.9 ± 0.2 | 0.7 ± 0.2 | 3.2 ± 0.3 |
| HFD-CRMP | 3.4 ± 0.8 | 2.5 ± 0.7 | 1.0 ± 0.2 | 1.0 ± 0.2 | 3.4 ± 0.9 |

| | [6-$^{13}$C] Glucose | [2-$^{13}$C] Glutamate | [3-$^{13}$C] Glutamate | $V_{PDH}/V_{CS}$ (%) | $V_{PK+ME}/V_{PC+PDH}$ (%) |
|---|---|---|---|---|---|
| Control | 7.8 ± 0.4 | 7.3 ± 0.4 | 7.1 ± 0.4 | 3.4 ± 0.1 | 5.9 ± 0.1 |
| ME inhibitor | 4.5 ± 0.5 | 4.4 ± 0.7 | 4.5 ± 0.6 | 2.0 ± 1.1 | 7.9 ± 2.1 |
| Glucagon | 6.0 ± 0.4 | 4.6 ± 0.5 | 4.8 ± 0.6 | 2.7 ± 0.1 | <2% |
| Epinephrine | 6.8 ± 0.4 | 5.5 ± 0.4 | 5.5 ± 0.2 | 4.3 ± 1.0 | 5.4 ± 0.1 |
| Hyperinsulinemic-euglycemic clamp | 4.9 ± 0.5 | 5.4 ± 0.5 | 5.3 ± 0.5 | 3.8 ± 0.5 | 14.8 ± 4.6 |
| HFD | 4.4 ± 0.7 | 4.8 ± 0.6 | 4.8 ± 0.4 | 2.6 ± 0.4 | 6.6 ± 1.2 |
| HFD-CRMP | 4.2 ± 1.0 | 4.6 ± 0.3 | 4.5 ± 0.4 | 4.1 ± 0.5 | 6.1 ± 0.6 |
| Average (all groups) | | | | 3.8 ± 0.5 | 5.8 ± 0.7 |

TABLE 2

Glucose enrichment in all groups of rats in Example 1.
Data are presented as the mean ± S.E.M. of
n = 16 (controls), n = 5 (HFD-CRMP), or
n = 6 (all other groups) rats per group.

| | Total [m + 1] Glucose | Total [m + 2] Glucose | C4C5C6 [m + 2] Glucose | $V_{PC}/V_{EGP}$ (%) |
|---|---|---|---|---|
| Control | 26.9 ± 1.0 | 5.7 ± 0.5 | 0.42 ± 0.06 | 72 ± 2 |
| ME inhibitor | 15.2 ± 1.7 | 2.1 ± 0.6 | 0.07 ± 0.04 | 50 ± 2 |
| Glucagon | 22.3 ± 2.2 | 4.2 ± 0.7 | 0.24 ± 0.06 | 65 ± 3 |
| Epinephrine | 22.2 ± 1.6 | 4.0 ± 0.8 | 0.25 ± 0.05 | 67 ± 2 |
| Hyperinsulinemic-euglycemic clamp | 11.2 ± 3.1 | 1.6 ± 0.7 | 0.16 ± 0.03 | 42 ± 6 |
| HFD | 24.0 ± 1.5 | 5.3 ± 0.6 | 0.64 ± 0.22 | 64 ± 5 |
| HFD-CRMP | 20.0 ± 4.2 | 3.9 ± 1.4 | 0.23 ± 0.10 | 58 ± 7 |

In the human studies, each subject participated in two studies, each following a 12 hr overnight fast, and received an IV infusion of [1-$^{13}$C]acetate [13 μmol (kg-min)$^{1}$] or [3-$^{13}$C]lactate [36.1 μmol (kg-min)$^{-1}$] on separate occasions. $V_{PC}/V_{CS}$ was determined by measuring the rate of incorporation of [1-$^{13}$C]acetate into [1-$^{13}$C] and [5-$^{13}$C] glutamate using in vivo MRS during the [1-$^{13}$C]acetate infusions, and by PINTA analysis of a plasma sample obtained at steady-state in the [3-$^{13}$C]lactate infusions. The $V_{PC}/V_{EGP}$ ratio was measured by PINTA analysis of steady-state plasma after a [3-$^{13}$C]lactate infusion.

Flux modeling: PINTA

The flux calculations required the following equations using [$^{13}$C] glucose positional enrichment in plasma or liver, determined by NMR and GC/MS mass spectrometry. The labeling patterns associated with the fluxes and the relevant pathways are shown in FIGS. 5A-5B. $V_{PC}$ is the rate of pyruvate carboxylase flux as determined from the anaplerotic flow into oxaloacetate (OAA). $V_{CS}$ is defined as the flux of the citrate synthase reaction in the citric acid cycle. The calculated anaplerotic flux can also include malic enzyme (ME) flux but under the conditions studied it was shown that ME flux was negligible compared to anaplerotic flux. Table 3 shows the equations used to calculate relative fluxes by PINTA. G2 denotes [m+2] glucose arising from the condensation of two singly-labeled trioses.

TABLE 3

Flux modeling ratios [$V_{PC}/V_{EGP}$, equation (1),
and $V_{PC}/V_{CS}$, equation (2)] used in the PINTA
method. The derivations and further definitions
of these equations are given elsewhere herein.

| Ratio | Calculation |
|---|---|
| $\dfrac{V_{PC}}{V_{CS}}$ | $\left(\dfrac{[5-^{13}C]\text{glucose}}{2*([4-^{13}C]\text{glucose})}\right) - 1$     (1) |
| $\dfrac{V_{PC}}{V_{EGP}}$ | $\dfrac{G2}{XFE^2}$     (2) | with G2 and XFE as defined in
equations (32) and (35).

Calculation of $V_{PC}/V_{CS}$

The ratio of $$\frac{V_{PC}}{V_{CS}} \qquad [\text{equation (1)}]$$

was calculated as described below based on a model of hepatic metabolism developed by Katz for radiolabeled isotopes (Katz, J., Am. J. Physiol. 248, R391-R399, 1985). In this calculation it is assumed that the flux from PC will continue through PEPCK and subsequent gluconeogenic reactions, and end up in liver glucose. This will be a maximum estimate of the PC contribution due to the possibility of futile cycling where PEP is converted by pyruvate kinase into pyruvate. Previous in vivo animal and human studies suggest that $V_{PK+ME}$ flux is relatively low compared to $V_{PC}$ flux under fasting conditions. Consistent with these prior studies $V_{PK+ME}$ flux/$V_{PC+PDH}$ flux is relatively low (<15%) under several physiologic conditions and that these low rates of pyruvate cycling have a minimal impact on the estimated $V_{PC}/V_{CS}$ ratio, as determined by a formula that takes this flux into account [formula (30)], the derivation of which is presented in the section "Expanded derivation of $V_{PC}/V_{CS}$."

In order to avoid any impact of pentose cycling on the estimate of the $V_{PC}/V_{CS}$ ratio only the relative $^{13}$C labeling in carbons C4 and C5 of glucose is examined. This ratio would not be expected to be significantly impacted by pentose cycling.

The isotope balance equation of the [1-$^{13}$C]oxaloacetate pool is given by equation (3):

$$\frac{\partial [1-^{13}C]OAA}{\partial t} = \frac{1}{2} * [1-^{13}C]\text{pyruvate} * V_{PC} + \qquad (3)$$

$$\frac{1}{2} * ([3-^{13}C]OAA + [1-^{13}C]acetylCoA) *$$

$$V_{CS} - [1-^{13}C]OAA * (V_{PC} + V_{CS})$$

Equation (3) may be simplified with the following assumptions: i) Metabolic and isotopic steady state.

ii) [1-$^{13}$C]pyruvate~~0.

iii) [1-$^{13}$C]acetyl-CoA~0.

iv) Complete scrambling of enrichment between [2-$^{13}$C] OAA and [3-$^{13}$C]OAA, as well as between [1-$^{13}$C] OAA and [4-$^{13}$C]OAA by fumarase.

Figure 6A:
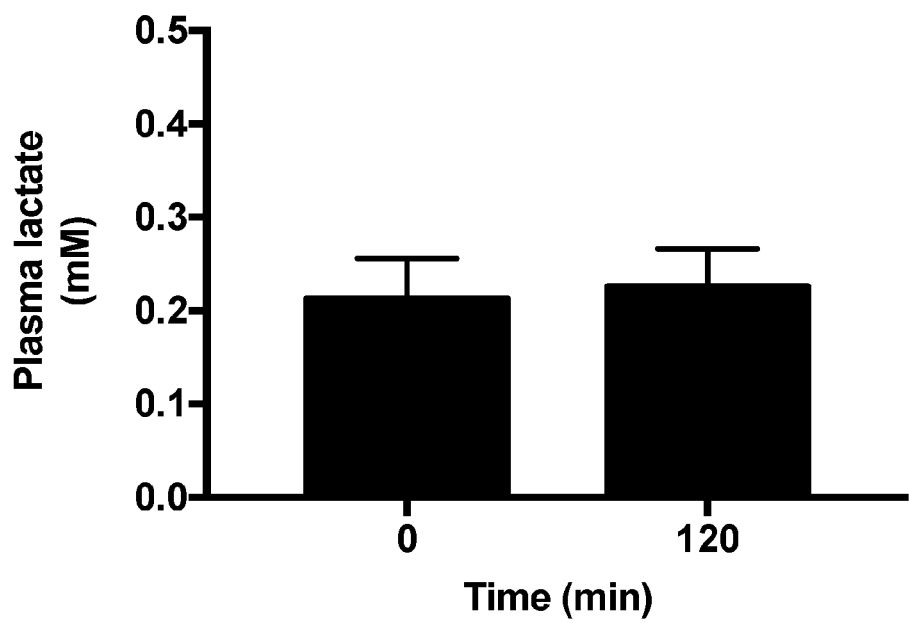
FIGS. 6A-6D are graphs showing that plasma glucose enrichment was a good surrogate for liver glucose enrichment in rats infused with [3-$^{13}C$]lactate at steady-state.
Figure 6B:
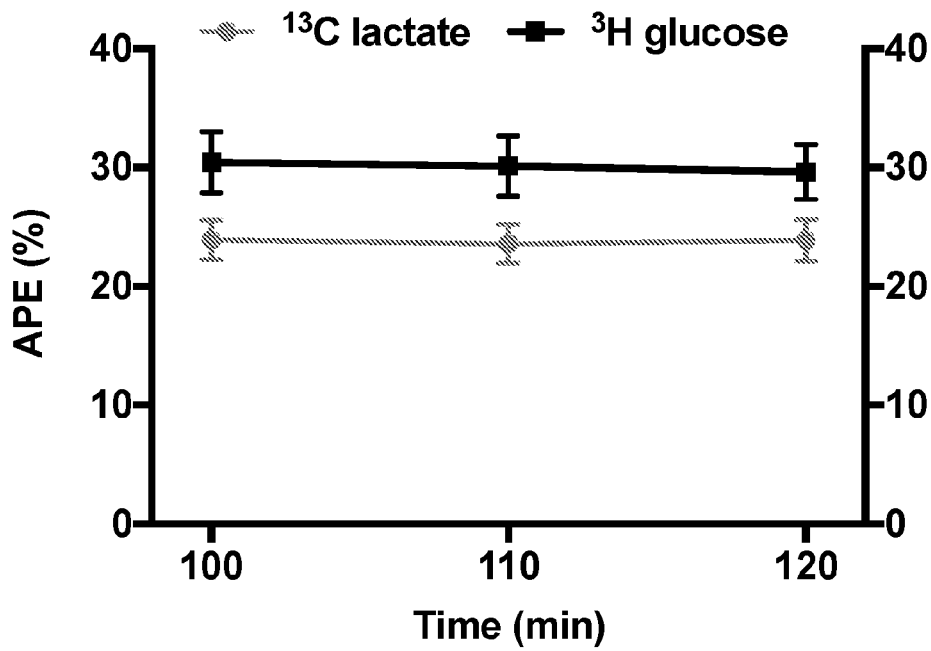
Figure 7A:
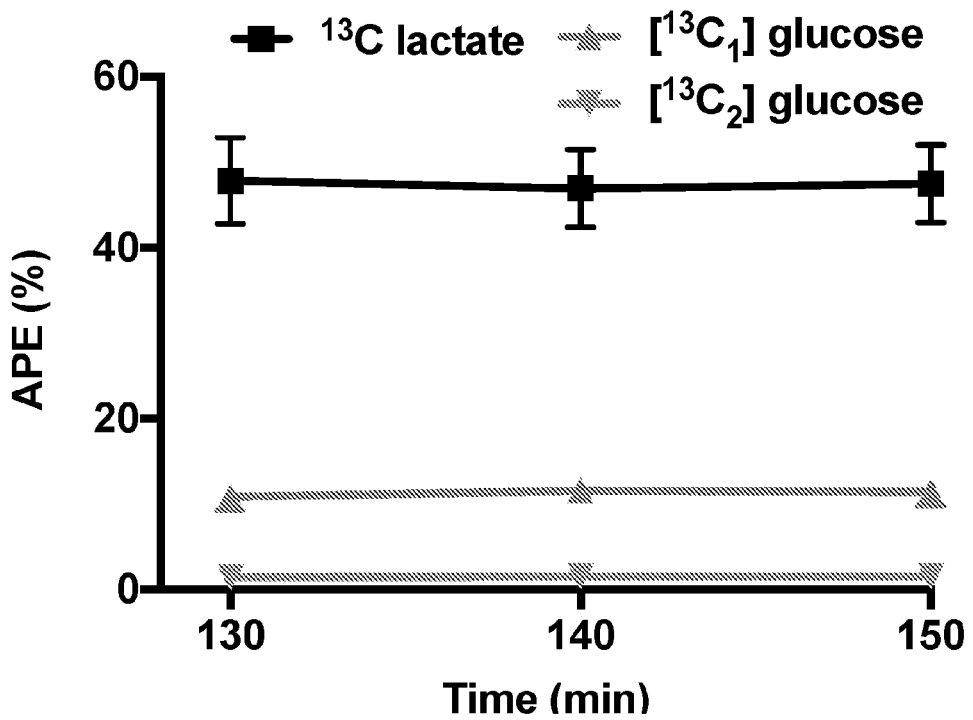
FIG. 7A is a graph showing plasma [$^{13}C$]lactate and m+1 and m+2 [$^{13}C$]glucose enrichments in non-diabetic, overnight fasted humans. Data are the mean±S.E.M. of three subjects.

The first assumption was tested by confirming the stability of the glucose labeling in the plasma at the time of sampling (FIG. 6B, FIG. 7A). The absence of significant label in bicarbonate (which was found to be 1.5±0.1% in rats infused with 40 μmol/(kg-min) of [3-$^{13}$C]lactate [plasma lactate enrichment ~45%]) supports assumptions (ii) and (iii). Assumption (iv) was tested by confirming equal enrichment in C2 and C3 glutamate (Table 2).

With these assumptions the equation reduces to equation (4):

$$\frac{\partial [1-^{13}C]OAA}{\partial t} = \frac{1}{2}*([3-^{13}C]OAA*V_{CS}) - [1-^{13}C]OAA*(V_{PC}+V_{CS}) \quad (4)$$

At steady-state, $$\frac{\partial [1-^{13}C]OAA}{\partial t} = 0.$$

Rearranging yields equation (5):

$$\frac{V_{PC}}{V_{CS}} = \left(\frac{[3-^{13}C]OAA}{2*[1-^{13}C]OAA}\right) - 1 \quad (5)$$

Substitution of the fractional C enrichment of C6 glucose for C3 OAA and the fractional enrichment of C4 glucose for C1 OAA into equation (5) yields equation (6):

$$\frac{V_{PC}}{V_{CS}} = \left(\frac{[6-^{13}C]\text{ glucose}}{2*([4-^{13}C]\text{ glucose})}\right) - 1 \quad (6)$$

To avoid any potential impact of glyceroneogenesis from [3-$^{13}$C]lactate, which would label C1 and C6 glucose, and based on assumption (iv), equation (6) was further modified to generate equation (7):

$$\frac{V_{PC}}{V_{CS}} = \left(\frac{[5-^{13}C]\text{ glucose}}{2*([4-^{13}C]\text{ glucose})}\right) - 1 \quad (7)$$

Expanded Derivation of $V_{PC}/V_{CS}$ Taking into Account Pyruvate Recycling and Other Minor Fluxes Below a complete derivation to assess the potential effect of pyruvate recycling and other minor fluxes not included in the ($V_{PC}/V_{CS}$) calculations is presented:
1. Dilution of labeling at the level of α-ketoglutarate (via unlabeled glutamine entering the glutamate pool and exchanging)
2. Production of labeled [1-$^{13}$C]pyruvate due to futile cycling between OAA and pyruvate through Malic Enzyme ($V_{ME}$) or the combined action of PEP carboxykinase and pyruvate kinase
3. Flow of unlabeled mass into the TCA cycle at the level of succinate ($V_{suc}$)

If pyruvate cycling is included there will be significant $^{13}$C enrichment in [1-$^{13}$C]pyruvate, [2-$^{13}$C]pyruvate, and [1-$^{13}$C]acetyl-CoA. The isotope balance equation of [1-$^{13}$C] OAA is given by equation (8):

$$\frac{\delta[1-^{13}C]OAA}{\delta t} = \frac{1}{2}*[1-^{13}C]\text{pyruvate}*V_{PC} + \quad (8)$$
$$\frac{1}{2}*([3-^{13}C]OAA + [1-^{13}C]\text{acetyl}-CoA)*$$
$$(V_{suc}+V_{CS}) - [1-^{13}C]OAA*(V_{PC}+V_{CS}+V_{suc})$$

Under conditions where a substrate such as propionate that enters the TCA cycle at the level of succinate is not infused, $V_{CS} \sim V_{CS}+V\text{suc}$ so that equation (8) can be simplified to equation (9):

$$\frac{\delta[1-^{13}C]OAA}{\delta t} = \frac{1}{2}*[1-^{13}C]\text{pyruvate}*V_{PC} + \quad (9)$$
$$\frac{1}{2}*([3-^{13}C]OAA + [1-^{13}C]\text{acetyl}-CoA)*$$
$$V_{CS} - [1-^{13}C]OAA*(V_{PC}+V_{CS})$$

Relationship Between α-Ketoglutarate and OAA Labeling

Dilution of label at the level of α-ketoglutarate due to unlabeled glutamine entering glutamate and exchanging with α-ketoglutarate through AAT is given by equation (10):

$$K1 = \frac{[2-^{13}C]\alpha KG}{[3-^{13}C]OAA} \quad (10)$$

Relationship Between [1-$^{13}$C]Acetyl-CoA and [2-$^{13}$C]Pyruvate Labeling

The labeling of acetyl-CoA relative to pyruvate is reduced by the fraction of acetyl-CoA coming from unlabeled sources such as lipids. Based on mass balance this reduction is given by equation (11):

$$[1-^{13}C]\text{acetyl} - \quad (11)$$
$$CoA = [2-^{13}C]\text{pyruvate}*\frac{V_{PDH}}{V_{CS}} = [2-^{13}C]\text{pyruvate}*K_2$$

$$K_2 = \frac{V_{PDH}}{V_{CS}} \quad (12)$$

Relationship Between [1-$^{13}$C]OAA and [1-$^{13}$C]Pyruvate

[1-$^{13}$C]pyruvate can be created from [1-$^{13}$C]OAA either through Malic Enzyme ($V_{ME}$) or the combined actions of PEP carboxykinase and pyruvate kinase ($V_{PK}$). One defines total pyruvate recycling as given by equation (13):

$$V_{PK+ME} = V_{PK} + V_{ME} \quad (13)$$

At steady state the isotope balance equation for [1-$^{13}$C] pyruvate is given by equation (14):

$$0 = [1-^{13}C]OAA \cdot V_{PK+ME} - [1-^{13}C]\text{pyruvate} \cdot (V_{PK+ME} + V_{PDH} + V_{PC} + V_{Lacr}) \quad (14)$$

Which can be rearranged to equation (15):

$$[1-^{13}C]\text{pyruvate} = [1-^{13}C]OAA*\left[\frac{V_{PK+ME}}{V_{PK+ME}+V_{PC}+V_{PDH}+V_{Lacr}}\right] \quad (15)$$

in which $V_{Lacr}$ denotes the loss of pyruvate from the liver via reverse transport of lactate and alanine.

The ratio in brackets in equation (15) can be expressed in terms of a constant $K_3$ yielding equation (16), $$[1-^{13}C]\text{pyruvate} = [1-^{13}C]OAA * K_3 \quad (16)$$

$$\text{where } K_3 = \frac{V_{PK+ME}}{V_{PK+ME} + V_{PC} + V_{PDH} + V_{Lacr}} \quad (17)$$

Relationship Between [3-$^{13}$C]OAA and [2-$^{13}$C]Pyruvate

Labeling in [2-$^{13}$C]pyruvate may also arise from pyruvate recycling as described below. At steady state the isotopic balance equation for [2-$^{13}$C]pyruvate is given by equation (18):

$$0 = [2-^{13}C]OAA \cdot V_{PK+ME} - [2-^{13}C]\text{pyruvate} \cdot (V_{PK+ME} + V_{PC} + V_{PDH} + V_{Lacr}) \quad (18)$$

Rearranging yields equation (19), $$[2-^{13}C]\text{pyruvate} = [2-^{13}C]OAA * \left[\frac{V_{PK+ME}}{V_{PK+ME} + V_{PC} + V_{PDH} + V_{Lacr}}\right] \quad (19)$$

The ratio in brackets can be expressed in terms of a constant $K_3$ yielding $$[2-^{13}C]\text{pyruvate} = K_3 \cdot [2-^{13}C]OAA \quad (20)$$

Due to fumarase and malic enzyme reversibility, [2-$^{13}$C]OAA~[3-$^{13}$C]OAA so that equation (19), substituting in $K_3$ from equation (17), can be replaced with equation (21):

$$[2-^{13}C]\text{pyruvate} = K_3 \cdot [3-^{13}C]OAA \quad (21)$$

Derivation of the Steady State Solution

Substituting for [1-$^{13}$C]pyruvate and [1-$^{13}$C]acetyl-CoA (~0 based on assumption i) in equation (3) at steady state using the relations derived above [equations (11) and (15)] gives equation (22):

$$0 = \frac{1}{2} * K_3 * [1-^{13}C]OAA * V_{PC} + \frac{1}{2} * K_1 * ([3-^{13}C]OAA + K_2 * K_3 * [3-^{13}C]OAA) * V_{CS} - [1-^{13}C]OAA * (V_{PC} + V_{CS})) \quad (22)$$

which can be rearranged to equation (23):

$$0 = [1-^{13}C]OAA \cdot (0.5 \cdot K_3 \cdot V_{PC} - V_{PC} - V_{CS}) + \frac{1}{2} \cdot K_1 \cdot [3-^{13}C]OAA \cdot (1 + K_2 \cdot K_3) \cdot V_{CS} \quad (23)$$

Dividing by $V_{CS}$ yields $$0 = [1-^{13}C]OAA * \left[\left(0.5 * K_3 * \frac{V_{PC}}{V_{CS}} - \frac{V_{PC}}{V_{CS}}\right) - 1\right] + \frac{1}{2} * [3-^{13}C]OAA * K_1(1 + K_2 * K_3) \quad (24)$$

$$0 = [1-^{13}C]OAA * \left[(0.5 * K_3 - 1) * \frac{V_{PC}}{V_{CS}} - 1\right] + \frac{1}{2} * [3-^{13}C]OAA * K_1(1 + K_2 * K_3) \quad (25)$$

Based on published work one expects minimal dilution at α-ketoglutarate under these conditions so that $$K_1 \sim 1 \quad (26)$$

Furthermore based on present results (Table 1):

$$K_2 = \frac{V_{PDH}}{V_{CS}} < 0.1 \quad (27)$$

$$K_3 = \frac{V_{PK+ME}}{V_{PK+ME} + V_{PDH} + V_{PC} + V_{Lacr}} < 0.1 \quad (28)$$

Substituting K1=1 and setting the $K_2K_3$ term to ~0 yields equation (29):

$$0 = [1-^{13}C]OAA * \left[(0.5 * K_3 - 1) * \frac{V_{PC}}{V_{CS}} - 1\right] + \frac{1}{2} * [3-^{13}C]OAA \quad (29)$$

which can be rearranged to $$\frac{V_{PC}}{V_{CS}} = \left[0.5 * \left(\frac{[3-^{13}C]OAA}{[1-^{13}C]OAA}\right) - 1\right] * \frac{1}{1 - 0.5 * K_3} \quad (30)$$

Equation (30) is seen to be the same as equation (7) other than a correction term which goes to 1 when there is no pyruvate recycling. Note that based on the experimental measurements of $V_{PK+ME}$ under these conditions (Table 1) one anticipates a 5% or less impact of pyruvate recycling on the calculated ($V_{PC}/V_{CS}$) ratio. In the maximum case where $V_{PC}=V_{PK}+ME$ (no gluconeogenesis, just pyruvate recycling) $K_3=1$ and $V_{PC}/V_{CS}$ will be underestimated by a factor of 2 using equation (30).

Calculation of $V_{PC}/V_{EGP}$

Endogenous glucose production (EGP) is the sum of gluconeogenesis (GNG) and glycogenolysis (GlyNG). The fractional contribution of GNG to EGP can be determined by an infusion of [3-$^{13}$C]lactate to label the triose pool, and the subsequent synthesis and Mass Isotopomer Distribution Analysis (MIDA) of plasma $^{13}$C-glucose. MIDA analysis is based on the probability of unlabeled (T), and singly-labeled triose phosphates (T*) combining to form unlabeled glucose (G0 from TT), singly-labeled glucose (G1 from TT* and T*T), and doubly-labeled glucose molecule (G2 from T*T*).

Since, the sum of the unlabeled, G0, and labeled, G1 and G2, glucose isotopomers is equal to 1, the distribution of the combination of T and T* can be described by the binomial relationship:

$$1 = T^2 + 2(T*T) + (T*)^2 \quad (31)$$

This can also be expressed in terms of the p, the probability of triose phosphate enriched with $^{13}$C above natural abundance, and q=(1-p), the probability of triose phosphate that is not enriched above natural abundance.

As glucose is synthesized from combining two trioses with enrichments of p and q, the isotopomer distribution of glucose (G0, G1, and G2) is:

$$(p+q)^2 = p^2 + 2pq + q^2 \quad (32)$$

Where, G2=$p^2$, G1=2pq, and G0=$q^2$.

From the mass spectrum, one can determine the ratio of G2/G1.

And from above, one has:

$$G2/G1 = p^2/2pq \quad (33)$$

Substituting (1-p) for q, one has:

$$G2/G1 = p^2/2p(1-p) = p/2(1-p) \quad (34)$$

Solving for p, or XFE, the fractional triose enrichment, in terms of the ratio of the enrichments of doubly-labeled $^{13}$C-glucose, G2, and singly-labeled $^{13}$C-glucose, G1, one has:

$$p = XFE = 1/((1+(1/(2G2/G1)))) \quad (35)$$

The contribution of pyruvate carboxylase flux to EGP, $V_{PC}/V_{EGP}$, is then:

$$V_{PC}/V_{EGP} = G2/XFE^2 \quad (36)$$

where G2 denotes glucose [m+2] arising from the condensation of two [m+1] trioses.

The key assumptions are:
  i. A binomial probability analysis describes the distribution of $^{13}$C-glucose isotopomers resulting from the synthesis of two $^{13}$C-labeled trioses.
  ii. One gluconeogenic precursor pool enrichment (if not, $V_{PC}/V_{EGP}$ is underestimated).
  iii. Triose phosphates are equilibrated (if not, $V_{PC}/V_{EGP}$ is overestimated).
  iv. Using [$^{13}$C]lactate as the tracer to label the triose pool does not include the contribution of glycerol to gluconeogenesis, and hence represents $V_{PC}/V_{EGP}$, as validated in FIG. 2.

In addition to these assumptions, the MIDA calculation assumes that G2 (i.e. any glucose enriched with 2-$^{13}$C atoms is due to the condensation of 2 trioses, each labeled with a single $^{13}$C-atom. However, the use of $^{13}$C-lactate as the tracer, and its subsequent passage through the TCA cycle (with entry through PC and PDH) will lead to trioses containing two $^{13}$C atoms. Therefore in addition to determining the total m+1 and m+2 enrichment in glucose (GC-MS:CI of glucose pentaacetate, m/z 331→338), enrichment in the glucose C4-C5-C6 fragment was determined by GC-MS analysis in the EI mode of the glucose aldonitrile pentapropionate derivative by monitoring m/z 259→265. One corrects for any [m+2] glucose synthesized from $^{13}C_2$-trioses by analysis of the enrichment in the glucose C4C5C6 fragment according to the following equation:

$$\text{Corrected}[m+2]\text{glucose} = \text{Measured}[m+2]\text{glucose} - 2*C4C5C6[m+2]\text{glucose} \quad (37)$$

Flux Modeling. Ex Vivo NMR of Hepatic Tissue

The flux calculations employ the following equations (Table 4).

TABLE 4

Flux modeling ratios used in the ex vivo NMR method.

| Ratio | Calculation | |
|---|---|---|
| $\dfrac{V_{PC}}{V_{EGP}}$ | $\dfrac{C5 \text{ glucose}}{C2 \text{ malate}}$ | (38) |
| $\dfrac{V_{PC}}{V_{CS}}$ | $\dfrac{\frac{1}{2}*(C2 \text{ malate} + C3 \text{ malate}) - 4 \text{ glutamate}}{C3 \text{ alanine} - (C2 \text{ malate} + C3 \text{ malate})}$ | (39) |

Absolute $V_{PC}$ and $V_{CS}$ Flux Rates

In rats, in which [3-$^3$H]glucose was used as the tracer for glucose turnover, EGP was measured. Based on a previous study in which net renal gluconeogenesis was found to be negligible, it can be assumed that all gluconeogenesis occurs in the liver.

Combining the relative flux estimations for $$\frac{V_{PC}}{V_{EGP}} \text{ and } \frac{V_{CS}}{V_{PC}}$$

described above with rates of endogenous glucose production ($V_{EGP}$) yields absolute flux rates for $V_{PC}$ and $V_{CS}$ as follows (Table 5):

TABLE 5

Calculation of hepatic mitochondrial fluxes ($V_{PC}$, $V_{CS}$) with PINTA.

| Flux | Calculation | |
|---|---|---|
| $V_{PC}$ | $V_{EGP} * \dfrac{V_{PC}}{V_{EGP}}$ | (40) |
| $V_{CS}$ | $V_{PC} * \left(\dfrac{V_{CS}}{V_{PC}}\right)$ | (41) |

AMR, GC/MS, and LC/MS-MS Analyses

GC/MS was used to measure m+1 and m+2 [$^{13}$C]glucose enrichment. The total m+1 and m+2 [$^{13}$C]glucose enrichment was measured using a pentaacetate derivative: plasma or liver samples were deproteinized using 5 volumes of methanol, dried, and derivatized with 75 µL of 1:1 acetic anhydride:pyridine. After heating to 65° C. for 20 min, the reaction was terminated by adding 25 µL methanol, and m+1 and m+2 (as well as m+3 ... m+6) were determined by GC/MS (CI mode, m/z 331 [m], 332 [m+1], 333 [m+2], ... 337 [m+6]). The m+1 and m+2 [$^{13}$C] enrichments of the glucose C4C5C6 fragment were determined by generating the aldonitrile pentapropionate derivative: plasma or NMR liver extract samples were dried under $N_2$ gas, and 50 µl hydroxylamine hydrochloride (20 mg/ml in pyridine) were added. The samples were heated at 90° C. for 60 min, then 100 µl propionic anhydride was added, after which the samples were heated at 60° C. for 30 min. Finally, the samples were evaporated under $N_2$ gas, resuspended in ethyl acetate, and the m+1 and m+2 enrichment of the glucose C4C5C6 fragment was measured by GC/MS.

[$^{13}$C]malate enrichment was also measured by GC/MS. A 50-100 mg liver tissue sample was weighed in a 2.0 mL microcentrifuge tube with a metal bead, and 1.0 mL of pre-chilled methanol/water (50:50, v/v) solution was added, followed by disruption at 30 Hz for 1.0 min (QIAGEN TissueLyser, Valencia, Calif.) and centrifugation (4000 rpm) at 4° C. for 10 min. The supernatant was dried in a Speed Vac, and 75 µL n-butanol 4N HCl was added into each residual sample. The resulting mixtures were heated for 30 min at 65° C. The solvent was removed by a steady-flow of nitrogen gas at room temperature and the dried samples were acetylated with 100 L trifluoroacetic anhydride in methylene chloride (1:7 v/v) solution. The total and C2+C3 malate enrichments were determined by GC/MS (EI mode, m/z 213 for the total and 186 for the C1C2C3 fragment). The C2+C3 malate enrichment was determined according to equation (42), which relies on the assumption that the C4 enrichment is approximately equal to the C1 enrichment of malate:

$$APE_{C2C3} = APE_{total} - 2*(APE_{total} - APE_{C1C2C3}). \quad (42)$$

[$^{13}$C]alanine enrichment was measured by GC/MS. [$^{13}$C] NMR spectroscopy using the BRUKER TOPSPIN® system was utilized to measure relative positional 13C-enrichment of glucose, and combined with the total [$^{13}$C]glucose enrichment ([m+1]+2*[m+2]) measured by GC/MS to calculate the positional enrichment of [13C]glucose.

Total [$^{13}$C]glutamate enrichment was determined by LC-MS/MS. Approximately 100 mg of liver tissue was weighed out and homogenized in 500 μl ice-cold methanol using a TissueLyser, then centrifuged at 4000 rpm for 10 minutes. The supernatant was then purified by centrifugation (4000 rpm, 10 min) through the PALL NANOSEP® filter (100K) (Port Washington, N.Y.). Glutamate 13C enrichment ([m+1], [m+2]) was then assessed by LC-MS/MS using an AB SCIEX QTRAP 6500 (Framingham, Mass.), equipped with a SHIMADZU ultra-fast liquid chromatography (UFLC) system (Columbia, Md.) and electrospray ionization (ESI) source with negative-ion detection. The measured ion pairs were 146/128 (m0), 147/129 (m+1), and 148/130 (m+2).

Positional enrichment of glucose, glutamate, and alanine was measured by 13C NMR. The samples were run on the AVANCE 500-MHz NMR spectrometer (BRUKER INSTRUMENTS, Billerica, Mass.). Spectra were acquired with relaxation time=1 sec, dummy scans=4, and number of scans=25,000. Correction factors for differences in $T_1$ relaxation times were determined from fully relaxed spectra of standard glucose, glutamate, and alanine solutions. The total enrichment measured by GC/MS (glucose, alanine) or LC/MS/MS (glutamate) was divided algebraically between the carbons of each molecule based on the relative areas of the 13C NMR peaks: the NMR-determined fraction of $^{13}$C at each carbon position was calculated, and then multiplied by the total enrichment ([m+1] APE+2*[m+2] APE+1.1% APE*n, where n is the number of carbons in the molecule of interest). The chemical shifts of each peak are shown in Table 6.

$^{13}$C enrichment in C1 alanine was assumed to be negligible and the total alanine $^{13}$C enrichment was divided between carbons 2 and 3.

TABLE 6

Chemical shifts of peaks examined by $^{13}$C NMR.

| Peak | Chemical Shift (ppm) |
|---|---|
| α-C1 glucose | 92.3 |
| α-C1 glucose | 96.8 |
| α-C2, α-C5 glucose | 72.5 |
| β-C2 glucose | 75.0 |
| α-C3 glucose | 73.6 |
| β-C3 glucose | 76.6 |
| α,β-C4 glucose | 70.5 |
| β-C5 glucose | 76.8 |
| α,β-C6 glucose | 61.5 |
| C1 glutamate | 175.8 |
| C2 glutamate | 55.6 |
| C3 glutamate | 28.5 |
| C4 glutamate | 34.6 |
| C5 glutamate | 182.0 |
| C2 alanine | 51.7 |
| C3 alanine | 17.3 |

Liver Glycogen Content

Hepatic glycogen concentrations were analyzed following amyloglucosidase digestion and measurement of glucose concentrations in the digest.

Statistical Analysis

GraphPad Prism version 7.0 was used to perform all statistical analysis. Comparisons of two groups were performed using the 2-tailed unpaired Student's t-test, while a simple linear regression was performed to analyze linear correlations. Differences with P-value less than 0.05 were considered significant. GraphPad Prism software confirmed that the variances were not significantly different between groups compared using a student t-test, and a normal distribution was assumed.

$V_{PC}/V_{CS}$ and $V_{PC}/V_{EGP}$ are Similar by PINTA and Ex Vivo NMR

Figure 1:
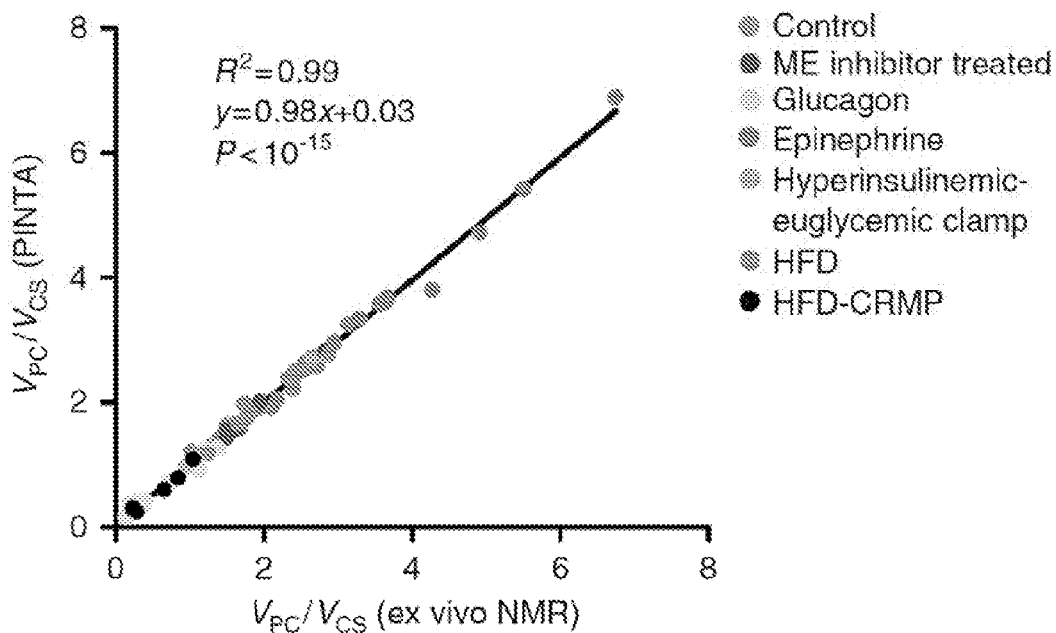
FIG. 1 is a graph showing $V_{PC}/V_{CS}$ ratios measured by PINTA and ex vivo NMR. This ratio was identical whether measured by PINTA or ex vivo NMR analysis of rat livers.
Figure 2:
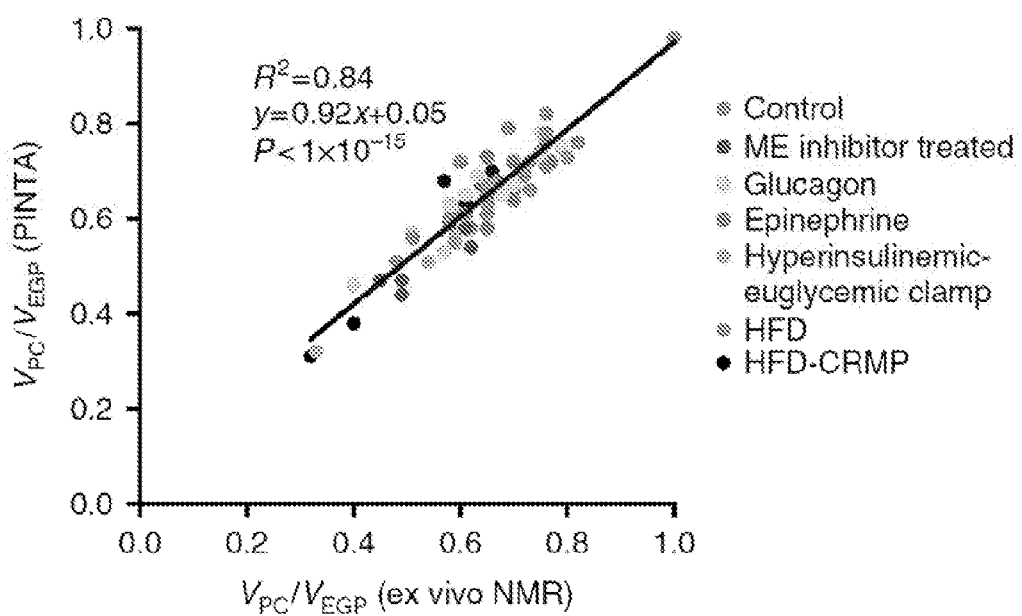
FIG. 2 is a graph showing $V_{PC}/V_{EGP}$ ratios measured by PINTA and ex vivo NMR. There was a close between the ratio measured by PINTA and the $V_{PC}/V_{EGP}$ ratio determined using ex vivo NMR analysis.

Analysis of plasma lactate and glucose enrichment in rat studies confirmed unchanged plasma lactate concentrations and steady-state enrichment after two hours of isotope infusion (FIGS. 6A-6B). The hepatic glucose and glutamate data obtained from all rats in this study are shown in Tables 1-2. Linear regression analysis demonstrated a strong correlation between the hepatic $V_{PC}/V_{CS}$ ratio measured with PINTA and that generated with a previously established ex vivo NMR method ($R^2$=0.99, slope=0.98) in 7 different groups of rats: 1) chow fed rats, 2) high fat fed rats, 3) rats undergoing a hyperinsulinemic-euglycemic clamp studies to mimic postprandial hyperinsulinemia, and separate groups of rats treated with: 4) glucagon, 5) epinephrine, 6) malic enzyme inhibitor, and 7) CRMP to promote increased hepatic mitochondrial oxidation (FIG. 1). The correlation between $V_{PC}/V_{EGP}$ ratios measured with ex vivo and PINTA analysis was compared, confirming a strong linear relationship between the two ratios ($R^2$=0.84, slope=0.92) (FIG. 2).

Plasma can be Used for PINTA Analysis

Figure 3:
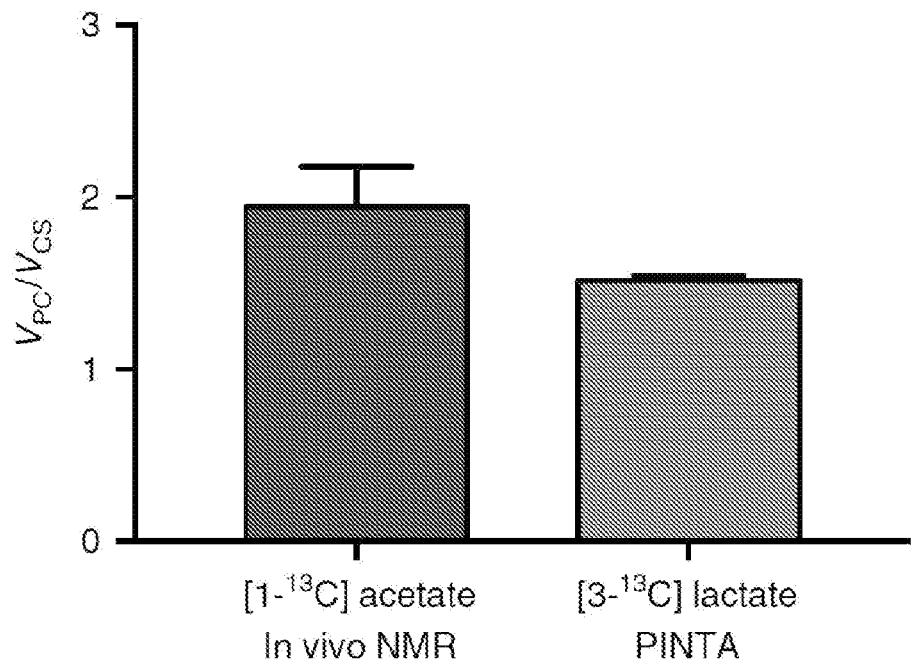
FIG. 3 is a graph comparing $V_{PC}/V_{CS}$ ratios in healthy human control subjects. The measured ratios were comparable when measured by in vivo NMR at 4 T or by PINTA. Data are presented as the mean±S.E.M. of n=3.
Figure 6C:
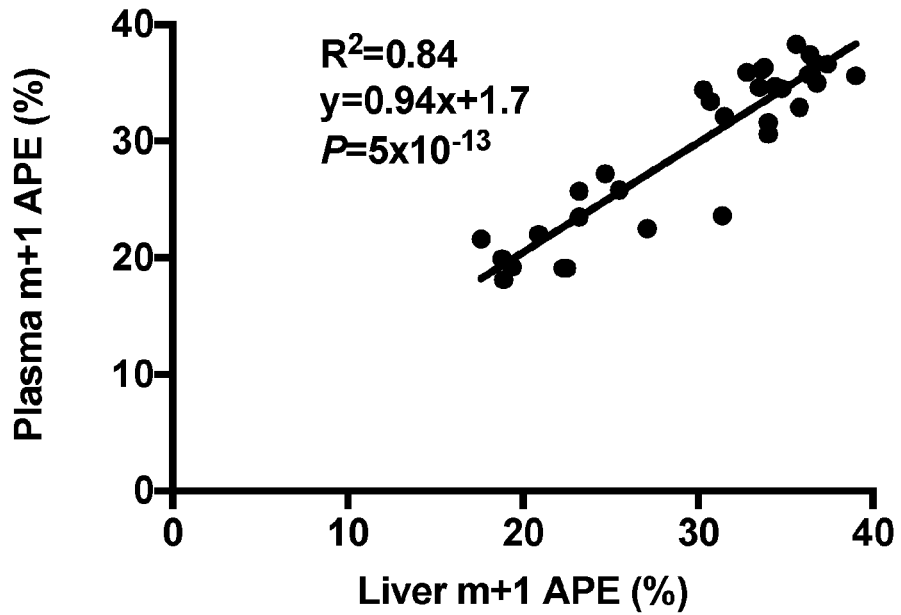
Figure 6D:
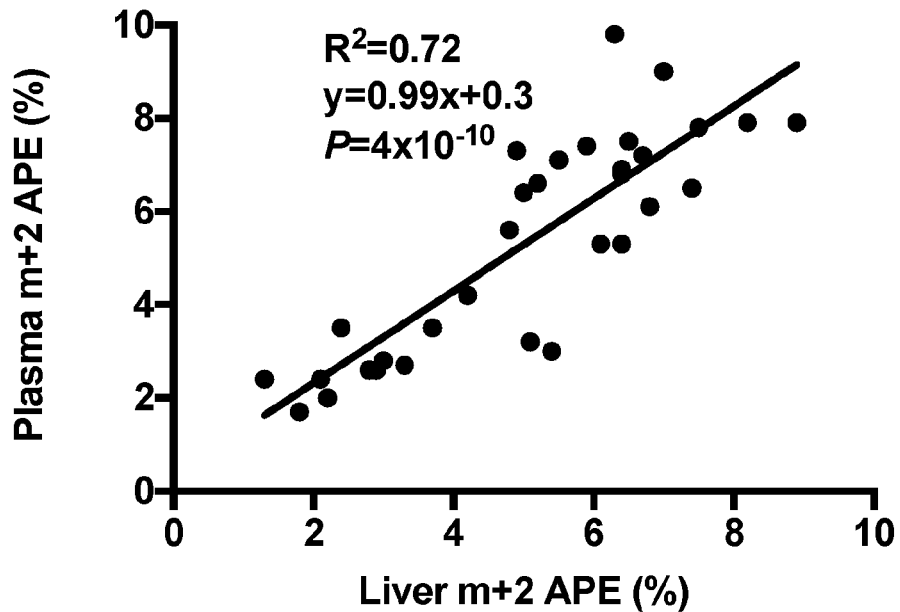
Figure 7B:
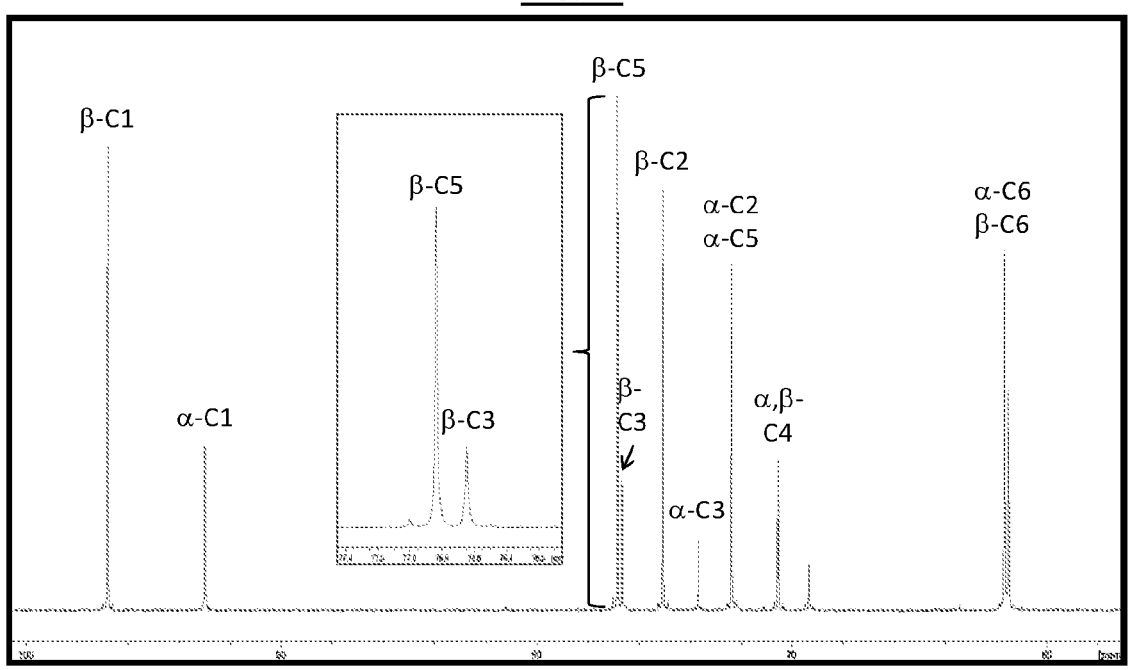
FIG. 7B is a representative $^{13}C$ NMR spectrum of plasma glucose from a non-diabetic, overnight fasted human.

In order to investigate whether this method can be applied to non-invasively measure hepatic fluxes in humans, a strong correlation between liver and plasma glucose enrichment in rat samples was first confirmed (FIGS. 6C-6D), demonstrating that the plasma glucose enrichment can be used as a surrogate for hepatic glucose enrichment in cases where non-invasive measurement of fluxes is of particular importance. The $V_{PC}/V_{CS}$ ratio was measured in three healthy human subjects following a 12 hr overnight fast. The two methods (in vivo NMR analysis of positional glutamate enrichment or PINTA analysis of plasma glucose) gave similar results, with $V_{PC}/V_{CS}$~1.5-1.9 using both methods (FIG. 3, FIGS. 7A-7B). The $V_{PC}/V_{EGP}$ ratio was 0.50±0.02, consistent with previous measurements of gluconeogenic contributions to endogenous glucose production in humans following an overnight fast.

PINTA Yields Expected Changes in Fluxes with Known Perturbations

Figure 4:
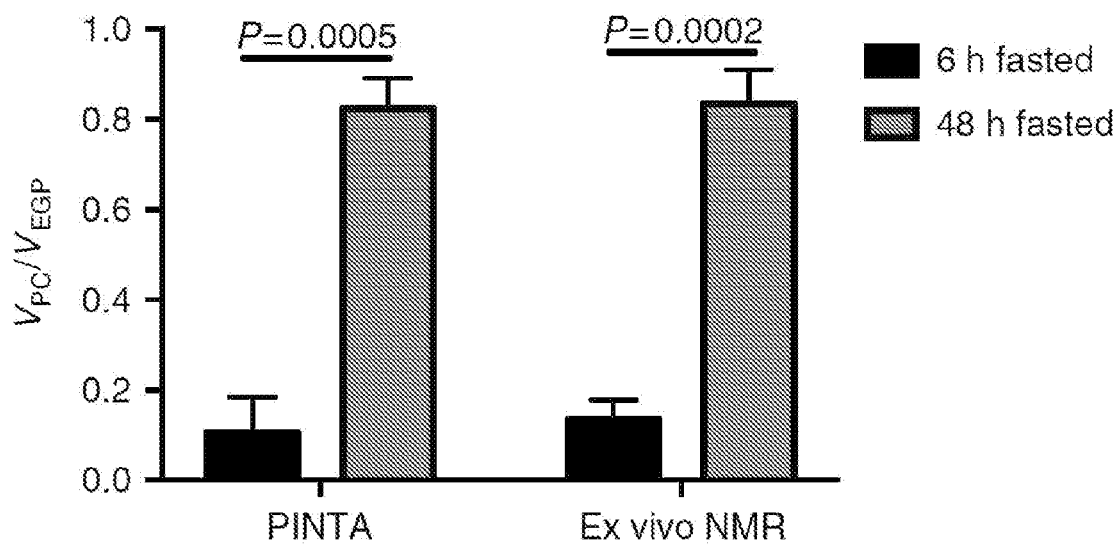
FIG. 4 is a graph showing that $V_{PC}/V_{EGP}$ increased with an extended fast. The $V_{PC}/V_{EGP}$ ratios measured using the two techniques were identical in both 6 and 48 hr fasted rats. Data are the mean±S.E.M. of n=4 rats per time point.
Figure 8:
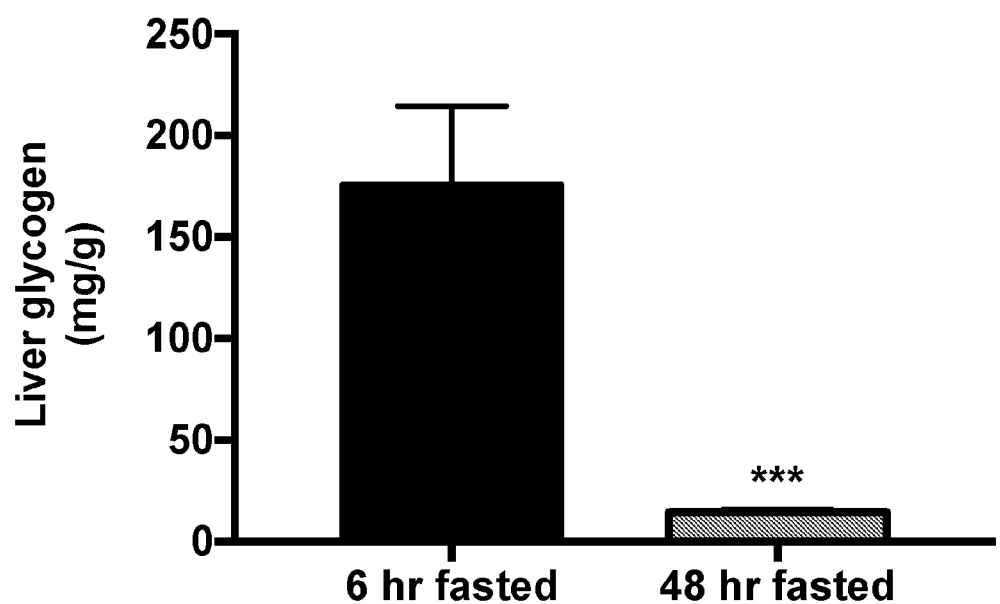
FIG. 8 is a graph showing that hepatic glycogen content was reduced after a 48 hr fast. Data are the mean±S.E.M. of n=5 per group.

In order to validate that the PINTA method is sensitive enough to detect expected differences in fluxes with alterations in hepatic mitochondrial oxidation, the effect of a Controlled-Release Mitochondrial Protonophore, which safely promotes liver-targeted mitochondrial uncoupling in vivo, was assessed, showing that this intervention increased $V_{CS}$ flux two-fold and suppressed both EGP and $V_{PC}$ fluxes (Table 7). The $V_{PC}/V_{EGP}$ ratio was measured in glycogen-depleted rats fasted for 48 hrs and the $V_{PC}/V_{EGP}$ flux ratio was compared to rats that had fasted for just six hours, after a prior fast and refeeding to increase liver glycogen content similar to the recently-fed state (FIG. 8). PINTA measurements demonstrated that $V_{PC}/V_{EGP}$ increased six-fold in hepatic glycogen-depleted rats fasted for 48 hrs, with the percentage of glucose production from pyruvate carboxylase flux increasing from ~13% to ~80% (FIG. 4).

TABLE 7

PINTA detects increased $V_{CS}$ flux in high fat fed rats treated with a liver-targeted mitochondrial uncoupler.
$V_{PC}/V_{CS}$ and $V_{PC}/V_{EGP}$ ratios, as well as absolute rates of endogenous glucose production, $V_{PC}$, and $V_{CS}$ flux were all measured using PINTA analysis of livers from rats infused with [3-$^{13}$C]lactate. *P < 0.05, **P < 0.01 by the 2-tailed unpaired Student's t-test.
Data are the mean ± S.E.M. of n = 5-6.

| Parameter | Control | CRMP |
|---|---|---|
| $V_{PC}/V_{CS}$ | 1.50 ± 27 | 0.48 ± 0.12** |
| $V_{PC}/V_{EGP}$ | 0.79 ± 0.05 | 0.60 ± 0.06* |
| EGP [μmol/(kg BW-min)] | 39 ± 1 | 33 ± 1** |
| $V_{PC}$ [μmol/(kg BW-min)] | 31 ± 3 | 20 ± 2** |
| $V_{CS}$ [μmol/(kg BW-min)] | 23 ± 4 | 49 ± 9* |

Selected Discussion

Alterations in hepatic fatty acid metabolism play a critical role in the pathogenesis of hepatic insulin resistance and increased rates of gluconeogenesis in patients with T2D and alterations in hepatic mitochondrial metabolism can play a key role in the pathogenesis of NAFLD and NASH. Furthermore liver-targeted agents to promote increased hepatic fatty acid oxidation through inhibition of acetyl-CoA carboxylase and liver-targeted and untargeted mitochondrial uncoupling agents are currently being developed to treat NAFLD/NASH and T2D. Thus there is great interest in developing noninvasive methods to assess rates of hepatic mitochondrial fatty acid oxidation and gluconeogenesis in vivo. The present invention discloses that, by assessing the positional isotopomer enrichments of the C4 and C5 carbons of plasma glucose by a combined $^{13}$C NMR/GC-MS method following an infusion of [3-$^{13}$C]lactate, one can noninvasively assess rates of hepatic mitochondrial oxidative ($V_{CS}$) and gluconeogenic fluxes from pyruvate ($V_{PC}$) in awake rodents and humans. Furthermore, by combining these $V_{PC}/V_{CS}$ relative flux measurements with assessment of endogenous glucose production and assessment of the ratio of $V_{PC}/V_{EGP}$ enrichment calculated from the m+1 and m+2 enrichments of glucose, one can estimate absolute rates of $V_{CS}$ flux and $V_{PC}$ flux.

In order to validate this method, the ratio of hepatic pyruvate carboxylase flux to hepatic citrate synthase flux ($V_{PC}/V_{CS}$) was measured using two methods following a steady-state infusion of [3-$^{13}$C]lactate and [3-$^{3}$H]glucose, comparing data obtained using a previously established ex vivo NMR analysis to the newly developed PINTA analysis (Tables 1-2) in seven groups of rats undergoing various physiological perturbations which could alter hepatic mitochondrial activity: 1) control chow fed rats, 2) insulin resistant high fat-fed rats, 3) hyperinsulinemic-euglycemic clamped rats, 4) glucagon infused rats, 5) epinephrine infused rats, 6) malic enzyme inhibitor treated rats and 7) liver-targeted mitochondrial uncoupler (CRMP) treated rats. Using this approach, a 1:1 correlation (FIG. 1; $R^2$=0.99, slope=0.98) for $V_{PC}/V_{CS}$ was observed using these two methods. Both methods rely on a similar small set of assumptions, including having reached steady state in the metabolites of interest and negligible enrichment in [1-$^{13}$C] pyruvate, alanine, and acetyl-CoA. These assumptions in the current study were validated by demonstrating stability of glucose enrichment in both rats and humans (FIGS. 6B and 7A) and confirming minimal hepatic bicarbonate enrichment (1.5±0.1%).

Next, the PINTA and ex vivo NMR methods were used to calculate the ratio of $V_{PC}/V_{EGP}$. A strong correlation (FIG. 2; $R^2$=0.84, slope=0.92) between ratios calculated was observed using the two methods in all groups of rats. The calculation of this flux required a different but related set of assumptions. PINTA measurement of $V_{PC}/V_{EGP}$ assumes, in addition to achievement of steady state, a binomial probability analysis describing the distribution of $^{13}$C-glucose isotopomers resulting from the synthesis of two $^{13}$C-labeled trioses, and the presence of just one gluconeogenic precursor pool enrichment. The ex vivo NMR method assumes the presence of rapidly equilibrating small pools in the TCA cycle that are unperturbed by the tracer, complete equilibration of C2 and C3 OAA, and that the enrichment of malate reflects that of OAA. The strong correlation between two methods with differing assumptions supports the applicability of each method. Taken together these data demonstrate that the analysis of glucose by the PINTA method (Tables 1-2) closely approximates the $V_{PC}/V_{CS}$ and $V_{PC}/V_{EGP}$ ratios measured using an invasive method that requires rapidly snap freezing 3-4 gram of liver tissue in rodents that have been anesthetized within 10 seconds of intravenously administered anesthesia.

A non-limiting goal of this report is to present a non-invasive method to measure hepatic oxidative and gluconeogenic fluxes that can be applied to humans. To examine the potential of PINTA to serve this purpose, two independent and complementary methods were used to calculate the ratio of $V_{PC}/V_{CS}$ in humans infused with [1-$^{13}$C]acetate and [3-$^{13}$C]lactate in separate studies. The studies demonstrate that PINTA measures the ratio $V_{PC}/V_{CS}$ similar to that determined using in vivo NMR analysis.

Next, in order to confirm the sensitivity of PINTA measurements to expected changes in mitochondrial flux rates, a validation study was performed utilizing treatment with a liver-targeted mitochondrial uncoupling agent, CRMP, which can selectively increase rates of hepatic mitochondrial oxidation in vivo without inducing hyperthermia or any associated hepatic or systemic toxicities. As compared to vehicle-treated control rats, animals treated with CRMP exhibited a 2.5-fold increase in hepatic $V_{CS}$ flux consistent with its effects to increase hepatic tricarboxylic acid cycle activity through uncoupling of mitochondrial oxidative-phosphorylation activity. This 2.5-fold increase in rates of hepatic mitochondrial oxidation induced by CRMP was associated with a ~70% reduction in the $V_{PC}/V_{CS}$ ratio and ~10% and ~30% reductions in rates of endogenous glucose production and $V_{PC}$ flux, respectively (Table 7). Finally, $V_{PC}/V_{EGP}$ flux was examined in glycogen-repleted rats fasted for 6 hrs and this ratio was compared to glycogen depleted rats fasted for 48 hr. An extended fast increased $V_{PC}/V_{EGP}$ flux six-fold, consistent with a shift in reliance upon increased mitochondrial pyruvate carboxylase flux for glucose production in the absence of hepatic glycogen. These data demonstrate that the PINTA method is sufficiently sensitive to detect expected differences in both relative and absolute $V_{PC}/V_{CS}$ fluxes as well as in the ratio $V_{PC}/V_{EGP}$ with previously characterized physiologic perturbations.

The selection of isotope is always a critical factor in any tracer metabolic study and [3-$^{13}$C]lactate has many advantages over other stable isotopes that have been used to assess hepatic mitochondrial and glucose metabolism. First, plasma lactate concentrations are 10-100 fold greater than the plasma concentrations of glycerol, acetate or propionate and therefore significant $^{13}$C enrichment in hepatic lactate and its intrahepatocellular metabolites can be achieved without significantly perturbing whole body lactate metabolism. Furthermore, compared to glycerol, acetate and propionate, lactate has the lowest periportal-perivenous gradient across the liver bed and therefore hepatocellular flux determinations using this isotope are least impacted by any heterogeneity of mixing of tracer between periportal and perivenous hepatocytes. In addition, the minimal impact of [3-$^{13}$C]lactate on hepatic metabolism stands in contrast to [U-$^{13}$C] propionate which, when administered at doses commonly used to trace hepatic mitochondrial metabolism in human and animal studies, markedly increases concentrations of plasma propionate and of hepatic propionyl-CoA and TCA cycle intermediates. As a potent allosteric activator of pyruvate carboxylase, increased propionyl-CoA may lead to profound alterations in hepatic mitochondrial fluxes. In contrast [3-$^{13}$C]lactate can be infused at a rate that provides sufficient label to measure hepatic mitochondrial fluxes without significantly altering hepatocellular mitochondrial metabolites/fluxes. Because of its reliance on the assumption that pyruvate cycling is minimal the PINTA method would be of limited utility in settings where pyruvate kinase (PK) and/or malic enzyme (ME) flux is high relative to pyruvate carboxylase flux. However, rates of $V_{PK+ME}$ flux were found to be very low compared to rates of $V_{PC+PDH}$ flux in healthy control subjects and insulin resistant subjects with NAFLD following an overnight fast. Consistent with these prior studies, $V_{PK+ME}$ flux relative to $V_{PC+PDH}$ flux is less than 6% in overnight fasted rodents (Table 1); using a complete equation including these fluxes it was found to have minimal impact on the estimates of $V_{PC}$ and $V_{CS}$ fluxes. Without intending to be limited to any particular theory, this finding makes teleological sense in that rates of hepatic glycolysis ($V_{PK}$) would be expected to be minimal relative to rates of $V_{PC}$ flux under fasting conditions in order to provide maximal net flux through gluconeogenesis to support obligate glucose-utilizing organs like the CNS while minimizing energy dissipation due to futile cycling. However, under other conditions such as hyperthyroidism, which significantly increases rates of hepatic pyruvate cycling due to increased $V_{ME}$ flux, as well as under hyperglycemic-hyperinsulinemic conditions, when rates of hepatic glycolysis would be expected to be significantly increased, it is necessary to adjust these PINTA determined rates of $V_{PC}/V_{CS}$ flux accordingly using equation (30).

The use of the PINTA method to measure $V_{PC}$ flux also has advantages over the $^{2}H_{2}O$ method to measure gluconeogenic flux rates. In addition to the improved specificity afforded by measuring $V_{PC}$ instead of total gluconeogenesis, infusion of [3-$^{13}$C]lactate is practically simpler for both investigator and subject: the $^{2}H_{2}O$ method requires dosing of $^{2}H_{2}O$ several hours prior to assessment of gluconeogenesis in order to allow adequate time for $^{2}H_{2}O$ equilibration in the whole-body water space. Furthermore, $^{2}H_{2}O$ administration is often associated with dizziness, nystagmus, nausea and occasional vomiting, which can be a limiting factor in the clinical setting.

The present disclosure describes a non-invasive (PINTA) method to measure rates of hepatic mitochondrial oxidation and pyruvate carboxylase flux in vivo during an infusion of [3-$^{13}$C]lactate in combination with a glucose tracer to assess rates of endogenous glucose production. This method will provide investigators with a simple and widely available means of examining the role of altered hepatic mitochondrial and glucose metabolism in various physiologic and pathophysiologic states in humans and rodent models of diabetes as well as to examine target engagement for novel therapies that are currently being developed to promote increased rates of hepatic fatty acid oxidation for the treatment of NASH and type 2 diabetes.

Example 2: Leptin Mediates a Glucose-Fatty Acid Cycle to Maintain Glucose Homeostasis in Starvation Mammals have evolved robust mechanisms to maintain sufficient substrate supply to meet the prodigious energy demands of the brain during starvation. Chief among them is a shift from carbohydrate to fat metabolism to preserve essential protein stores necessary for survival that would otherwise be catabolized for gluconeogenesis. In the transition from the fed to the early fasted state, there is a shift from substrate absorption to hepatic glycogenolysis and de novo synthesis of glucose from non-carbohydrate precursors, such as lactate, alanine, and glycerol (gluconeogenesis). In contrast, in the prolonged fasted state, when hepatic glycogen stores have been depleted, hepatic gluconeogenesis and ketogenesis supply substrate to the brain and other obligate glucose utilizers, such as erythrocytes and the renal medulla. The shift from glucose metabolism to fat and ketone metabolism is thought to be primarily orchestrated by a decrease in plasma insulin concentrations and, to a lesser extent, an increase in plasma glucagon concentrations, which in turn are thought to modulate hepatic gluconeogenesis principally by the transcriptional regulation of key unidirectional enzymes, such as phosphoenolpyruvate carboxykinase (PEPCK), fructose-1,6-bisphosphatase and glucose-6-phosphatase by forkhead box protein O1 (FOXO1), peroxisome proliferator-activated receptor gamma coactivator 1-alpha (PGC-1a), hepatocyte nuclear factor-4 alpha (HNF-4a), and other factors.

Prolonged starvation has also been shown to reduce plasma leptin concentrations in both humans and mice, which in turn has been shown to alter reproductive, thyroid, and adrenal function. However, the effect of starvation-induced hypoleptinemia on glucose and fat metabolism has not been conclusively demonstrated. In this regard, it is possible that hypoleptinemia may be a critical signal to increase white adipose tissue (WAT) lipolysis through activation of the hypothalamic-pituitary-adrenal (HPA) axis, resulting in increased hepatic acetyl-CoA content and pyruvate carboxylase activity, thereby maintaining glucose homeostasis and increasing hepatic ketogenesis during starvation.

In order to address this hypothesis, a positional isotopomer nuclear magnetic resonance (NMR) tracer analysis (PINTA) method (see Example 1) was used to assess in vivo rates of mitochondrial pyruvate carboxylase flux ($V_{PC}$) and mitochondrial oxidation ($V_{CS}$) along with stable isotope infusions to assess rates of whole-body glucose turnover, WAT lipolysis, hepatic ketogenesis, glucose-alanine cycling, and glucose-lactate cycling in awake rats during the transition from the fed state to the prolonged fasted state. Using this comprehensive metabolic approach, it has been shown that hypoleptinemia drives a glucose-fatty acid cycle mediated by activation of the hypothalamic-pituitary-adrenal axis, resulting in increased rates of WAT lipolysis, b-oxidation, ketogenesis, and hepatic acetyl-CoA content, which are necessary to maintain glucose homeostasis and adequate substrate supply to the brain during prolonged starvation.

Materials and Methods

Animal Studies

Male Sprague-Dawley rats were ordered from Charles River Laboratories (Wilmington, Mass.) at ~250 g and were group housed (3 per cage) for 1-2 weeks until they underwent surgery under general isoflurane anesthesia for placement of polyethylene catheters in the common carotid artery (PE50 tubing, Instech Solomon, Plymouth Meeting, Pa.), and the jugular vein (PE90 tubing, Instech), and/or the portal vein (PE50 tubing, Instech), after which they were singly housed until sacrifice. Unless otherwise specified, rats were fed a regular chow diet (Harlan Teklad #2018, Indianapolis, Ind.) throughout, and fasted as described below. High fat fed rats were given ad lib access to a safflower oil-based high fat diet containing 60% calories from fat (Dyets #112245, Bethlehem, Pa.) for 4 weeks prior to sacrifice, before which they were fasted as described above. In order to induce T1D, rats were injected with streptozotocin (65 mg/kg IP, Sigma Aldrich, St. Louis, Mo.) 24 hr prior to the start of a leptin infusion study and were fasted overnight 12 hr after streptozotocin injection. T1D was confirmed by the combination of hyperglycemia (>17 mM) and insulinopenia (<30 pM) after the overnight fast; all rats that did not meet both criteria (~25% of those injected with streptozotocin) were excluded from analysis.

Rats were randomly assigned to fasting time points following a 24 hr fast-refeeding protocol designed to maximize whole-body glycogen content prior to the fast, as occurs following a large meal. The feeding and fasting times for each group of rats are listed in Table 8.

TABLE 8

Fasting, refeeding, and fasting timelines.

| Fasting time (hr) | Fast start | Refeed start | Fast start | Sacrifice |
|---|---|---|---|---|
| 0 | 12:00 (Day 0) | 12:00 (Day 1) | N/A | 14:00 (Day 1) |
| 1 | 11:00 (Day 0) | 11:00 (Day 1) | 13:00 (Day 1) | 14:00 (Day 1) |
| 6 | 6:00 (Day 0) | 6:00 (Day 1) | 8:00 (Day 1) | 14:00 (Day 1) |
| 7 | 5:00 (Day 0) | 5:00 (Day 1) | 7:00 (Day 1) | 14:00 (Day 1) |
| 8 | 4:00 (Day 0) | 4:00 (Day 1) | 6:00 (Day 1) | 14:00 (Day 1) |
| 16 | 20:00 (Day 0) | 20:00 (Day 1) | 22:00 (Day 1) | 14:00 (Day 2) |
| 17 | 19:00 (Day 0) | 19:00 (Day 1) | 21:00 (Day 1) | 14:00 (Day 3) |
| 47 | 13:00 (Day 0) | 13:00 (Day 1) | 15:00 (Day 1) | 14:00 (Day 3) |
| 48 | 12:00 (Day 0) | 12:00 (Day 1) | 14:00 (Day 1) | 14:00 (Day 3) |

Following the fasting period designated, rats underwent studies as described in the following sections. They were euthanized with IV pentobarbital at the conclusion of each study, and their tissues rapidly freeze-clamped (liver freeze-clamped in situ) in tongs pre-cooled in liquid nitrogen.

In all studies, rats were sacrificed with tissues and plasma collected for analysis at 14:00 hr, removing any impact of diurnal variation on the measurements taken. All tracers were infused through a catheter placed ~1 week prior in the carotid artery, and blood was obtained from a catheter in the jugular vein. Measurements of portal vein glucose concentrations were performed on blood samples taken from a catheter in the portal vein; unless otherwise specified, all blood was drawn from the jugular vein. All studies began 1 hr after catheters were connected, reducing any impact of stress from handling on the physiology assessed.

Tracers

Primed-continuous infusions of tracers were performed at the following rates. In each case, the prime was for 5 min, with the continuous infusion spanning 5-120 min. Tracer infusion rates are shown in Table 9. A bolus of [6,6-$^{14}$C]2-deoxyglucose was administered in 48 hr fasted control rats and 48 hr fasted rats infused with glucose to increase plasma glucose concentrations to 6 mM and gastrocnemius muscle and epididymal white adipose tissue were harvested and processed to determine basal glucose uptake in both tissues by comparing the plasma [$^{14}$C] specific activity decay curve to tissue [$^{14}$C] specific activity, both measured using a scintillation counter.

TABLE 9

Tracer infusion rates used in this study.

| Tracer | Prime infusion rate [μmol/(kg-min)] | Continuous infusion rate [μmol/(kg-min)] | Source |
|---|---|---|---|
| [1,2,3,4,5,6,6-$^2$H$_7$]glucose | 1.8 | 0.6 | Cambridge Isotopes |
| [U-$^{13}$C$_{16}$]palmitate | 2.1 | 0.7 | Cambridge Isotopes |
| [1,1,2,3,3-$^2$H$_5$]glycerol | 4.5 | 1.5 | Sigma |
| [U-$^{13}$C$_4$]β-OHB | 3.0 | 1.0 | Cambridge Isotopes |
| [2,3,3,3-$^2$H$_4$]alanine | 15.0 | 5.0 | Cambridge Isotopes |
| [3-$^{13}$C]lactate | 120 | 40 | Cambridge Isotopes |

Leptin Infusions

In order to examine the physiologic impact of varying doses of leptin on glucose, hormones, and lipolysis, rats were infused with stepwise increasing doses of leptin during a continuous infusion of [1,2,3,4,5,6,6-$^2$H$_7$]glucose, [U-$^{13}$C$_{16}$]palmitate, [1,1,2,3,3-$^2$H$_5$] glycerol, and [U-$^{13}$C$_4$] β-hydroxybutyrate starting at hour 42 of a 48 hr fast. From 42-43.5 hr of the fast rats were infused with tracer only, from hours 43.5-45 they were infused with 20 pmol/(kg-min) leptin, from hours 45-46.5 they were infused with 60 pmol/(kg-min) leptin, and from 46.5-48 hr the infusion rate was 600 pmol/(kg-min). Blood samples were taken at 43.5, 45, 46.5, and 48 hr for measurement of substrate/hormone concentrations and turnover of each tracer, as described below. In the T1D leptin dose response studies, overnight (12 hr) fasted rats were infused with stepwise increasing dose of leptin during the same tracer infusion as described above. From 12-14 hr of the fast rats were infused with tracer only, from 14-16 hr they were infused with 50 pmol/(kg-min) leptin, and from hours 16-18 they were infused with 600 pmol/(kg-min) leptin. Blood samples were taken at 14, 16, and 18 hr of the fast for measurement of substrate/hormone concentrations and turnover of each tracer, as described below.

Pharmacologic Manipulation of Glycogen and Acetyl-CoA 8, 16, and 48 hr fasted rats were injected with a small molecule inhibitor of glycogen phosphorylase, 1-(3-(3-(2-Chloro-4,5-difluorobenzoyl) ureido)-4-methoxyphenyl)-3-methylurea (Sigma #361515; 5 mg/kg IV) and a tracer infusion of [2,3,3,3-$^2$H$_4$]alanine (15 mmol/[kg-min]prime for 5 min and 5 mmol/[kg-min] continuous) and [3-$^3$H] glucose (0.3 μCi/min prime for 5 min and 0.3 μCi/min continuous) as well as [$^{13}$C4] β-hydroxybutyrate, [1,1,2,3,3-$^2$H$_5$]glycerol, and [$^{13}$C$_{16}$]palmitate at the rates listed in Table 9, for 120 min. Blood samples were obtained before (time zero) and 120 min after treatment with the glycogen phosphorylase inhibitor for measurement of turnover rates and plasma hormone/substrate concentrations. Hepatic acetyl-CoA content was altered by treatment with a CPT-1 inhibitor (etomoxir, 8 mg/kg) or an ATGL inhibitor (atglistatin, 200 mmol/kg) in 0, 6, 16, and 48 hr fasted rats. Both agents were solubilized by suspending the drug in 4% ethanol/96% normal saline, heating to 60° C., and sonicating, and were cooled to room temperature before they were injected intraperitoneally. Intra-arterial infusion of a small amount of glucose was required to avoid hypoglycemia in 48 hr fasted, atglistatin-treated rats. In these animals plasma glucose concentrations were measured every 15 minutes and a variable infusion of 20% glucose (Pfizer Hospira, Lake Forest, Ill.) was used to maintain plasma glucose concentrations ~3.6-3.7 mM. The physiologic role of glucocorticoids was assessed in 6 and 48 hr fasted rats by treatment with a glucocorticoid receptor antagonist, mifepristone. Following a 2 hr tracer infusion at the rates described above to assess fatty acid, glycerol, glucose, and β-hydroxybutyrate turnover, rats were injected with mifepristone (40 mg/kg) IV. The tracer infusion was continued and the tracer of each of the above substrates was again measured 2 hr after treatment with mifepristone.

Glucose Clamps

Alanine turnover was determined in 48 hr fasted rats following a 2 hr infusion of [2,3,3,3-$^2$H$_4$]alanine as described below (Alanine Replacement). In order to match plasma glucose concentrations to those of 16 hr fasted rats, a variable infusion of glucose was begun through an arterial catheter in the same rats, with plasma glucose concentrations checked every 15 min and adjusted to maintain plasma glucose concentrations ~6.0 mM. With the glucose infusion continuing, a tracer dose of [6,6-$^{14}$C$_2$]2-deoxyglucose was administered through a venous catheter and tissue glucose uptake was determined as described below. In the hyperinsulinemic-euglycemic clamps, glucose turnover was measured during a basal infusion of [1,2,3,4,5,6,6-$^2$H$_7$]glucose as described above. A primed-continuous infusion of Regular insulin (prime 40 mU/kg, continuous infusion rate 4 mU/[kg·min]) was initiated for 150 min, during which plasma glucose concentrations were measured every 10-15 min and a variable infusion of 20% glucose (2.5% [1,2,3, 4,5,6,6-$^2$H$_7$] enriched) was infused to maintain euglycemia (~6 pM). The rats were euthanized with IV pentobarbital immediately at the conclusion of the clamp.

Alanine Replacement 48 hr fasted rats were infused with alanine [45 mmol/(kg-min)] during an infusion of [$^2$H$_7$]glucose and [3-$^{13}$C]lactate at the infusion rates listed in Table 9. Hepatic fluxes (whole-body glucose turnover, VPC and VCS), liver TCA cycle intermediate concentrations, and plasma metabolites and hormones were measured as described below (Flux Measurements).

Flux Measurements

All whole-body substrate turnover rates were calculated using the equation Turnover=([Tracer APE/Plasma APE]−1)*Infusion rate, where APE designates the atom percent enrichment measured by mass spectrometry as described below (Biochemical Analysis). All chemicals used for flux analysis were obtained from SIGMA. Turnover of glucose, glycerol, and β-hydroxybutyrate were determined by gas chromatography-mass spectrometry (GC-MS). Briefly, both glucose and glycerol were deprotonized with 5 volumes of methanol, derivitized with 3 volumes of 1:1 acetic anhydride:pyridine, heated to 65° C. for 20 min, and 1 volume of methanol was added, then GC-MS was used in CI mode to measure glucose enrichment and EI mode to measure glycerol enrichment, with turnover calculated using the equation above. β-Hydroxybutyrate was deprotonized with 5 volumes of methanol and derivitized with 3 volumes of n-butanol 4N HCl, after which the samples were heated to 65° C. for 60 min, evaporated under N$_2$ gas, and re-suspended in 100 mL of trifluoroacetic acid:methylene chloride (1:7). Fatty acid turnover was measured by determining the plasma palmitate enrichment by GC-MS. Samples were prepared for measurements of palmitate enrichment by evaporating 25 mL plasma, dissolving in 750 mL 1:1 chloroform:methanol and derivitizing with 250 mL boron trifluoride/methanol, then heating to 100° C. for 5 min, adding 2 mL pentane and 1 mL water, and centrifuging at low speed for 5 min. The supernatant was transferred to another vial, dissolved, and resuspended in 100 mL hexane for measurement of palmitate enrichment by GC-MS (CI mode). the percent fatty acids (30%-40% in each study) comprised by palmitate was then corrected for, in order to measure total fatty acid turnover. Alanine turnover was determined in rats infused with [2,3, 3,3-$^2$H$_4$]alanine by preparing samples to measure alanine enrichment by GC/MS (CI mode) using the same protocol as was employed to measure β-hydroxybutyrate enrichment. GC-MS was then used to determine the m+4 alanine enrichment (retention time ~4.1 min, m/z 242 [m0], 243 [m+1], 244 [m+2], 245 [m+3], 246 [m+4]). Lactate turnover was determined in rats infused with [3-$^{13}$C]lactate by performing the same extraction as for alanine and measuring the m+1 lactate enrichment (retention time ~2.8 min, m/z 243 [m0] and 244 [m+1]). VPC and VCS flux rates were determined by PINTA in rats infused with [3-$^{13}$C]lactate at the rates described above. Flux analysis was performed in rats confirmed post-absorptive (≥8 hr fasted) based on the absence of a portal-systemic glucose gradient (FIG. 10B). The equations used for calculation of flux ratios, which use the positional enrichment of glucose and isotopomers of total and C4C5C6 glucose to calculate these relative fluxes, are as follows:

$$\frac{V_{PC}}{V_{CS}} = \left(\frac{[5-^{13}C]\text{glucose}}{2*([4-^{13}C]\text{glucose})}\right) - 1 \quad (101)$$

$$\frac{V_{PC}}{V_{EGP}} = \frac{G2}{XFE^2} \quad (102)$$

where G2 denotes glucose [m+2] arising from the condensation of two [m+1] trioses as follows:

$$G2 = \text{Measured}[m+2] \text{ glucose} - 2*C4C5C6[m+2] \text{ glucose} \quad (103)$$

$$\text{and } XFE = \frac{1}{1 + \frac{G_1}{2*G_2}} \quad (104)$$

where G1 denotes glucose [m+1] and G2 is as calculated in Equation (103).

The derivations of these equations can be found in Example 1. Absolute V$_{PC}$ flux was measured by multiplying the V$_{PC}$/V$_{EGP}$ ratio by the VEGP (whole-body glucose turnover) measured by dilution of [$^2$H$_7$] glucose. Absolute V$_{CS}$ flux was calculated by dividing V$_{PC}$ by the ratio V$_{PC}$/V$_{CS}$. Rates of net hepatic glycogenolysis were calculated by measuring liver glycogen concentrations at the time points indicated and at one hour before or after the relevant time point. Assuming a constant rate of glycogenolysis during that hour, glycogenolysis rates were calculated by measuring the difference in liver glycogen between these time points and dividing by 60 min. The contribution of glycerol to gluconeogenesis was calculated as the difference between EGP and the sum of V$_{PC}$ and the rate of net hepatic glycogenolysis. The V$_{PDH}$/V$_{CS}$ flux was measured as the ratio of [4,5-$^{13}$C$_2$]glutamate/[$^{13}$C3]alanine in liver, brain, heart, skeletal muscle (gastrocnemius), kidney, WAT, and BAT after a 2 hr infusion of [1,2,3,4,5,6-$^{13}$C6]glucose (16.7 umol/[kg-min] prime for 5 min, 5.6 umol/[kg-min] continuous infusion). Alanine enrichment was measured by GC-MS as described above, and glutamate by LC-MS/MS: the samples were homogenized in 500 mL ice-cold methanol using a TissueLyser and filtered through a Nanosep filter. LC-MS/MS (AbSCIEX 6500 QTRAP with a Shimadzu ultrafast liquid chromatography system, negative ion mode) was used to monitor the relevant ion pairs: [m0] C4-5 glutamate, 146/41, [m+1] C4-5 glutamate, 147/47, and [m+2] C4-5 glutamate, 148/48.

Biochemical Analysis

Plasma glucose was measured enzymatically using the YSI Glucose Analyzer (Yellow Springs, Ohio). Plasma lactate, triglyceride, and β-hydroxybutyrate concentrations were measured by COBAS (Roche Diagnostics, Indianapolis, Ind.). Plasma NEFA were measured enzymatically using a Wako reagent (Wako Diagnostics, Mountain View, Calif.). Plasma glycerol and alanine concentrations were measured by GC-MS: samples were spiked with a $^2$H (alanine) or $^{13}$C (glycerol) internal standard and prepared for GC-MS using the protocols described above, with the ratio of labeled to unlabeled substrate compared to a standard curve to measure absolute concentrations. Plasma amino acid concentrations (glycine, alanine, serine, leucine, isoleucine, aspartate+asparagine, phenylalanine, glutamate+glutamine) were measured by GC-MS after spiking with $^2$H or 13C internal standards and derivitizing using the protocol described above for β-hydroxybutyrate measurements. Plasma insulin, leptin, CRH, ACTH, corticosterone, corticosteroid binding globulin, epinephrine, norepinephrine, growth hormone, T3, and FGF-21 concentrations were measured by ELISA (Mercodia, Winston-Salem, N.C.; Abcam, Cambridge, Mass.; MyBioSource, San Diego, Calif.; MyBioSource; Alpco, Salem, N.H.; MyBioSource; Abnova; Abnova; Millipore, Billerica, Mass.; MyBioSource; and R&D Systems, Minneapolis, Minn., respectively). Plasma insulin concentrations in the hyperinsulinemic-euglycemic clamps (and corresponding basal plasma) were measured by radioimmunoassay by the Yale Diabetes Research Center Radioimmunoassay Core. Samples used for measurement of epinephrine and norepinephrine were collected into pre-chilled EDTA-coated tubes. Plasma glucagon was measured in plasma samples collected in pre-chilled tubes containing aprotinin (0.5 mg/ml), by RIA through the Yale Diabetes Research Center Radioimmunoassay Core.

Tissue Analysis

Liver and muscle glycogen concentrations were assessed using amyloglucosidase digestion. Liver TAG content was measured using the method of Bligh and Dyer (Bligh and Dyer, Can. J. Biochem. Physiol. 37, 911-917, 1959): lipids were extracted from livers using 2:1 chloroform:methanol, and the Sekisui triglyceride-SL reagent was used to measure triglyceride content spectrophotometrically. Liver and muscle DAG content and liver acetyl- and malonyl-CoA concentrations were measured by LC-MS/MS as described by Yu and Perry (Yu, et al. J. Biol. Chem. 2002, 277, 50230-50236; Perry, et al., J. Clin. Invest. 2017, 127, 657-669). Concentrations of TCA cycle intermediates (citrate, malate, succinate) were measured by LC-MS/MS: ~100 mg of tissue were weighed out, and a solution containing 0.1 mmol of internal standards ([13C$_6$]citrate, [13C$_4$]succinate, and [$^{13}$C$_4$] L-malate, all from Sigma) was added. The samples were homogenized in 500 mL ice-cold methanol using a TissueLyser and filtered through a Nanosep filter. LC-MS/MS (AbSCIEX 6500 QTRAP with a Shimadzu ultrafast liquid chromatography system, negative ion mode) was again used to monitor the relevant ion pairs: succinate and [$^{13}$C4]succinate, 117/99 and 121/103, respectively; malate and [$^{13}$C$_4$]malate, 133/115 and 137/119, respectively; and citrate and [13C$_6$]citrate, 191/173 and 197/179, respectively. Liver alanine concentrations were measured by GC/MS after spiking liver samples with an internal standard ([$^{13}$C$_3$]alanine). Hepatic PKCε translocation, gluconeogenic enzyme protein expression, ApoB (antibody from Meridian Life Science, Memphis, Tenn.), and PGC1α (antibody from Santa Cruz Biotechnology, Dallas, Tex.) protein expression were assessed by western blot. Expression of each of these proteins was normalized to GAPDH.

Quantification and Statistical Analysis

Comparisons were performed using the 2-tailed Student's t test (if two groups were compared) or ANOVA (if more than two groups were compared), paired or unpaired as specified in the figure legends, with significance defined as a p value <0.05. GraphPad Prism 7.0 (San Diego, Calif.) was used for all statistical analysis. In most cases, n=6-8 rats per group, unless otherwise indicated in the figure legends. Data are presented as the mean±SEM.

Depletion of Hepatic Glycogen During Starvation Induces Hypoleptinemia

Figure 9A:
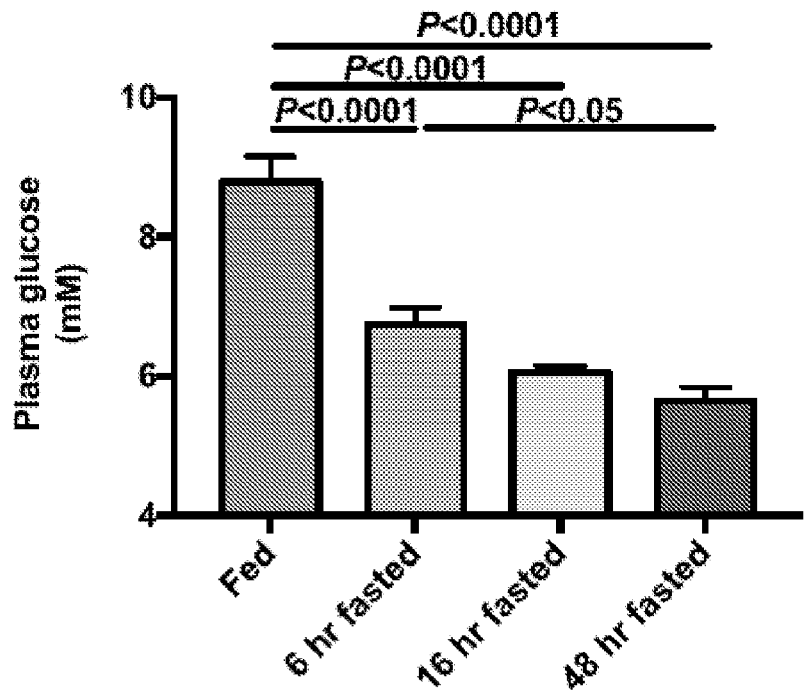
Figure 9B:
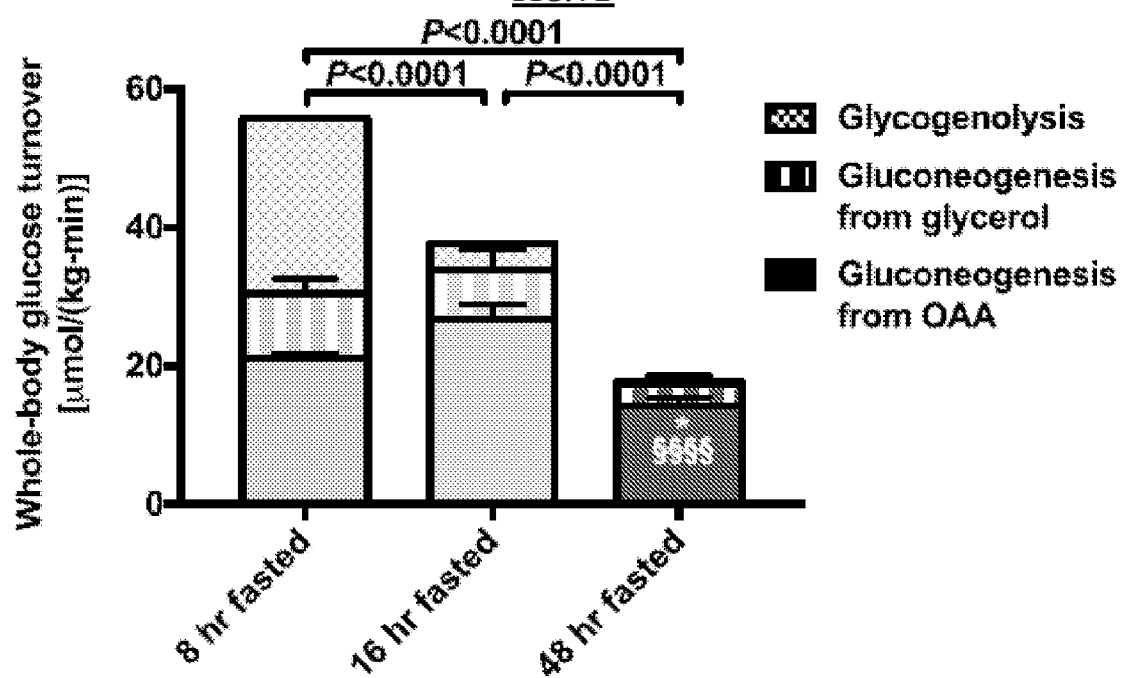
Figure 9E:
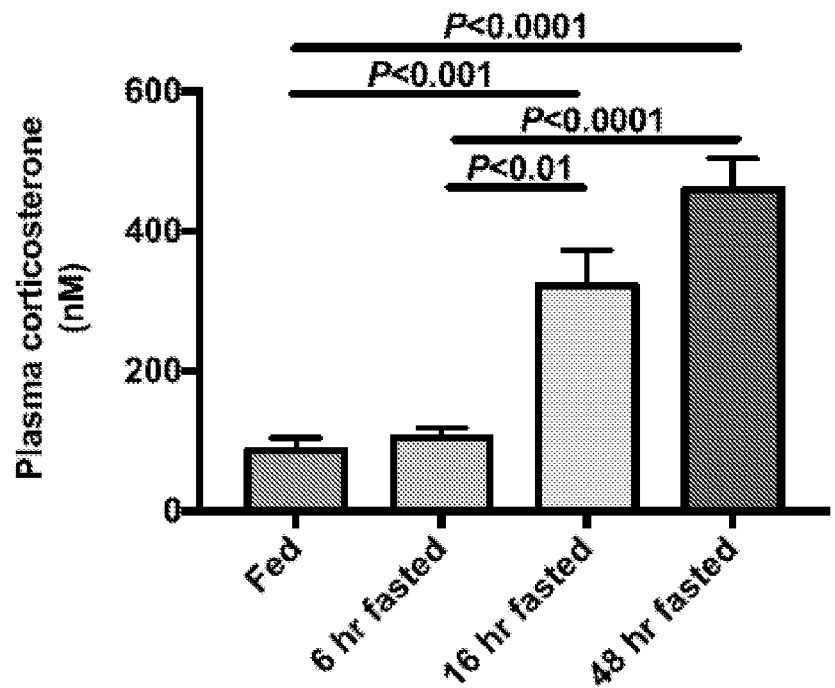
Figure 10A:
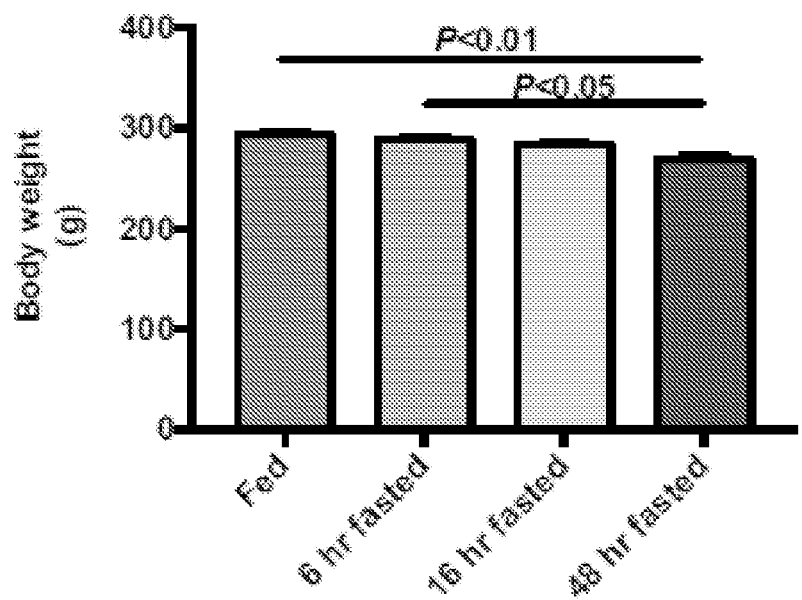
FIGS. 10A-10W are graphs showing that depletion of hepatic glycogen content lowered plasma glucose and insulin concentrations, caused hypoleptinemia, and activated the HPA axis in starvation.
Figure 10B:
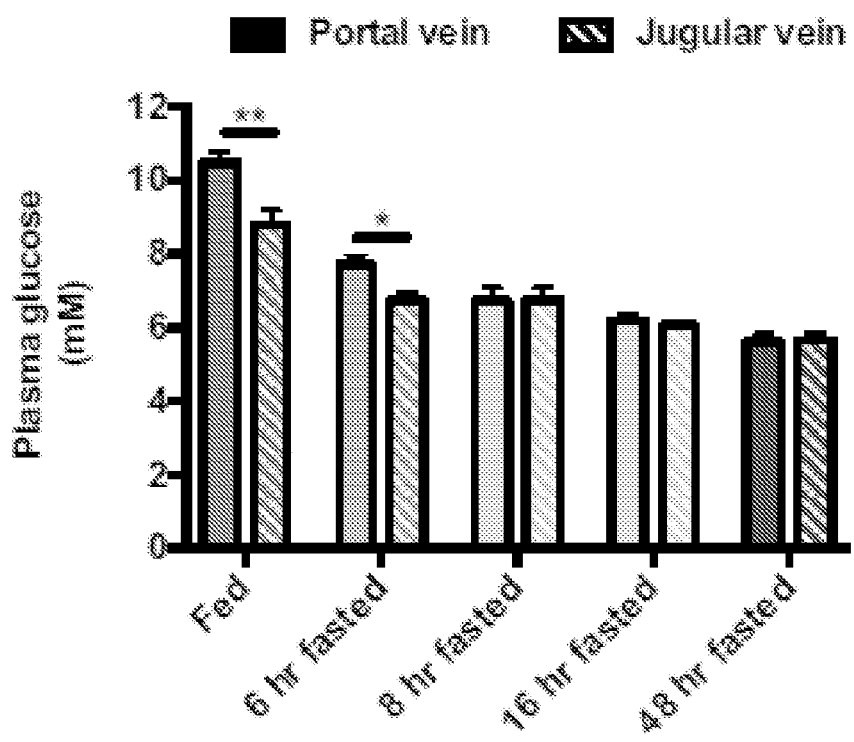
FIG. 10B is a graph of plasma glucose concentrations in the jugular vein and portal vein. Jugular vein concentrations are duplicated from FIG. 9A. *p<0.05, **p<0.01 by the 2-tailed unpaired Student's t test.
Figure 10C:
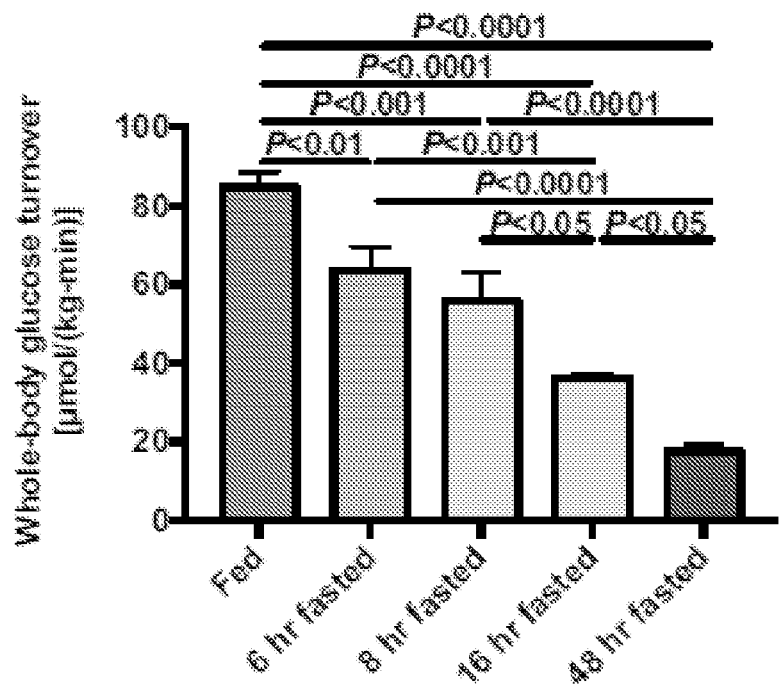
FIG. 10C is a graph showing rates of whole-body glucose turnover.
Figure 10D:
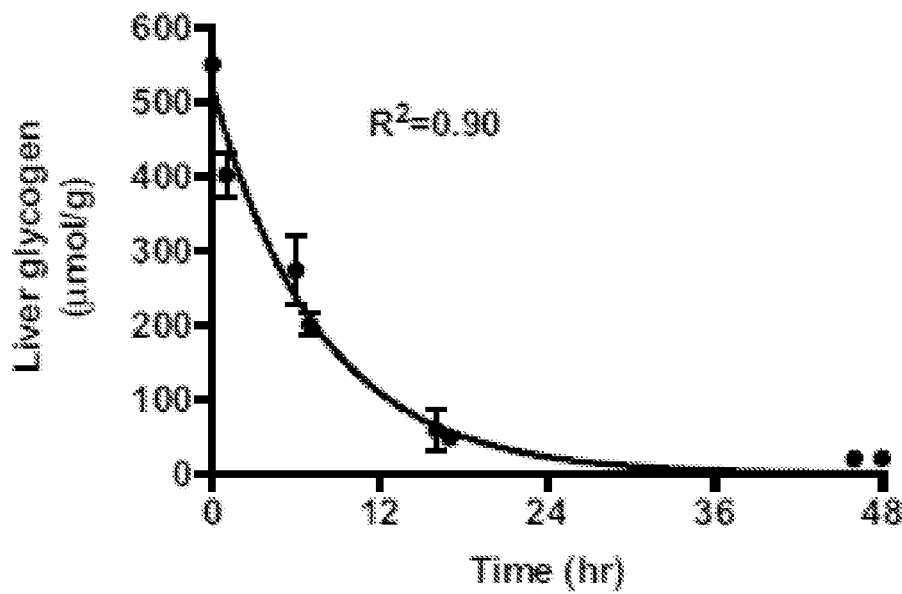
FIG. 10D is a graph of liver glycogen concentrations.
Figure 10E:
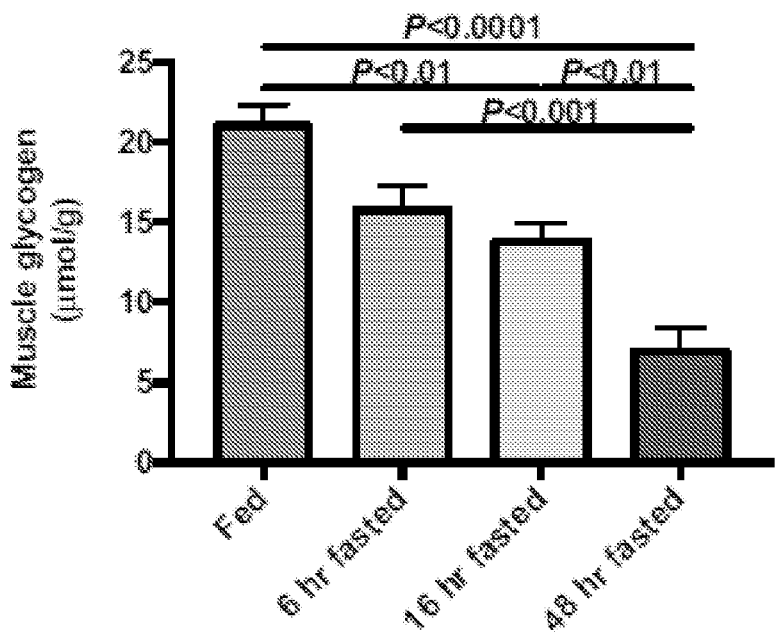
FIG. 10E is a graph showing muscle glycogen content.
Figure 10F:
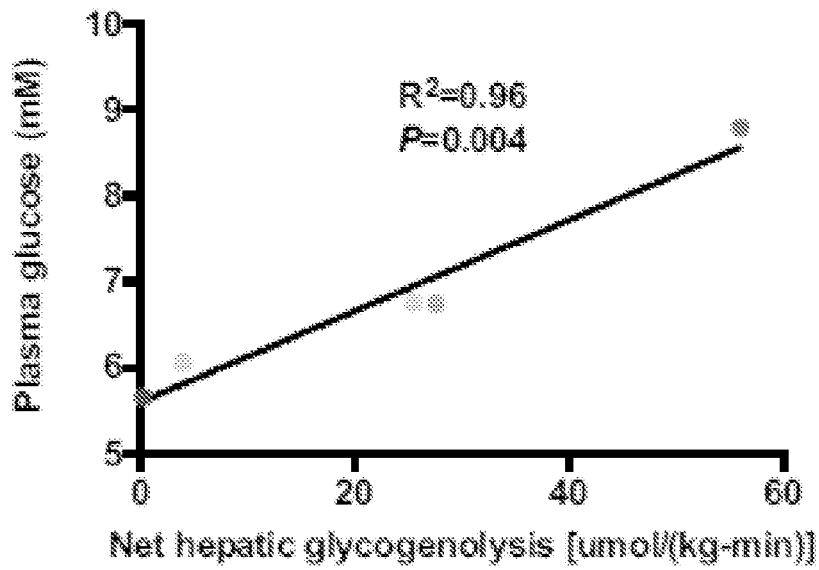
FIG. 10F is a graph of the correlation between plasma glucose concentrations and hepatic glycogenolysis rates.

Following food removal, plasma glucose concentrations progressively declined despite minimal differences in body weight and rats were found to be post-absorptive at 8 hr of fasting, as indicated by the absence of a glucose concentration gradient between the portal vein and the jugular vein (FIGS. 9A, 10A, and 10B). This progressive reduction in plasma glucose concentrations in the early post-absorptive state (8-16 hr) could be entirely attributed to reductions in rates of net hepatic glycogenolysis, as reflected by the strong correlation between plasma glucose concentrations and rates of net hepatic glycogenolysis (R2=0.96, p=0.003) (FIG. 9B and FIGS. 10C-10F). In contrast, plasma glucose concentrations were dissociated from rates of hepatic gluconeogenesis, which increased between 8 and 16 hr but decreased between 16 and 48 hr (FIG. 9B). In addition, the progressive reduction in rates of net hepatic glycogenolysis during the fast was associated with a shift from glucose to fat/ketone oxidation, demonstrated by fasting duration-dependent reductions in the ratio of pyruvate dehydrogenase flux to citrate synthase flux (VPDH/V$_{CS}$) in liver, kidney (cortex), skeletal muscle, WAT, brown adipose tissue (BAT), heart, and brain (FIG. 9C).

Figure 10G:
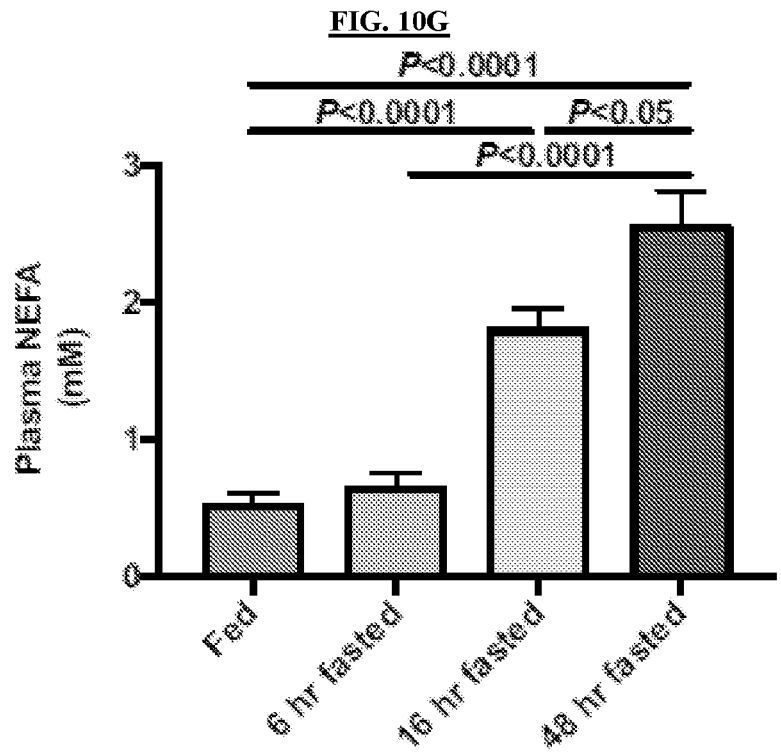
FIGS. 10G-10I are graphs showing plasma non-esterified fatty acid (FIG. 10G), glycerol (FIG. 10H), and β-hydroxybutyrate (FIG. 10I) concentrations.
Figure 10H:
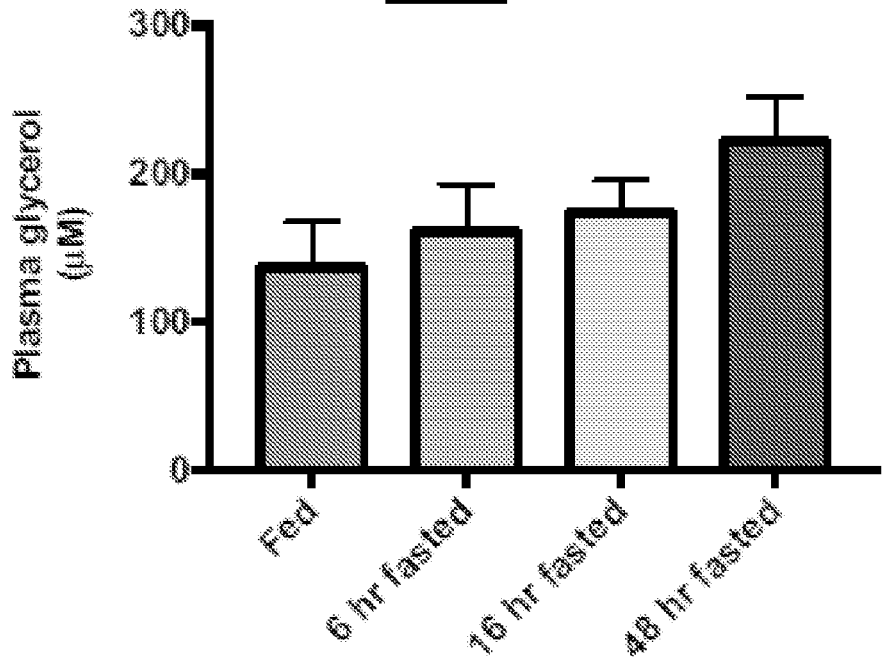
Figure 10I:
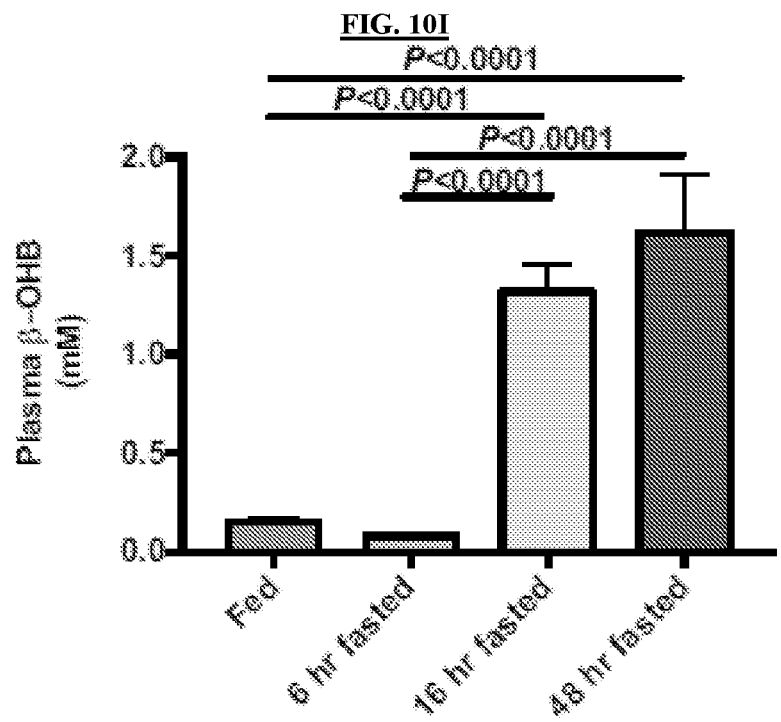
Figure 10J:
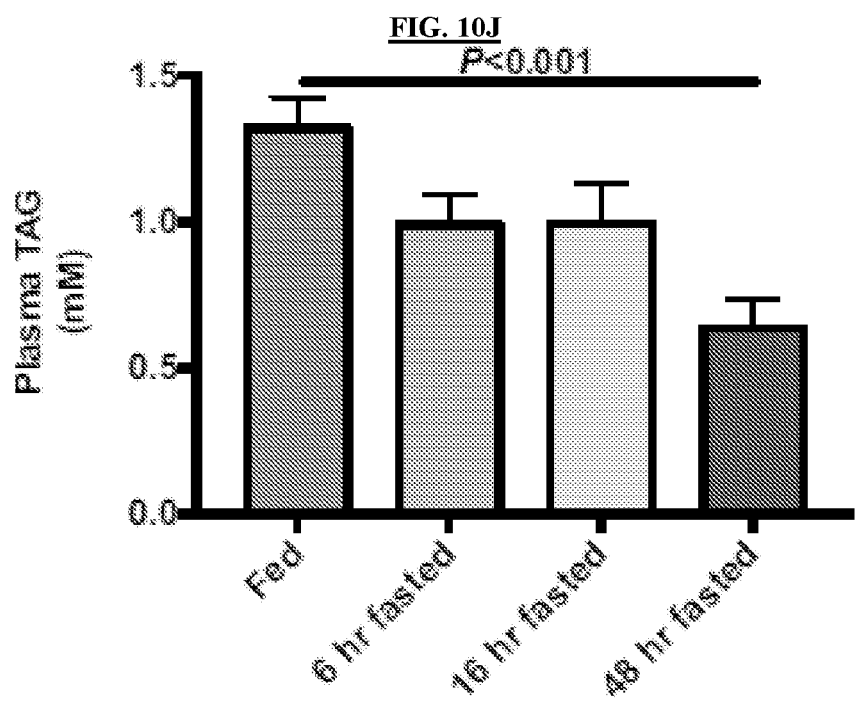
FIGS. 10J-10K are graphs showing plasma (FIG. 10J) and liver (FIG. 10K) triglyceride content.
Figure 10K:
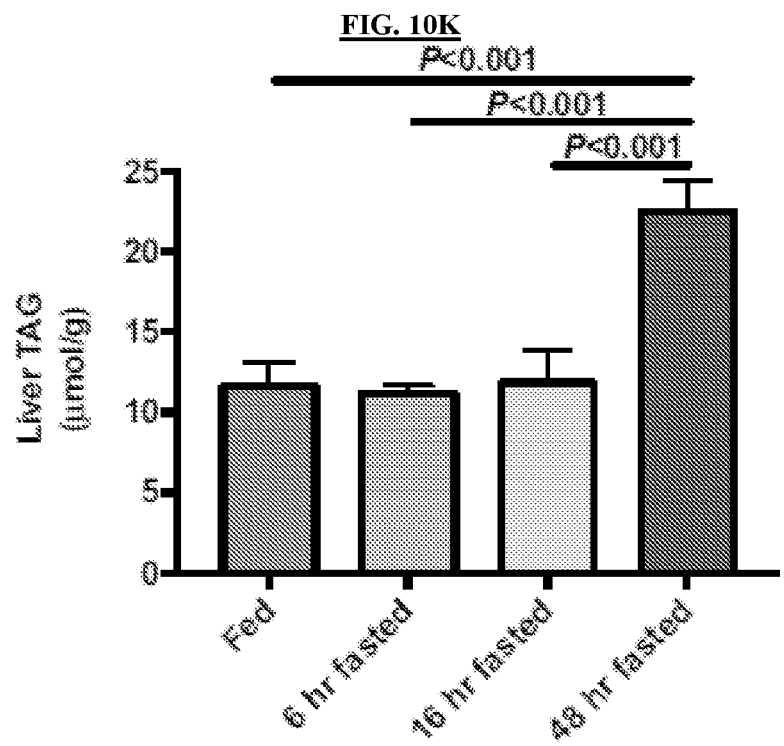
Figure 10L:
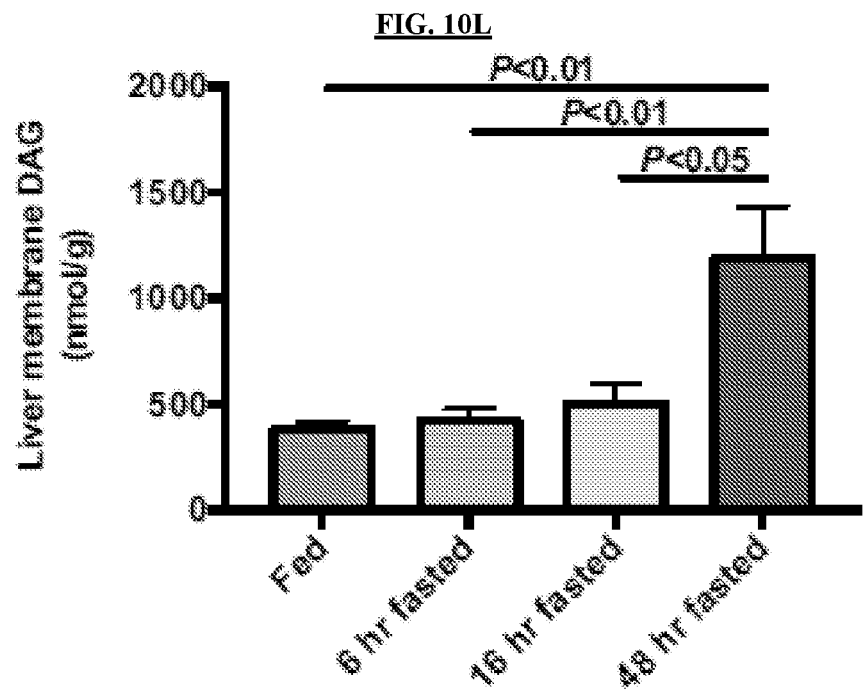
FIG. 10L is a graph showing liver membrane diacylglycerol.
Figure 10O:
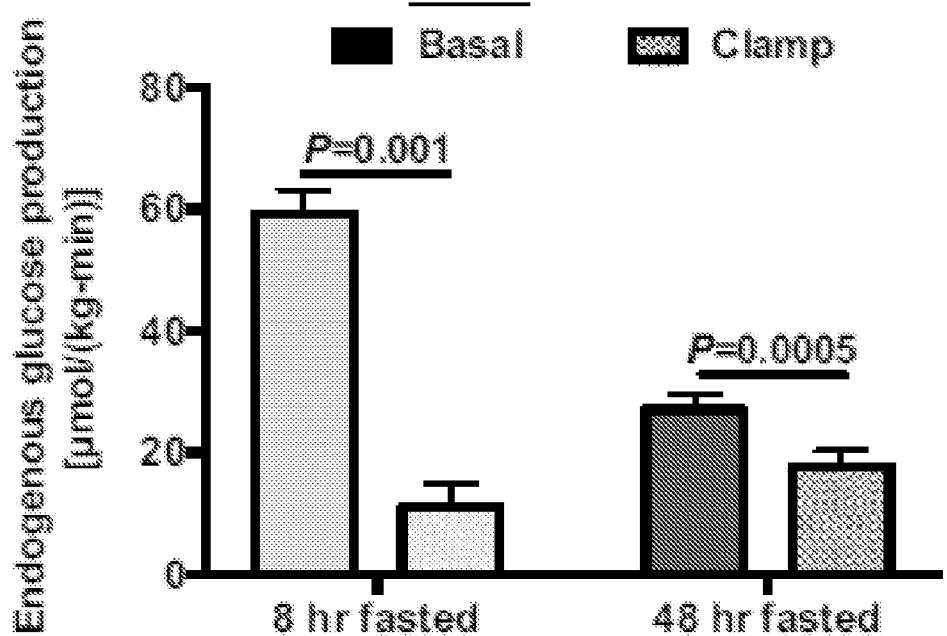
FIG. 10O is a graph showing basal and clamp endogenous glucose production.
Figure 10P:
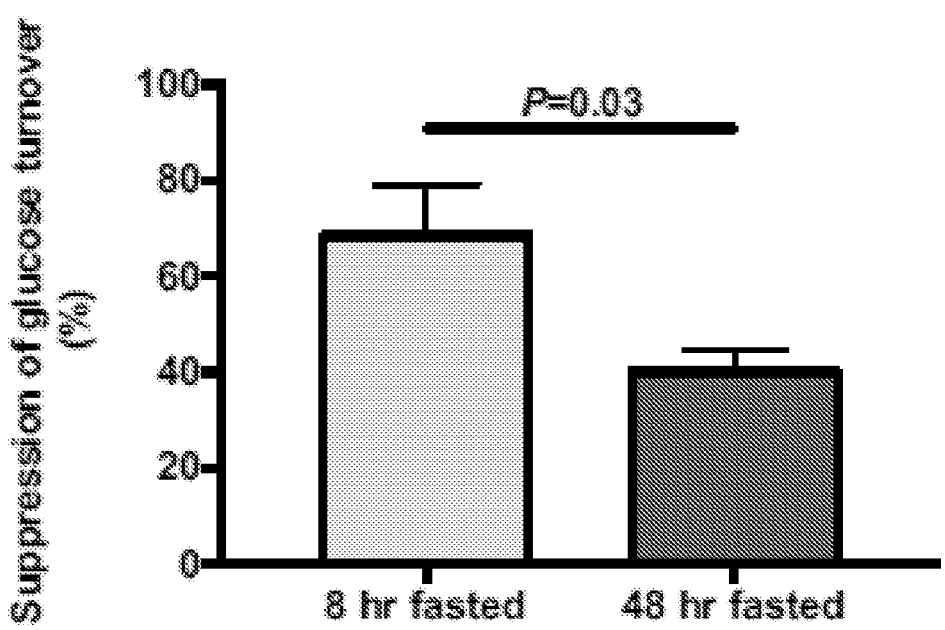
FIG. 10P is a graph showing suppression of endogenous glucose production during the clamp.
Figure 10Q:
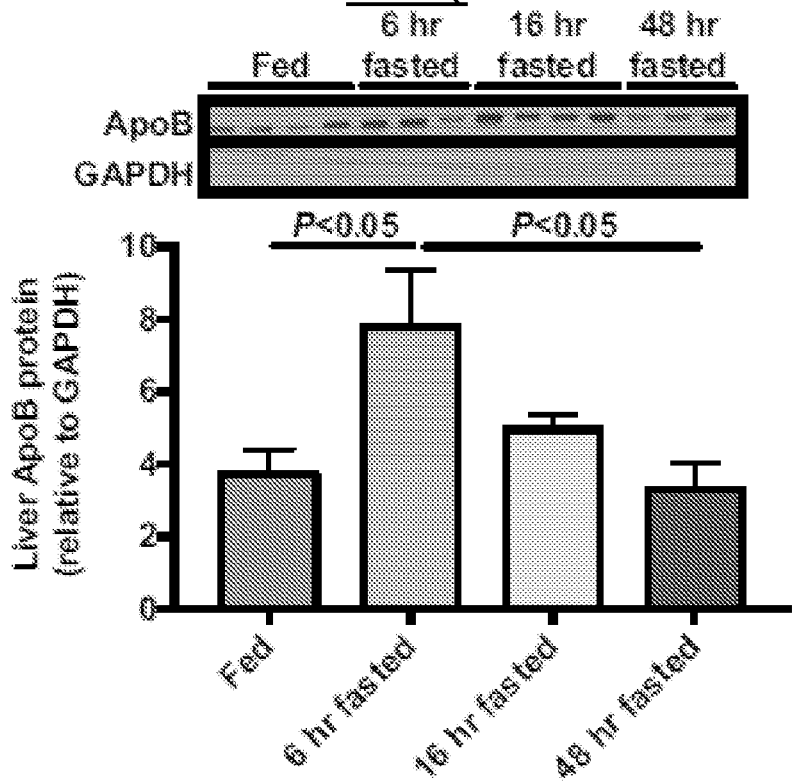
FIG. 10Q is a graph showing liver ApoB protein expression.
Figure 10R:
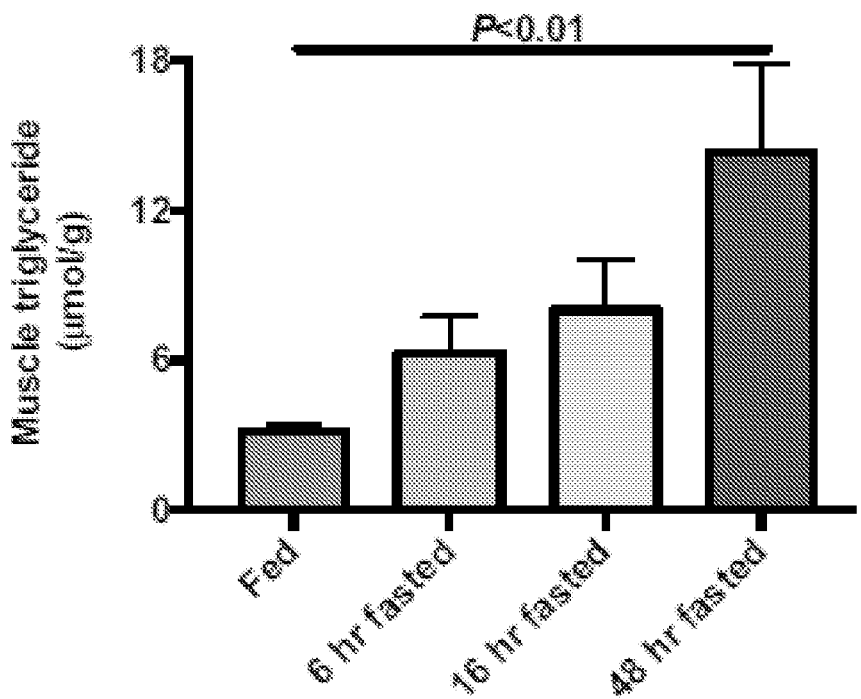
FIG. 10R is a graph showing muscle triglyceride content.
Figure 10S:
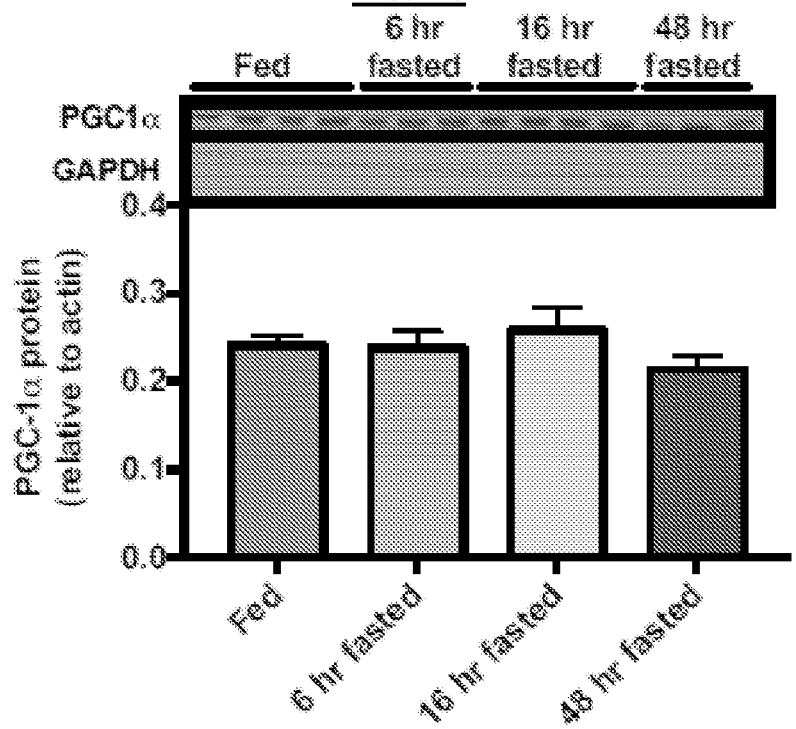
FIG. 10S is a graph showing hepatic PGC-1a protein expression.
Figure 10T:
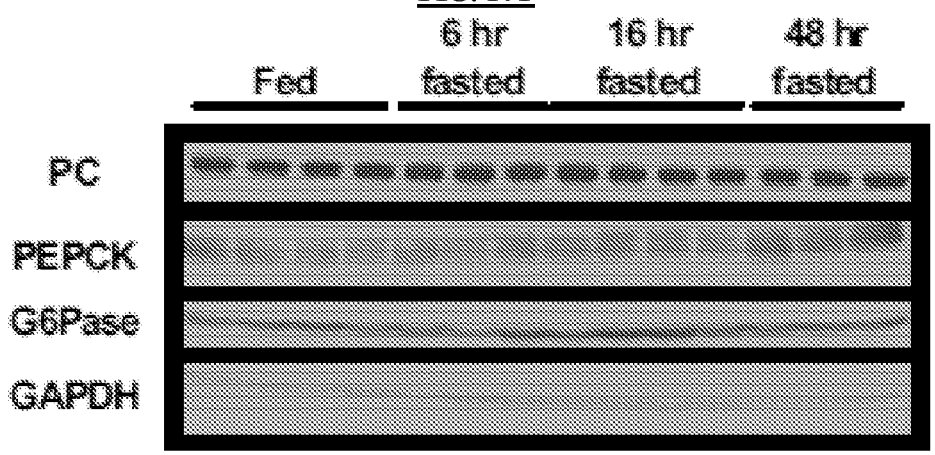
FIG. 10T is a set of Western blots measuring gluconeogenic protein expression.
Figure 10U:
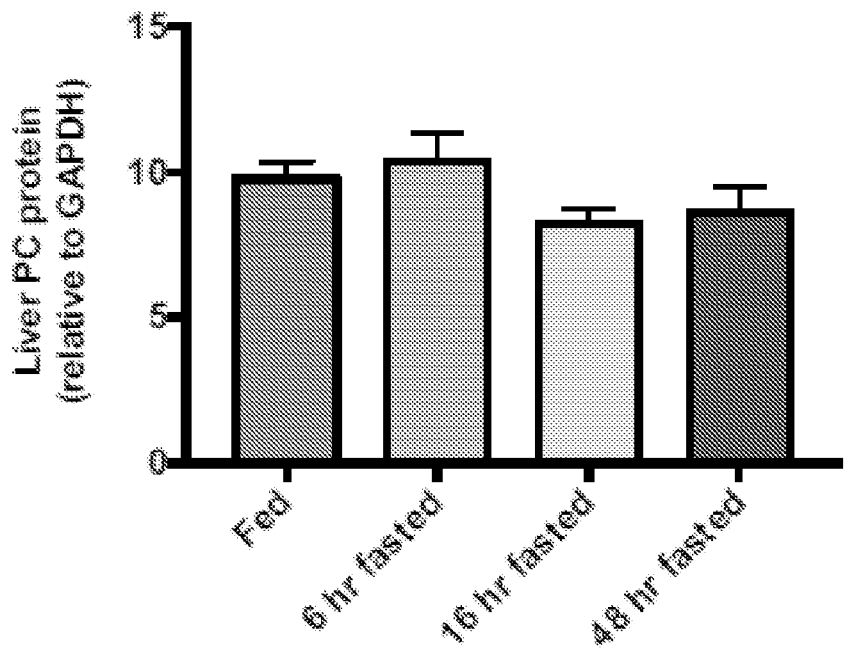
Figure 10V:
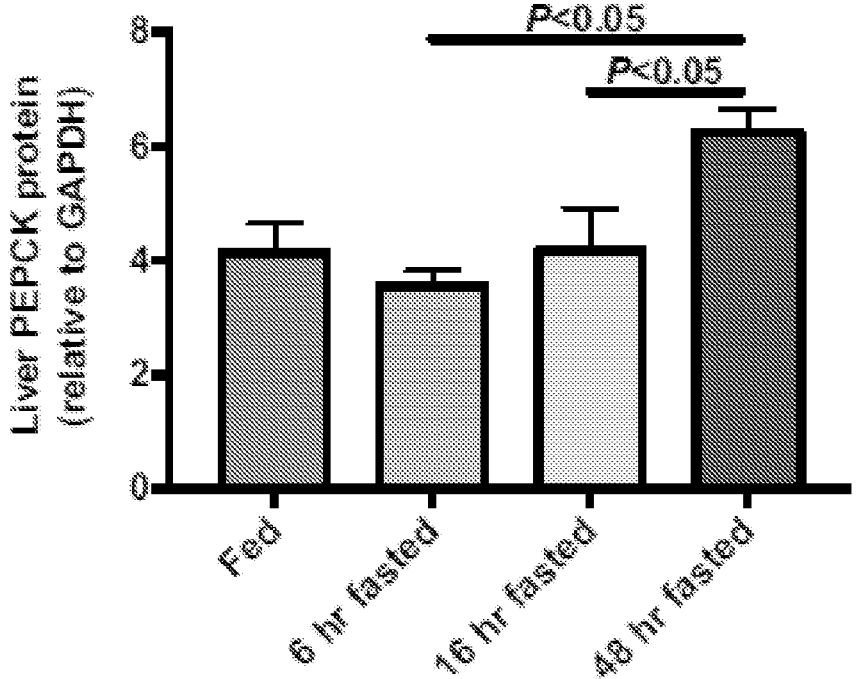
Figure 10W:
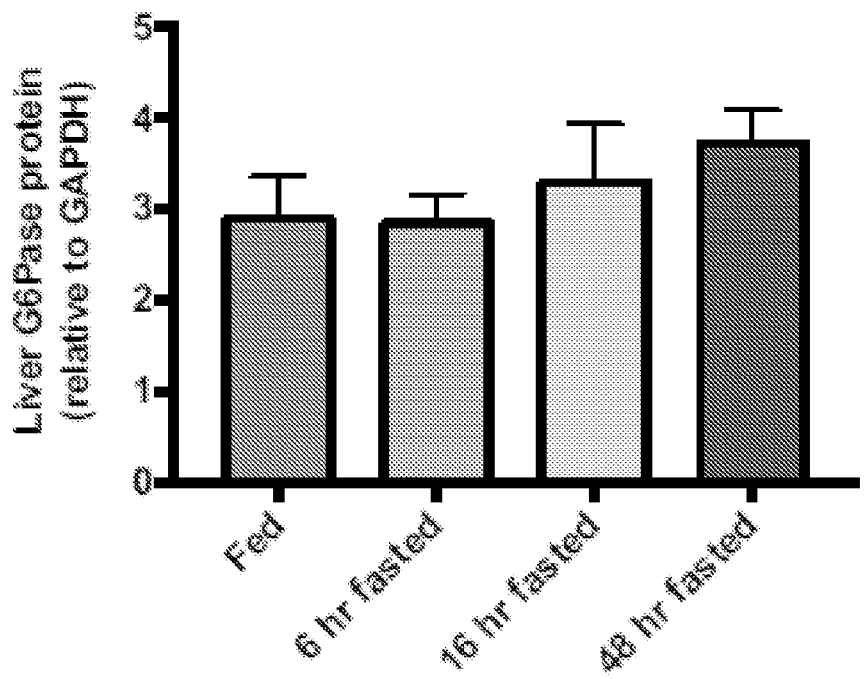

Plasma non-esterified fatty acid (NEFA), glycerol, and β-hydroxybutyrate concentrations increased progressively throughout the fast (FIGS. 10G-10I). During starvation, plasma triglyceride (TAG) concentrations were reduced at 48 hr of fasting, whereas liver TAG and diacylglycerol (DAG) content were increased. This increase in hepatic DAG content was associated with increased protein kinase C-epsilon (PKCε) translocation (FIGS. 10J-10M), which in turn was associated with reduced percent suppression of endogenous glucose production during a hyperinsulinemic-euglycemic clamp (FIGS. 10N-10P). The dissociation between plasma and liver TAG can likely be explained in part by increased hepatic esterification of fatty acids into hepatic TAG driven by increased WAT lipolysis combined with reduced hepatic TAG export, which may be in part attributed to reductions in liver apolipoprotein B (ApoB) concentrations (FIG. 10Q). Similarly, skeletal muscle TAG content increased in fasted rats as the fast progressed (FIG. 10R). In addition, there was no change in peroxisome proliferator-activated receptor-gamma coactivator-1 alpha (PGC-1α) expression with starvation, and gluconeogenic enzyme (phosphoenolpyruvate carboxykinase, pyruvate carboxylase, glucose-6-phosphatase) expression did not correlate with the measured changes in gluconeogenic flux (FIGS. 10S-10W).

Figure 11A:
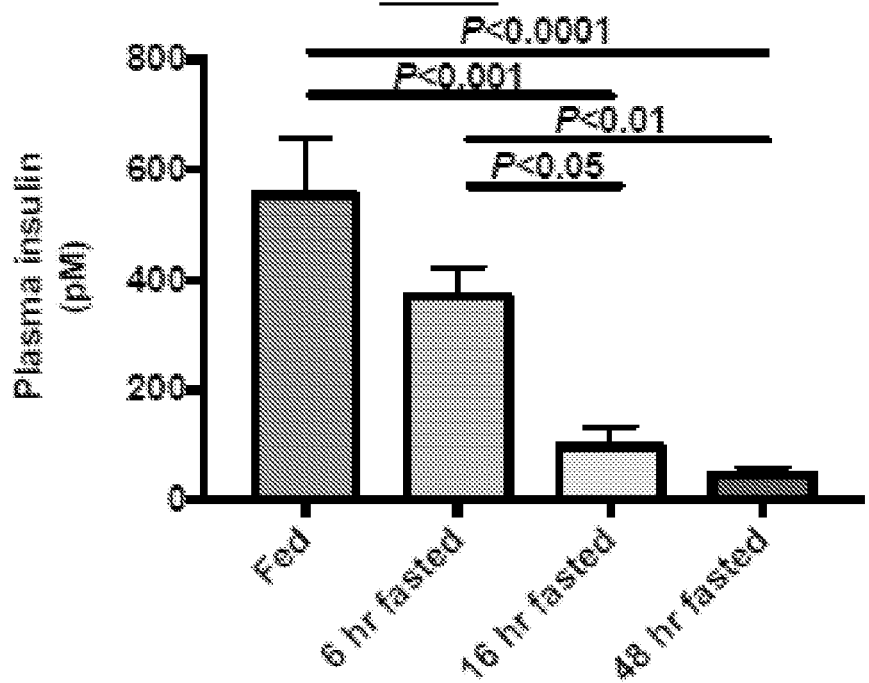
FIGS. 11A-11W are graphs showing depletion of hepatic glycogen content lowers plasma glucose and insulin concentrations, causes hypoleptinemia, and activates the hpa axis in starvation.
Figure 11B:
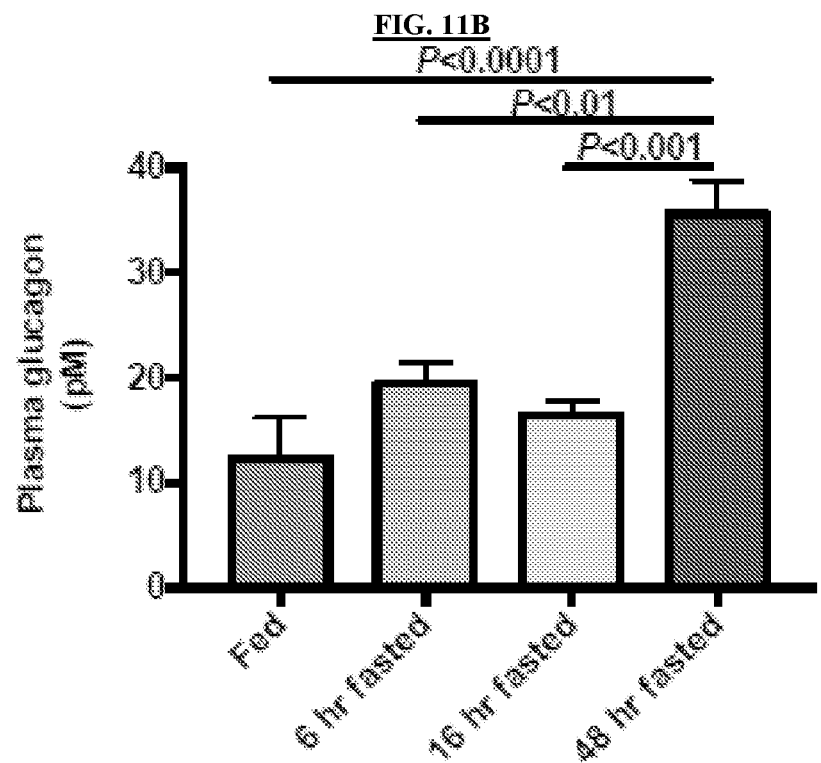
Figure 11C:
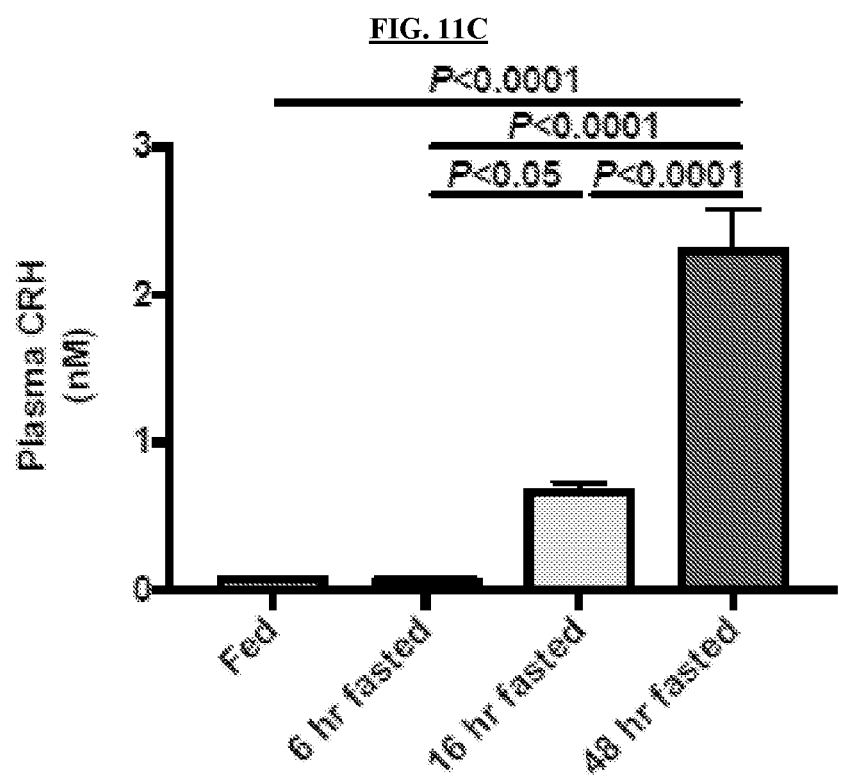
FIGS. 11C-11J are graphs showing plasma CRH (FIG. 11C), ACTH (FIG. 11D), CBG (FIG. 11E), epinephrine (FIG. 11F), norepinephrine (FIG. 11G), growth hormone (FIG. 11H), FGF-21 (FIG. 11I), and T3 (FIG. 11J) concentrations.
Figure 11D:
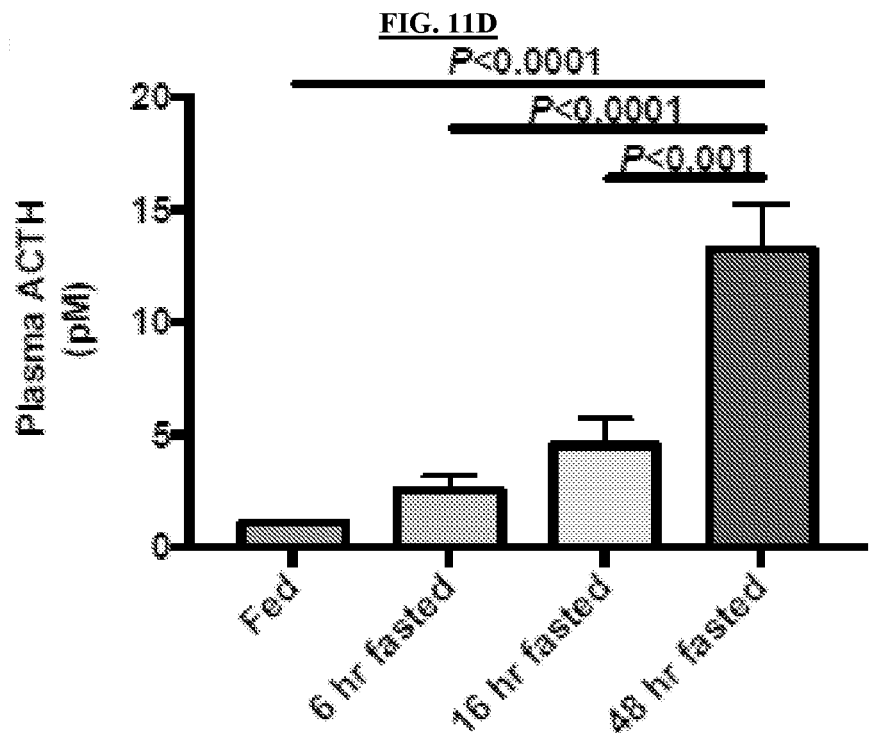
Figure 11E:
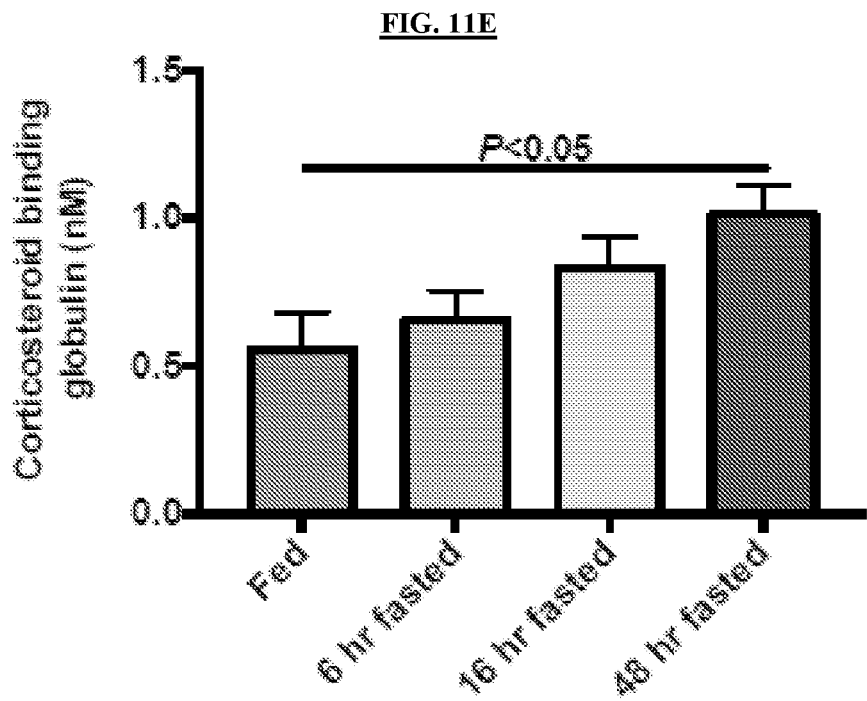
Figure 11F:
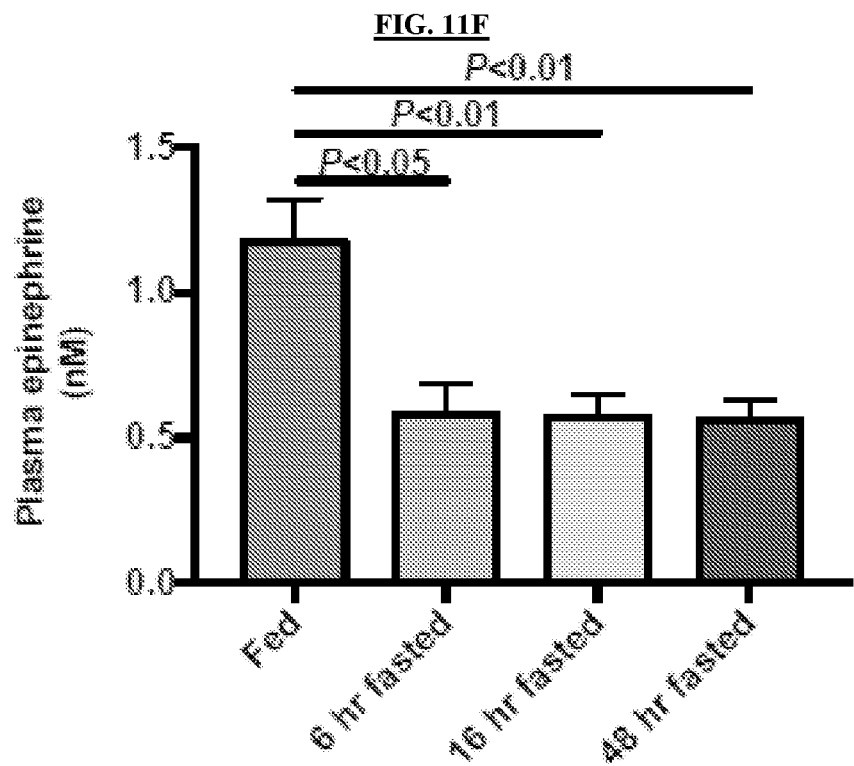
Figure 11G:
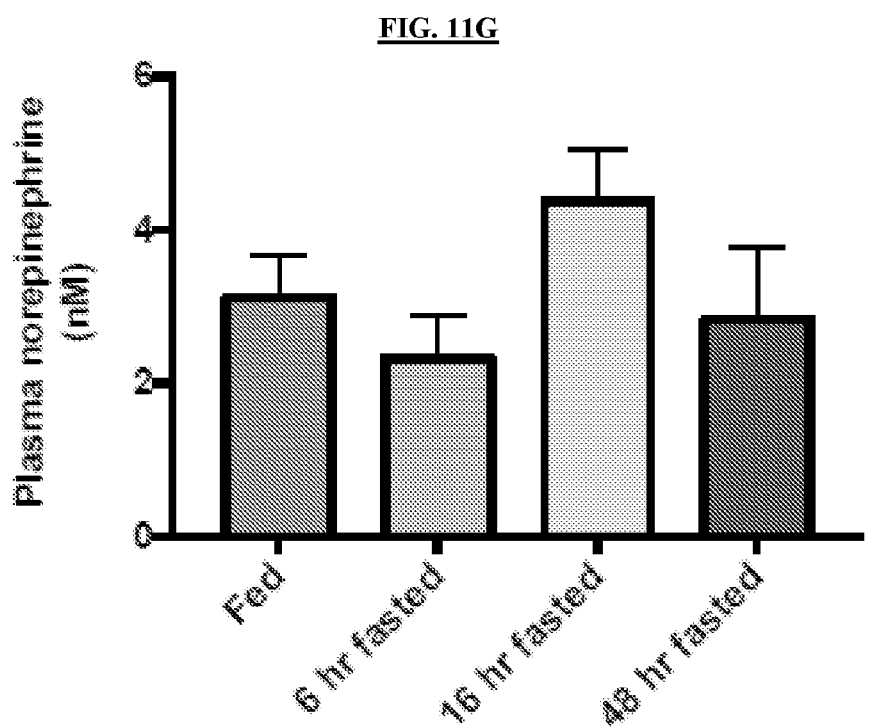
Figure 11H:
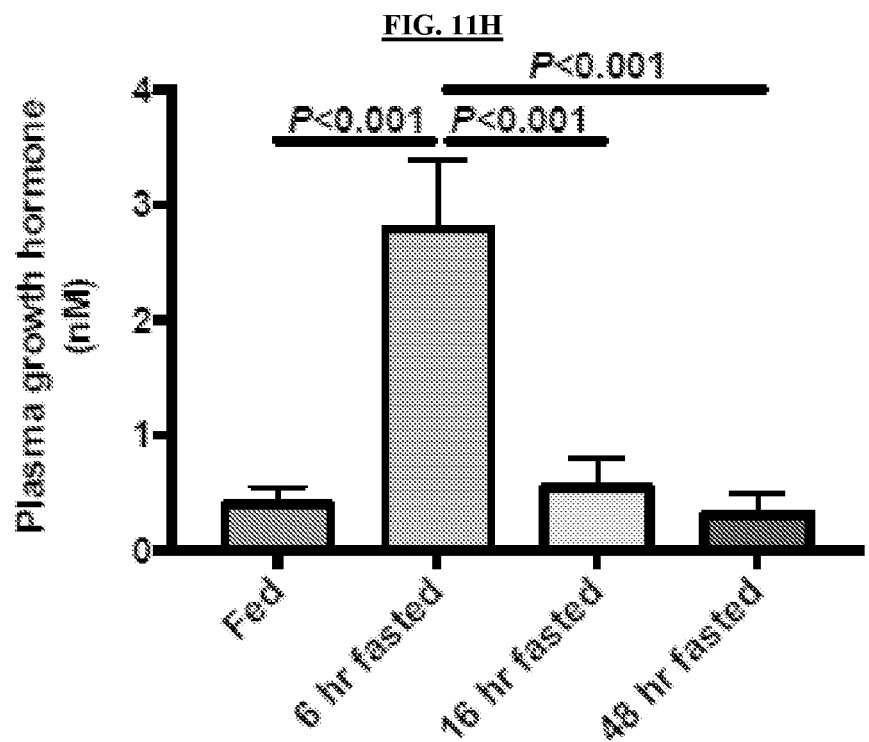
Figure 11I:
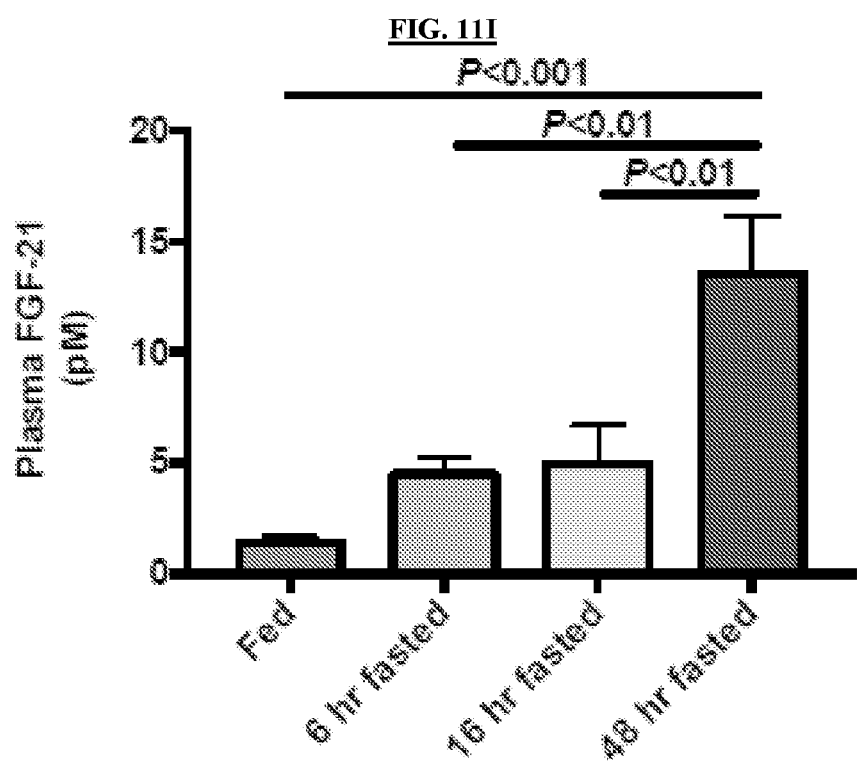
Figure 11J:
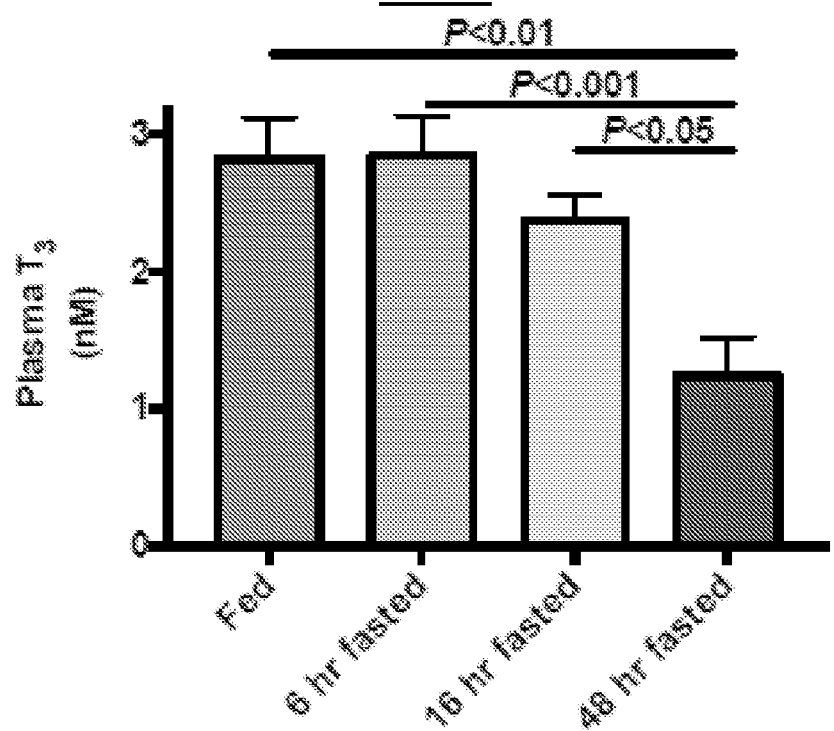
Figure 11K:
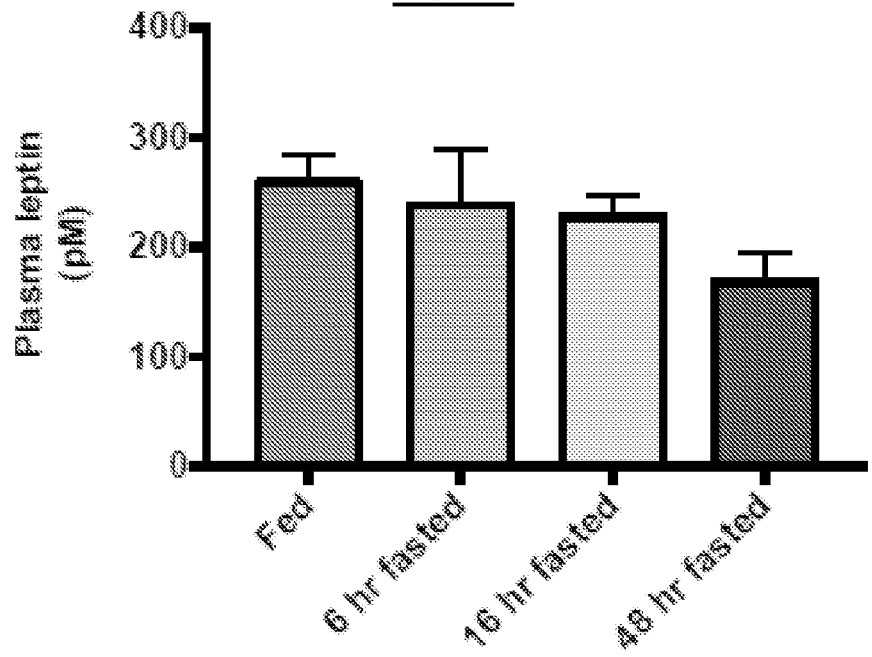
FIGS. 11K-11L are graphs showing plasma leptin (FIG. 11K) and corticosterone (FIG. 11L) concentrations in 4-week high fat fed rats.
Figure 11L:
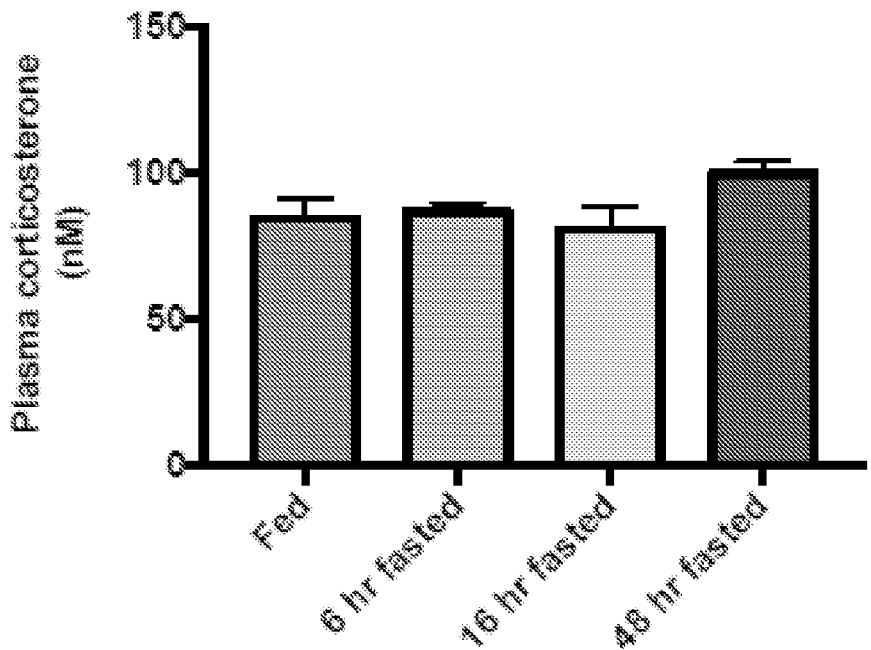
Figure 11M:
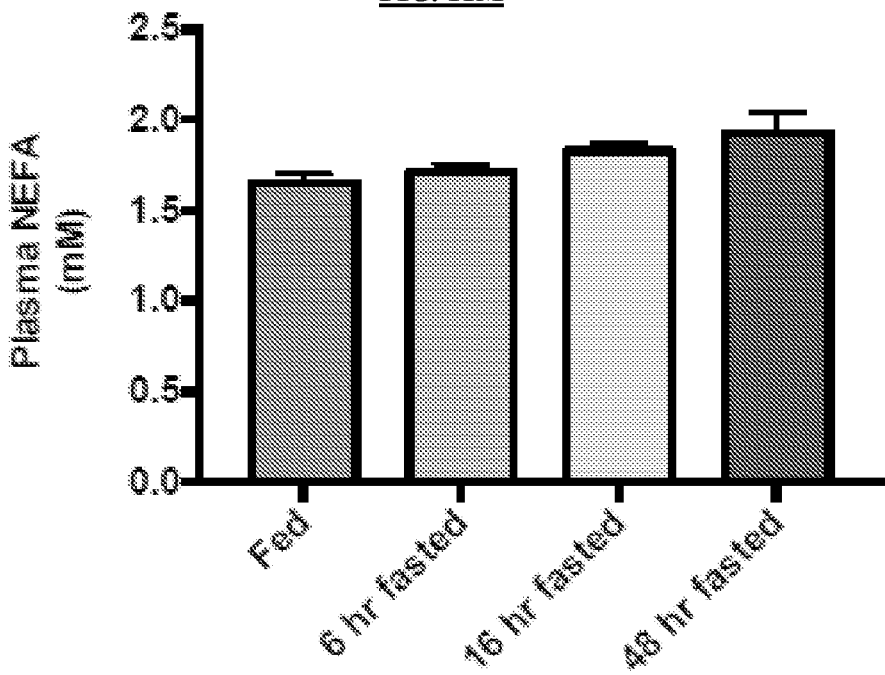
FIGS. 11M-11N are graphs showing plasma NEFA (FIG. 11M) and β-hydroxybutyrate (FIG. 11N) concentrations in 4-week high fat fed rats.
Figure 11N:
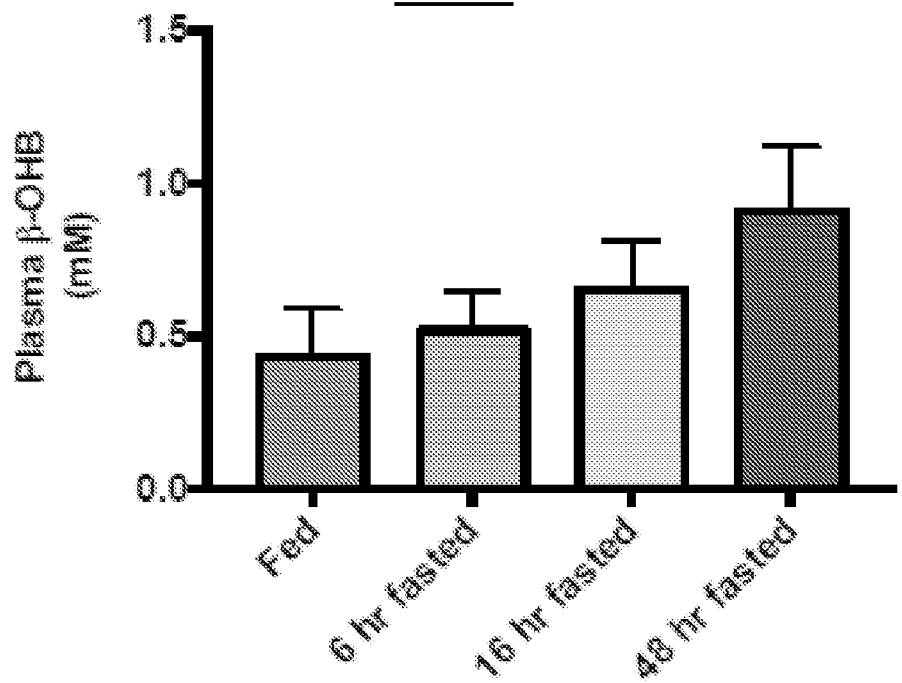
Figure 11O:
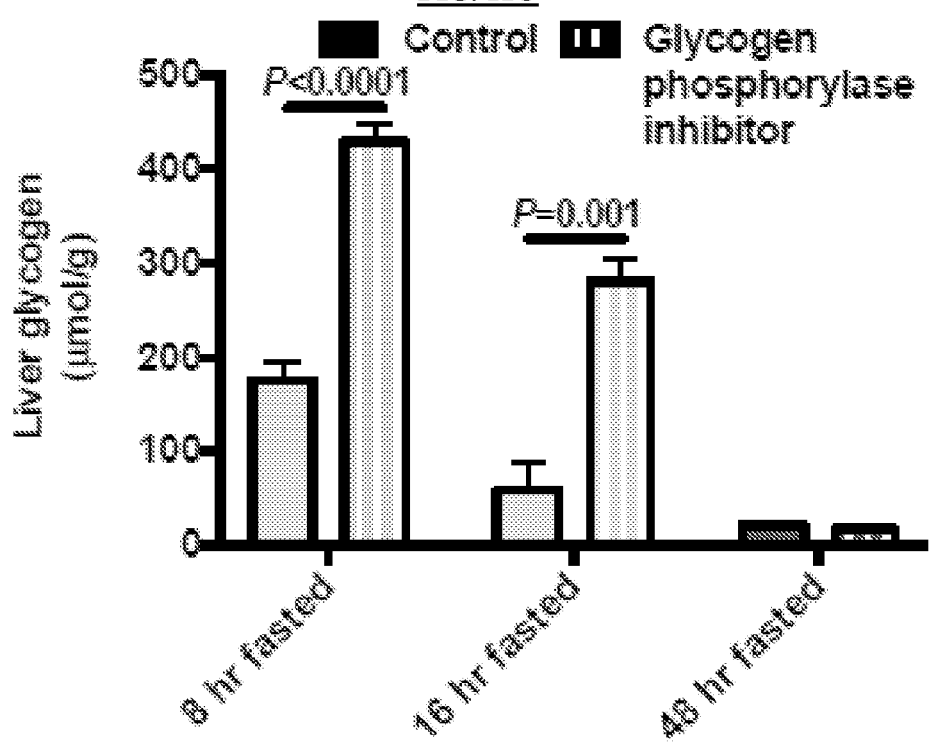
FIG. 11O is a graph showing liver glycogen in rats treated with a glycogen phosphorylase inhibitor as compared to controls (control data duplicated from FIG. 10D). The 2-tailed unpaired Student's t test was used to compare glycogen concentrations with or without the inhibitor at each time point.
Figure 11P:
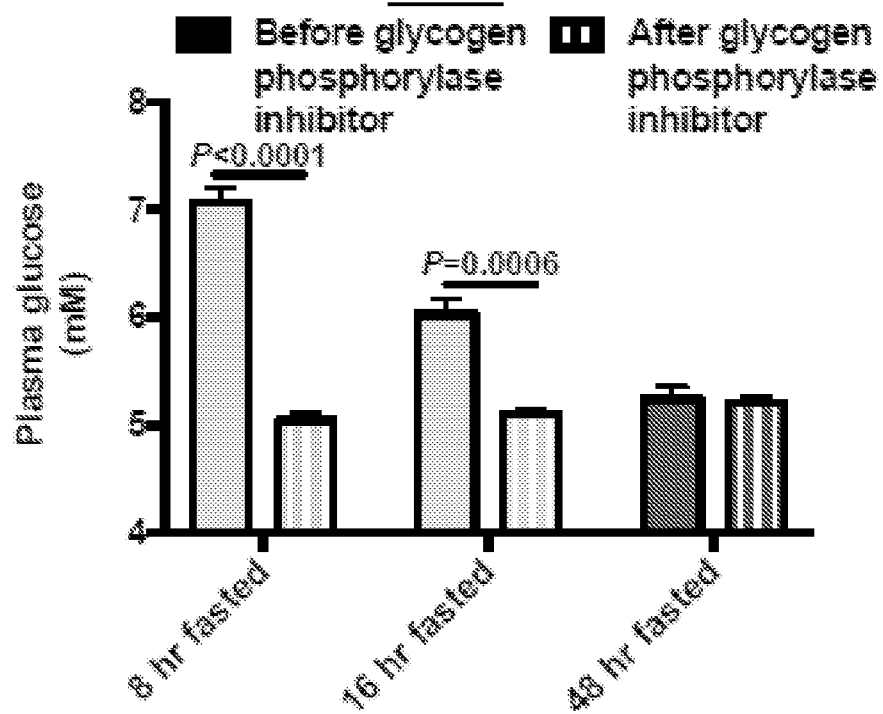
Figure 11Q:
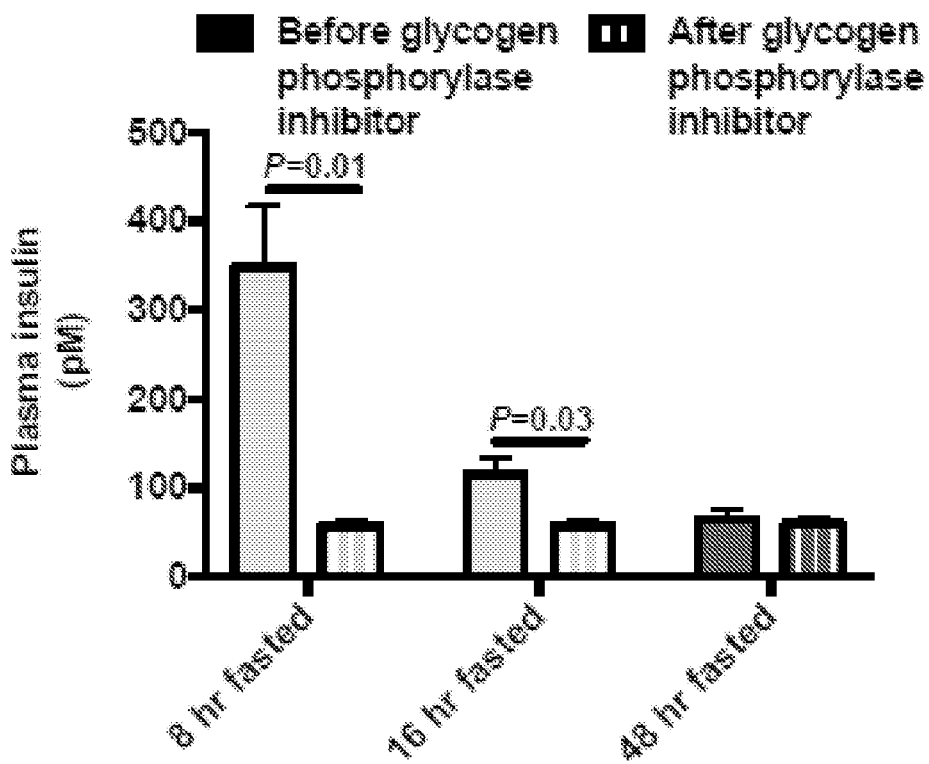
Figure 11R:
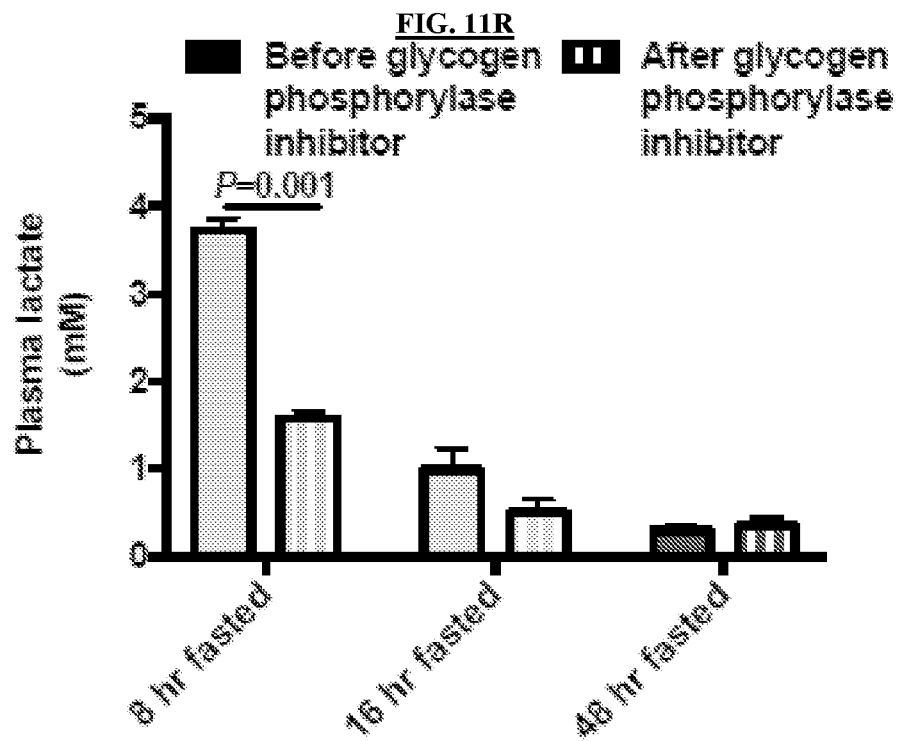

The reduction in plasma glucose concentrations that occurred as the fast progressed was accompanied by reductions in plasma insulin concentrations and increases in plasma glucagon concentrations (FIGS. 11A and 11B). Plasma leptin concentrations decreased by 80% between fed and 48-hr fasted rats; this was associated with activation of the HPA axis, as indicated by increases in plasma corticotropin-releasing hormone (CRH), adrenocorticotropic hormone (ACTH), and corticosterone concentrations (FIGS. 9D, 9E, 11C, and 11D). Corticosteroid-binding globulin also increased modestly, but there were no differences in plasma epinephrine or norepinephrine concentrations and a transient increase in plasma growth hormone concentration after a short-term, but not a long-term, fast (FIGS. 11E-11H). Consistent with previous reports, starvation was also associated with an increase in plasma fibroblast growth factor-21 (FGF-21) concentrations (Kim and Lee, Diabetes Metab. J. 38, 245-251, 2014; Kliewer and Mangelsdorf, Am. J. Clin. Nutr. 91, 254S-257S, 2010) (FIG. 11I) and a reduction in plasma triiodothyronine (T3) concentrations (Flier et al., J. Clin. Invest. 105, 859-861, 2000) (FIG. 11J). In contrast to in lean-chow-fed rats, plasma leptin, corticosterone, NEFA, and ketone concentrations did not change significantly with a 48-hr fast in hyperleptinemic, diet-induced obese rats (FIGS. 11K-11N).

Figure 9F:
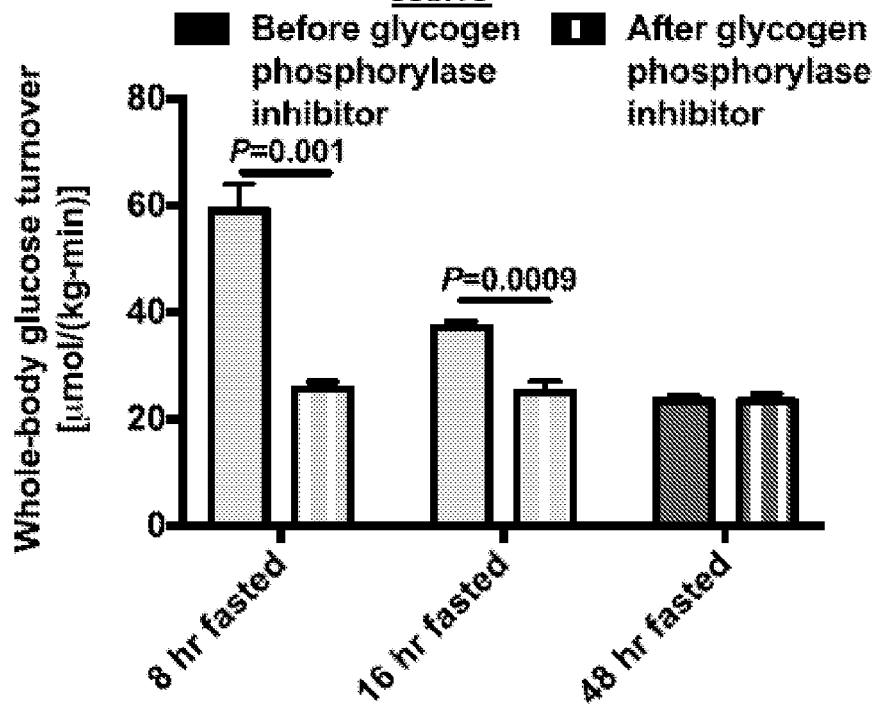
Figure 9G:
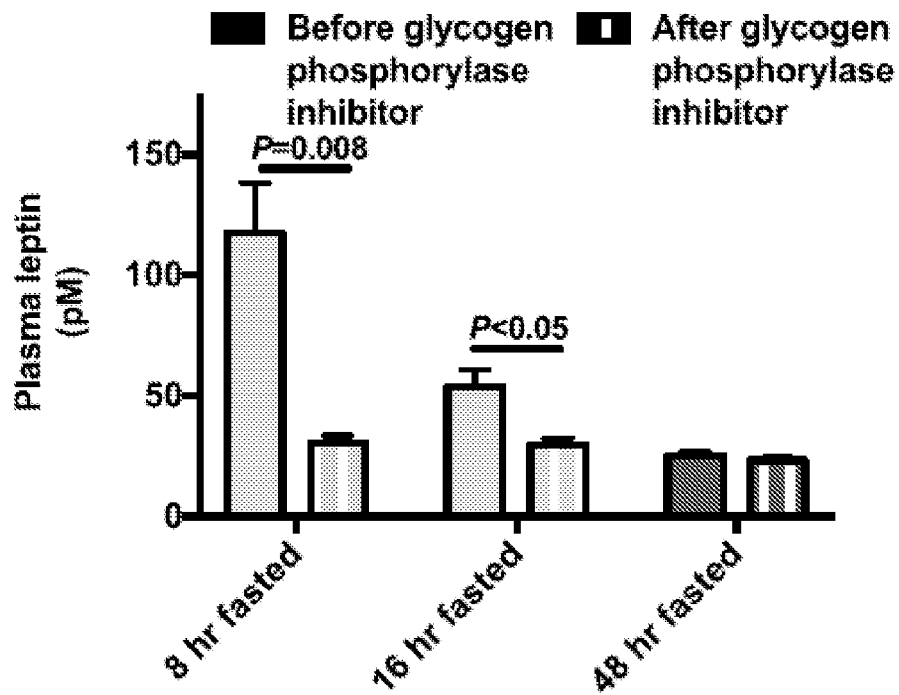
Figure 9H:
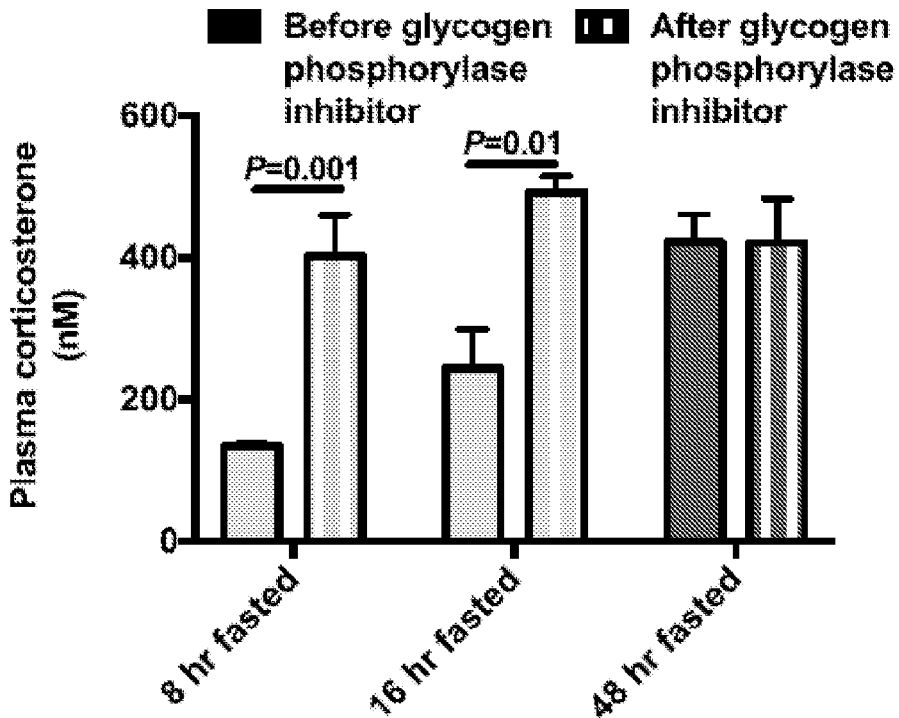
Figure 11S:
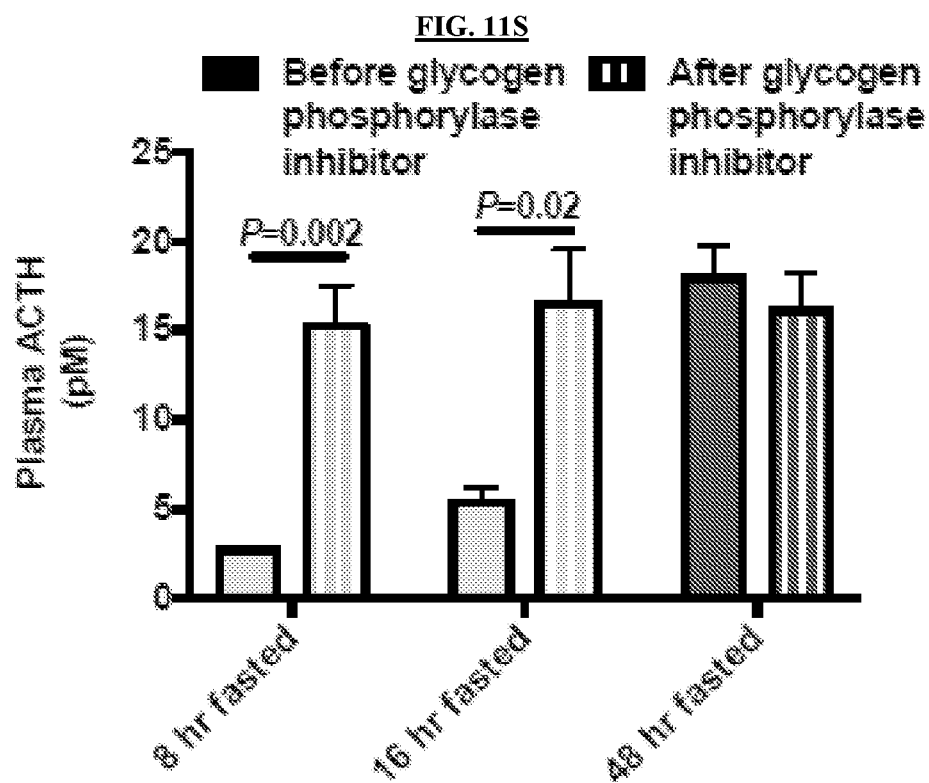
Figure 11T:
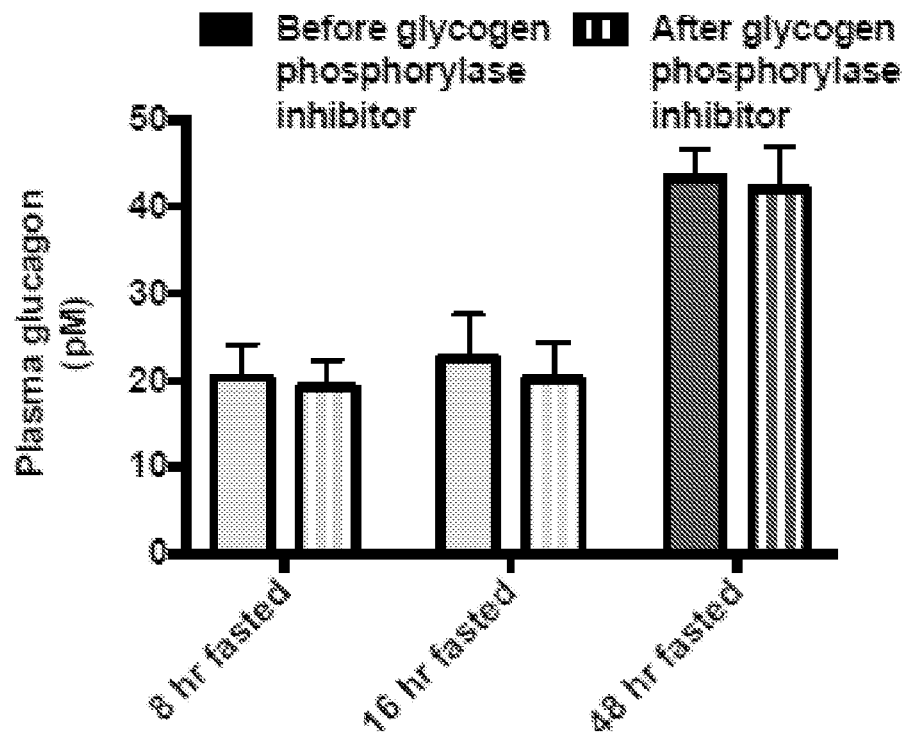
Figure 11U:
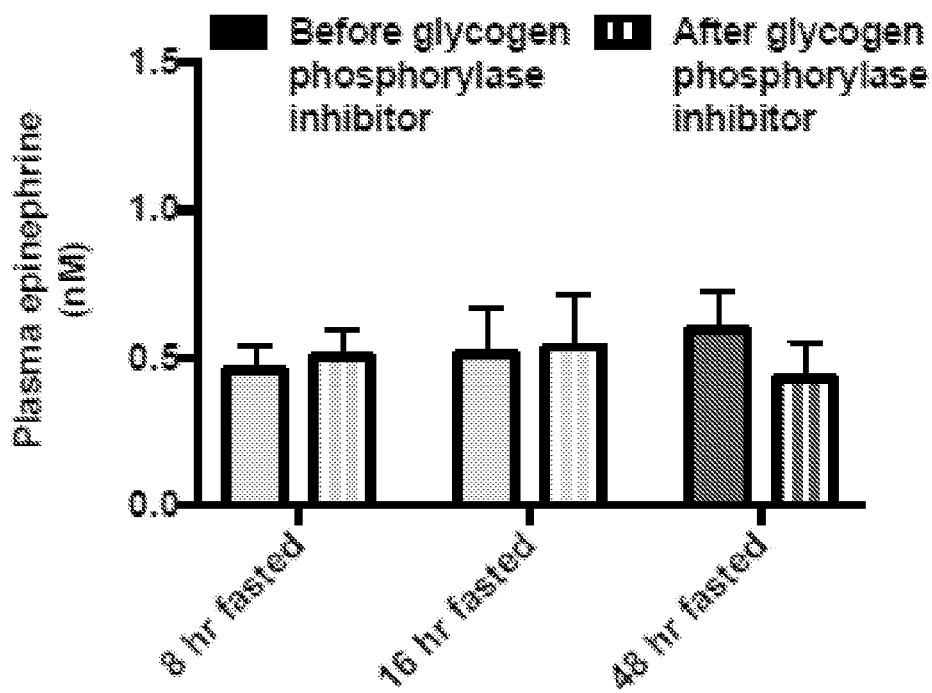
Figure 11V:
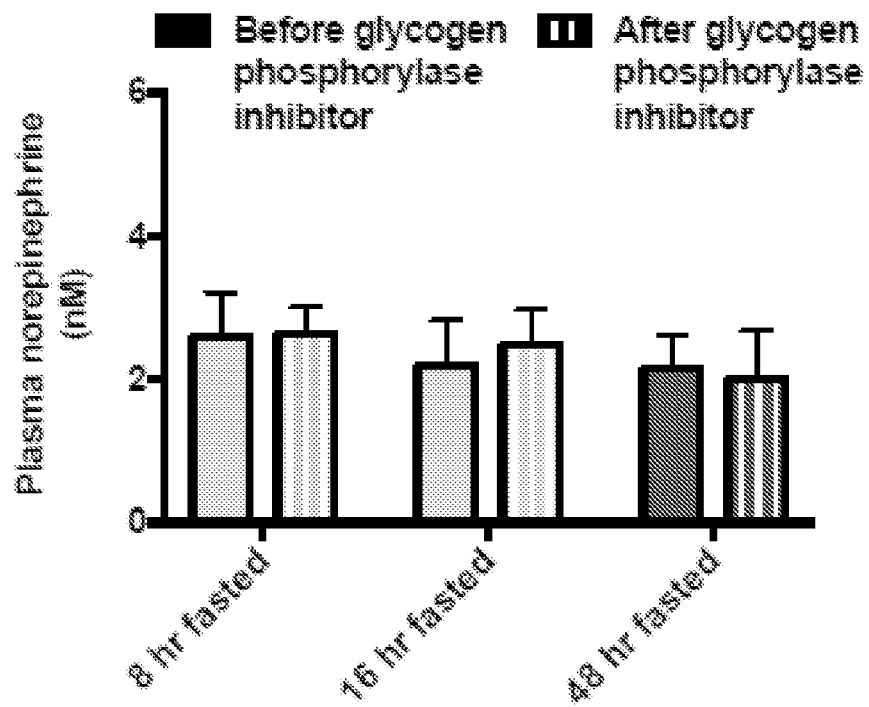
Figure 11W:
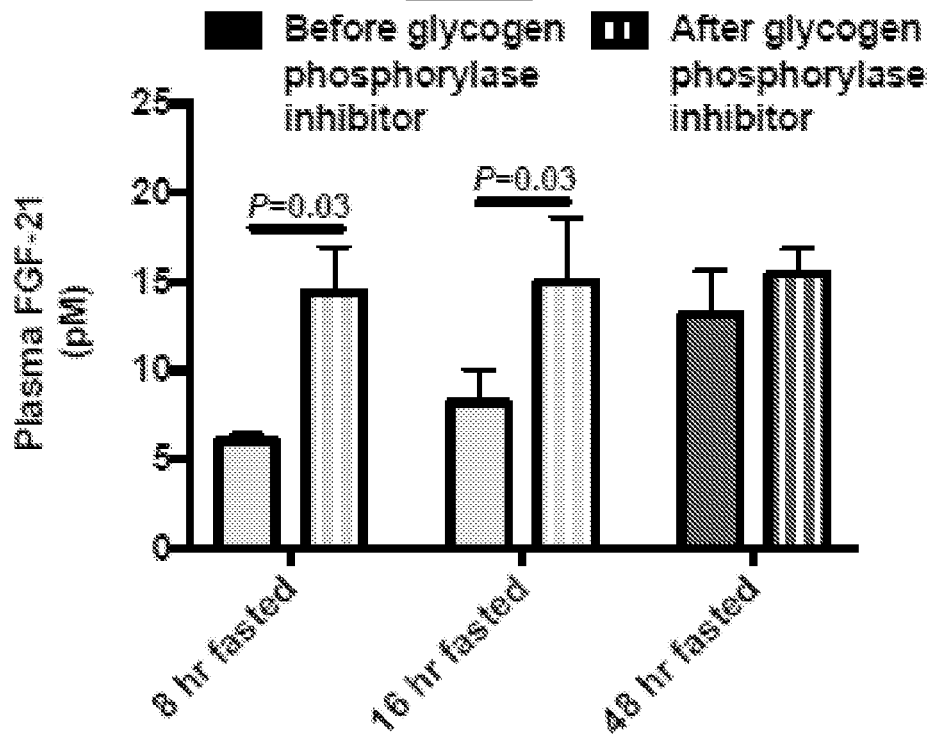

To more specifically investigate the impact of reductions in net hepatic glycogenolysis on rates of endogenous glucose production, plasma leptin concentrations, and activation of the HPA axis, post-absorptive rats fasted for 8, 16, and 48 hr were treated with a small molecule inhibitor of glycogen phosphorylase. Inhibition of hepatic glycogenolysis lowered plasma glucose, lactate, and insulin concentrations and whole-body glucose turnover in the short-term (8 and 16 hr) fasted rats, but not in the 48-hr fasted rats, consistent with the negligible contributions that hepatic glycogenolysis would be expected to have on plasma glucose concentrations in this glycogen-depleted state (FIGS. 9F and 11O-11R). The reductions in plasma glucose and insulin concentrations in 8- and 16-hr fasted rats treated with the glycogen phosphorylase inhibitor were associated with reductions in plasma leptin concentrations and increases in HPA axis activity, as reflected by increases in plasma corticosterone and ACTH concentrations in these groups (FIGS. 9G, 9H, and 11S). In contrast, plasma glucagon and catecholamine concentrations were not altered by treatment with the glycogen phosphorylase inhibitor, despite increased plasma FGF-21 concentrations in 8 and 16-hr fasted rats (FIGS. 11T-11W).

Figure 12A:
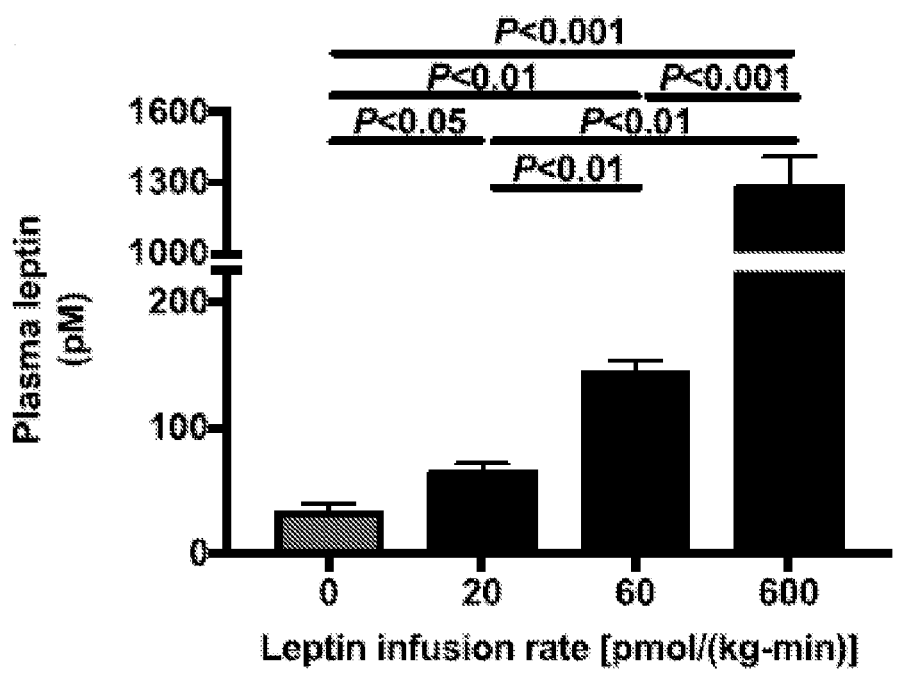
Figure 12B:
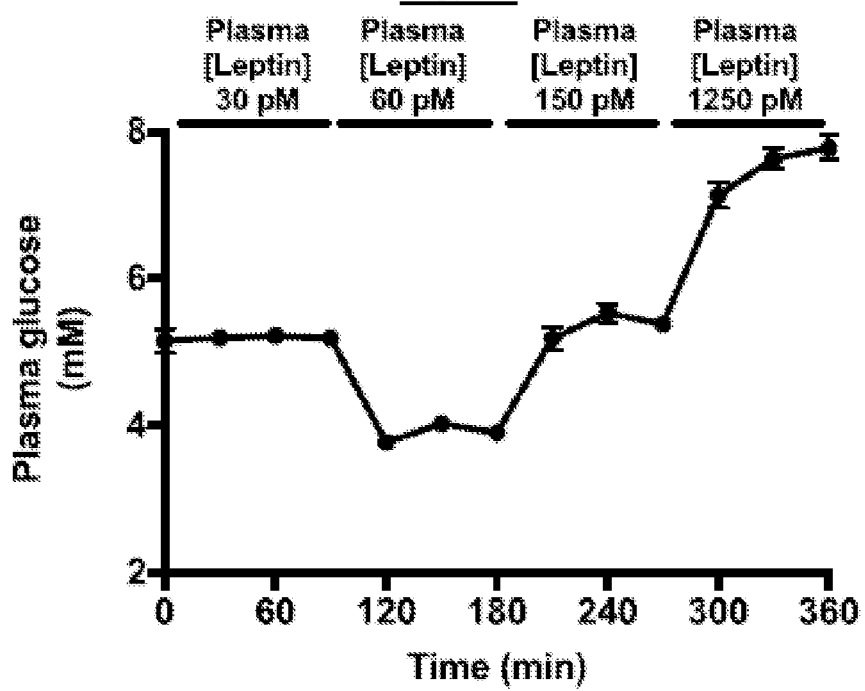
Figure 12E:
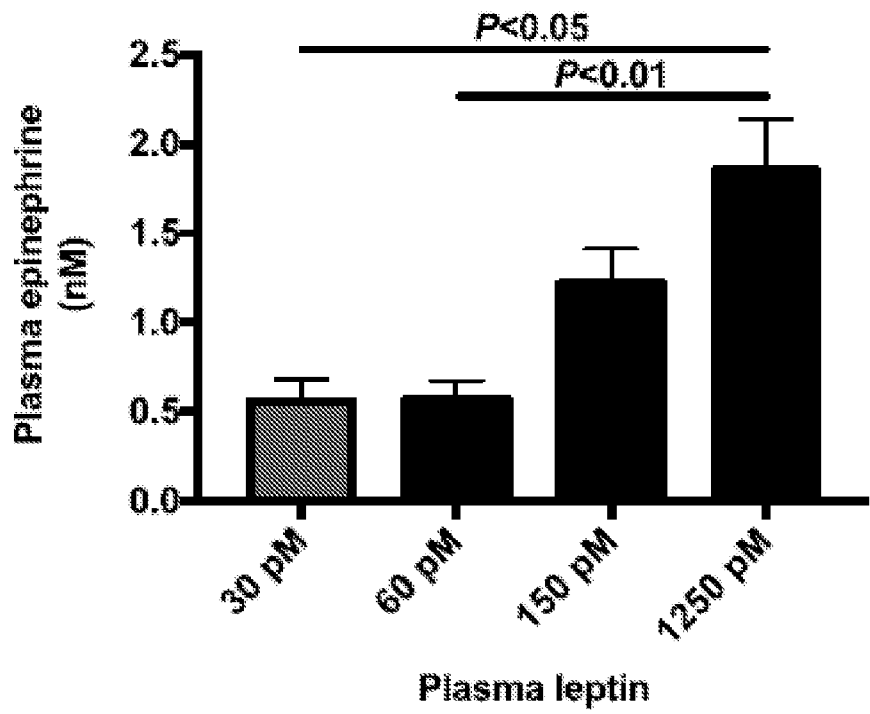
Figure 12F:
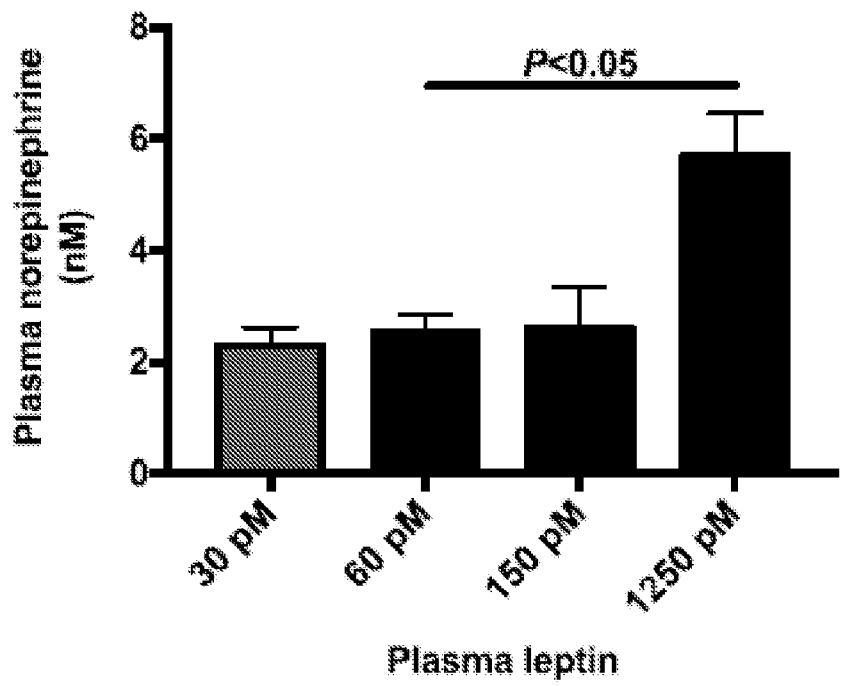
Figure 12G:
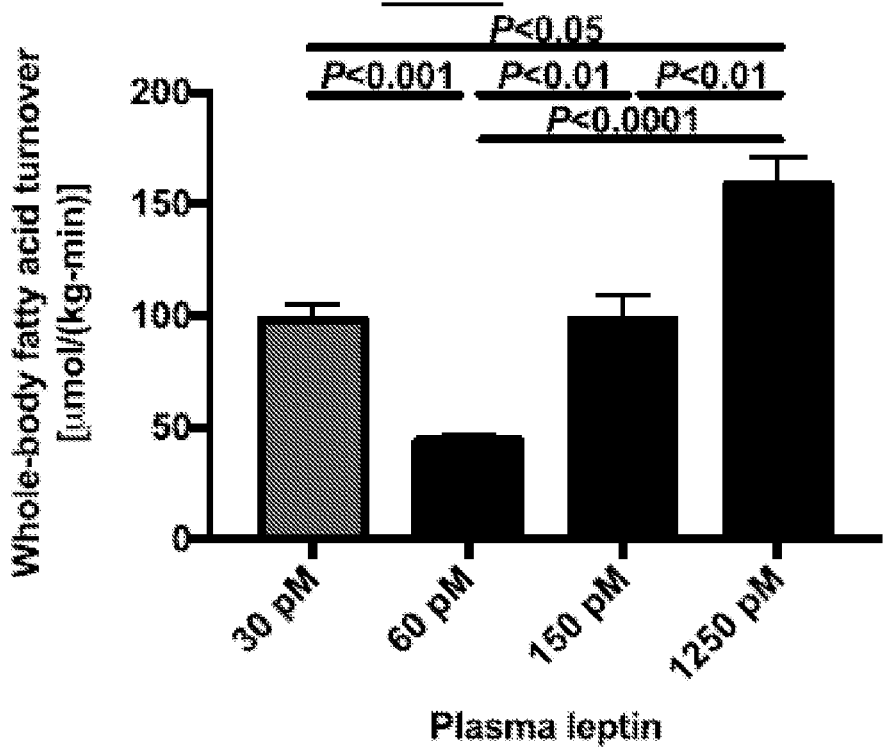
Figure 12H:
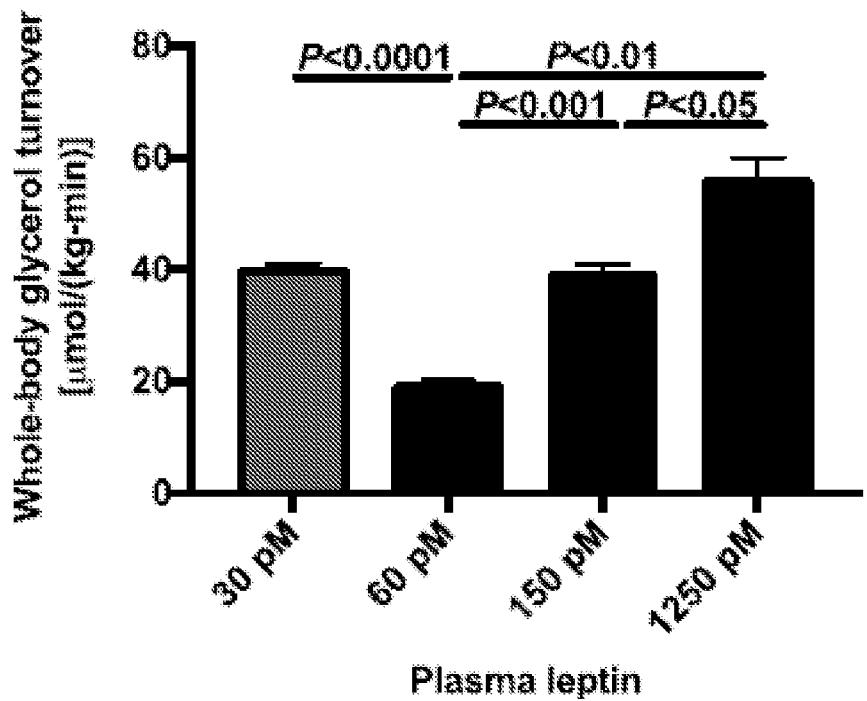
Figure 12I:
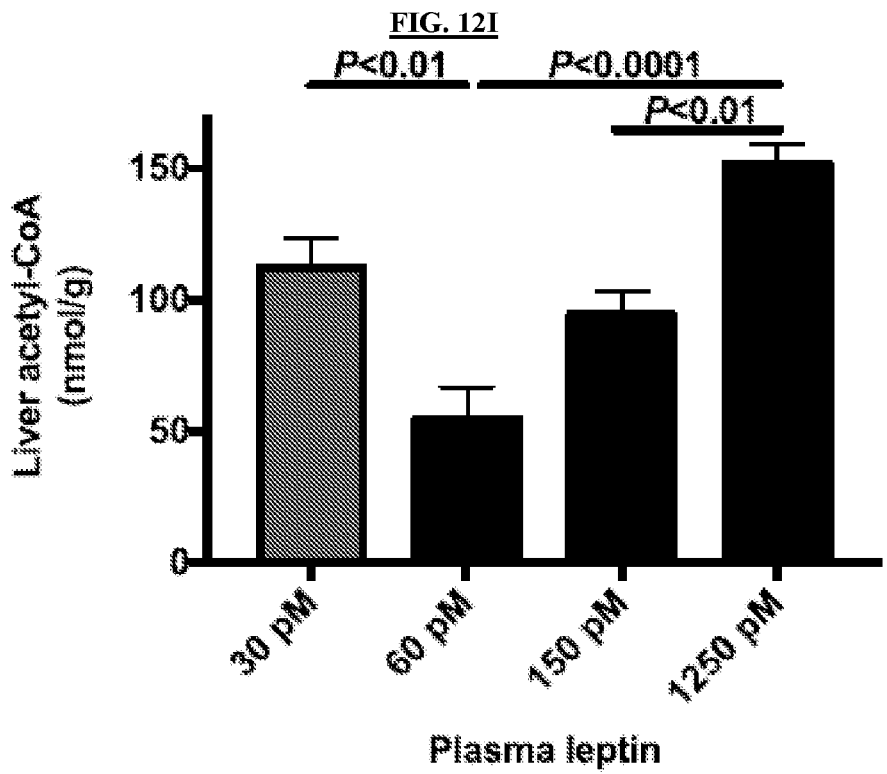
Figure 12J:
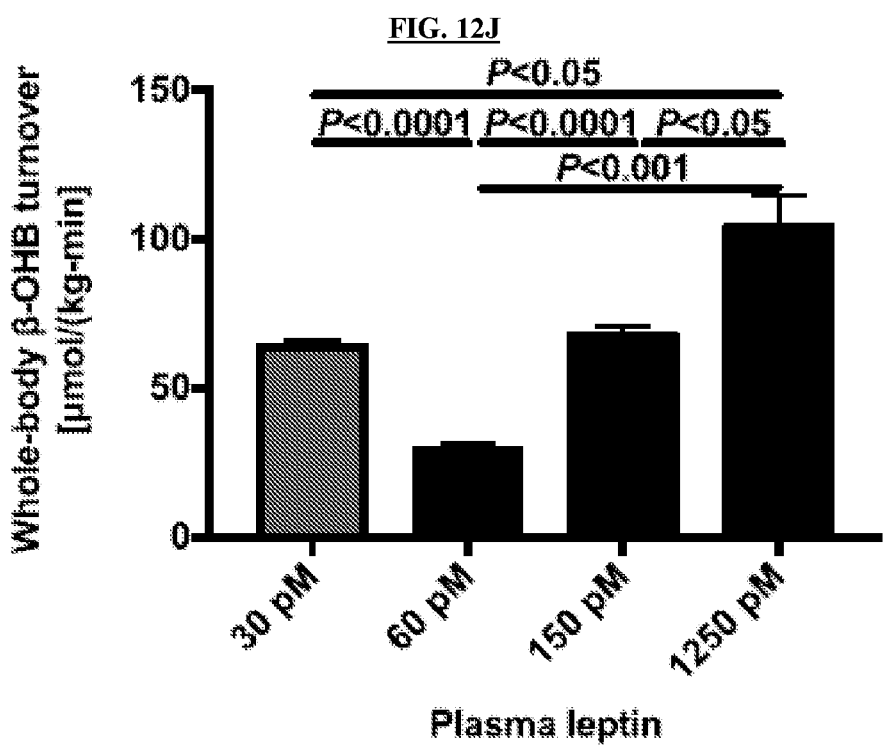
Figure 13A:
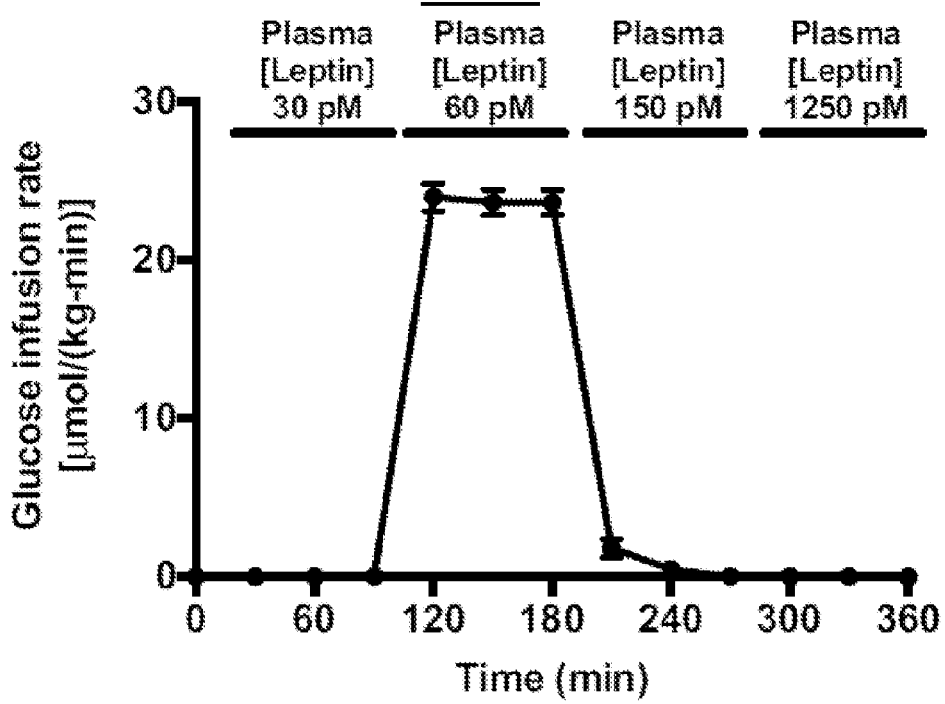
FIGS. 13A-13U are graphs showing that physiologic leptin replacement reduced WAT lipolysis and hepatic glucose production, and that leptin reversed this effect by stimulation of catecholamine secretion in 48-hr fasted normal chow-fed rats and type 1 diabetic rats.
Figure 13B:
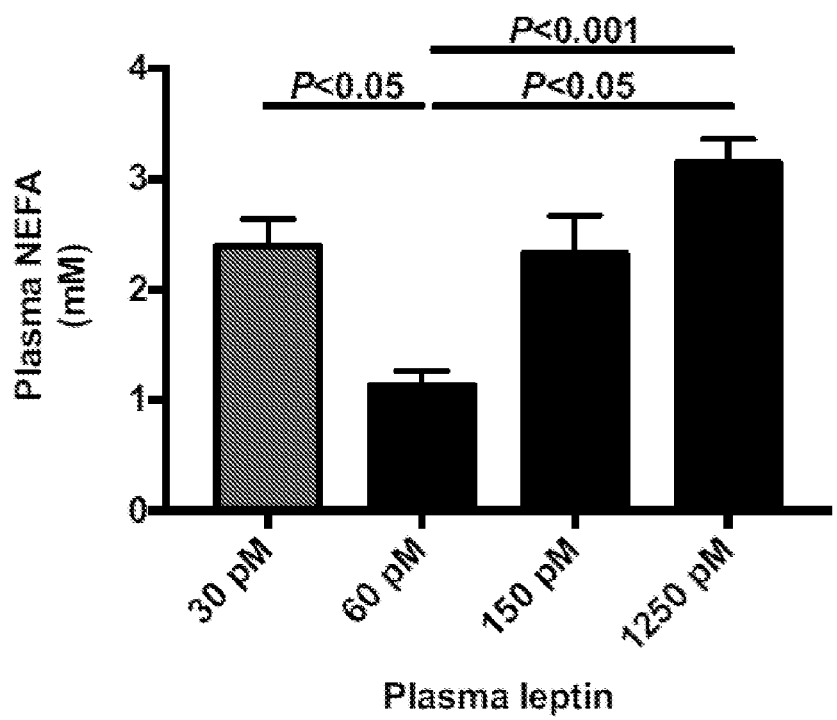
Figure 13C:
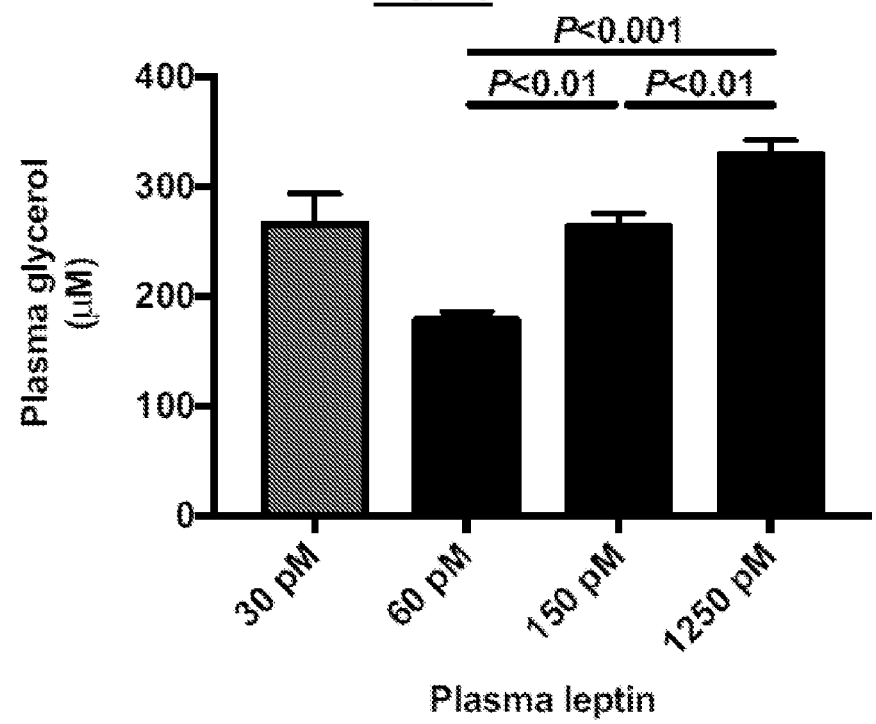
Figure 13D:
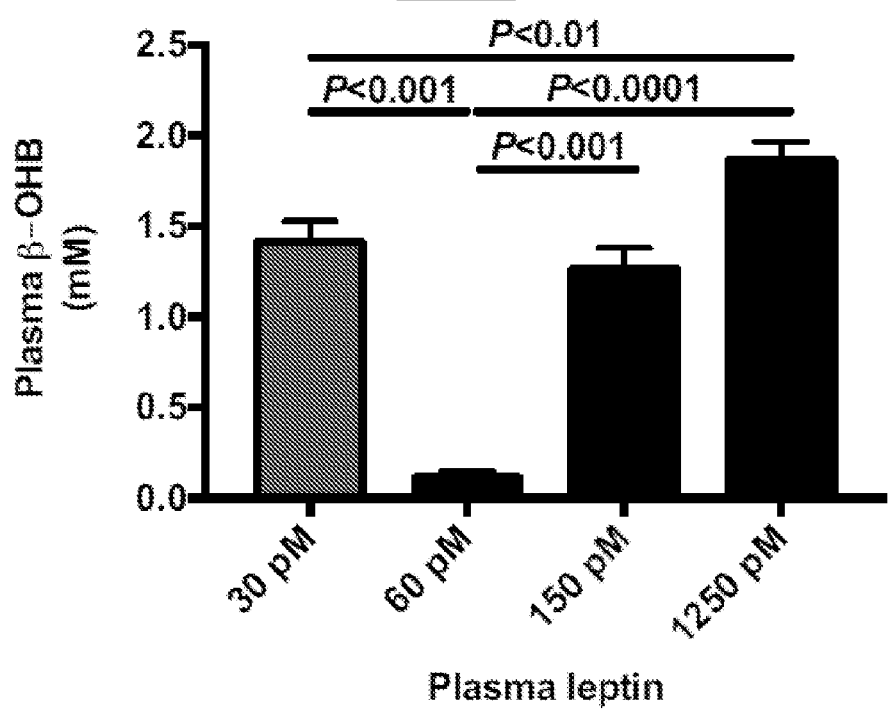
Figure 13E:
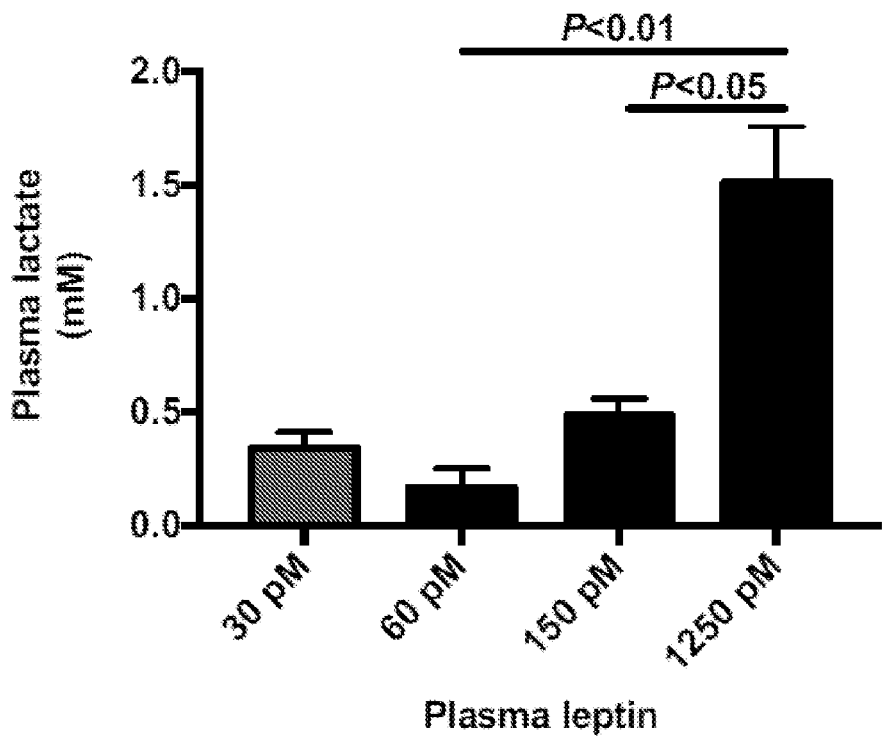
Figure 13F:
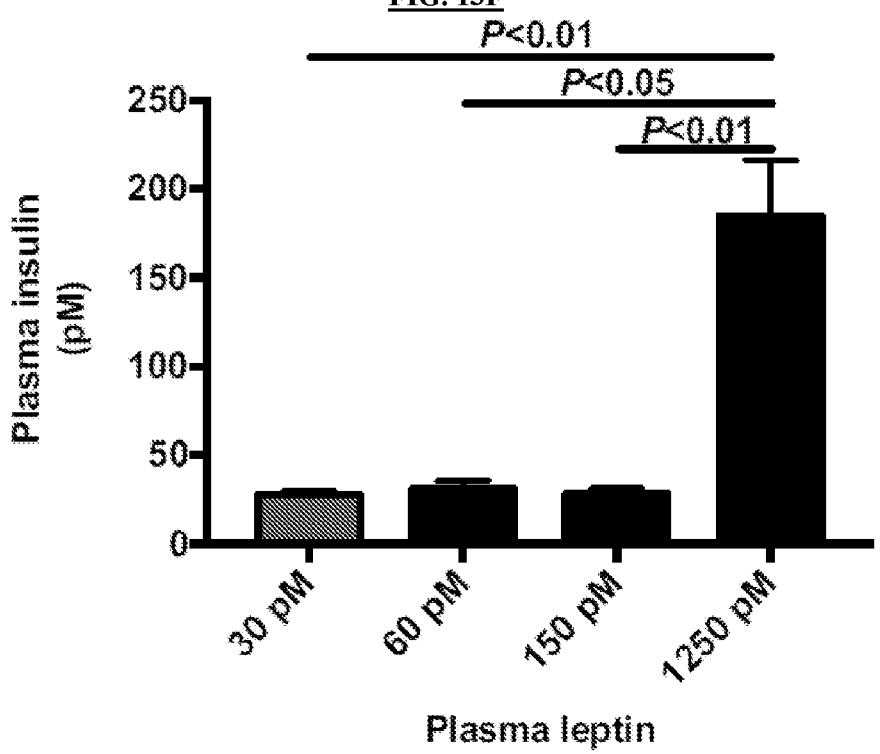
Figure 13G:
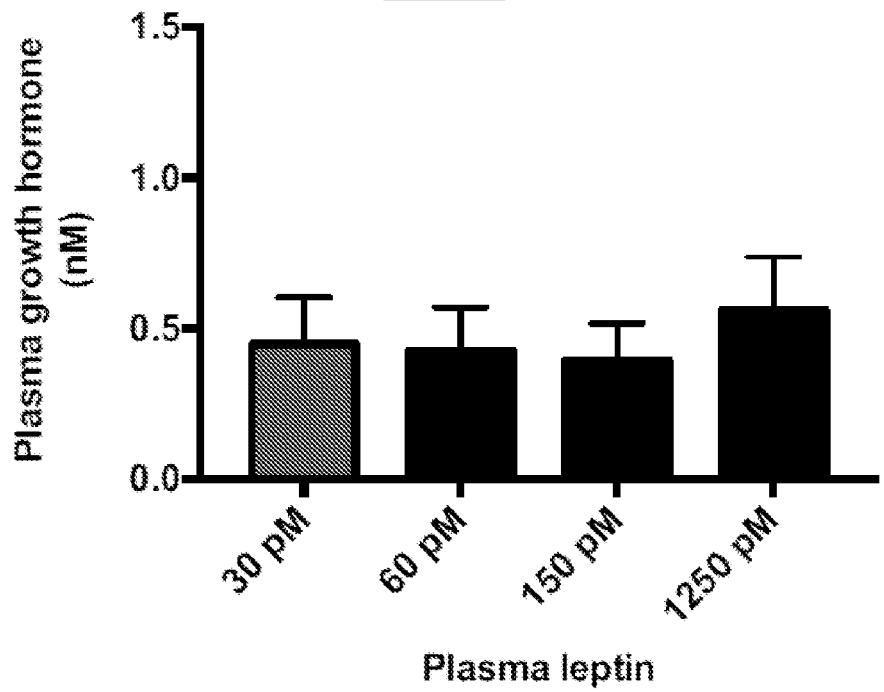
Figure 13H:
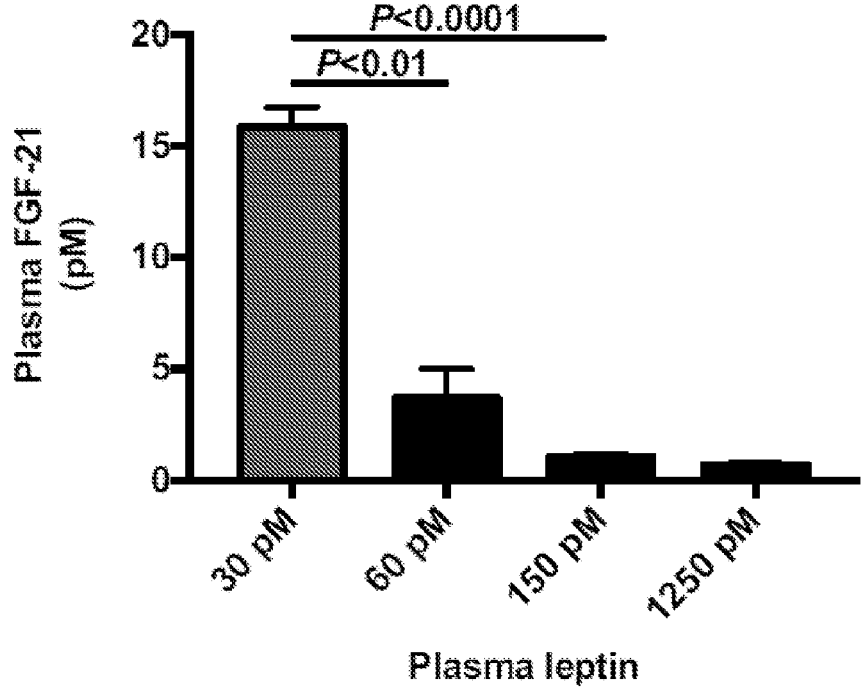
Figure 13K:
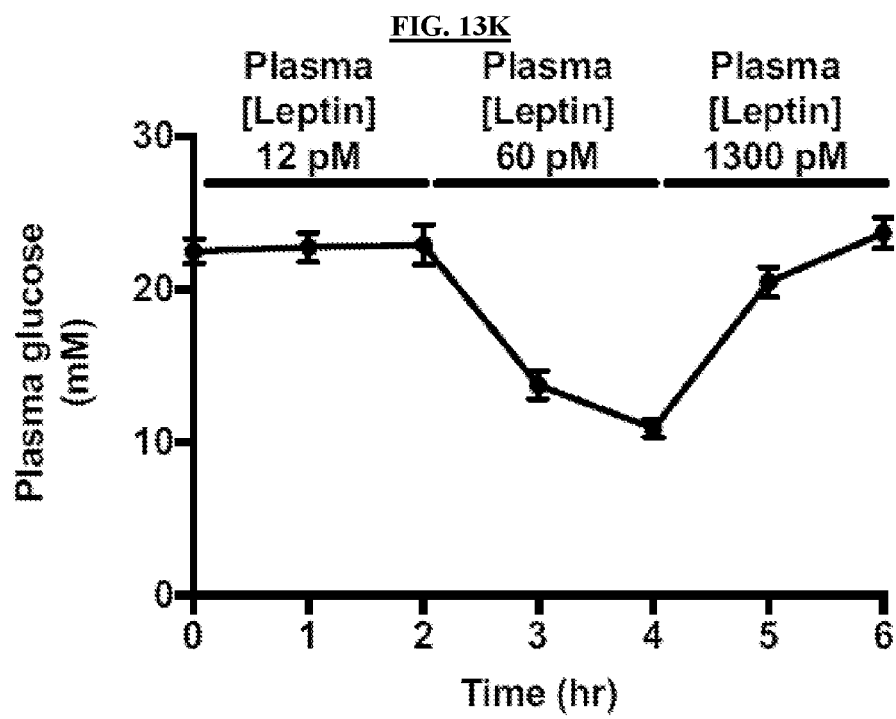
Figure 13L:
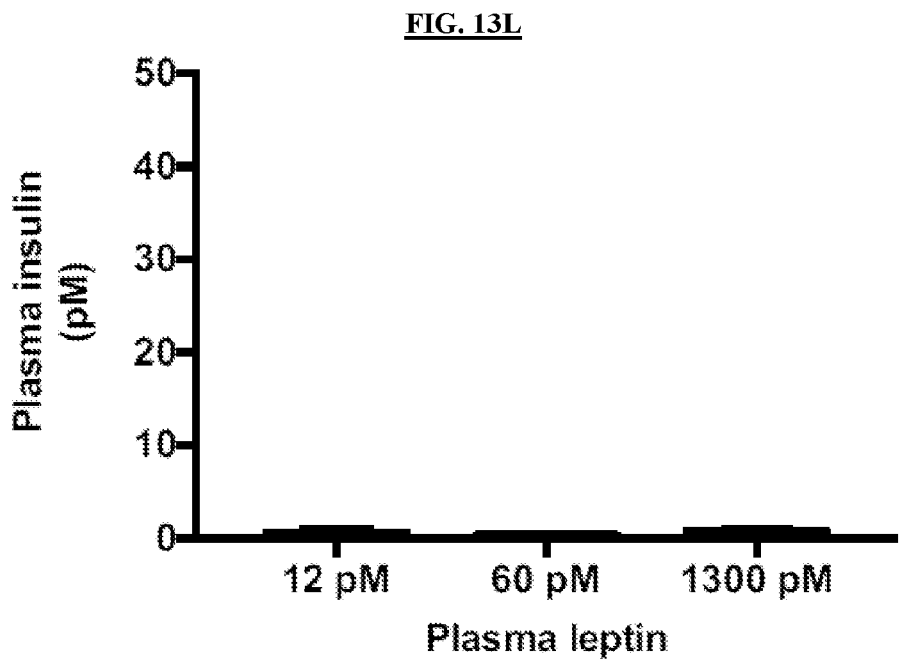
Figure 13O:
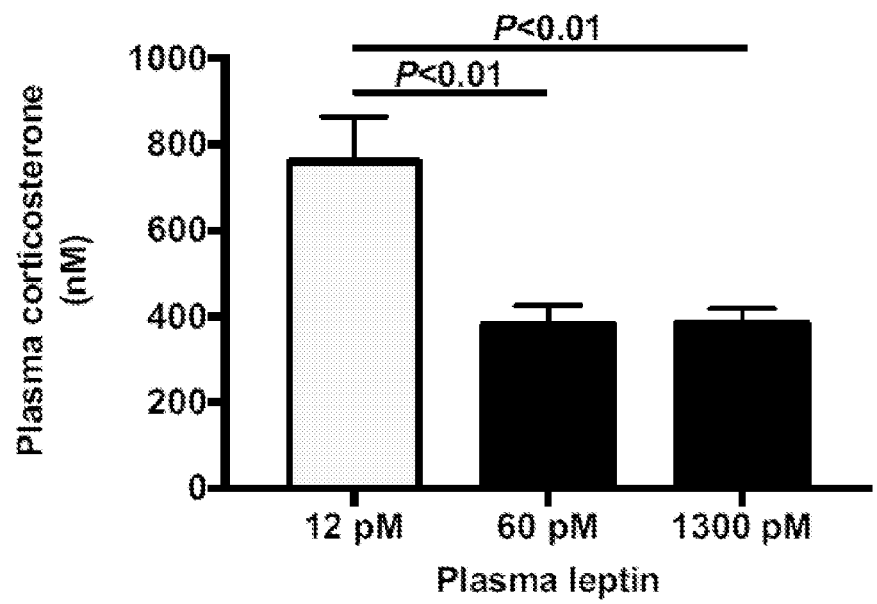
Figure 13P:
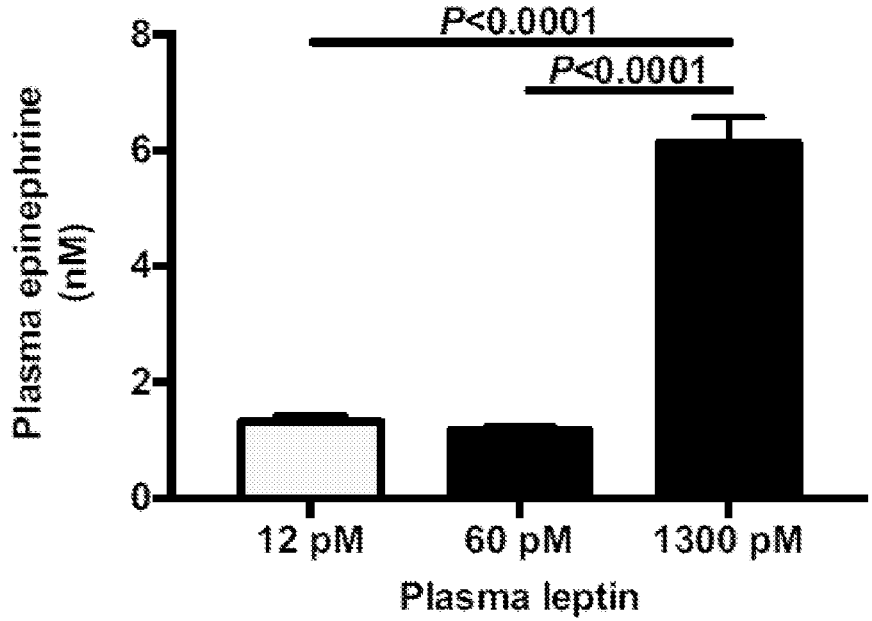

Physiologic Leptin Replacement Suppresses Lipolysis and Reduces Plasma Glucose, but Supraphysiologic Leptin Stimulates Lipolysis and Increases Plasma Glucose In order to explore the physiologic role of the reductions in plasma leptin concentrations associated with prolonged starvation on the HPA axis, WAT lipolysis, and hepatic gluconeogenesis, leptin was infused into 48-hr fasted rats at three infusion rates. The infusion rates were designed to increase plasma leptin to physiologic concentrations observed in a 16-hr fast (~60 pM) to concentrations similar to those observed in obese rats (FIG. 11K) and in fed rats (~150 pM) and to supraphysiologic concentrations (~1250 pM) similar to or lower than those measured with leptin infusion in previous (FIG. 12A). Physiologic leptin replacement (~60 pM) lowered plasma glucose concentrations and hepatic glucose production, requiring an infusion of glucose to prevent hypoglycemia and counter-regulation. Infusions of leptin to raise plasma leptin concentrations to ~150 pM and ~1250 pM were unable to lower either parameter (FIGS. 12B, 12C, and 13A). The reductions in plasma glucose concentrations with physiologic leptin replacement (plasma leptin concentration, ~60 pM) and increases in plasma glucose concentrations with supraphysiologic leptin treatment (plasma leptin concentrations, ~150 pM and ~1250 pM) were mirrored in suppression of plasma NEFA, glycerol, β-hydroxybutyrate, and lactate concentrations with physiologic leptin replacement and increases with supraphysiologic leptin infusions (FIGS. 13B-13E). Consistent with leptin's effect to suppress HPA axis activity, plasma corticosterone was suppressed by all three infusion rates of leptin. However, plasma catecholamine concentrations increased dose dependently with increasing leptin infusion, with the highest infusion rate of leptin raising plasma epinephrine and norepinephrine concentrations 2- to 3-fold (FIGS. 12D-12F). Plasma insulin concentrations also increased at the highest dose of leptin, most likely secondary to the increased rates of hepatic glucose production and resultant hyperglycemia. In contrast, there was no difference in plasma growth hormone concentrations (FIGS. 13F and 13G). However, leptin infusion caused a dose-dependent reduction in plasma FGF-21 concentrations, suggesting that the increase in plasma FGF-21 concentrations observed in fasted rats was secondary to hypoleptinemia and the resulting changes in the HPA axis, WAT lipolysis, and hepatic fat oxidation (FIG. 13H). Both fatty acid and glycerol turnover were suppressed with physiologic leptin replacement in 48-hr fasted rats and increased with supraphysiologic leptin treatment, resulting in increases in hepatic acetyl-CoA content and (3-hydroxybutyrate turnover (FIGS. 12G-12J and 13I).

Figure 13S:
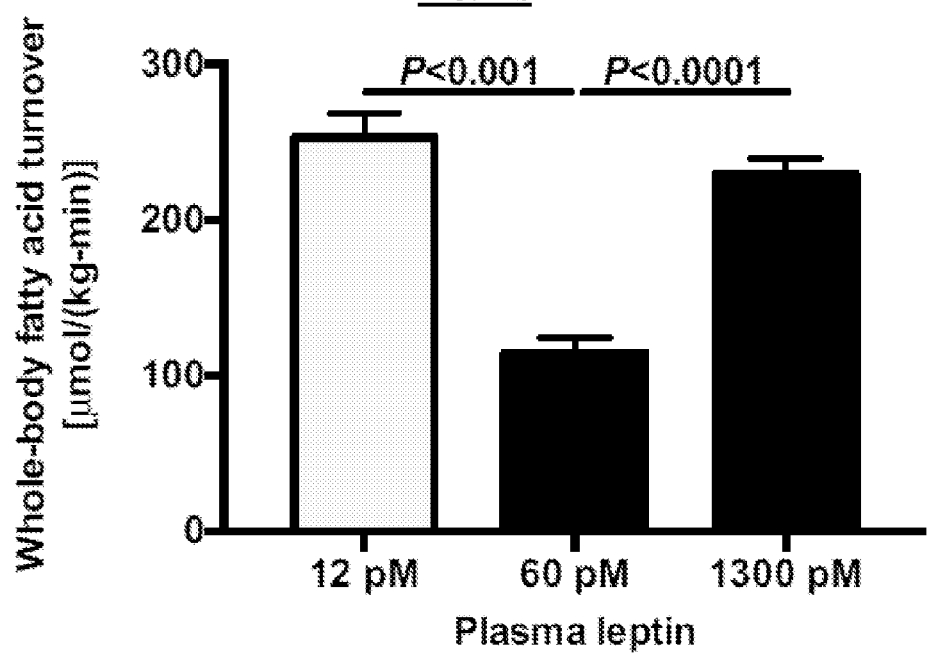
Figure 13T:
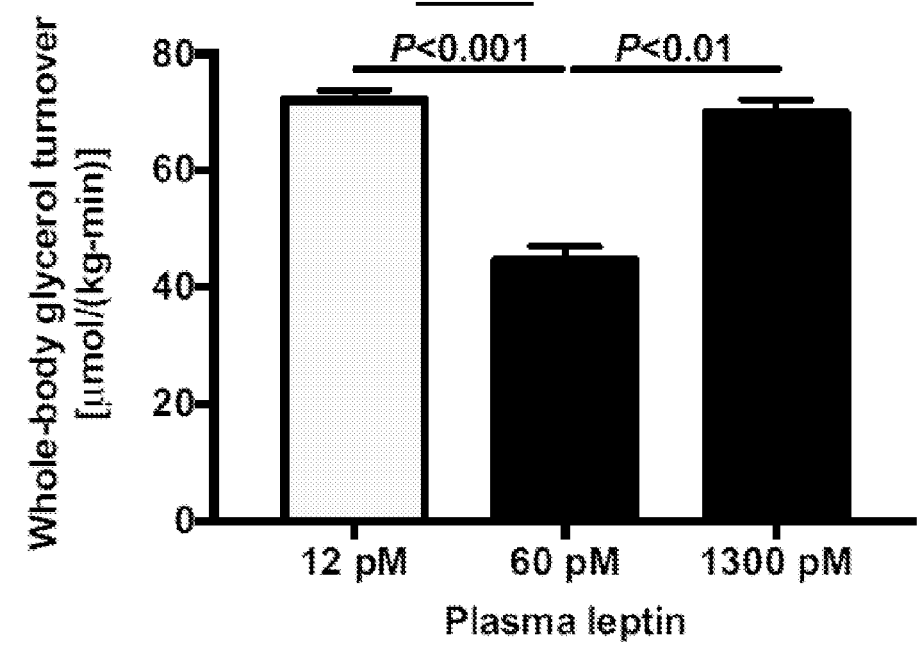
Figure 13U:
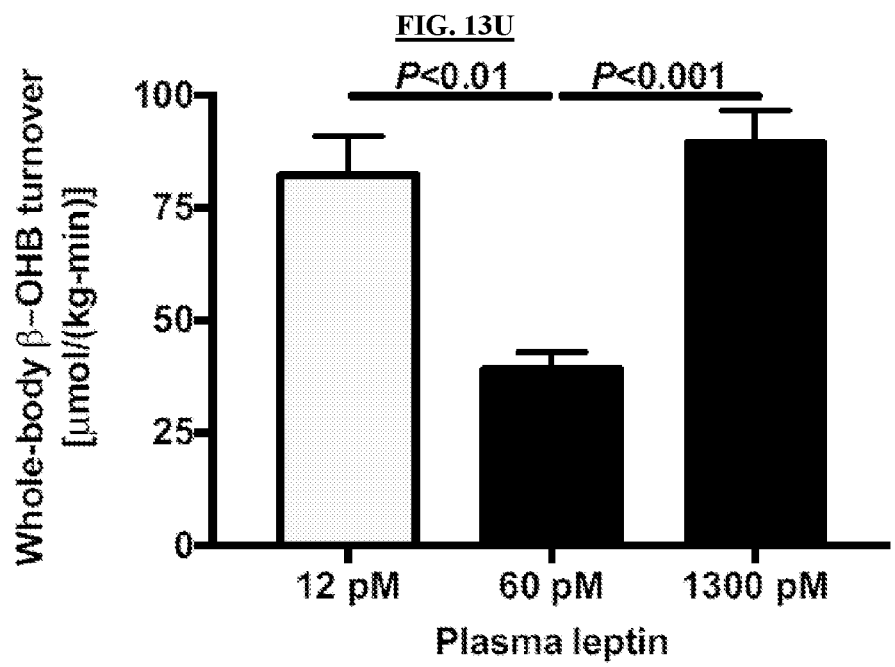

To examine the potential insulin dependence of the ability of leptin to suppress HPA-axis-mediated WAT lipolysis under physiologic conditions but promote WAT lipolysis under supraphysiologic conditions, leptin dose-response studies were conducted. A severely insulinopenic streptozotocin-induced rat model of type 1 diabetes (T1D) that almost entirely lack plasma leptin was used. Similar to what was observed in the starved normal rats, physiologic leptin replacement (~60 pM) in the T1D rats promoted a marked reduction in plasma glucose concentrations and endogenous glucose production rates, but supraphysiologic leptin concentrations (~1300 pM) promoted increases in both plasma glucose concentrations and endogenous glucose production (FIGS. 13J-13M). Both doses of leptin suppressed HPA axis activity, but supraphysiologic leptin concentrations (~1300 pM) were associated with a 4-fold increase in plasma catecholamine concentrations without any change in growth hormone concentrations (FIGS. 13N-13R). These alterations in HPA axis activity and catecholamine concentrations were associated with suppression of WAT lipolysis in T1D rats infused with leptin to achieve physiologic replacement leptin concentrations (~60 pM), an effect which was abrogated in rats infused with leptin to reach supraphysiologic plasma leptin concentrations (~1300 pM) (FIGS. 13S-13U).

Figure 14A:
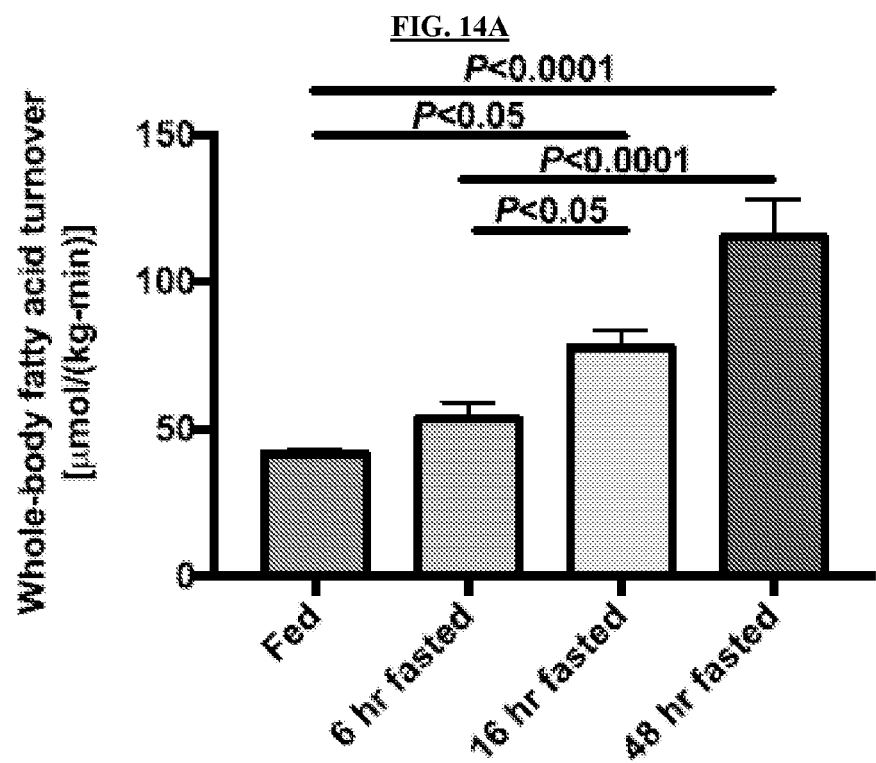
Figure 14B:
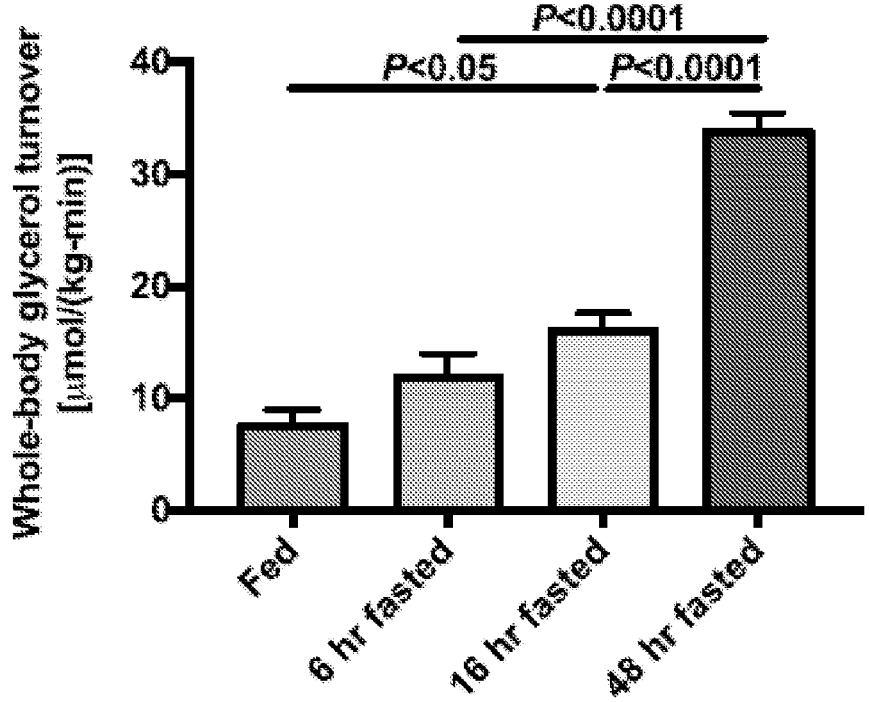
Figure 14C:
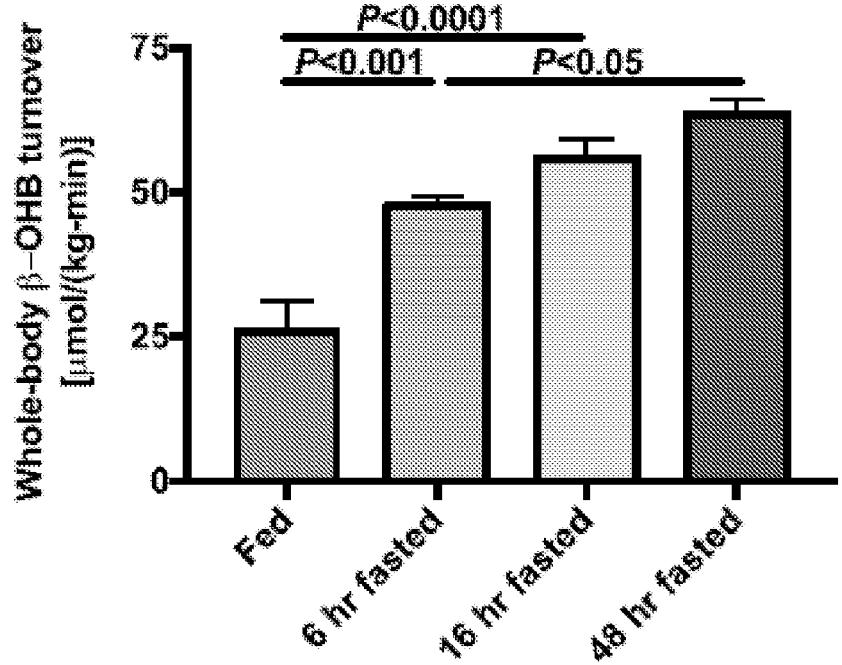
Figures 14D, 14E:
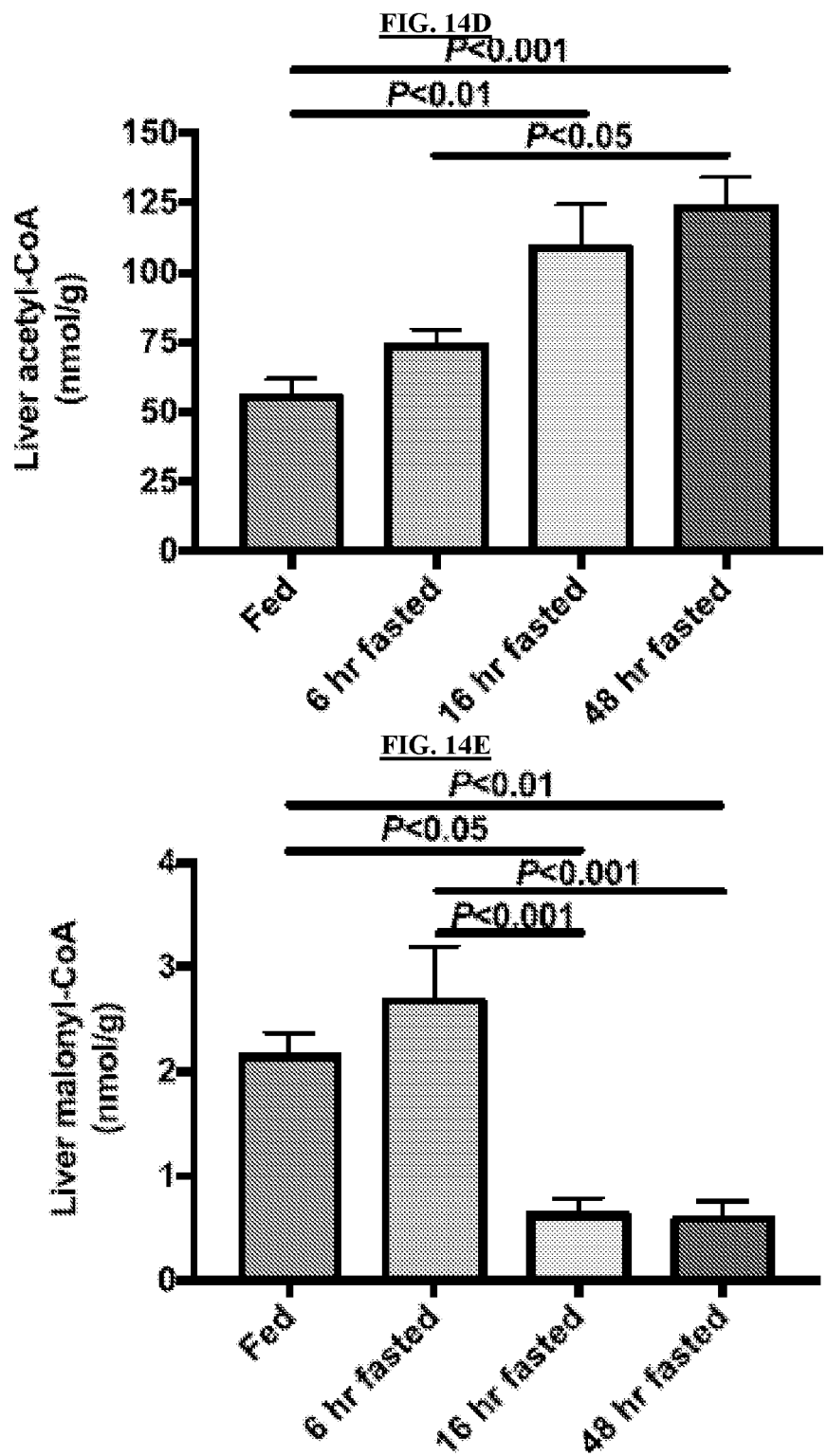
Figure 14H:
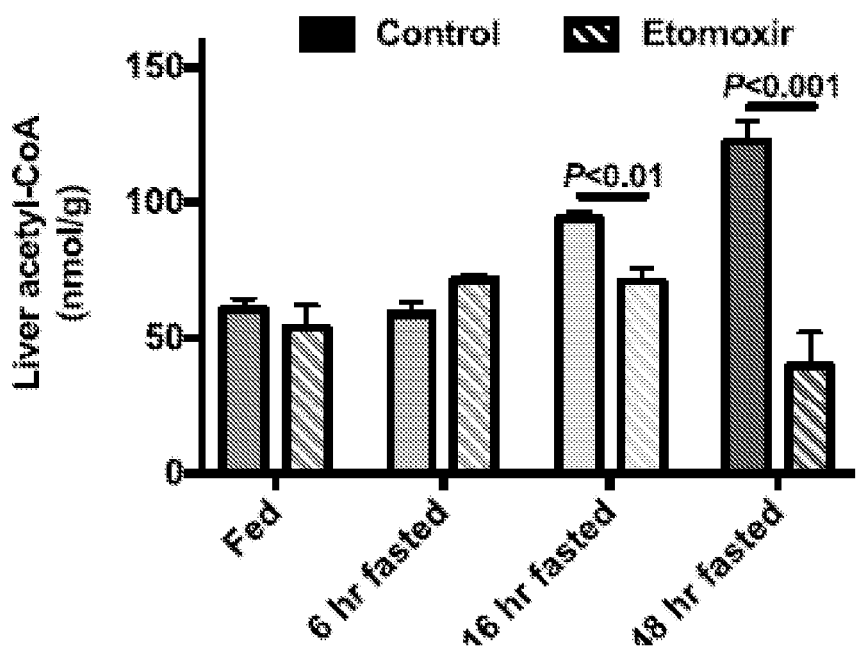
Figure 14I:
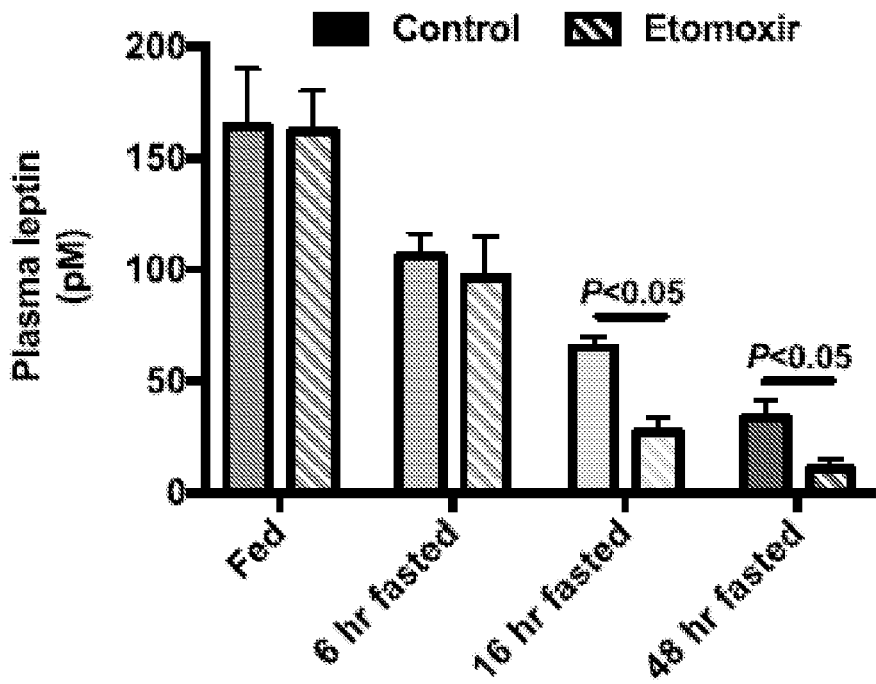
Figure 14J:
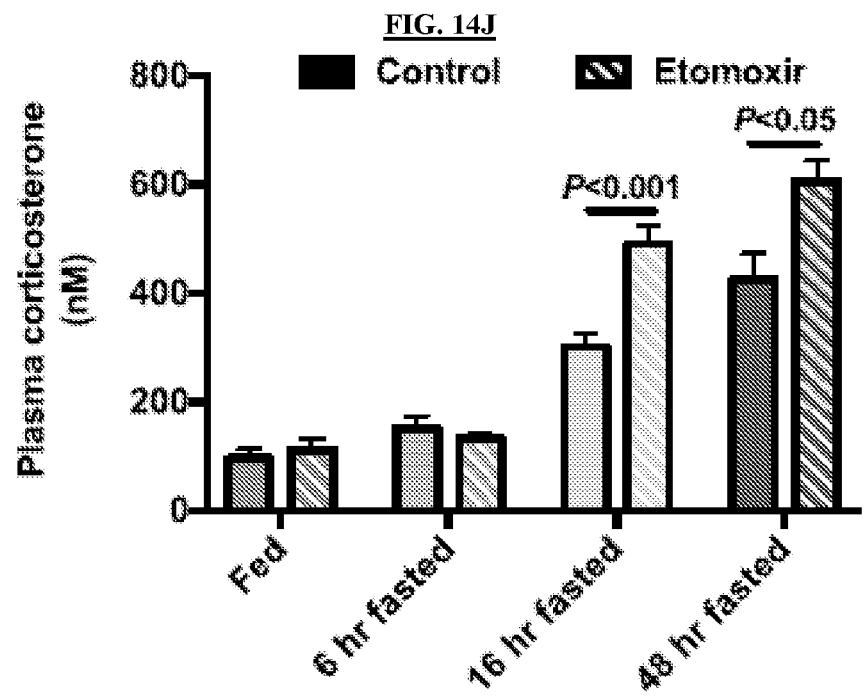
Figure 16A:
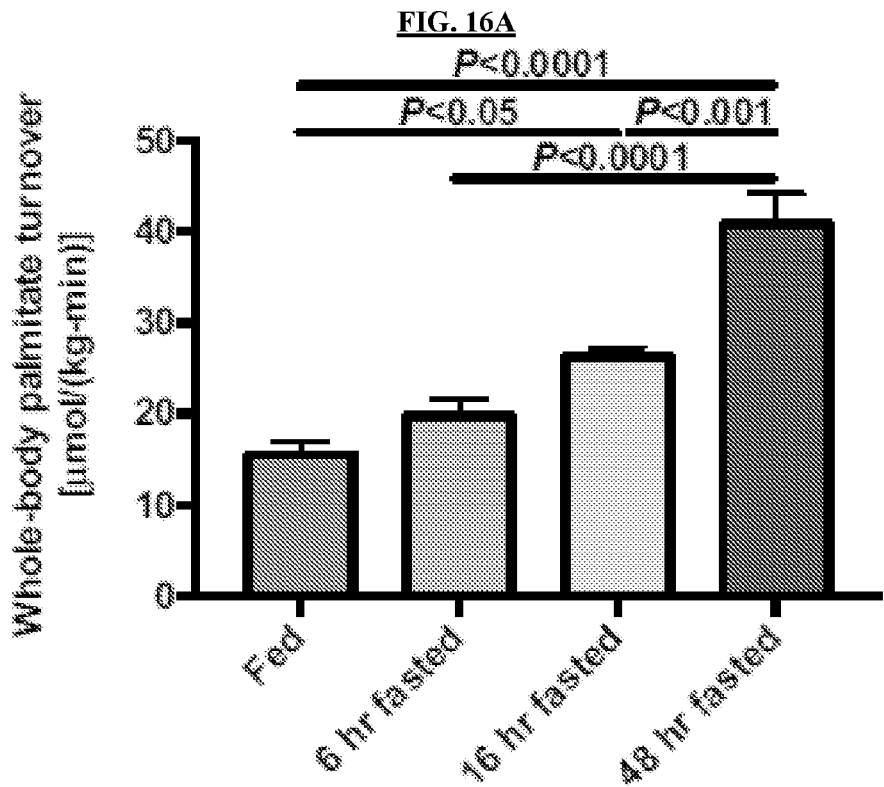
Figure 16F:
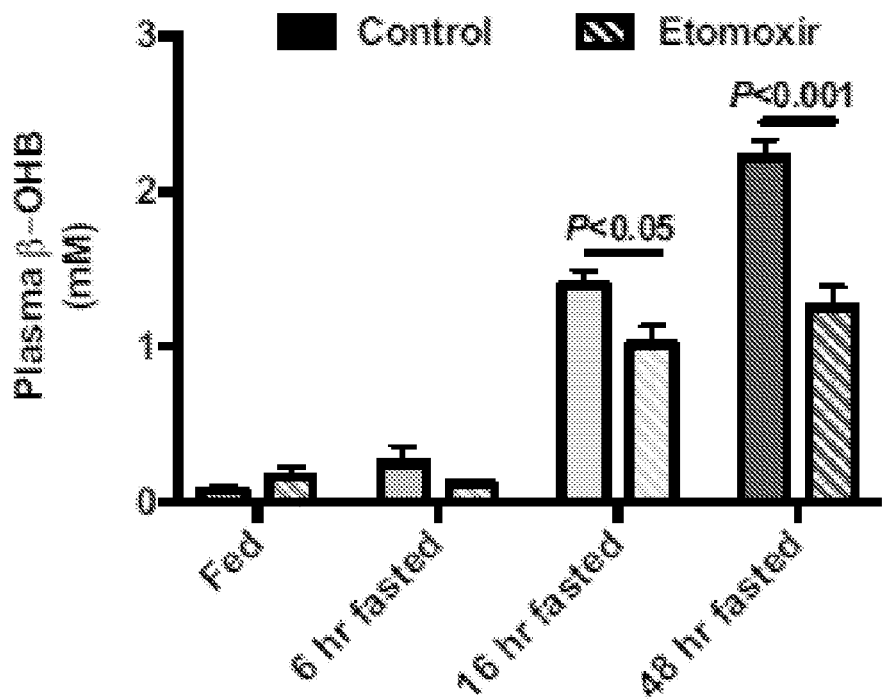
Figure 16G:
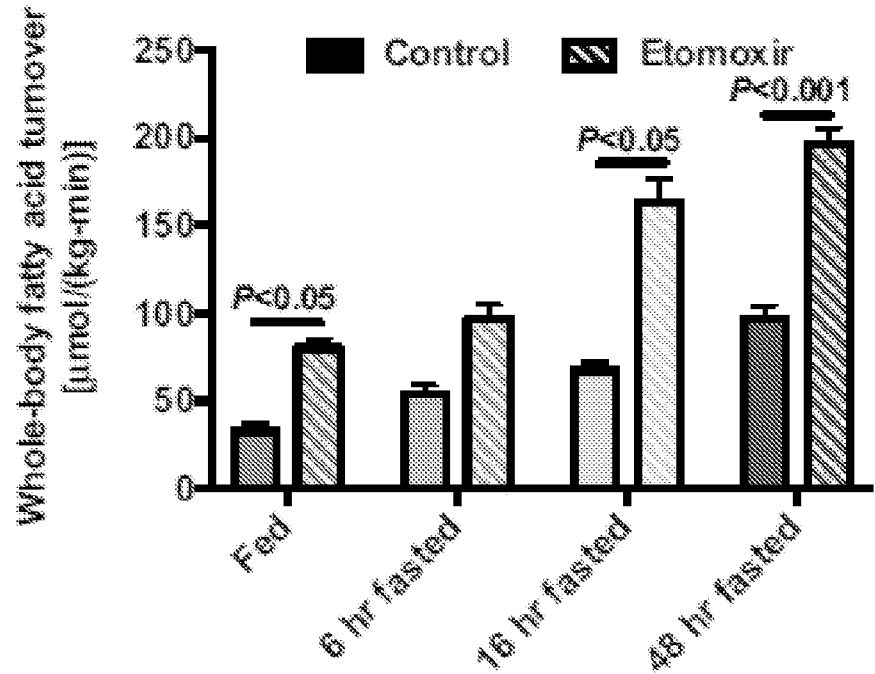
Figure 16H:
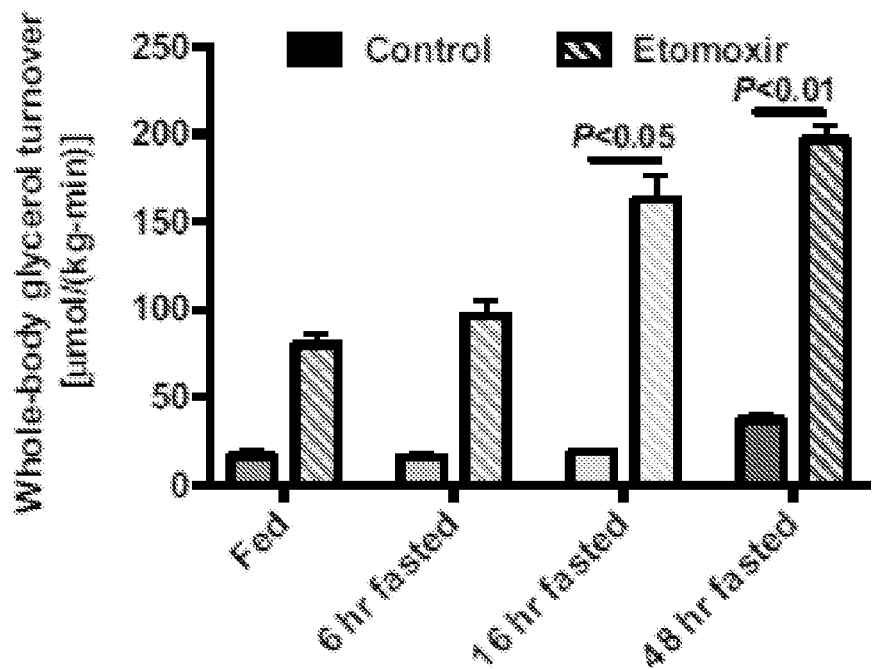
Figure 16I:
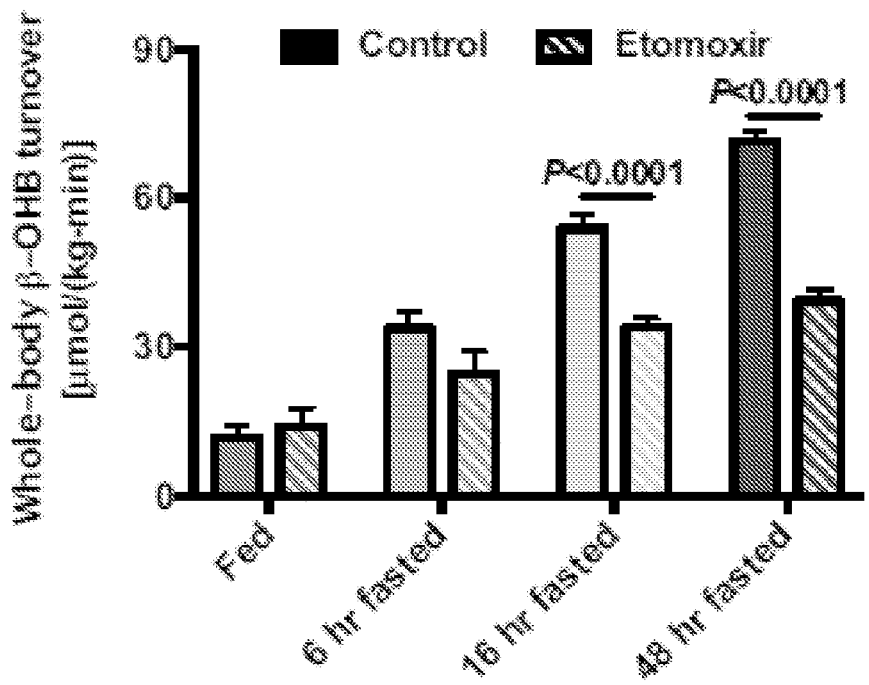
Figure 16J:
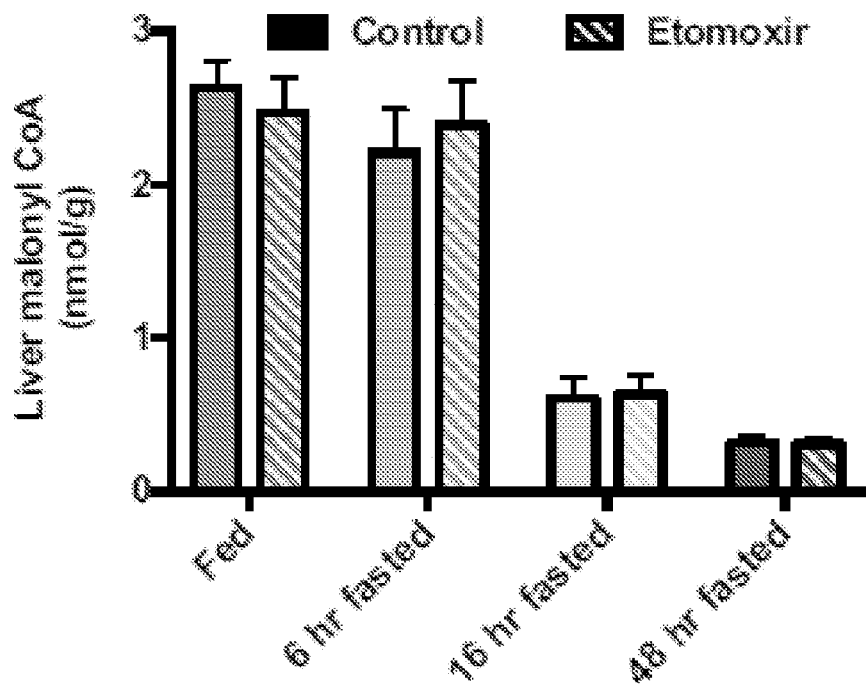
Figure 16K:
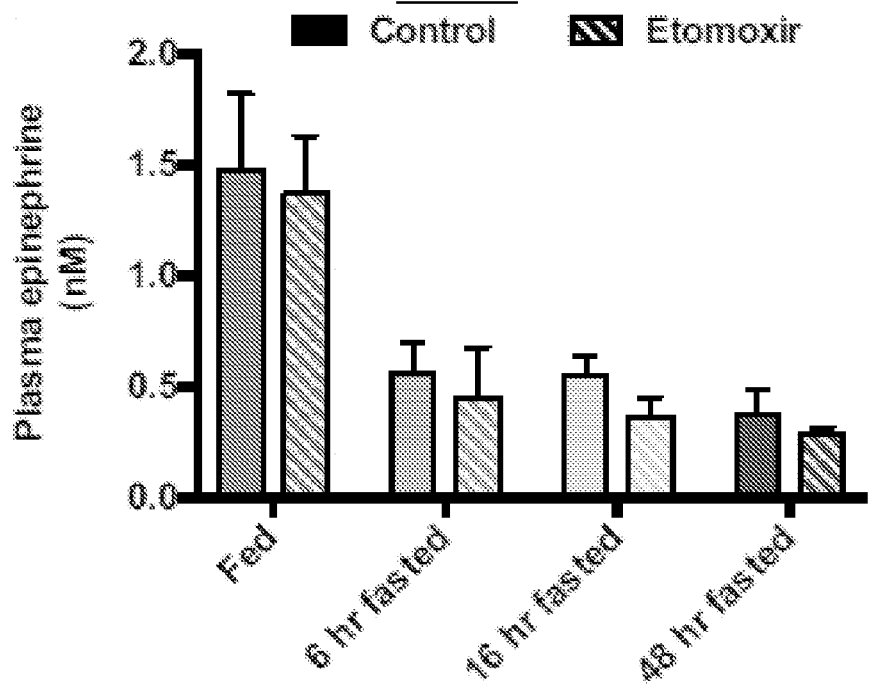
Figure 16L:
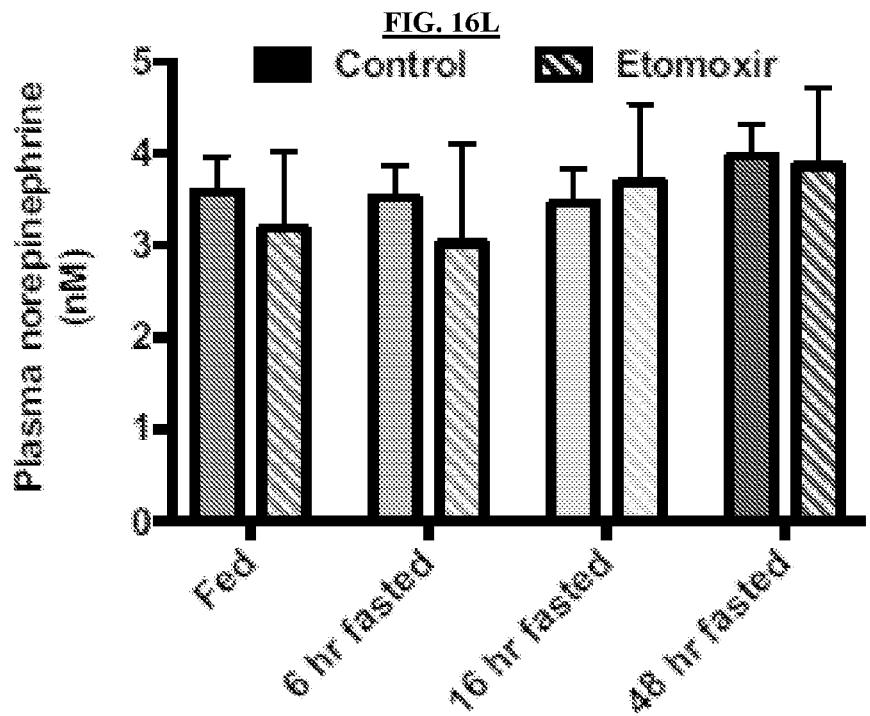
Figure 17A:
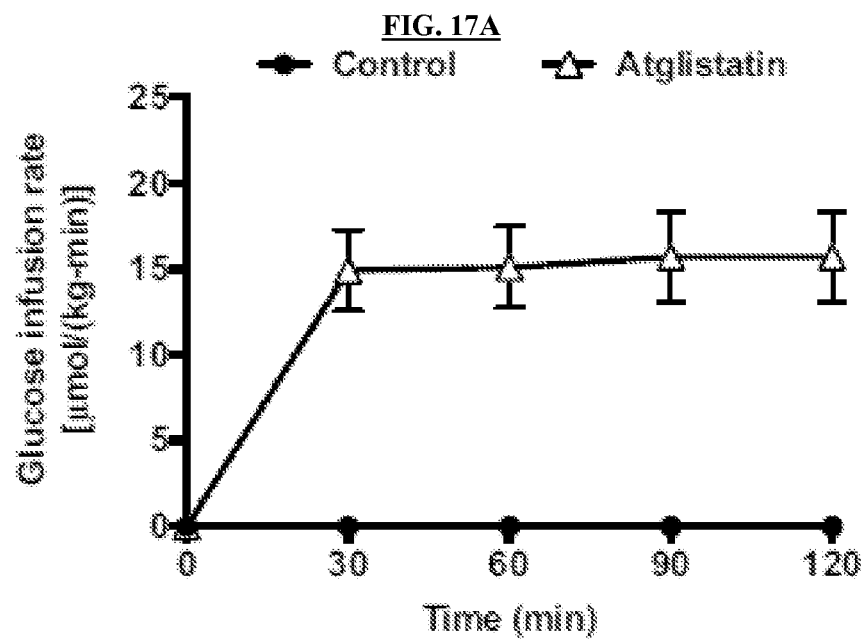
FIGS. 17A-17I are graphs showing that increased WAT lipolysis was necessary to increase hepatic acetyl-CoA content and maintain euglycemia in the starved state.
Figure 17B:
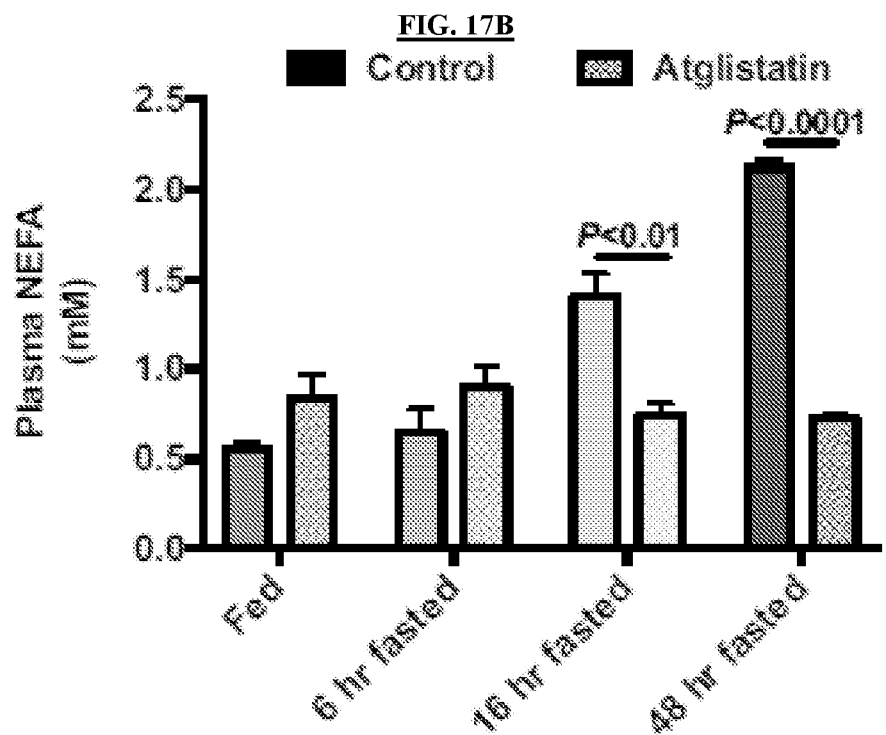
Figure 17C:
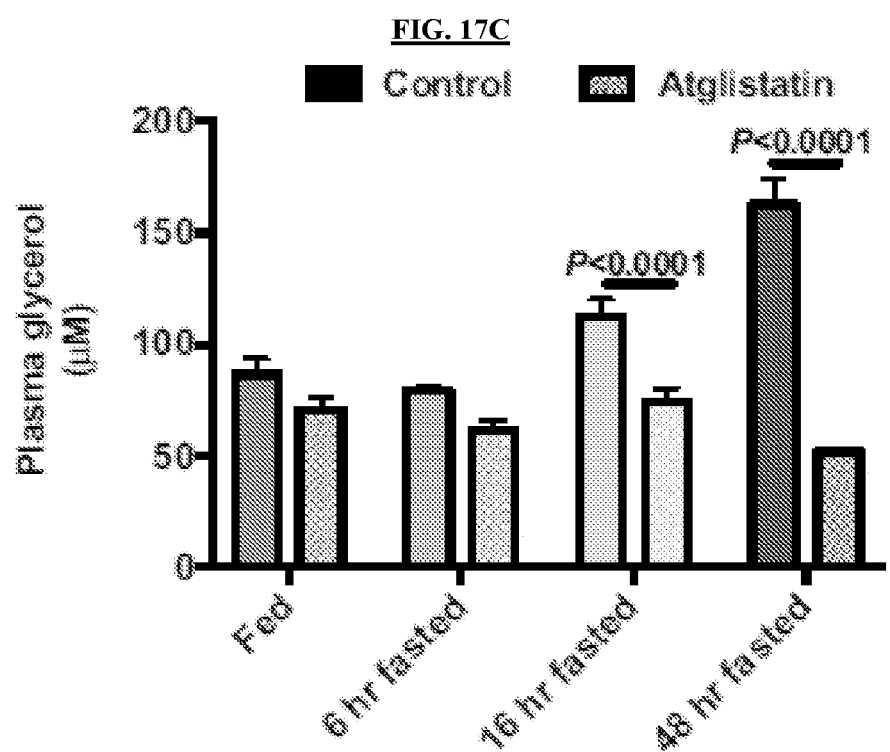
Figure 17D:
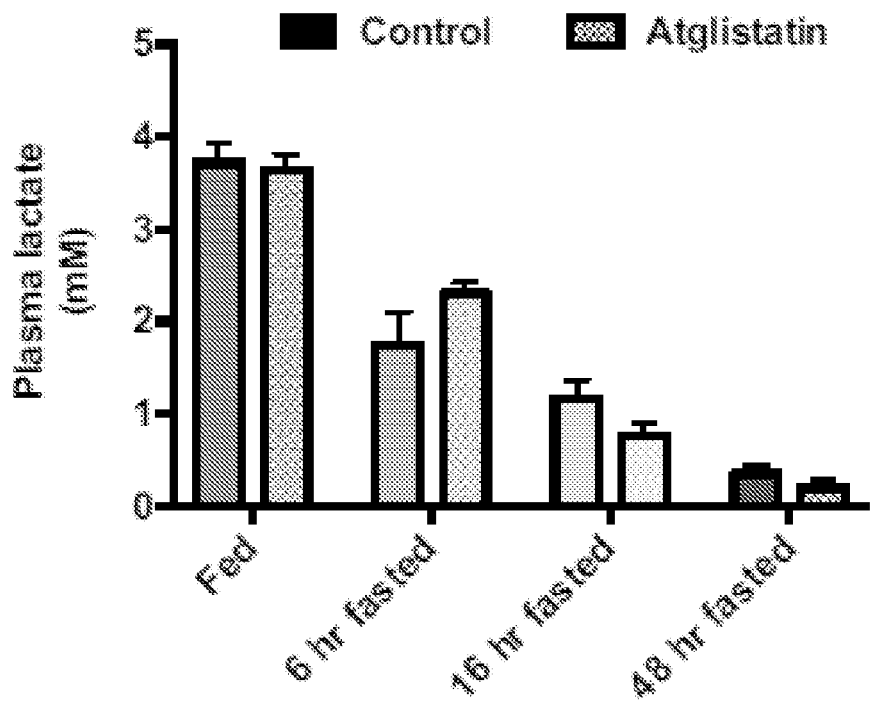
Figure 17E:
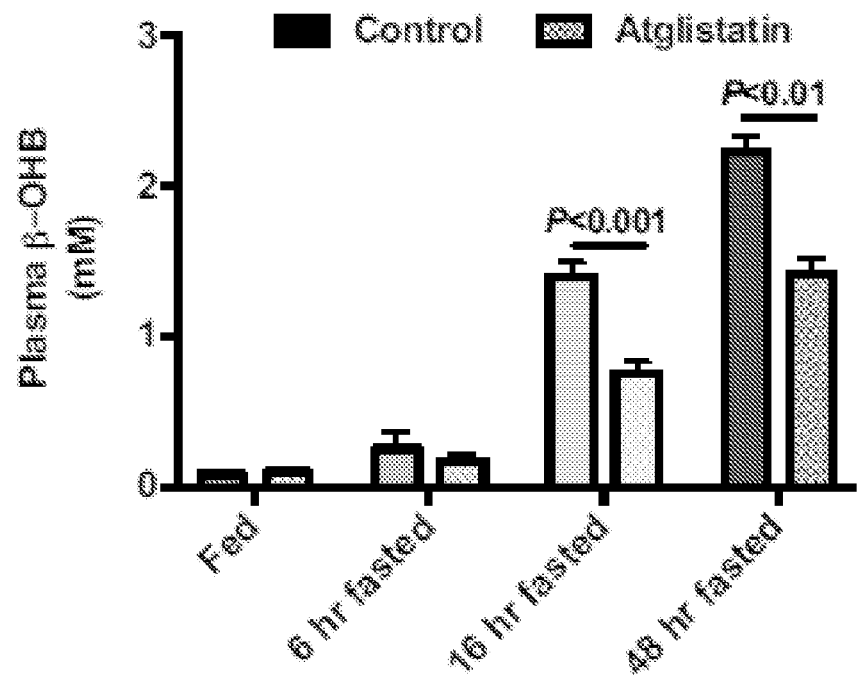
Figure 17F:
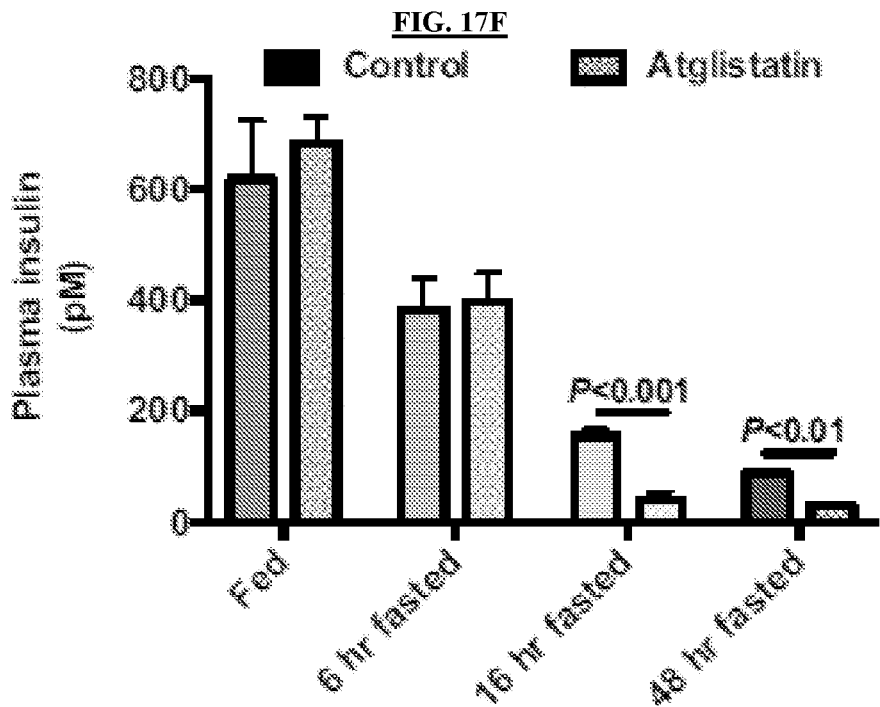
Figure 17G:
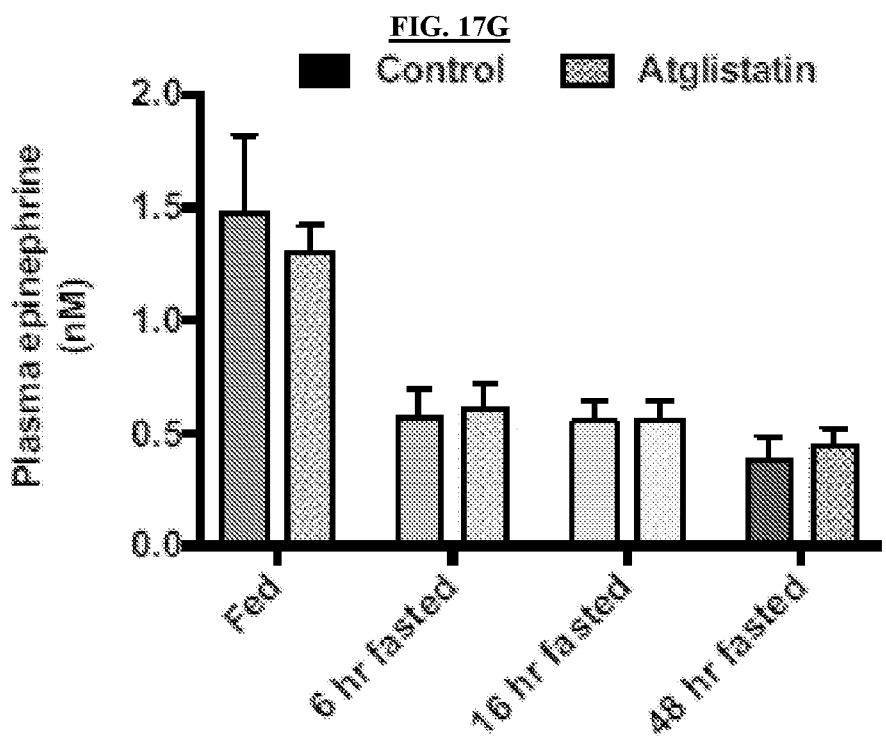
Figure 17H:
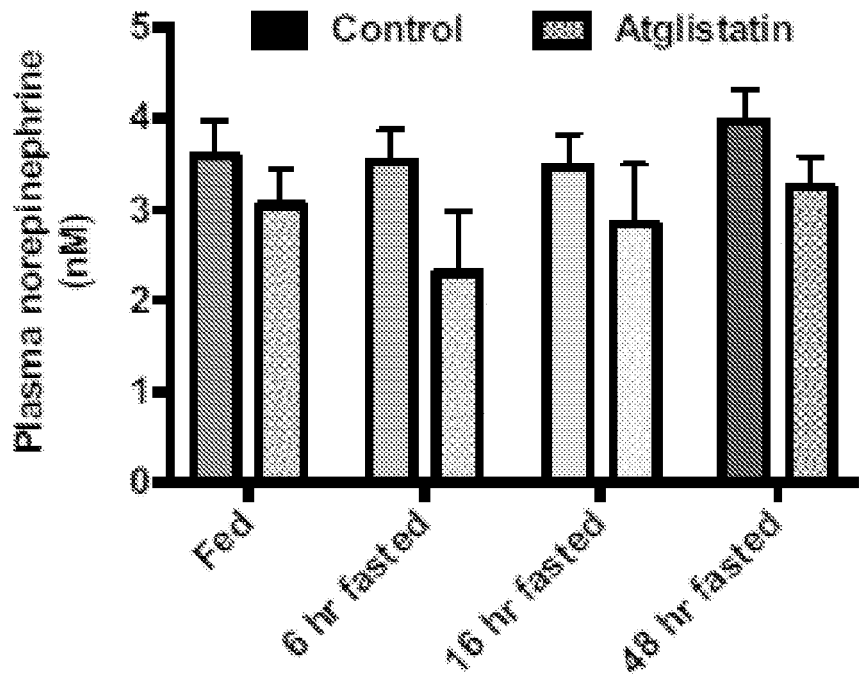
Figure 17I:
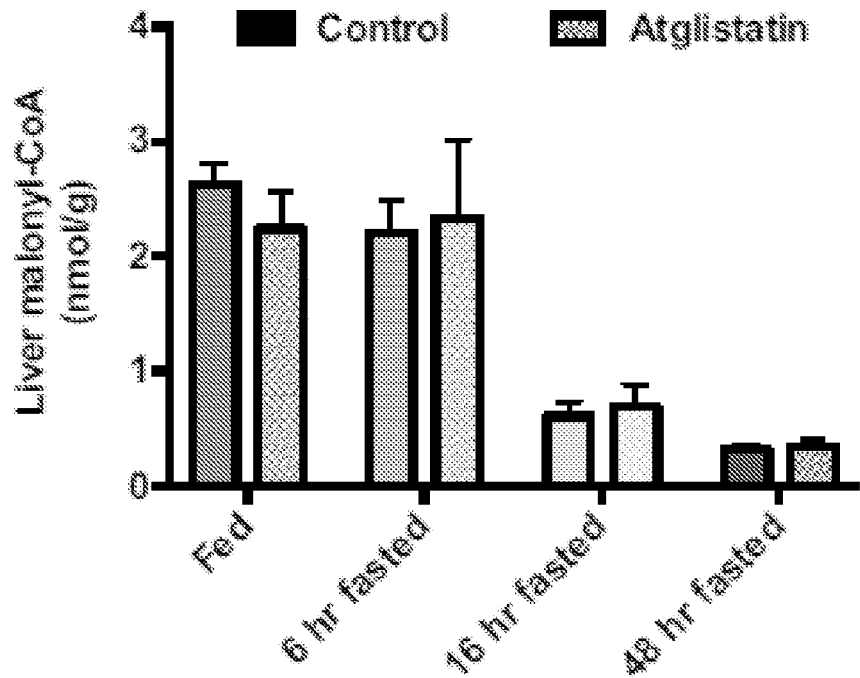

Increases in Leptin/HPA Axis-Mediated WAT Lipolysis and Hepatic Acetyl-CoA Content Maintain Euglycemia During the Early Stages (6-16 hr) of Fasting Having observed that variations in plasma leptin concentrations are associated with alterations in plasma glucocorticoid and catecholamine concentrations, as well as WAT lipolysis, we next asked how WAT lipolysis changes during the fast. Using stable isotope ([$^{13}C_{16}$]palmitate, [$^{2}H_5$]glycerol, and [$^{13}C_4$] β-hydroxybutyrate) infusions, we found a progressive increase in turnover of fatty acids, glycerol, and ketones (FIGS. 14A-14C and 16A). As predicted by the increase in β-hydroxybutyrate turnover observed with increasing duration of fasting, hepatic acetyl-CoA concentrations also increased as the fast progressed, whereas hepatic malonyl-CoA content was reduced by 75% between 6 and 16 hr of fasting, but did not change between the 16 and 48 hr time points (FIGS. 14D and 14E), suggesting that inhibition of carnitine palmitoyltransferase-1 (CPT-1) activity by hepatic malonyl-CoA content reached a nadir by 16 hr of fasting. Next, to directly assess the impact of increases in hepatic acetyl-CoA content on hepatic glucose metabolism, we treated rats fasted for 0, 6, 16, and 48 hr with etomoxir, a small-molecule inhibitor of CPT-1. In fasted rats, CPT-1 inhibition lowered plasma glucose and insulin concentrations and whole body glucose turnover associated with suppression of hepatic acetyl-CoA content and β-hydroxybutyrate turnover despite increased WAT lipolysis and unchanged plasma lactate and hepatic malonyl-CoA concentrations (FIGS. 14F-14H and FIGS. 16B-16J). Without intending to be limited to any particular theory, this result is potentially a consequence of the reductions in plasma insulin concentrations observed with inhibition of CPT-1. To examine whether the reductions in plasma glucose and insulin measured with CPT-1 inhibition were associated with alterations in HPA axis activity, plasma leptin and corticosterone concentrations were measured. It was found that etomoxir treatment was associated with 50% reductions in plasma leptin concentrations, as well as increases in plasma corticosterone concentrations in 16- and 48-hr fasted rats (FIGS. 14I and 14J). In contrast, there were no differences in plasma epinephrine or norepinephrine concentrations (FIGS. 16K and 16L).

Figure 15A:
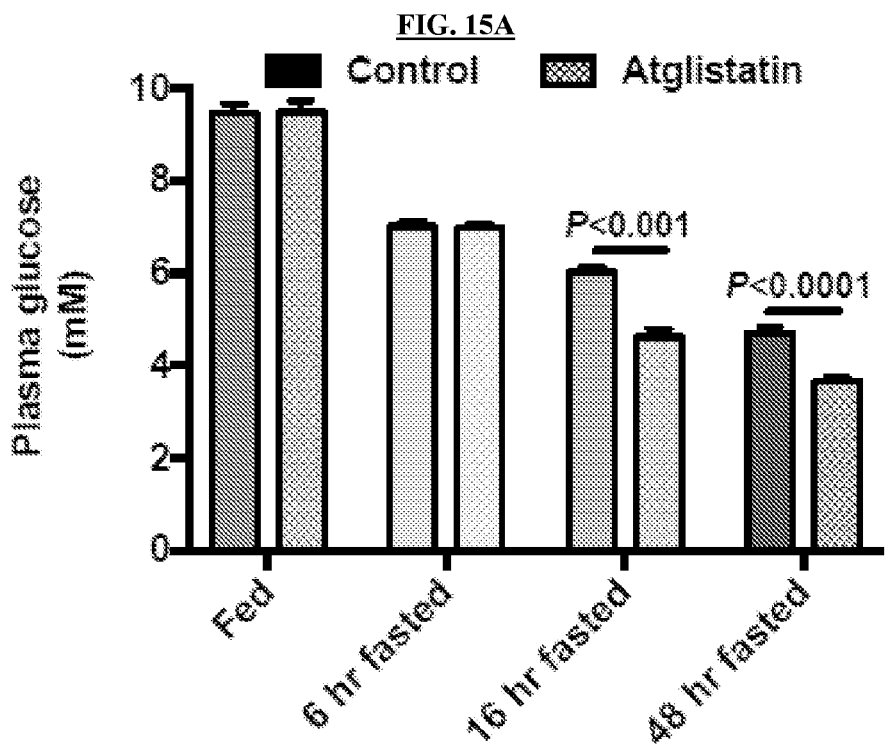
Figure 15B:
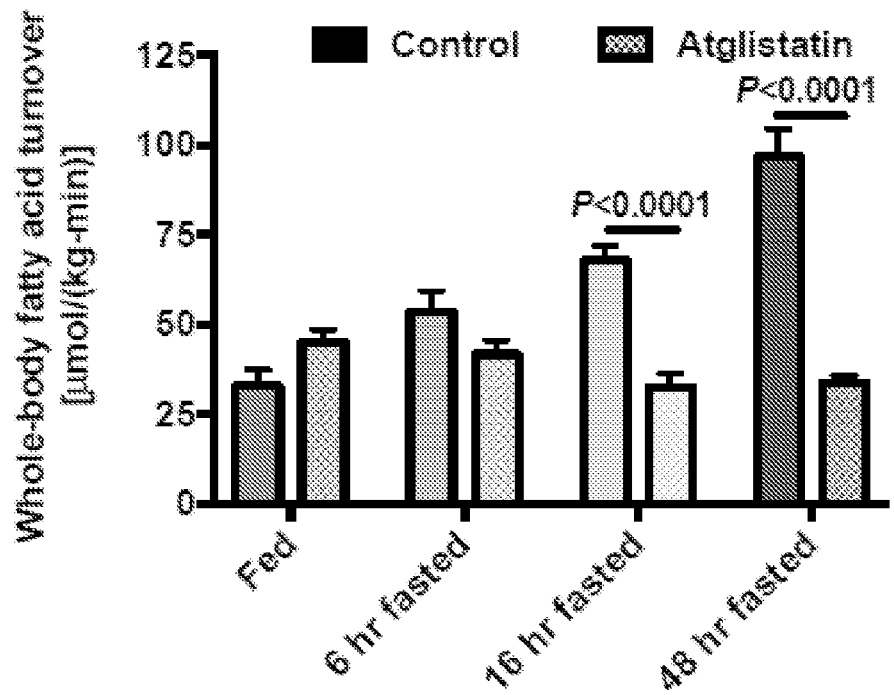
Figure 15C:
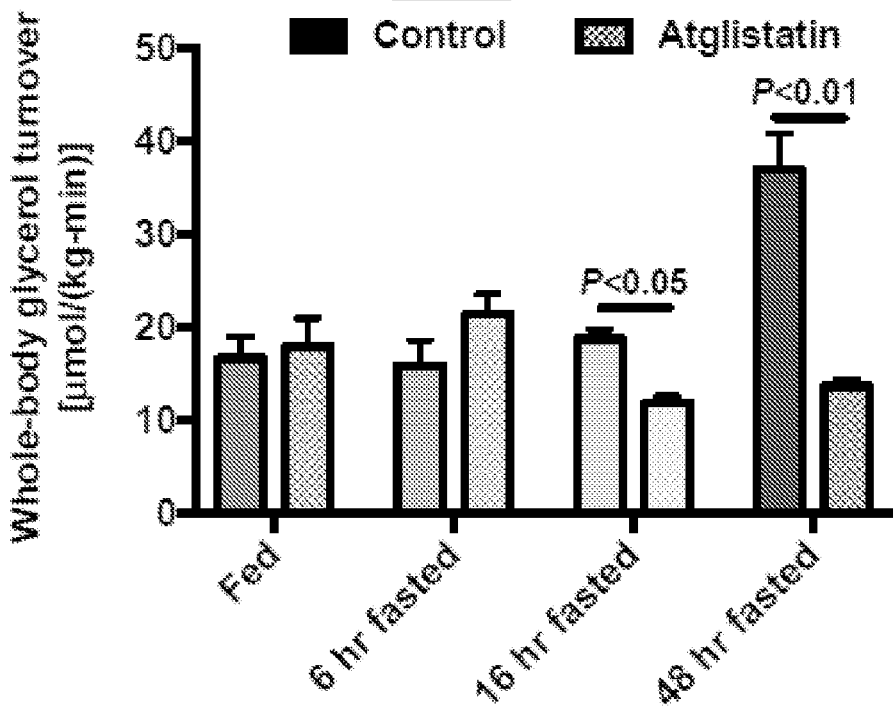
Figure 15H:
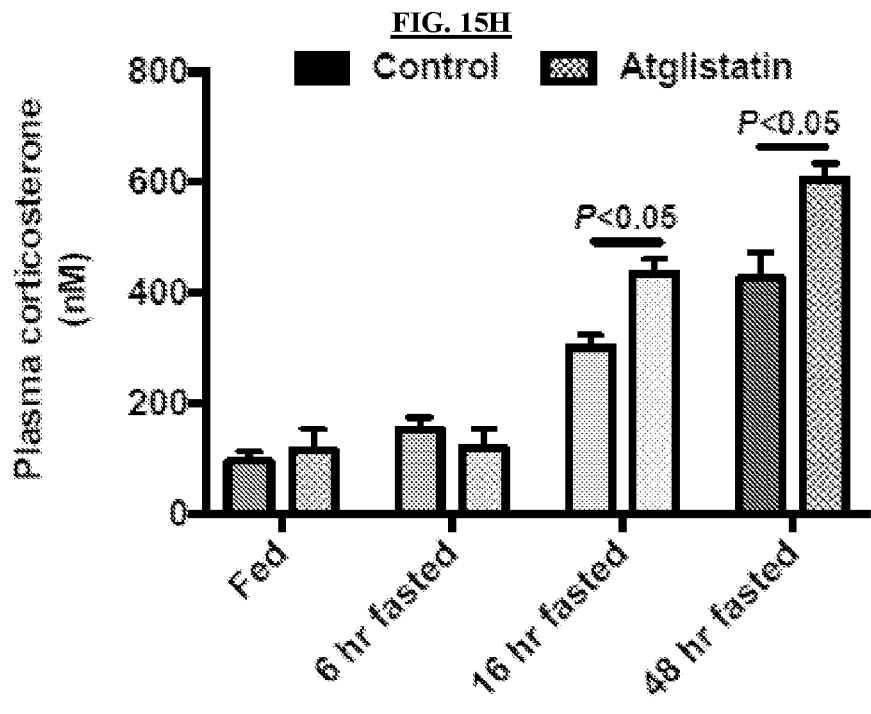
Figure 18A:
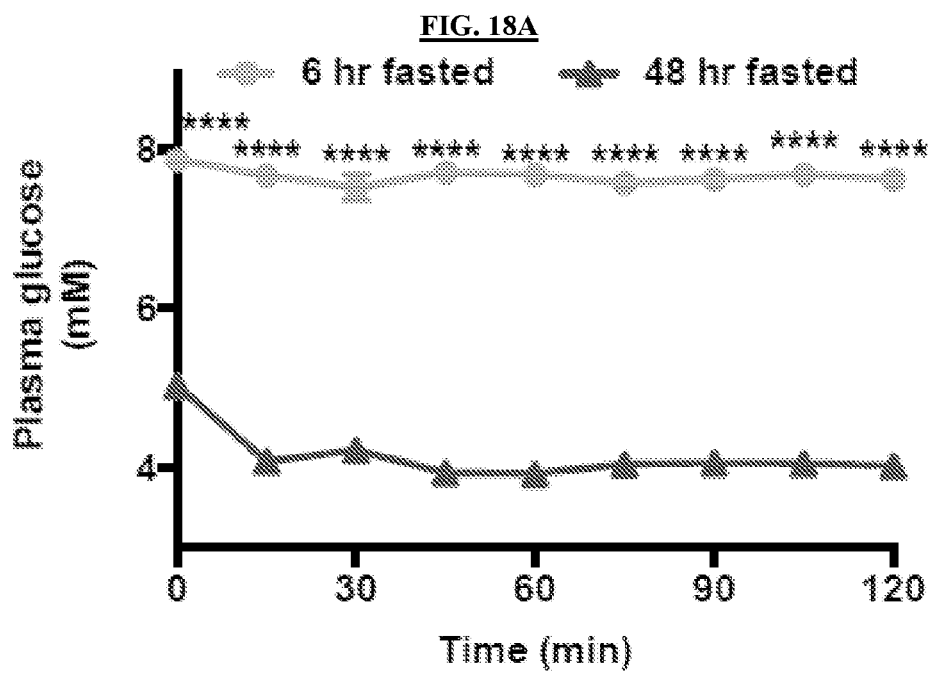
Figure 18B:
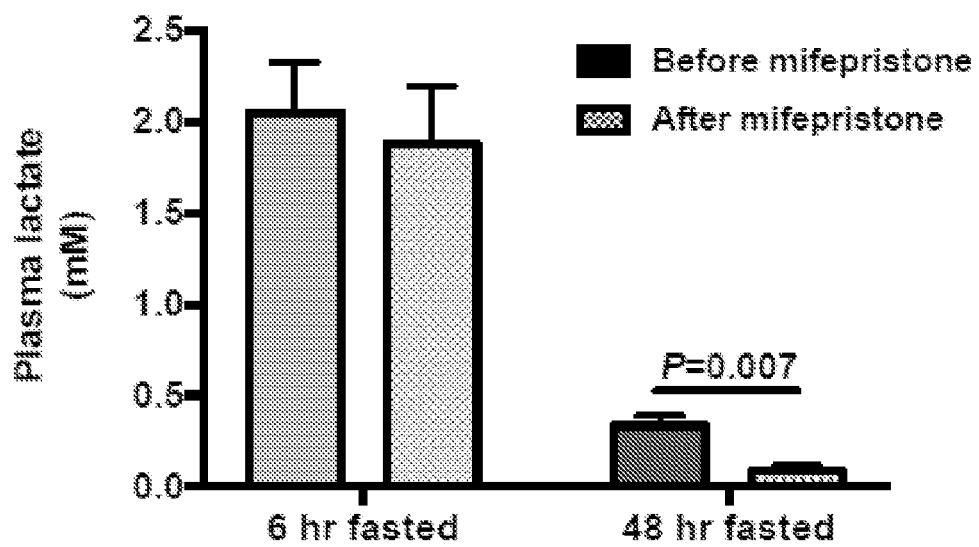
Figure 18C:
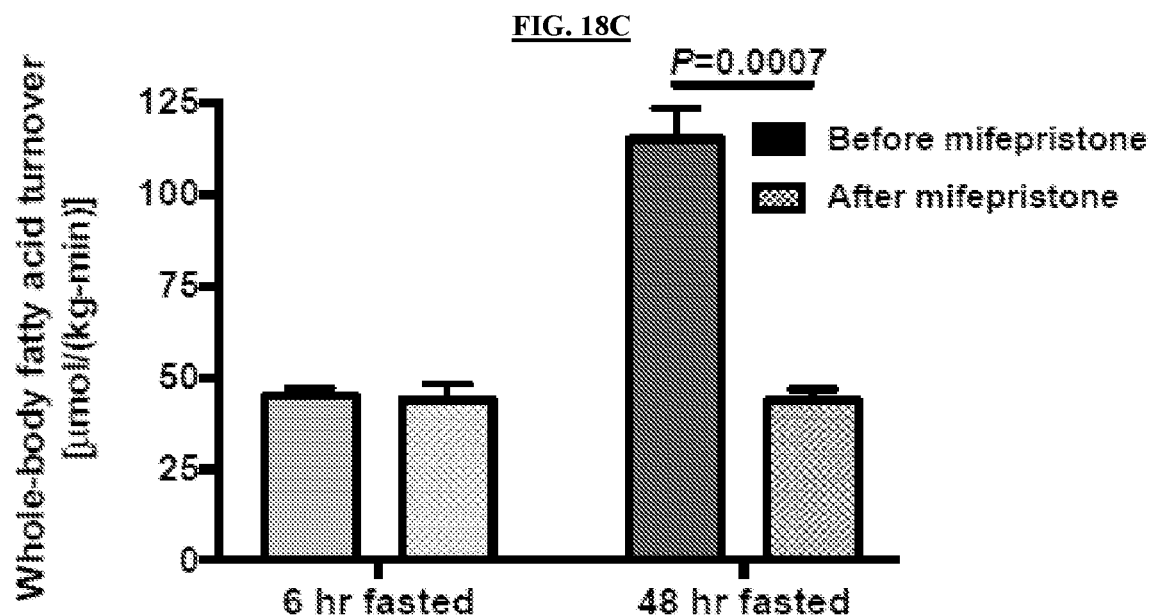
Figure 18D:
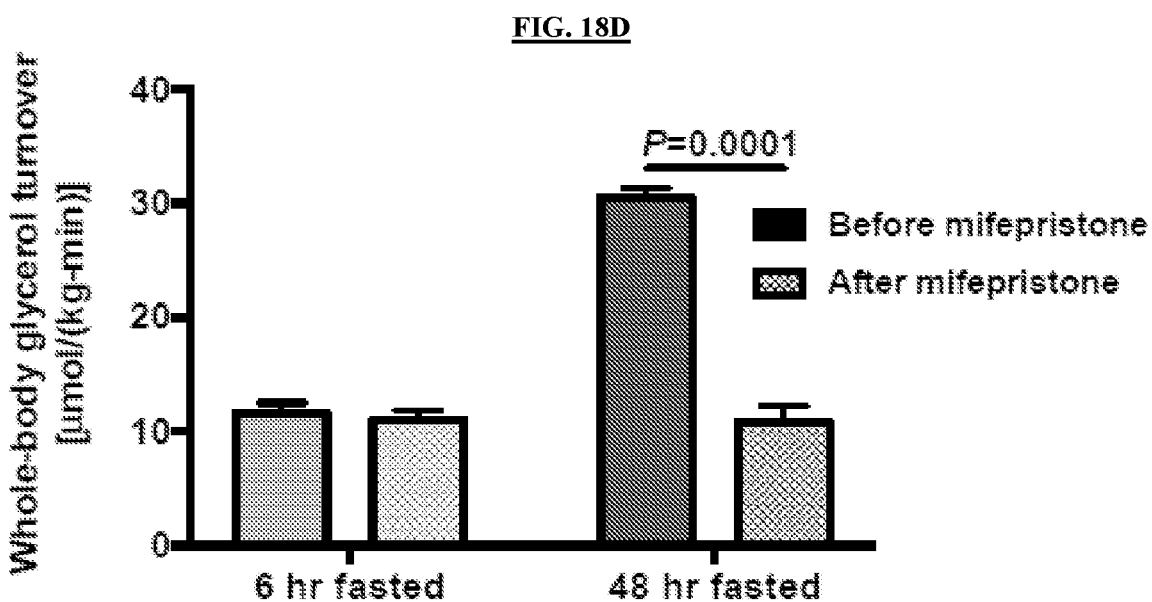
Figure 18G:
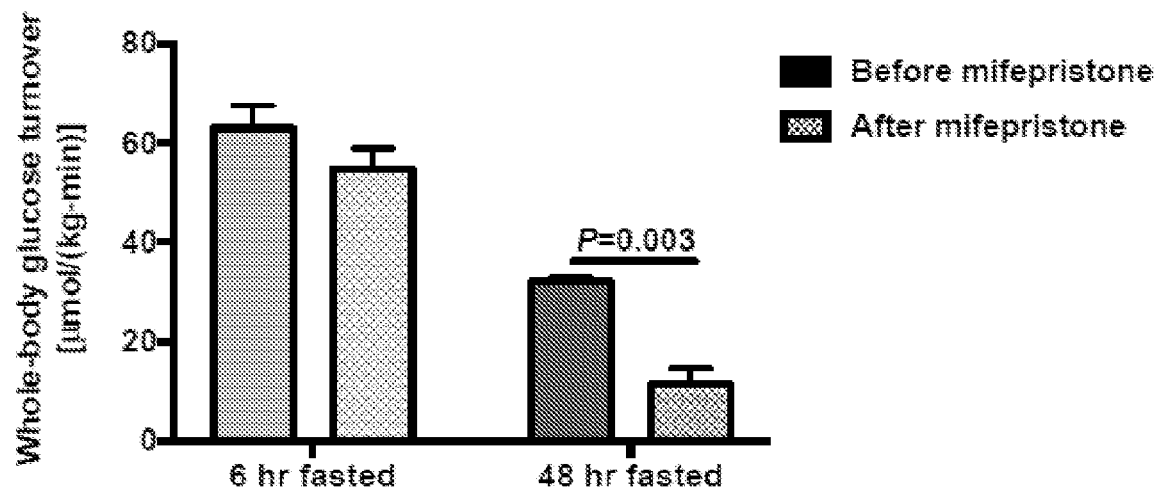
Figure 18H:
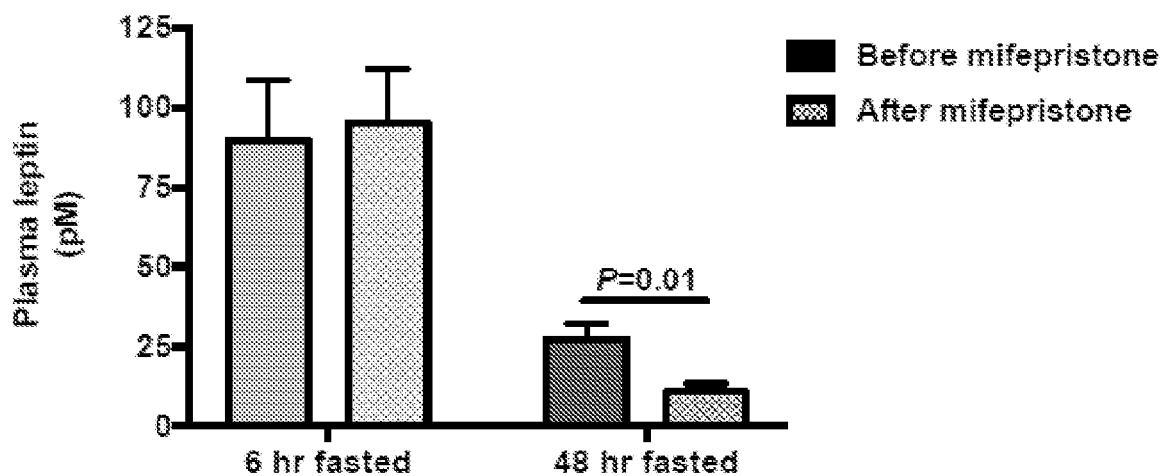
Figure 19A:
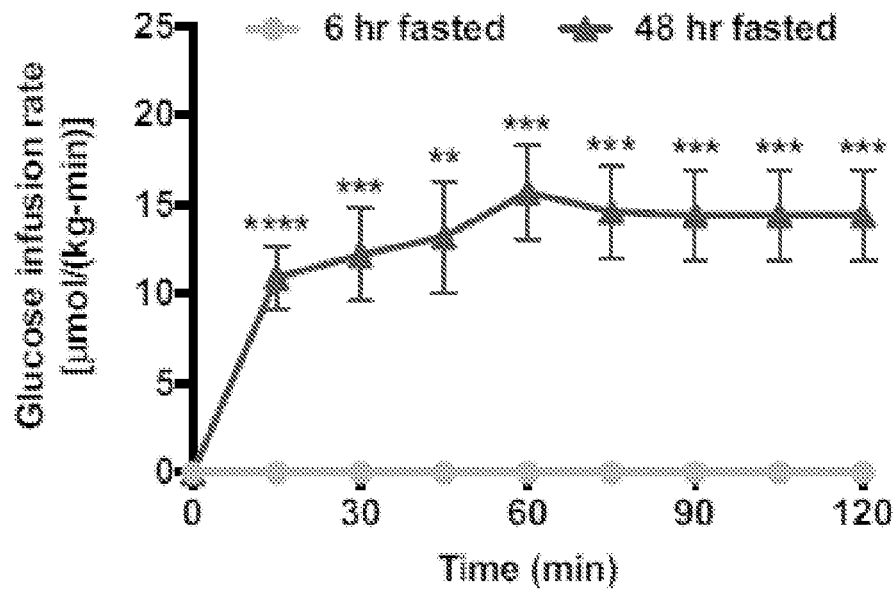
Figure 19B:
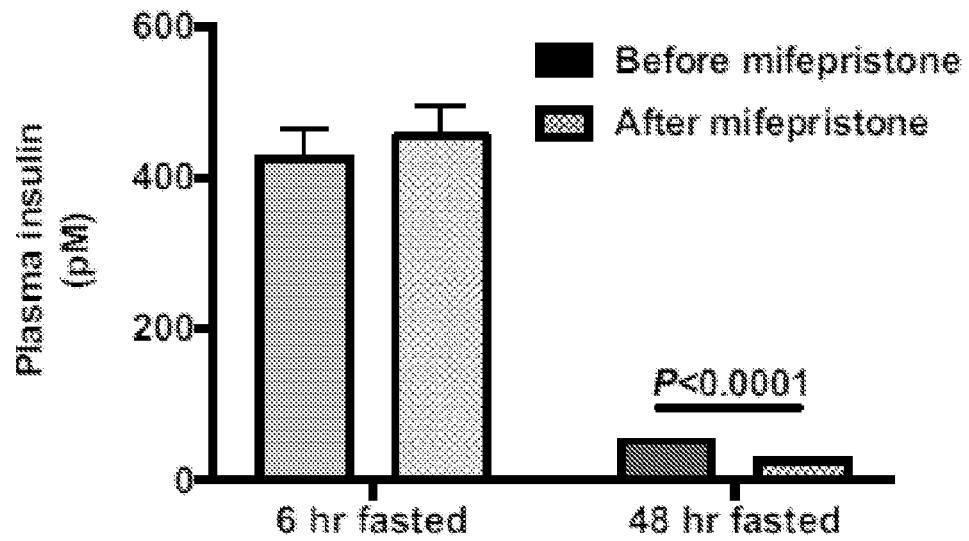
Figure 19E:
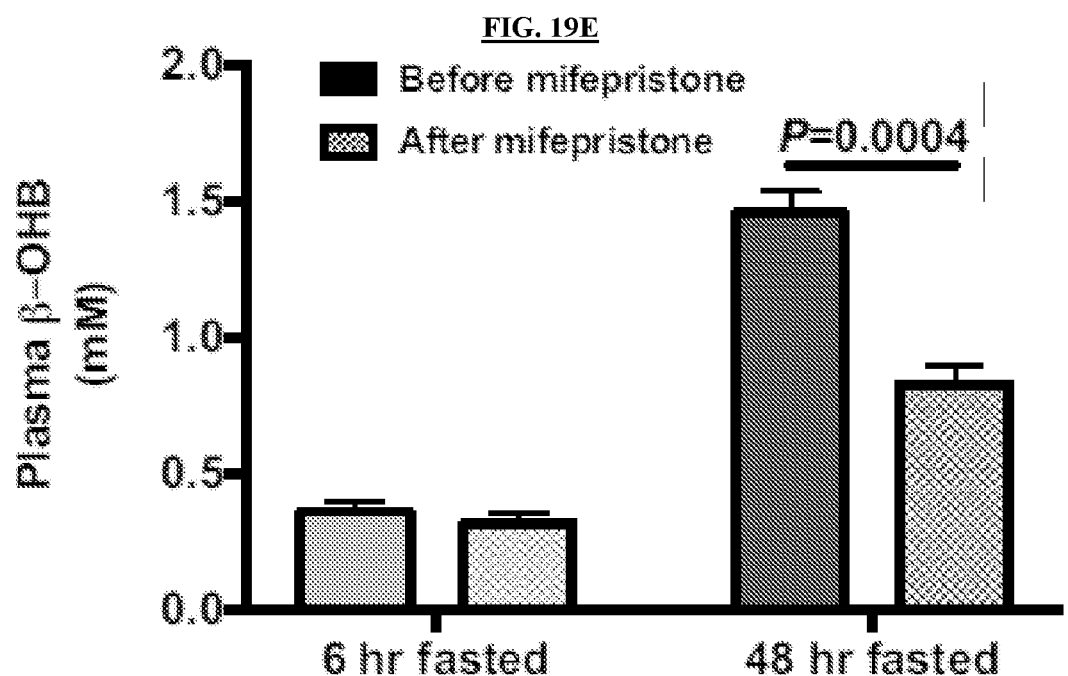
Figure 19F:
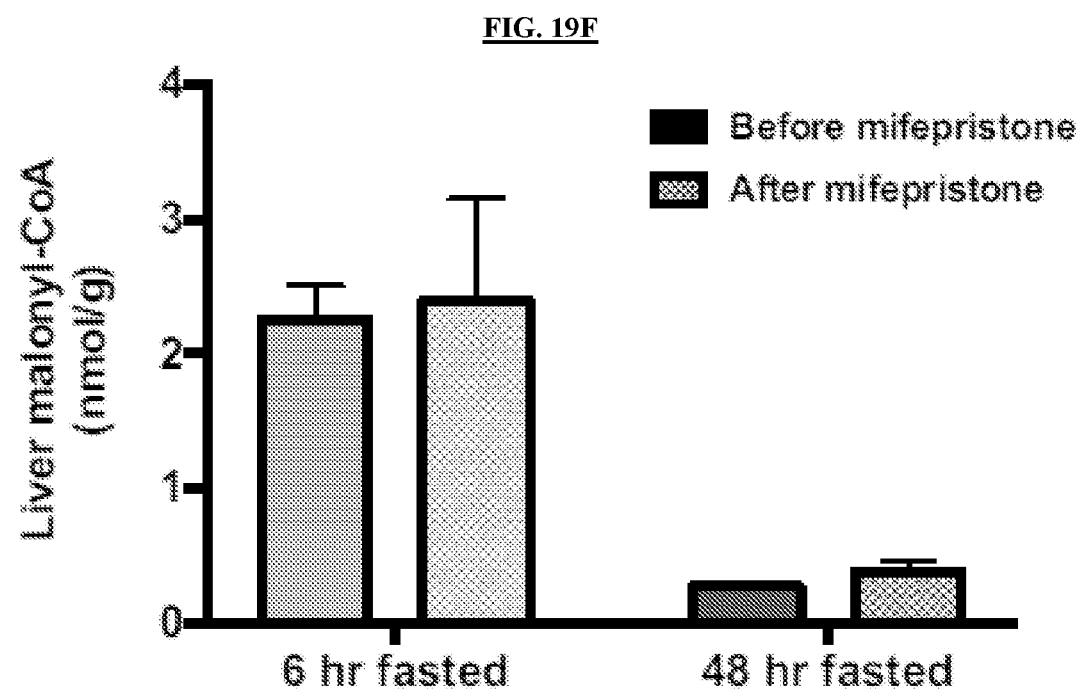
Figure 20A:
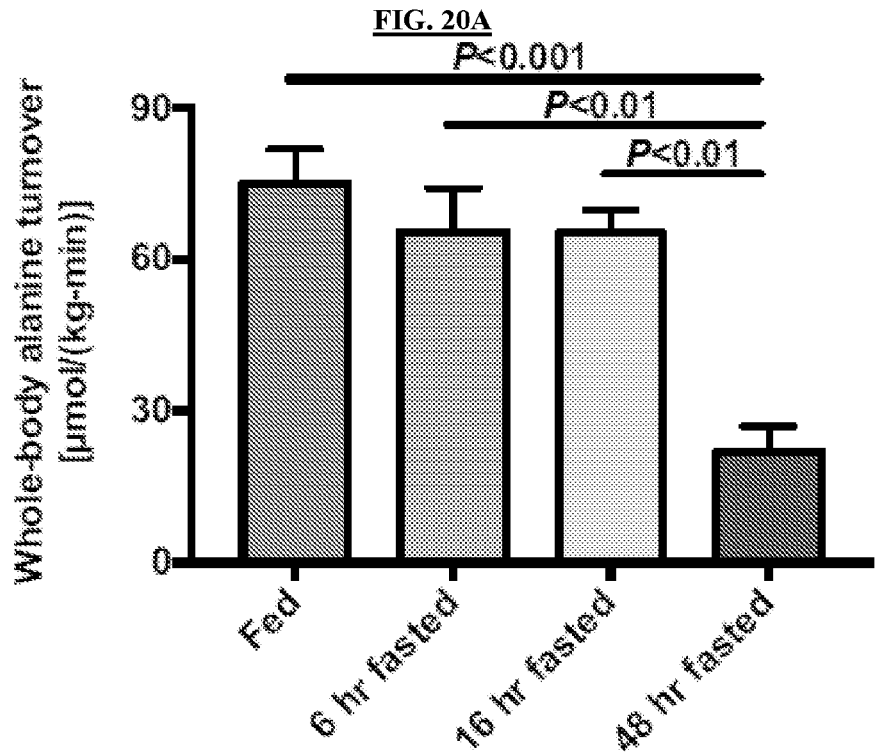
Figure 20B:
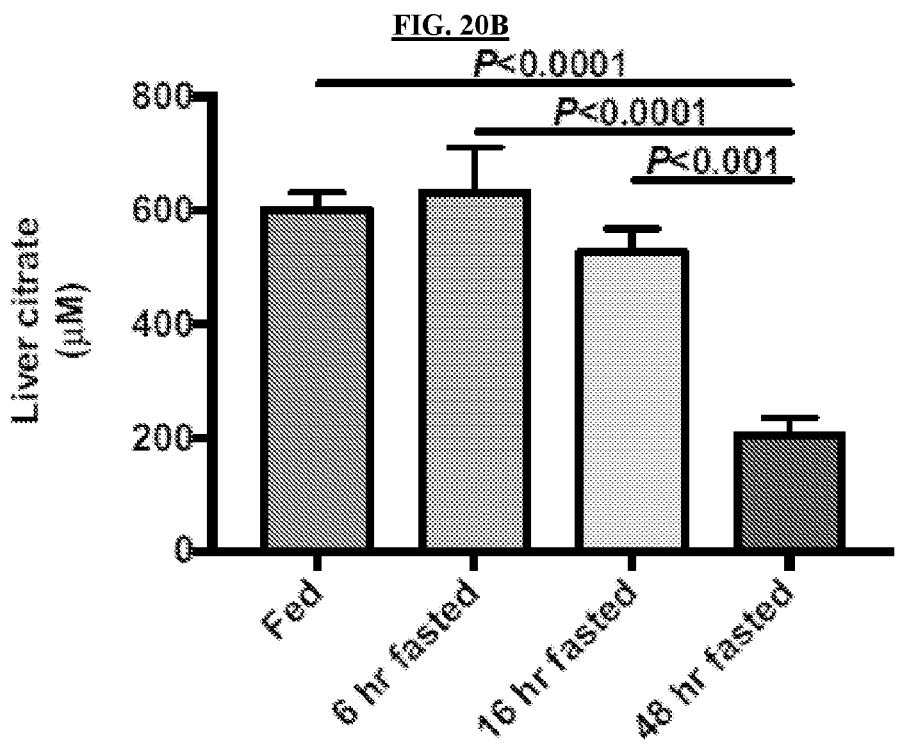
Figure 20C:
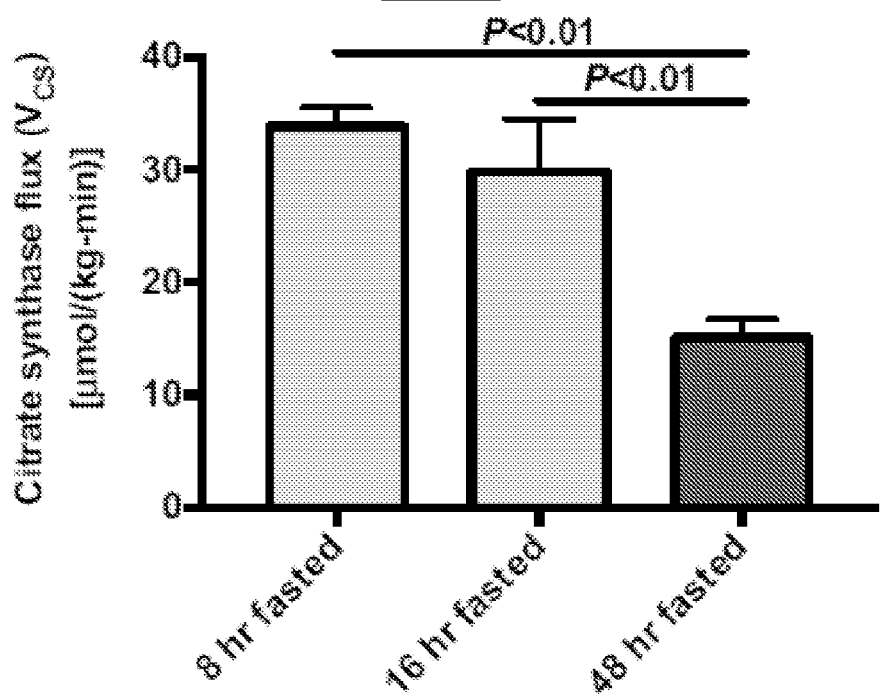
Figure 20D:
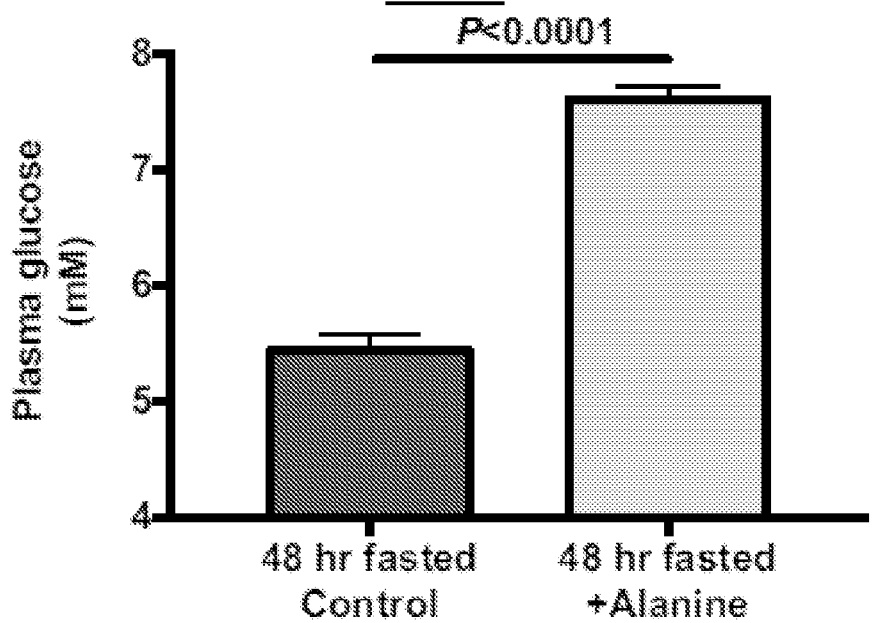
Figure 20G:
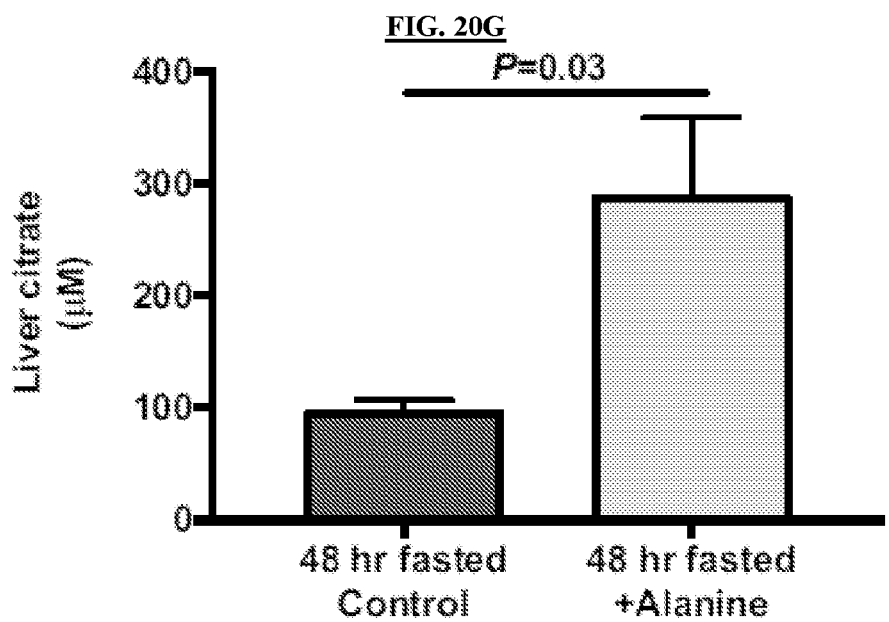
Figure 20H:
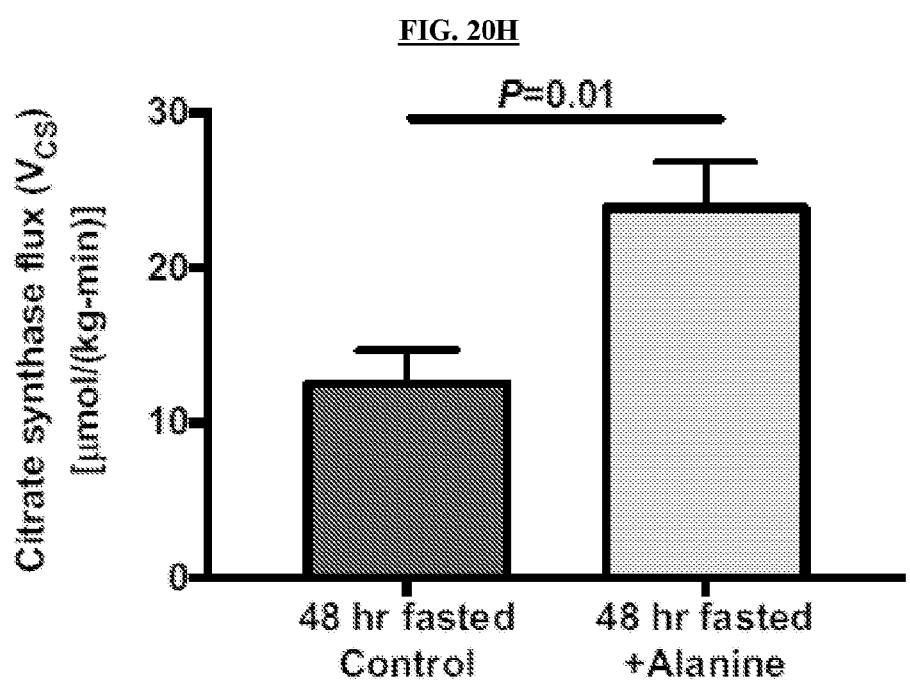

Next, to more directly assess the role of increased WAT lipolysis in the maintenance of hepatic gluconeogenesis by hepatic acetyl-CoA in starvation, rats were treated with atglistatin, a small molecule inhibitor of adipose triglyceride lipase (ATGL). Atglistatin treatment rapidly decreased plasma glucose concentrations in 16- and 48-hr fasted rats, and an infusion of glucose was required to avoid severe hypoglycemia due to suppression of WAT lipolysis and hepatic acetyl-CoA content in the latter group, despite unchanged plasma lactate, epinephrine, and norepinephrine concentrations and hepatic malonyl-CoA content (FIGS. 15A-15F and 17A-17I). As in etomoxir-treated rats, 16- and 48-hr fasted, atglistatin-treated rats exhibited reductions in plasma leptin and increases in plasma corticosterone concentration (FIGS. 15G and 15H), consistent with plasma glucose/insulin regulation of leptin release from the adipocyte. To assess whether increased plasma corticosterone concentrations were necessary to maintain euglycemia in the starved state, rats were treated with a glucocorticoid receptor antagonist, mifepristone. Despite infusion of glucose to avoid hypoglycemia provoking a counter regulatory response, mifepristone treatment decreased plasma glucose concentrations, whole-body glucose turnover, WAT lipolysis, and ketogenesis in 48-hr fasted rats, but not in recently fed rats (FIGS. 18A-18G and 19A-19F). Finally, consistent with data in rats treated with etomoxir and atglistatin, the lower plasma glucose and insulin concentrations caused by treating 48-hr fasted rats with mifepristone were associated with a 60% reduction in plasma leptin concentrations (FIG. 18H). Taken together, these data demonstrate the key role for hepatic acetyl-CoA in supporting hepatic gluconeogenesis during starvation. Furthermore, they demonstrate the critical role for hypoleptinemia-mediated increases in HPA axis activity in promoting increased WAT lipolysis and hepatic ketogenesis in this process.

Figure 21A:
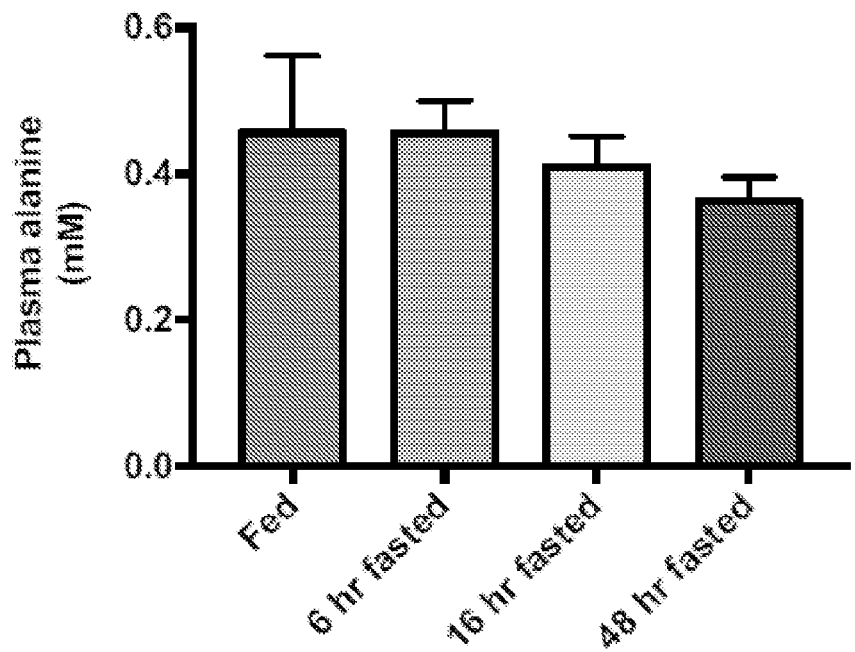
FIGS. 21A-21Y are graphs showing that reductions in glucose-alanine cycling with starvation led to suppression of hepatic glucose production and mitochondrial oxidation.
Figure 21B:
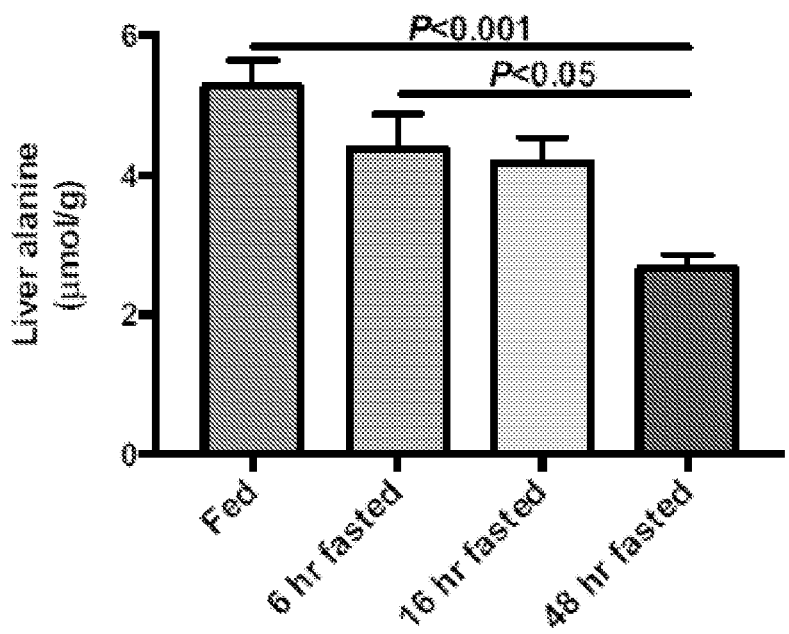
Figure 21C:
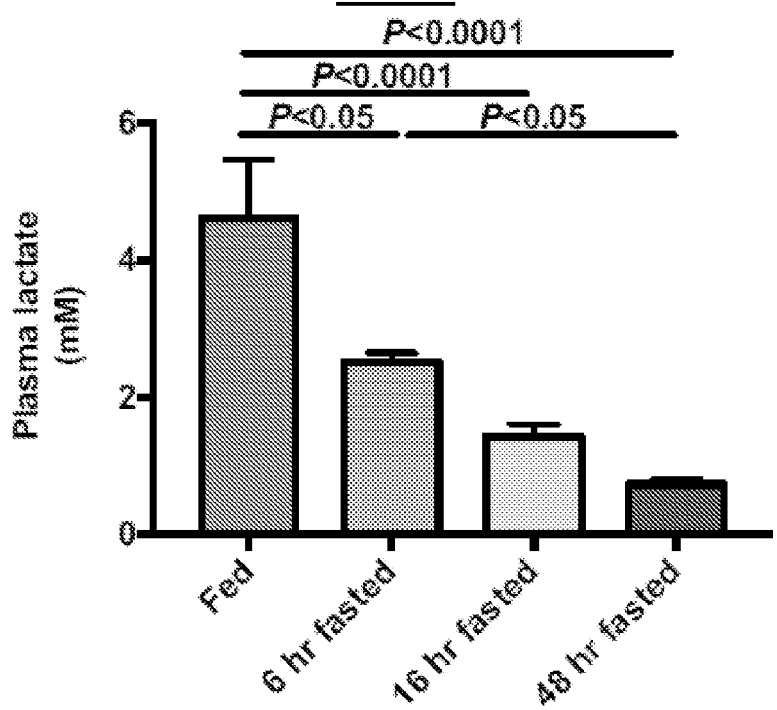
FIG. 21C is a graph showing plasma lactate concentrations.
Figure 21D:
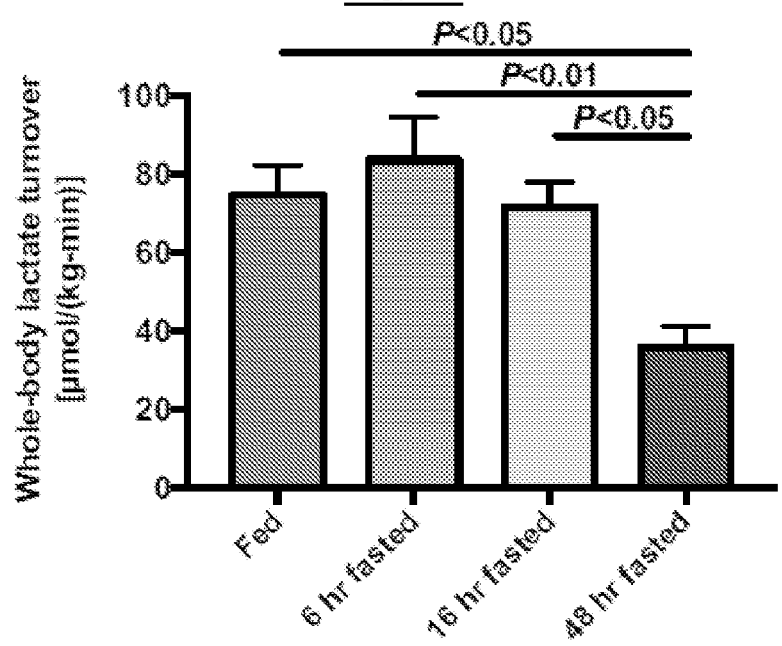
FIG. 21D is a graph showing whole-body lactate turnover.
Figure 21E:
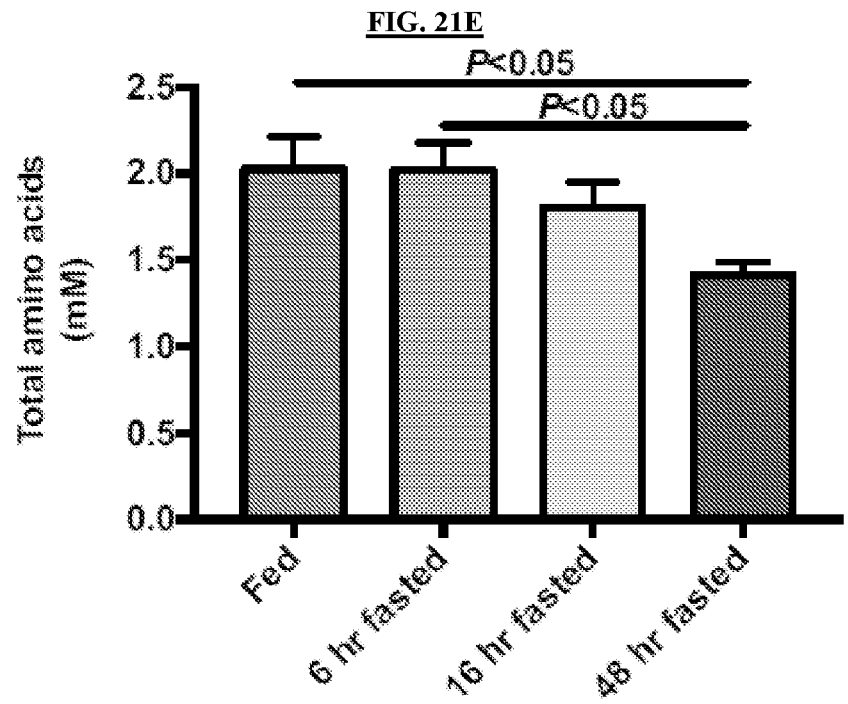
FIG. 21E is a graph showing total amino acid concentrations.
Figure 21F:
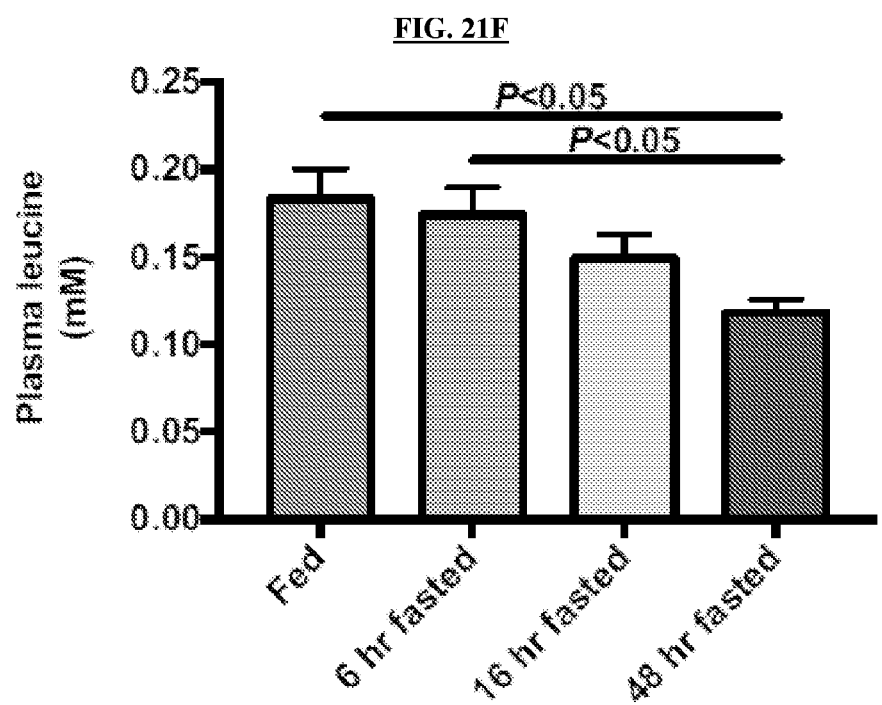
FIGS. 21F-21L are graphs showing plasma leucine (FIG. 21F), isoleucine (FIG. 21G), phenylalanine (FIG. 21H), glycine (FIG. 21I), aspartate/asparagine (FIG. 21J), glutamate/glutamine (FIG. 21K), and serine (FIG. 21L) concentrations.
Figure 21G:
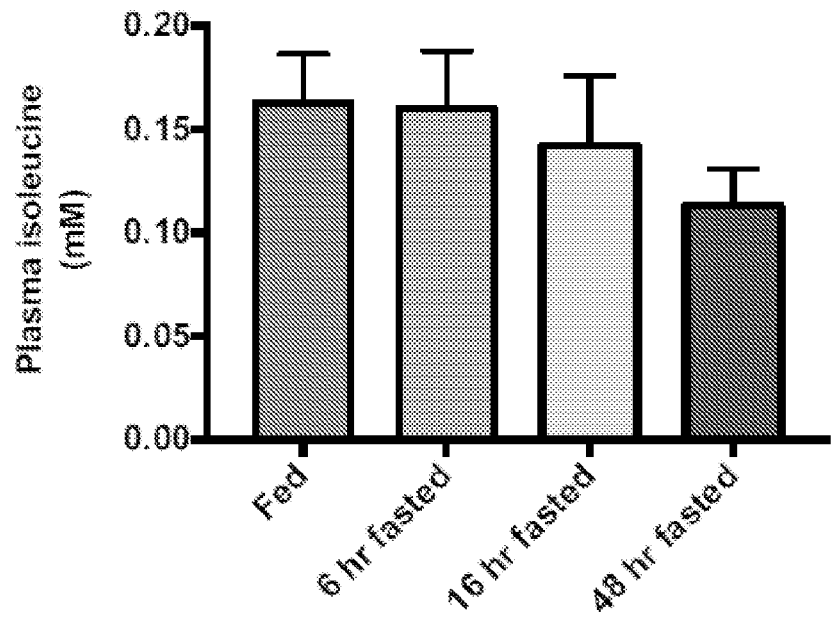
Figure 21H:
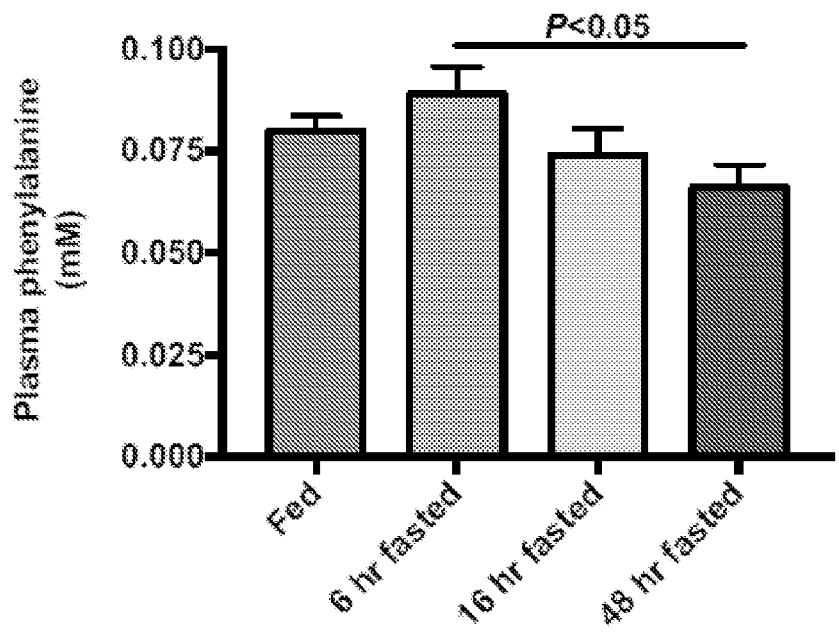
Figure 21I:
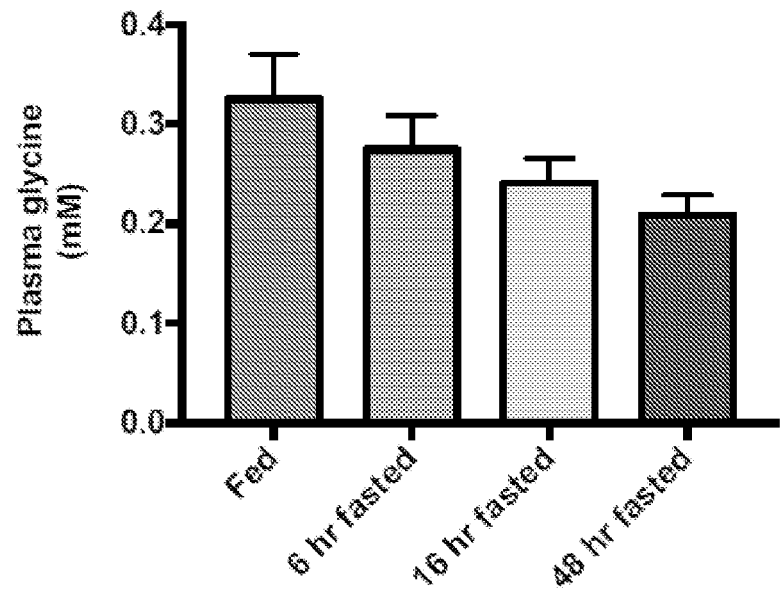
Figure 21J:
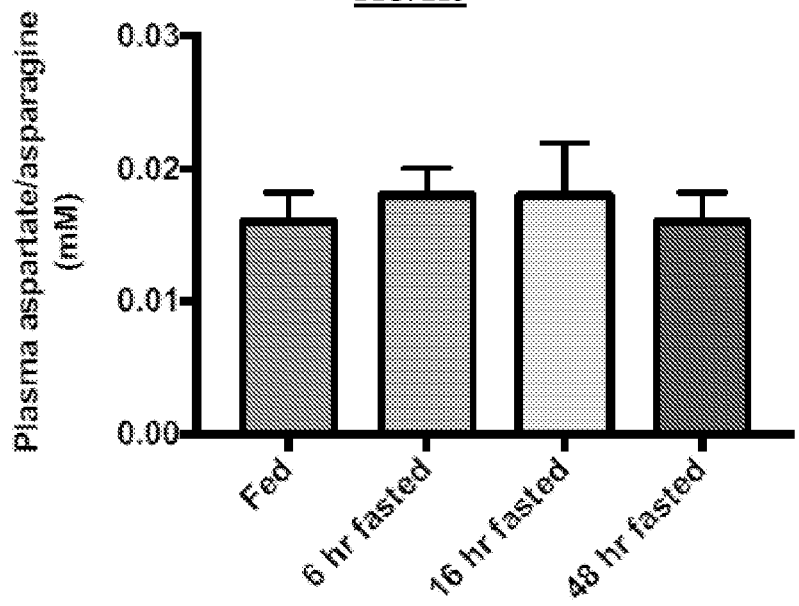
Figure 21K:
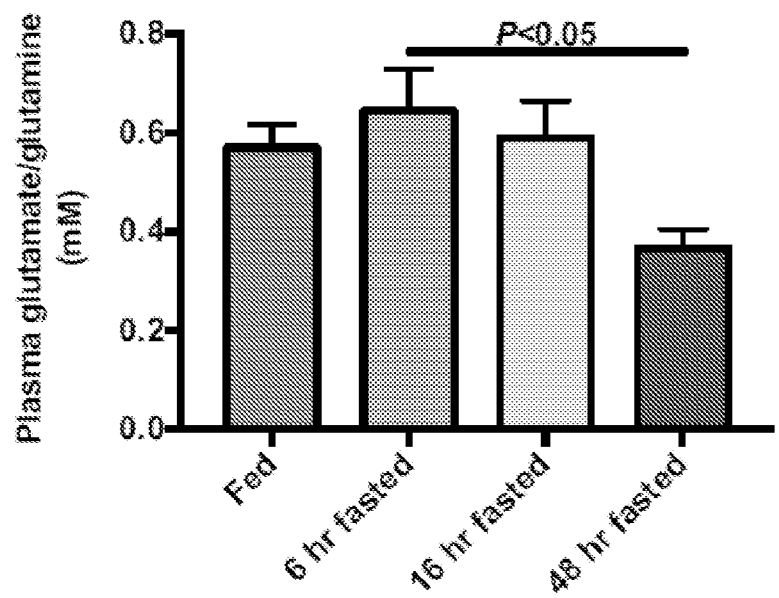
Figure 21L:
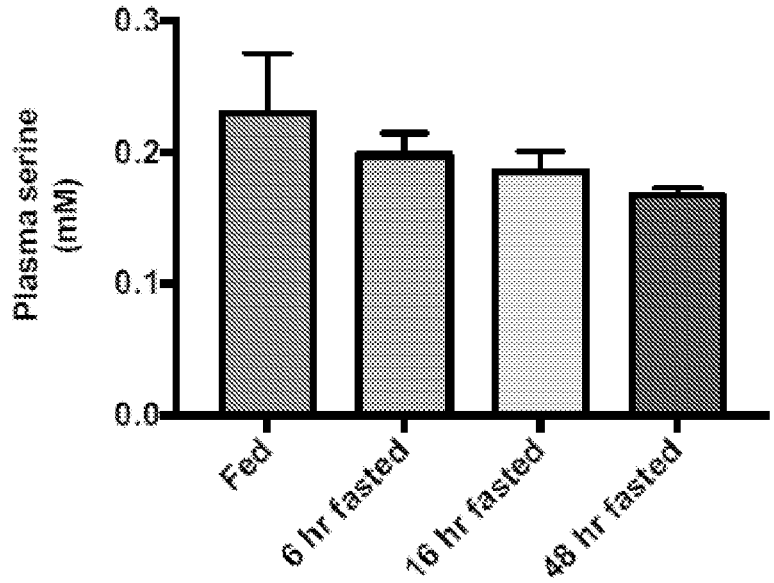
Figure 21M:
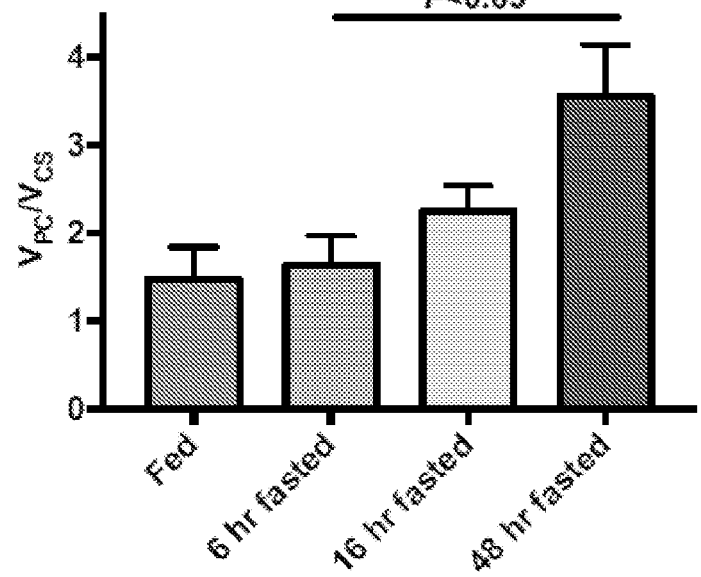
FIG. 21M is a graph showing VPC/VCS ratios at various time points.
Figure 21N:
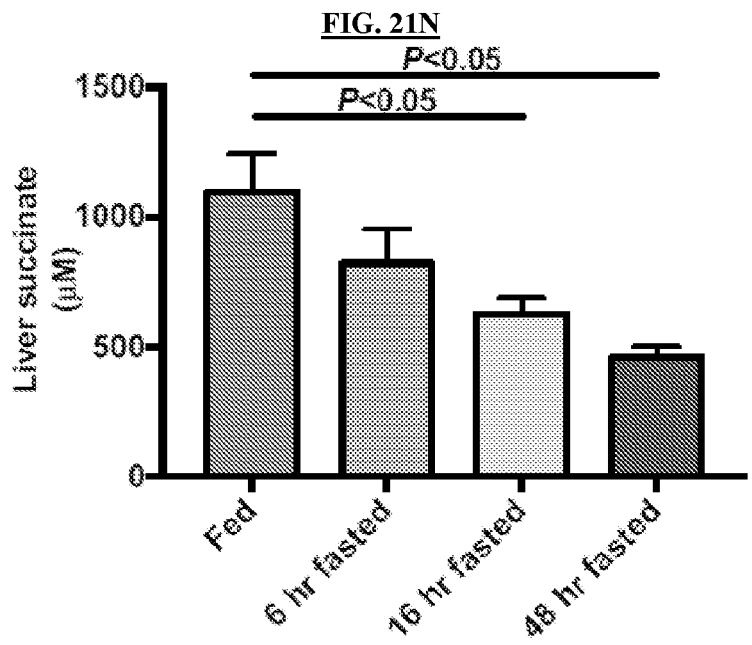
FIGS. 21N-21O are graphs showing liver succinate (FIG. 21N) and malate (FIG. 21O) concentrations.
Figure 21O:
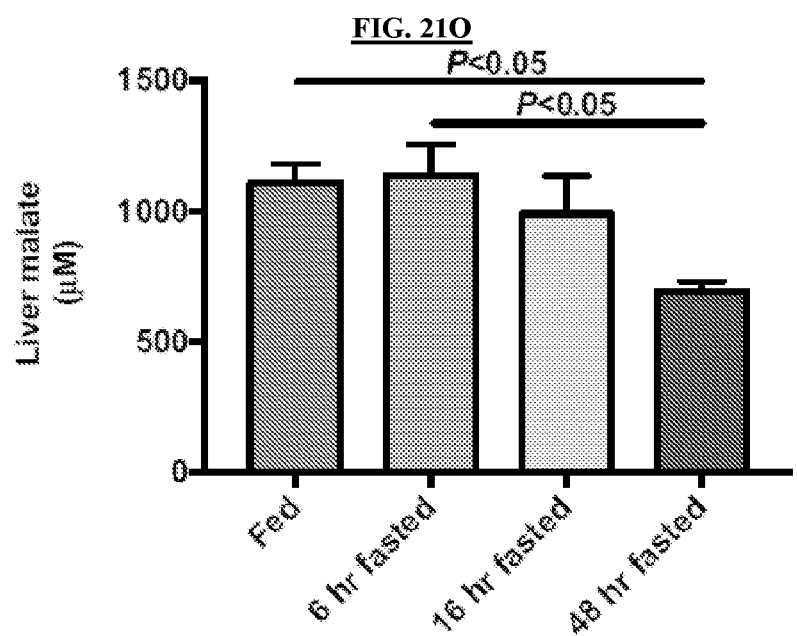
Figure 21P:
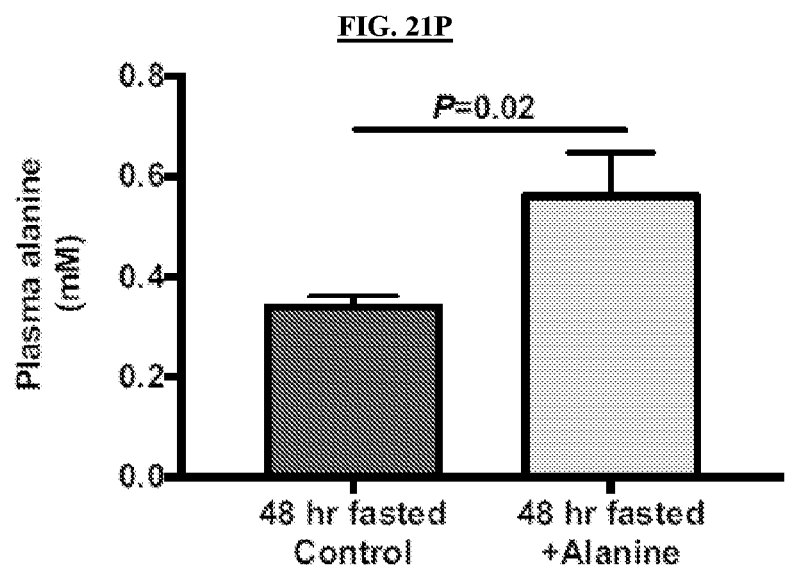
FIGS. 21P-21Q are graphs showing plasma (FIG. 21P) and liver (FIG. 21Q) alanine concentrations in 48 hr fasted rats infused with alanine (45 mmol/[kg-min]).
Figure 21Q:
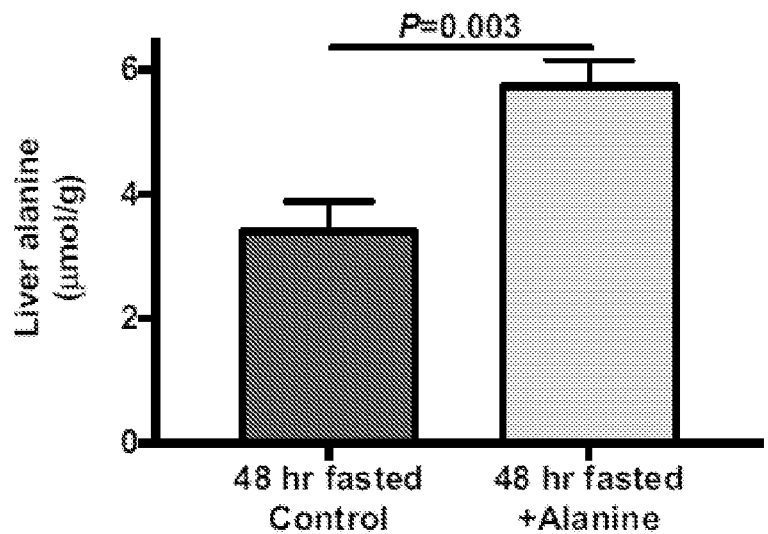
Figure 21R:
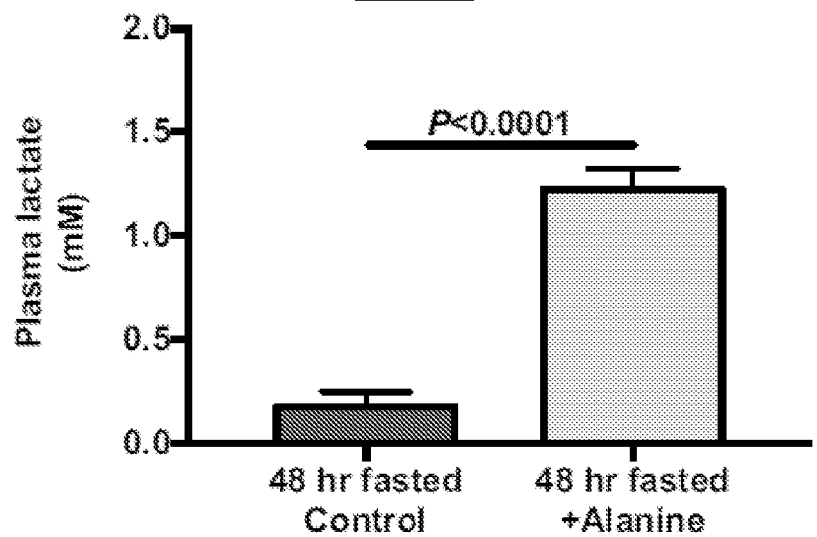
FIGS. 21R-21U are graphs showing plasma lactate (FIG. 21R), insulin (FIG. 21S), glucagon (FIG. 21T), and leptin (FIG. 21U) concentrations.
Figure 21S:
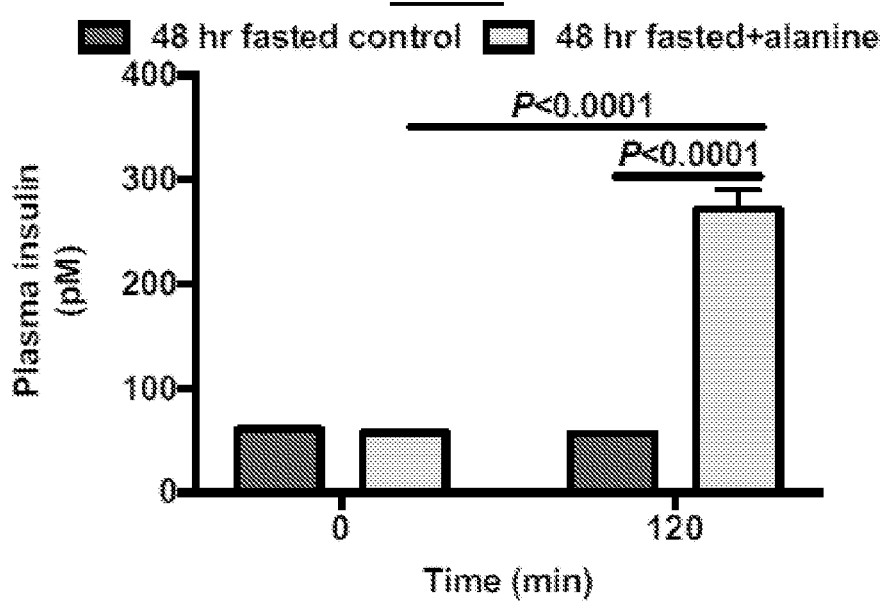
Figure 21T:
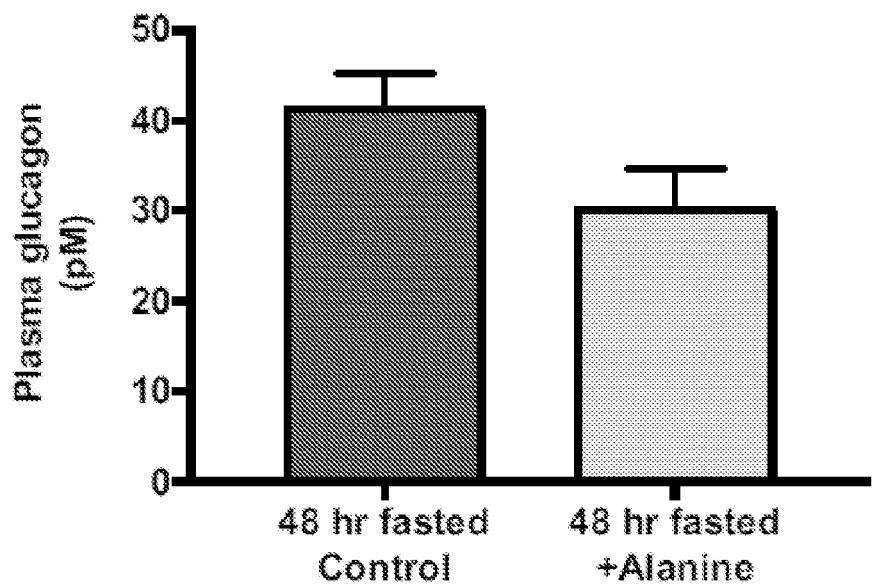
Figure 21U:
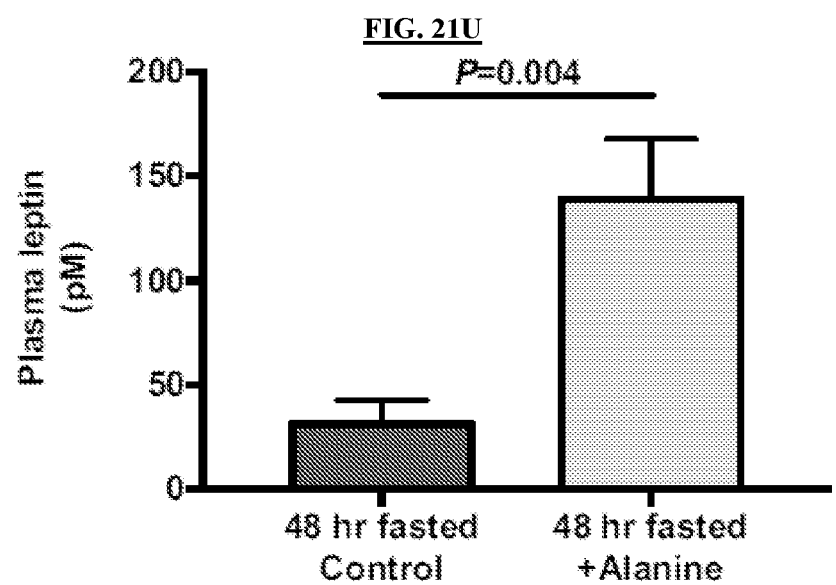
Figure 21V:
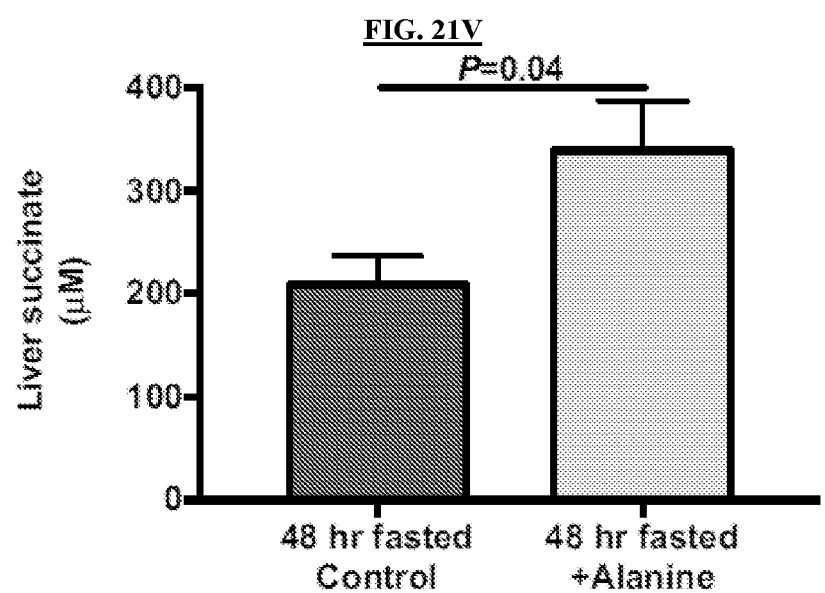
FIGS. 21V-21W are graphs showing liver succinate (FIG. 21V) and malate (FIG. 21W) concentrations.
Figure 21W:
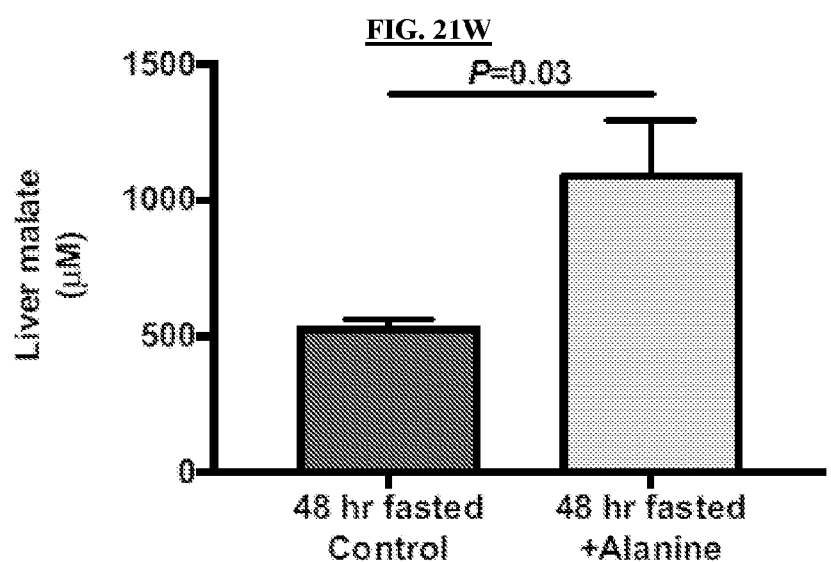
Figure 21X:
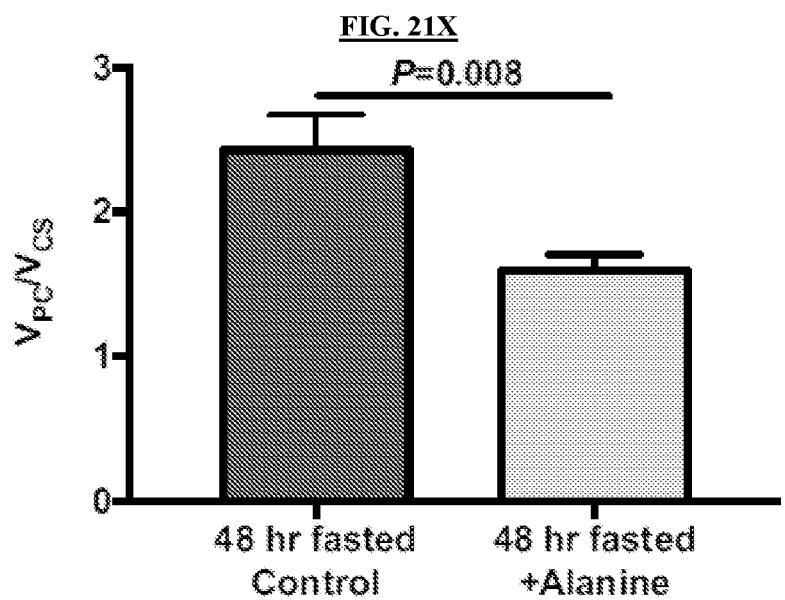
FIG. 21X is a graph comparing $V_{PC}/V_{CS}$ ratios between control rats and alanine infused rats.

Reductions in Muscle Glucose-Alanine Cycling Promote Decreased Rates of Hepatic Mitochondrial Oxidation and Gluconeogenesis in the Prolonged (48 hr) Fasted State Given the progressive increases in WAT lipolysis and hepatic acetyl-CoA content with increasing duration of the fast, it might be expected that hepatic pyruvate carboxylase flux ($V_{PC}$) would also continue to increase with an extended fast. Instead, a ~50% reduction in pyruvate carboxylase flux was observed between 16- and 48-hr fasted rats (FIG. 9B), despite a 15% increase in hepatic acetyl-CoA content during this time interval (FIG. 14D). To understand the reasons for the discordance between hepatic pyruvate carboxylase flux and hepatic acetyl-CoA content, plasma concentrations and turnover rates were assessed for the two predominant gluconeogenic substrates (lactate and alanine). 65% reductions in rates of whole-body alanine turnover, as well as 35% reductions in hepatic alanine concentrations were observed between 16- and 48-hr fasted rats, associated with smaller reductions in lactate turnover and plasma amino acid concentrations (FIGS. 20A and 21A-21L). PINTA analysis of hepatic mitochondrial oxidation rates also revealed a 50% reduction in rates of hepatic mitochondrial oxidation (VCS) associated with reductions in liver citrate, malate, and succinate concentrations. Taken together, these data suggest that prolonged (48 hr) starvation led to reductions in glucose-alanine cycling, which in turn resulted in decreased hepatic mitochondrial anaplerosis via pyruvate carboxylase, resulting in decreased rates of mitochondrial oxidation (FIGS. 20B, 20C, and 21M-21O). To test this hypothesis, alanine was infused in 48-hr fasted rats to match alanine turnover rates and hepatic alanine concentrations measured in 16-hr fasted rats (FIGS. 21P and 21Q). This intervention increased plasma glucose, insulin, and lactate concentrations; endogenous glucose production; and pyruvate carboxylase flux (VPC) associated with a 3-fold increase in plasma leptin concentrations but independent of any change in plasma glucagon (FIGS. 20D-20F and 21R-21U). In addition, normalizing alanine turnover increased liver tricarboxylic acid cycle intermediate concentrations and rates of hepatic mitochondrial oxidation (VCS) in 48-hr fasted rats independent of changes in plasma T3 concentrations (FIGS. 20G, 20H, and 21V-21Y).

Figure 22A:
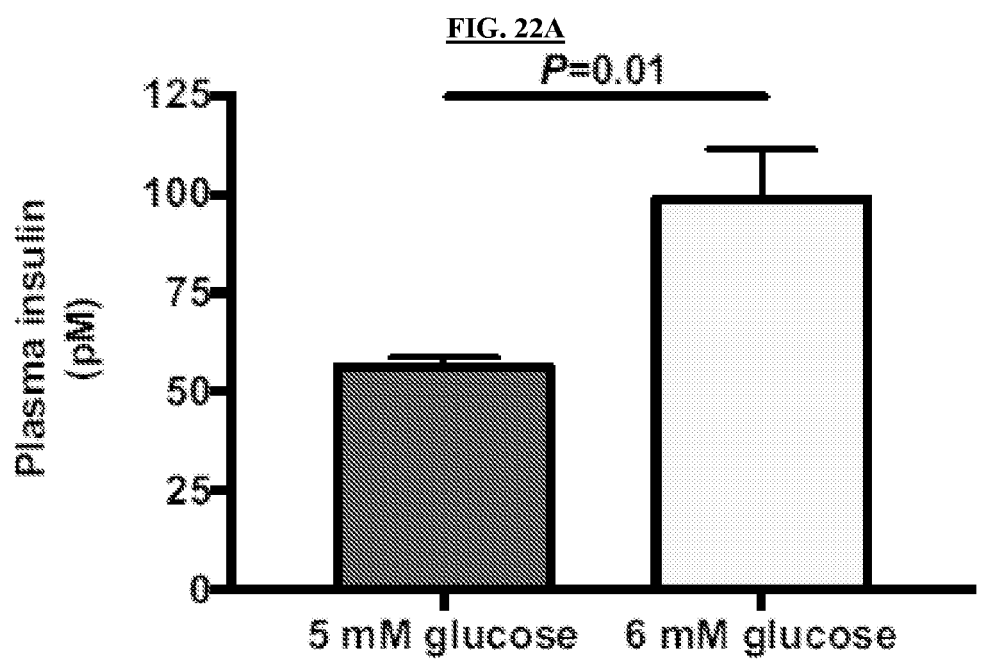
Figure 22B:
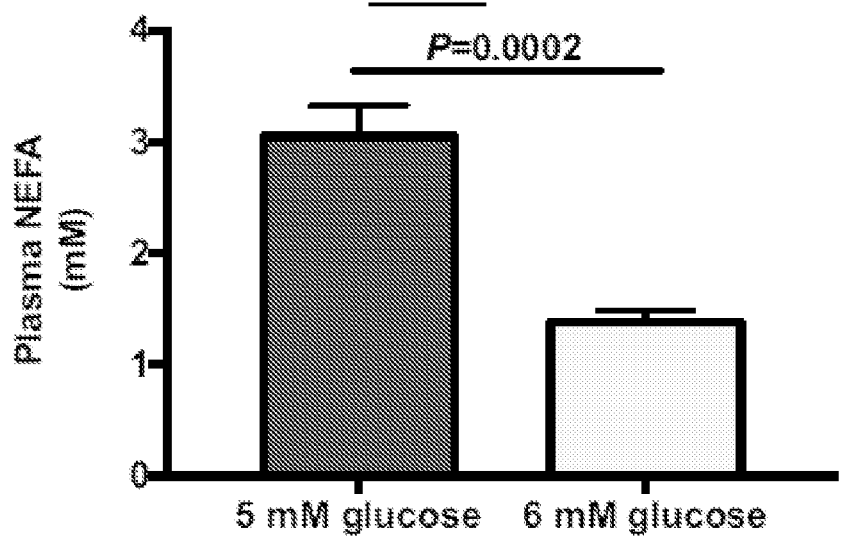
Figure 22C:
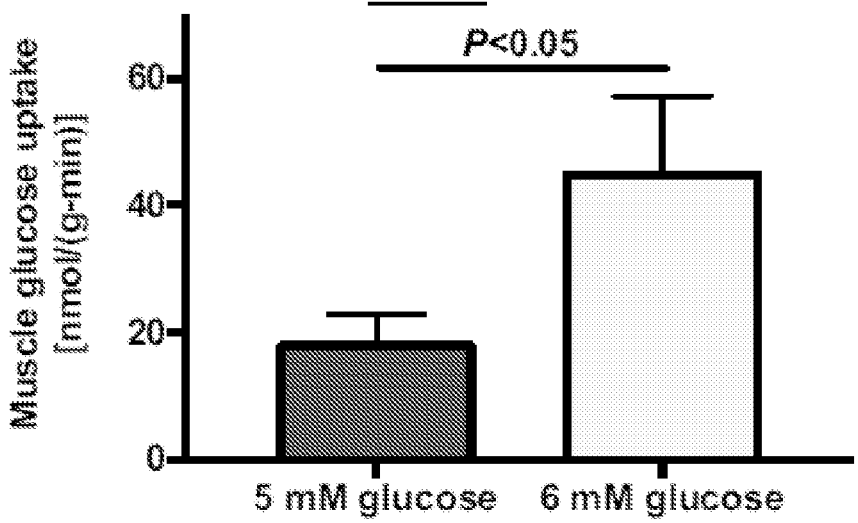

Small Reductions in Plasma Glucose (6-5 mM) Suppress Muscle Glucose-Alanine Cycling During Prolonged (48 hr) Starvation Subtle reductions in plasma glucose concentrations from 6 to 5 mM were hypothesized to promote hypoleptinemia, increase HPA axis activity, and reduce glucose-alanine cycling, as well as glucose-lactate cycling in the starved state. To test this, a low-dose glucose infusion was performed in 48-hr fasted rats to increase plasma glucose concentrations from 5 to 6 mM, as measured in 16-hr fasted rats (FIGS. 23A and 23B). This intervention increased plasma insulin concentrations by 75% and doubled plasma lactate concentrations while reducing plasma FGF-21 concentrations by 50%. Plasma NEFA concentrations and rates of endogenous glucose production were also reduced by 30-50% (FIGS. 22A, 22B, and 23C-23E). Increasing plasma glucose from 5 to 6 mM doubled both glucose uptake into skeletal muscle and whole-body alanine turnover (FIGS. 22C and 22D), increasing the latter to rates similar to those observed in 16-hr fasted rats. In addition, 48-hr fasted rats with plasma glucose concentrations ~6 mM exhibited a 2-fold increase in WAT glucose uptake as compared to 48-hr fasted rats with plasma glucose ~5 mM, doubling plasma leptin concentrations and suppressing HPA axis activity as reflected by 50%-60% reductions in plasma ACTH and corticosterone concentrations (FIGS. 22E-22H). Similarly, we found that treatment of short-term fasted rats (8 and 16 hr) with an inhibitor of glycogen phosphorylase resulted in hypoleptinemia and increased HPA axis activity, as well as increased rates of WAT lipolysis and decreased rates of alanine turnover (FIGS. 22I, 22J, and 23F-23J).

Selected Discussion

To prolong survival during an extended fast, mammals must shift from a primary reliance upon carbohydrate metabolism to a primary reliance upon fat and ketone metabolism in order to maintain adequate substrate supply to the brain, heart, and other organs, thus preserving essential protein stores that would otherwise be catabolized to support gluconeogenesis. While insulin and, to a lesser extent, glucagon have long been thought to be the major orchestrators of this transition from glucose to fat/ketone metabolism, the results presented herein demonstrate a leptin-mediated glucose-fatty acid cycle that is essential to support this process.

Consistent with previous in vivo $^{13}C$ nuclear magnetic resonance studies of hepatic glycogen metabolism in humans, the fraction of glucose production from hepatic glycogenolysis decreased over the course of a 48-hr fast in lean rats, while gluconeogenesis rates remained relatively constant until rats reached a state of prolonged starvation at 48 hr, whereupon gluconeogenic flux decreases by ~50%. Similar to data from fasting humans, hepatic glycogen concentrations in rats followed a pattern of exponential decay during fasting (FIG. 10D), and the reduction in rates of net hepatic glycogenolysis was the major determinant of the reduction in the rate of endogenous glucose production and plasma glucose concentration observed during a prolonged fast (FIGS. 9A-9C). To specifically test the physiologic impact of reductions in rates of hepatic glycogenolysis on leptin secretion, HPA axis activity, and WAT lipolysis, rats were treated with a small molecule inhibitor of glycogen phosphorylase. Consistent with a key role for hepatic glycogenolysis as the major determinant of endogenous glucose production and fasting plasma glucose concentrations in the early stages (0 to 16 hr) of the fast, 8- and 16-hr fasted rats treated with the glycogen phosphorylase inhibitor manifested rates of endogenous glucose production that were reduced by 60% and 30%, respectively (FIG. 9F). In contrast, 48-hr fasted rats treated with the glycogen phosphorylase inhibitor exhibited no difference in rates of endogenous glucose production, consistent with rates of net hepatic glycogenolysis being negligible by 48 hr of fasting.

In order to examine the ability of reductions in hepatic glycogenolysis to drive the HPA activation observed in the starved state, plasma lipolytic hormone concentrations and WAT lipolysis were assessed in rats treated with an inhibitor of glycogen phosphorylase. A reduction in plasma leptin concentrations and increases in plasma corticosterone concentrations and WAT lipolysis were observed, bringing each parameter to concentrations measured in 48-hr fasted rats despite unchanged plasma catecholamine concentrations in short-term fasted rats treated with the glycogen phosphorylase inhibitor (FIGS. 9G, 9H, 22J, 11S, 11U, 11V, and 23F-23J). These results suggest that hypoleptinemia-driven HPA axis activation could promote increased hepatic gluconeogenic flux by increasing WAT lipolysis, resulting in increased fatty acid delivery to liver and hepatic acetyl-CoA content to maintain euglycemia during prolonged (≥16 hr) fasting. Consistent with this hypothesis, both WAT lipolysis and hepatic acetyl-CoA content increased with increasing duration of the fast. Interestingly, these increases in WAT lipolysis were also associated with the development of severe hepatic steatosis, increases in hepatic DAG content, hepatic PKCε activation, and impaired percent suppression of endogenous glucose production during a hyperinsulinemic-euglycemic clamp (FIGS. 10K-10P). These results are consistent with prior studies demonstrating that increased fatty acid delivery to the liver can promote increased hepatic esterification and hepatic TAG synthesis in an insulin-independent fashion, as well as a causal role for hepatic DAG activation of PKCε in hepatic insulin resistance, through increased insulin receptor kinase threonine 1160 (murine 1150) phosphorylation.

In contrast to ectopic lipid content, which increased progressively through the fast, hepatic malonyl-CoA decreased between 6 and 16 hr of the fast, facilitating mitochondrial b-oxidation by reducing inhibition of CPT-1. To further examine the potential role of increasing hepatic acetyl-CoA concentrations in the maintenance of hepatic gluconeogenesis and endogenous glucose production, we treated rats with two agents to directly modulate hepatic acetyl-CoA content: ATGL inhibitor atglistatin and CPT-1 inhibitor etomoxir. Despite different mechanisms of action, both agents suppressed hepatic acetyl-CoA content, hepatic gluconeogenesis, and plasma glucose and insulin concentrations in 16- to 48-hr fasted rats, thus demonstrating a critical role for hepatic acetyl-CoA content in the maintenance of hepatic gluconeogenesis during starvation.

Taken together, these data challenge the canonical view of the primacy of insulinopenia-mediated transcriptional and/or translational regulation of gluconeogenic enzymes in increasing hepatic gluconeogenesis and maintaining euglycemia in starvation. Although PEPCK protein expression increased progressively during the fast, hepatic gluconeogenesis from oxaloacetate was reduced by 50% from 16 to 48 hr due to substrate limitation (FIGS. 9B, 20E, and 20F) in the setting of unchanged pyruvate carboxylase protein expression. These data raise the question of whether insulinopenia per se promotes WAT lipolysis and increases in hepatic acetyl-CoA content in the starved state or whether other factors such as HPA axis activation (FIG. 9D) are also required.

To answer that question, mifepristone, a selective glucocorticoid receptor antagonist, was administered to rats fasted for 6 and 48 hr. Although mifepristone had no impact on WAT lipolysis, whole body glucose turnover, or plasma glucose or insulin concentrations in recently fed rats (6 hr), inhibition of glucocorticoid action markedly suppressed each of these parameters, necessitating glucose infusion to avoid severe hypoglycemia and counter-regulation in prolonged (48 hr) fasted rats (FIG. 18). Because mifepristone treatment suppressed WAT lipolysis in the setting of reductions in plasma insulin concentrations, these data suggest that severe insulinopenia per se is not sufficient to promote increased WAT lipolysis and hepatic gluconeogenesis in starved rats. To further test the role of HPA axis activation and, specifically, the role of hypoleptinemia in driving this process, leptin was infused in a stepwise fashion to increase plasma leptin concentrations in 48-hr fasted rats to: (1) physiologic concentrations typical of overnight-fasted, chow-fed rats (~60 pM), (2) modestly elevated concentrations similar to those of high-fat fed (HFD) rats (~150 pM) (FIG. 11K), and (3) supraphysiologic concentrations (~1300 pM) similar to or lower than those measured in previous systemic leptin infusion studies in the literature. This study demonstrated that physiologic leptin replacement suppressed HPA axis activity, WAT lipolysis, hepatic acetyl-CoA content, and rates of hepatic gluconeogenesis in 48-hr fasted rats without altering plasma insulin concentrations, thereby demonstrating that insulinopenia per se is not sufficient to increase WAT lipolysis, hepatic acetyl-CoA content, and hepatic gluconeogenesis during starvation.

To further examine the role of insulin in mediating leptin's effect on WAT lipolysis, leptin dose-response studies were performed in a severely insulinopenic streptoztocin-induced rat model of T1D that is also severely leptinopenic. These data demonstrate the impact of the absence of leptin: with plasma leptin concentrations only ~12 pM (92% lower than fed rats) and severe insulinopenia (99% lower than fed rats), both WAT lipolysis and endogenous glucose production rates were markedly increased. Physiologic leptin replacement suppressed endogenous glucose production and WAT lipolysis in T1D rats (FIGS. 13J-13U), consistent with previous studies. However, in both fasting normal control rats and T1D rats, supraphysiologic leptin concentrations promoted increased catecholamine release, increasing WAT lipolysis and abrogating leptin's effect to lower rates of endogenous glucose production and plasma glucose concentrations. These data are consistent with prior studies demonstrating that leptin activates catecholamine synthesis, catecholamine signaling, and energy expenditure. Further, the ability of leptin to stimulate the sympathetic nervous system, WAT lipolysis, and hepatic glucose production at plasma concentrations ≥150 pM may explain the failure of previous studies to observe an effect of leptin to reduce hyperglycemia in fasted insulinopenic diabetic rodents through suppression of HPA axis activity. Without intending to be limited to any particular theory, hypoleptinemia-induced activation of HPA axis activity may not occur universally in starvation as was observed in 4-week HFD obese rats (FIGS. 11K-11N). In contrast to regular chow-fed lean control rats, HFD obese hyperleptinemic rats did not manifest reductions in plasma leptin concentrations and increases in HPA activity during 48 hr of fasting (FIGS. 11K-11N). This may explain why starvation-induced reductions in plasma leptin concentrations and increases in HPA activity have not always been observed in human studies. In contrast to young lean rodents, which have minimal fat mass after a 48-hr fast, most normal weight human subjects will still have substantial fat mass even after several days of starvation, which would not be expected to decrease plasma leptin concentrations to the critical threshold that maybe required to activate the HPA axis. In contrast, patients with anorexia nervosa often develop severe hypoleptinemia (due to depleted fat stores) which is associated with activation of the HPA axis and hypercortisolemia, suggesting that under conditions of severe depletion of adipose tissue mass, leptin may decrease sufficiently with starvation to activate HPA axis driven WAT lipolysis. In contrast, in overweight subjects or those undergoing caloric restriction instead of fasting in whom leptin may not be reduced sufficiently to produce increased HPA activity, this mechanism may not be as relevant or may take a longer time to occur in order to deplete the larger fat mass in these overweight/obese individuals. Consistent with this possibility, several recent studies do show an association between hypoleptinemia and increased plasma cortisol concentrations in high-normal weight humans during caloric deprivation. In addition, it is possible that the relative importance of insulinopenia- and hypoleptinemia-induced HPA axis activation in driving the shift from glucose to fat metabolism may differ between rodents and humans; in contrast to rodents, insulinopenia may be sufficient to produce most or all of the effect of starvation to increase WAT lipolysis in humans independent of increases in plasma cortisol concentrations.

Figure 22F:
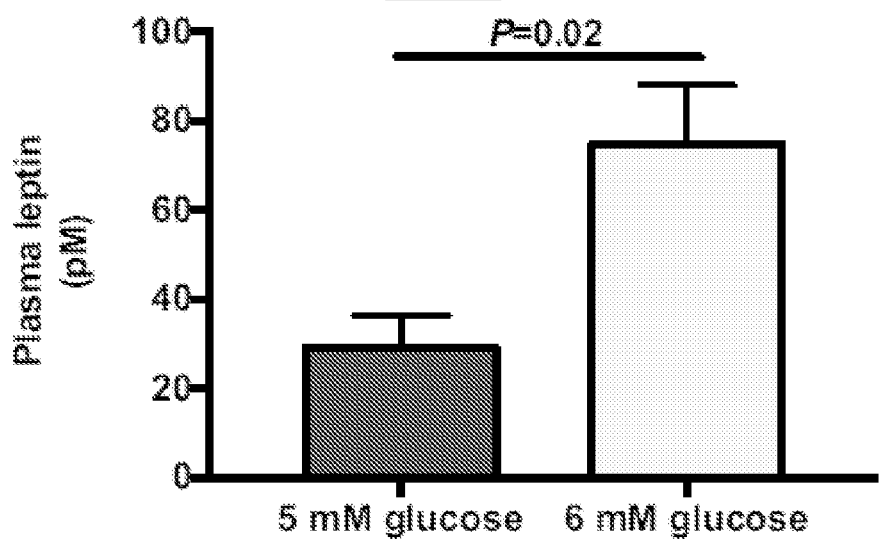
Figure 22G:
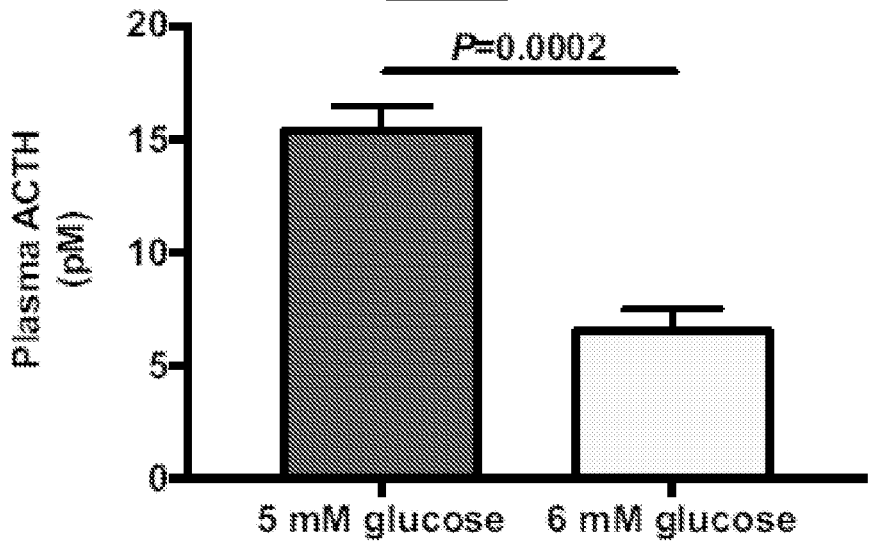
Figure 22H:
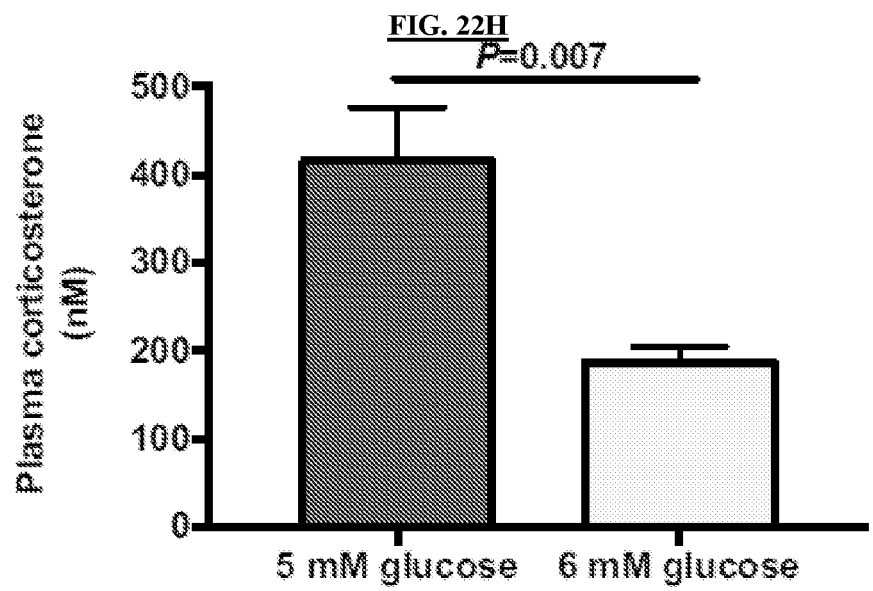
Figure 22I:
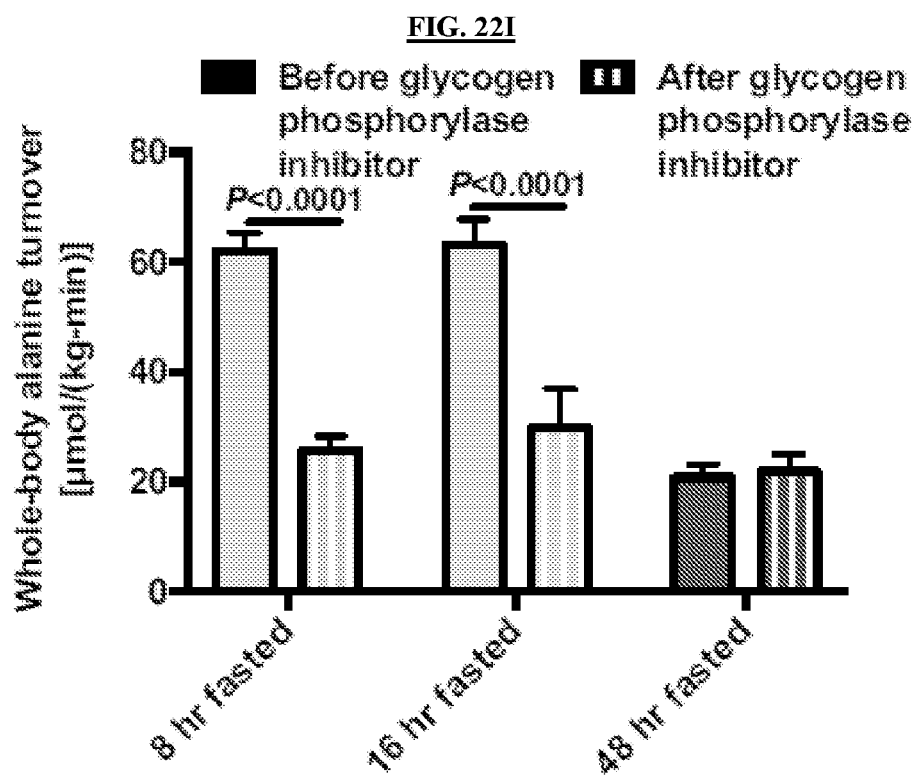
Figure 22J:
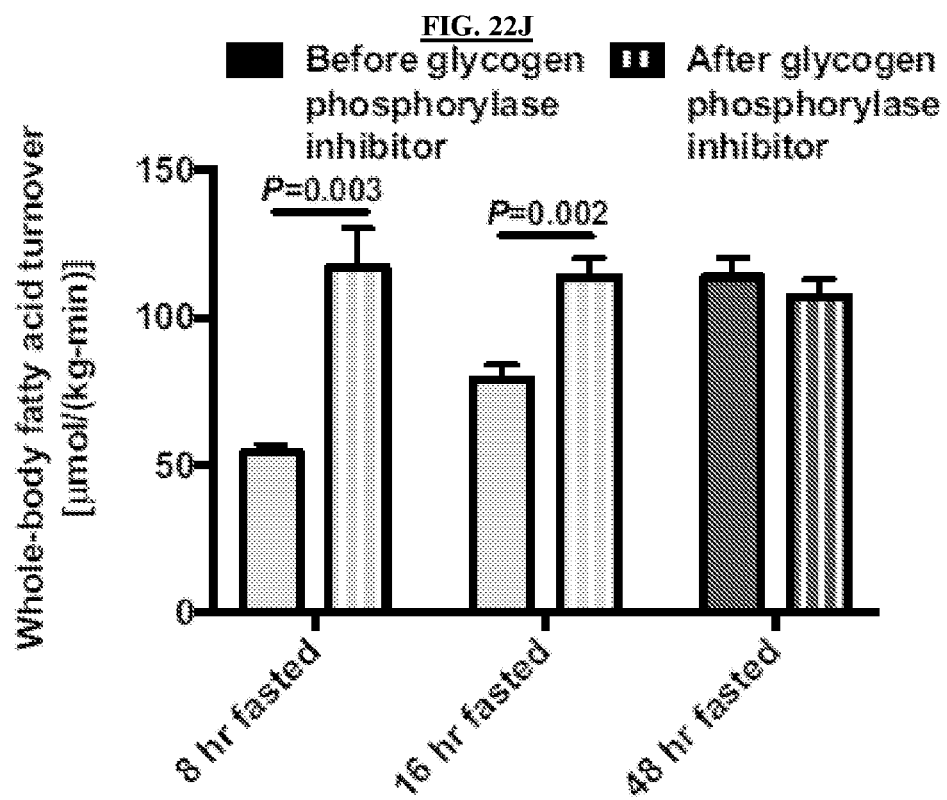
Figure 23A:
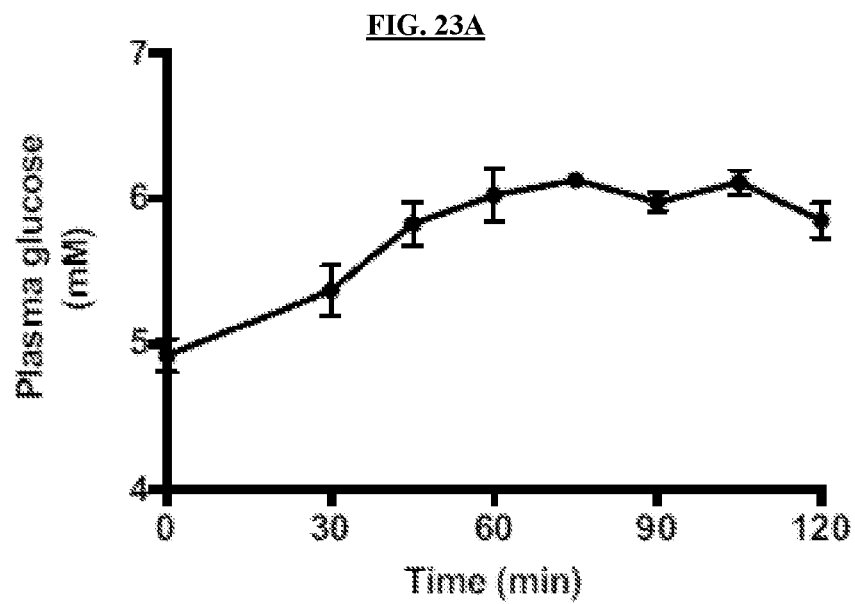
Figure 23B:
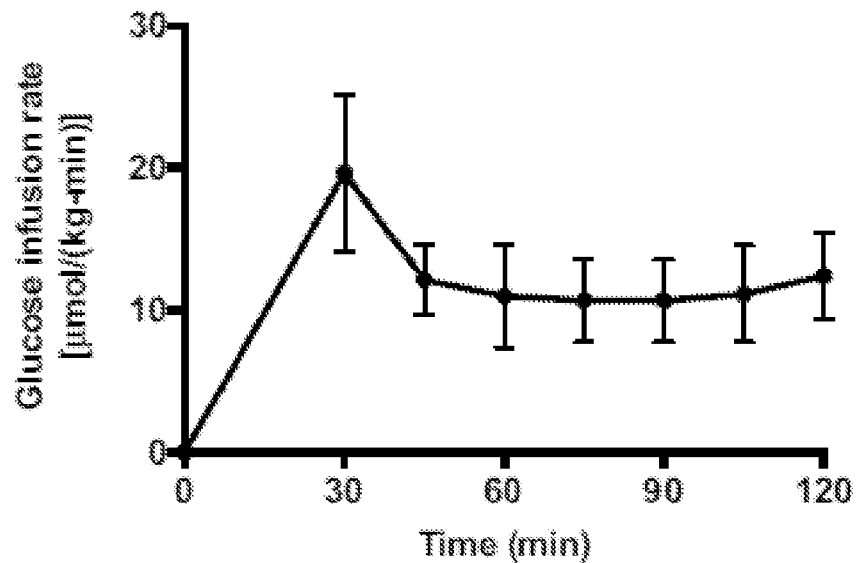
Figure 23C:
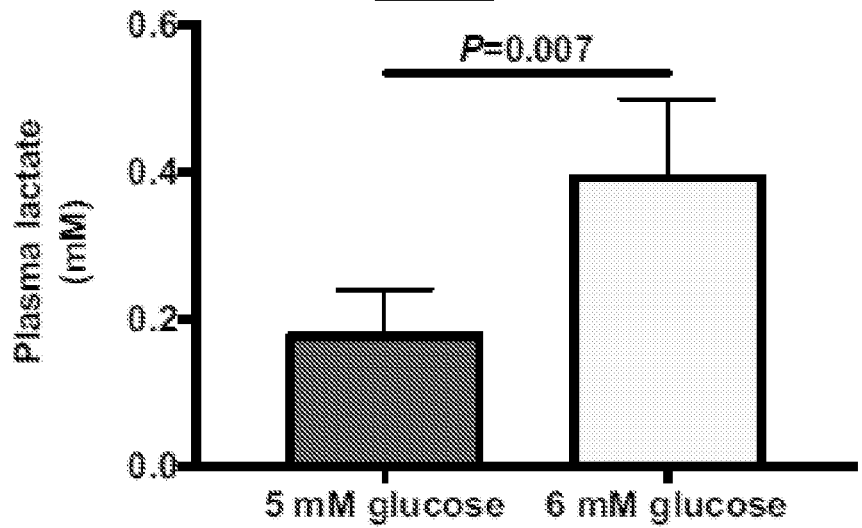

Several reports suggest that in lean and obese human subjects, plasma leptin concentrations decrease during caloric restriction out of proportion to the decline in total body weight or fat mass and increase with refeeding or long-term hyperinsulinemia, consistent with the data presented herein (FIGS. 9D, 22F, and 10A). These data pose the question of whether starvation regulates plasma leptin concentrations by an alternative mechanism in addition to reductions in total fat mass. Consistent with this possibility, acute treatment with inhibitors of glycogen phosphorylase, CPT-1, ATGL, and the glucocorticoid receptor all reduced plasma glucose, insulin, and leptin concentrations within just 2 hr, a time frame incompatible with similar reductions in body weight. Without intending to be limited to any particular theory, it is possible that a reduction in plasma glucose concentrations from 6 to 5 mM and consequent reductions in plasma insulin concentrations from ~100 to ~45 pM during prolonged fasting reduce plasma leptin concentrations from ~65 to ~35 pM. A small increase in plasma glucose concentrations from 5 to 6 mM in 48-hr fasted rats doubled glucose uptake into WAT, doubled plasma leptin concentrations, and reduced plasma corticosterone concentrations by 50% (FIGS. 22E-22H). These data demonstrate that progressive reductions in plasma glucose concentrations during the fed to fasted transition in lean, normal chow-fed rats signals the depletion of stored hepatic carbohydrate (glycogen) reserves and results in reduced WAT leptin secretion, which in turn stimulates the HPA axis activity to promote increased WAT lipolysis and the transition from whole body glucose oxidation to fat/ketone oxidation.

Figure 21Y:
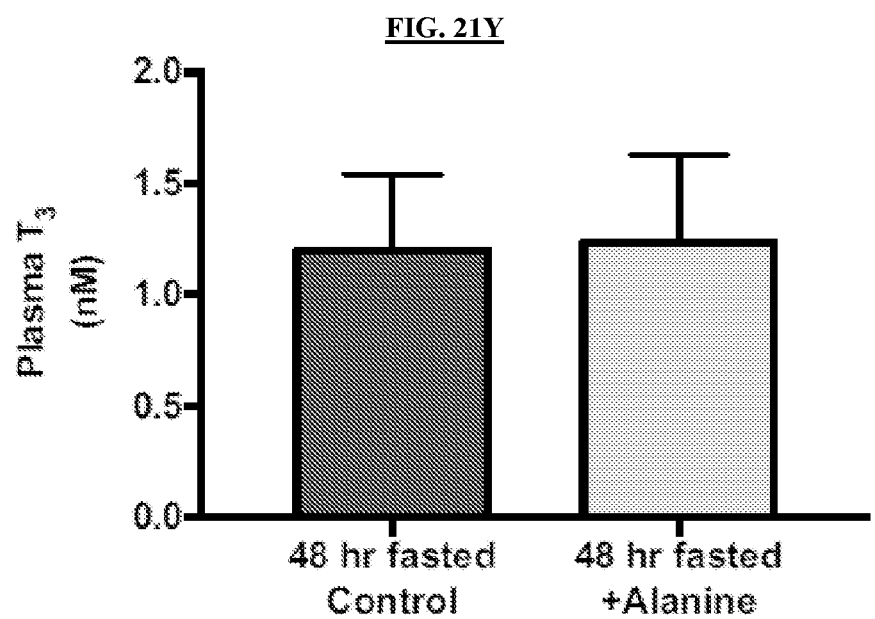

Despite increased or unchanged WAT lipolysis and hepatic acetyl-CoA content between 16 and 48 hr of fasting, rats exhibited a ~50% reduction in rates of hepatic gluconeogenesis after 48 hr of starvation. This result could be entirely attributed to reductions in rates of hepatic pyruvate carboxylase flux (VPC) between these time points (FIG. 9B). It is possible that reductions in alanine turnover, which was observed in 48-hr starved rodents (FIG. 20A) and which is consistent with previous studies demonstrating a reduction in alanine release from the forearm in fasted humans, may be responsible for reduced hepatic gluconeogenesis due to substrate limitation. To test that hypothesis, rats were infused with alanine to increase total alanine turnover to match rates of alanine turnover measured in 16-hr fasted rats. This intervention increased plasma glucose and insulin concentrations, hepatic glucose production, and hepatic pyruvate carboxylase flux similar to or greater than what was measured in 16-hr fasted rats. In addition, rates of hepatic mitochondrial oxidation (citrate synthase flux, VCS)—assessed by PINTA analysis-revealed suppression of hepatic mitochondrial oxidation flux (VCS) with 48 hr of fasting, but alanine replacement increased rates of hepatic mitochondrial oxidation (VCS) independent of changes in plasma T3 concentrations (FIGS. 11J and 21Y). Taken together, these data reveal that reductions in alanine turnover during prolonged starvation cause suppression of hepatic mitochondrial oxidation rates. The reductions in alanine turnover observed in the starved state would be expected to promote further increases in hepatic ketogenesis due to an expanding mismatch between rates of hepatic β-oxidation and hepatic mitochondrial oxidation (VCS), thereby providing increased ketones to serve as a substrate for brain mitochondrial oxidative metabolism, supplying ~45% of the brain's energy needs after 48 hr of starvation (FIG. 9C). The reductions in alanine turnover observed in the starved state were confirmed to result from reductions in plasma glucose concentrations from 6 to 5 mM: infusion of glucose to raise plasma glucose concentrations from 5 to 6 mM in 48-hr fasted rats increased whole-body alanine turnover to rates similar to those measured in 16-hr fasted rats (FIG. 22D). In summary, these data reveal several new concepts regarding leptin biology and the regulation of whole-body and tissue-specific substrate metabolism from the transition from the fed to fasted state in normal lean free-ranging rats, specifically:

(1) Progressive decreases in plasma glucose (9 to 6 mM) and insulin (500 to 100 pM) concentrations during early starvation (6-16 hr) can mostly be ascribed to reduced rates of net hepatic glycogenolysis (25 to 4 mmol/[kg, min]) because rates of hepatic gluconeogenesis during this period remain relatively constant, thus providing a systemic index of remaining stored hepatic carbohydrate (glycogen) reserves. This in turn promotes progressive reductions in plasma leptin concentrations (150 to 60 pM).

(2) Reductions in plasma leptin concentrations (150 to 60 pM) stimulate the HPA axis, thus increasing plasma corticosterone concentrations (100 to 450 nM), which, in the presence of hypoinsulinemia, results in stimulation of WAT lipolysis and the shift from whole-body carbohydrate oxidation to fat/ketone oxidation.

(3) Increases in WAT lipolysis increase hepatic acetyl-CoA content and allosterically stimulate hepatic pyruvate carboxylase flux, which is essential for the maintenance of hepatic glucose production and euglycemia during starvation.

(4) Insulinopenia is necessary, but not sufficient, for increased rates of WAT lipolysis, increased hepatic acetyl-CoA content, increased rates of hepatic ketogenesis, and the shift from carbohydrate oxidation to fat/ketone oxidation during starvation.

(5) Decreased glucose-alanine cycling, due to hepatic glycogen depletion, results in marked (~50%) reductions in rates of hepatic pyruvate carboxylase flux (VPC) and hepatic mitochondrial oxidative metabolism (VCS).

(6) Reductions in rates of hepatic mitochondrial oxidation (VCS) during prolonged (48 hr) starvation can be attributed in part to reductions in rates of hepatic anaplerosis (VPC).

(7) Physiologic replacement of plasma leptin concentrations (30 to 60 pM) during prolonged (48 hr) starvation inhibits WAT lipolysis and results in decreased rates of hepatic gluconeogenesis through reductions in HPA axis activity. In contrast, supraphysiologic plasma leptin concentrations stimulate WAT lipolysis and result in increased rates of hepatic gluconeogenesis and hyperglycemia through activation of the sympathetic nervous system and increased catecholamine secretion.

(8) Increased rates of WAT lipolysis promote increased hepatic fat (DAG) accumulation and PKCε activation during prolonged (48 hr) starvation.

Based on these findings, but without intending to be limited to any particular theory, it is possible that fasting-induced hepatic steatosis and lipid-induced hepatic insulin resistance may also play an important role in promoting survival during famine by minimizing hepatic glucose uptake and energy storage as glycogen, therefore sparing any ingested carbohydrate for the central nervous system and other obligate glucose-requiring tissues, thus providing an evolutionary basis for DAG-PKCε induced hepatic insulin resistance. Taken together, these data show that both insulinopenia and hypoleptinemia are necessary for maintenance of euglycemia during short-term (6-16 hr) starvation in lean rats, with insufficient anaplerosis from glucose-alanine cycling limiting both hepatic gluconeogenesis and mitochondrial oxidation in prolonged (48 hr) starvation. These data further identify a novel leptin-mediated glucose-fatty acid cycle that integrates responses of the muscle, white adipose tissue, and liver to maintain adequate substrate supply to the brain to promote survival during starvation.

Example 3: Glucagon Allosterically Stimulates Gluconeogenesis by InsP$_3$R-I Mediated Intrahepatic Lipolysis Glucagon has long been considered to be one of the major drivers of hyperglycemia in type 2 diabetes (T2D), and glucagon-blocking therapies have been pursued as adjuncts to therapy for both type 1 and type 2 diabetes. Glucagon antagonism using either antibodies against glucagon or its receptor, small molecule antagonists of the glucagon receptor, and antisense oligonucleotides to knock down expression of the glucagon receptor have all shown promising glucose-lowering effects in humans and in animal models of T2D. However, concerns have been raised regarding the potential of these agents to increase liver enzymes by an unknown mechanism. Conversely, a dual glucagon-like peptide-1/glucagon receptor agonist has recently been shown in rodents and non-human primates to lower blood glucose concentrations, associated with increased energy expenditure and weight loss. Taken together, these data suggest a potential role for glucagon to promote hepatic mitochondrial fat oxidation and suggest that a lack of glucagon action may suppress hepatic fat oxidation and predispose to ectopic hepatic lipid accumulation and non-alcoholic fatty liver disease (NAFLD).

Glucagon is a well-known stimulator of both hepatic glycogenolysis and gluconeogenesis; the former by cyclic AMP (cAMP)-mediated activation of glycogen phosphorylase, and the latter believed to occur largely through transcriptional regulation. Hepatic calcium signaling is integral to transcriptional regulation of hepatic gluconeogenesis: inhibition or deletion of liver $Ca^{2+}$/calmodulin-dependent protein kinase II (CaMKII) results in reduced gluconeogenic protein mRNA expression in mouse livers and associated reductions in plasma glucose and insulin concentrations. Similarly, it has been shown that knocking down InsP$_3$R-I, the main hepatic isoform of the cytosolic calcium-regulating inositol 1,4,5-trisphosphate receptor, reduced glucose production in isolated hepatocytes stimulated with glucagon, which can be attributed to downregulation of gluconeogenic gene expression due to calcineurin-mediated dephosphorylation of CREB-regulated transcriptional coactivator-2 (CRTC2).

Materials and Methods

Animals

All protocols were approved by the Yale University Animal Care and Use Committee. Liver-specific InsP$_3$R-I KO mice were generated as described (Feriod, et al. *Hepatology Communications* 1, 23-35, 2017) and in all experiments, littermates were studied at 10-12 weeks of age. They were fed standard chow (Teklad #2018) and housed on a 12 hr light/dark cycle in the Yale Animal Resources Center. To knock down ATGL in a liver-specific manner, an adeno-associated virus targeting ATGL (Vector BioLabs, $10^{12}$ gc per mouse) was administered by retro-orbital injection four weeks prior to studies. Male mice were used for in vivo studies, while female mice were used for in vitro studies, unless otherwise specified. One week prior to in vivo studies, mice underwent surgery under isoflurane anesthesia to place a catheter in the jugular vein. Post-surgical recovery was confirmed by regaining the pre-surgical body weight prior to any in vivo studies. They were fasted overnight, unless otherwise stated, prior to in vivo studies. In the acute glucagon infusion studies, mice were given an intra-venous infusion of glucagon (5 ng kg$^{-1}$ min$^{-1}$) for two hours, with tissue and plasma samples obtained after two hours of infusion. Mice were euthanized using IV pentobarbital at the conclusion of the terminal study.

Mice infused chronically with glucagon were fed a high fat diet (Research Diets D12492) for four weeks, after which they were implanted with an ALZET® pump providing glucagon continuously (0.15 ng min$^{-1}$) for another 3.5 weeks, during which time they were continued on a high fat diet. They underwent CLAMS metabolic cage analysis to assess energetics and food and water intake during the second week of glucagon infusion. After an overnight fast, 3 weeks after implantation of the glucagon pumps, mice underwent an intraperitoneal glucose tolerance test and were subsequently refed. 48 hr later, after a 6 hr fast, they were sacrificed under isoflurane anesthesia for measurement of hepatic lipid content as described below.

For the chronic glucagon infusion studies in rats, 300 g male Sprague-Dawley rats were obtained from Charles River Laboratories and fed a safflower oil-based high fat diet (HFD, 60% calories from fat, Dyets #112245) for 4 weeks. During week 3 of the diet, rats underwent surgery under isoflurane anesthesia to place catheters in the jugular vein and carotid artery, and recovery was confirmed by regaining the pre-surgical body weight prior to in vivo studies. After four weeks on HFD, rats were placed in a soft plastic harness to protect their catheters and infused continuously for 10 days with glucagon (5 ng kg$^{-1}$ min$^{-1}$, total volume 5 ml kg$^{-1}$ day$^{-1}$). The glucagon infusion was either continued throughout the terminal study (PINTA) or discontinued two hours before the start of the terminal study (GTT with hepatic lipid/acetyl-CoA/glycogen measurements), in separate groups of rats, as specified in the figure legends. Rats were fasted for 8 hr prior to sacrifice with IV pentobarbital.

In Vivo Studies

In all in vivo mouse studies, blood was collected from the tail vein, with the exception of portal vein glucagon measurements, in which a needle was inserted into the portal vein of anesthetized mice to collect blood. In the rat studies, blood was collected from the jugular venous catheter. In both species, samples were immediately centrifuged (12,000 rpm) to separate plasma from red blood cells. PINTA analysis of hepatic mitochondrial fluxes was employed in both rats and mice (see Example 1). Briefly, mice were infused with a two-hour primed (5 min, 3×)-continuous infusion of [$_3$-$^{13}$C] lactate (40 μmol kg$^{-1}$ min$^{-1}$) and [1,2,3,4,5,6,6-$^2$H$_7$] glucose (0.1 mg kg$^{-1}$ min$^{-1}$). Rats were infused with lactate at the same rate, as well as [3-$^3$H] glucose (0.1 mCi kg$^{-1}$ min$^{-1}$). At the conclusion of the study, animals were euthanized with IV pentobarbital.

Figure 30A:
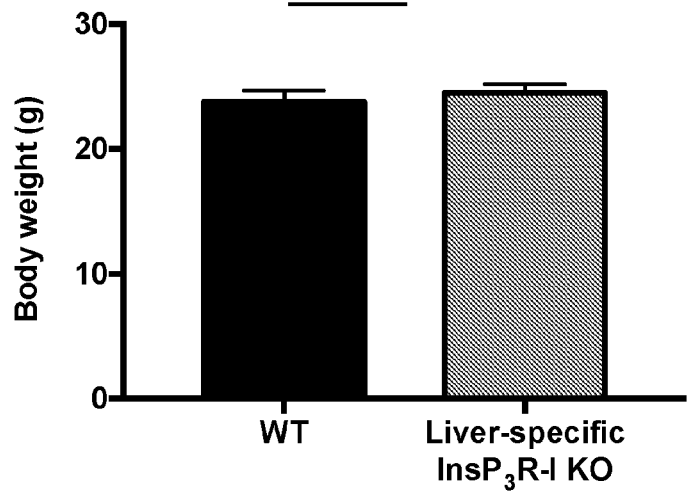
Figure 30B:
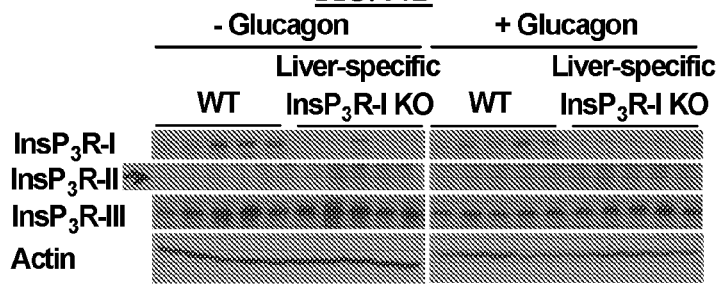
FIGS. 30B-30D are graphs showing liver InsP$_3$R protein expression.
Figure 30C:
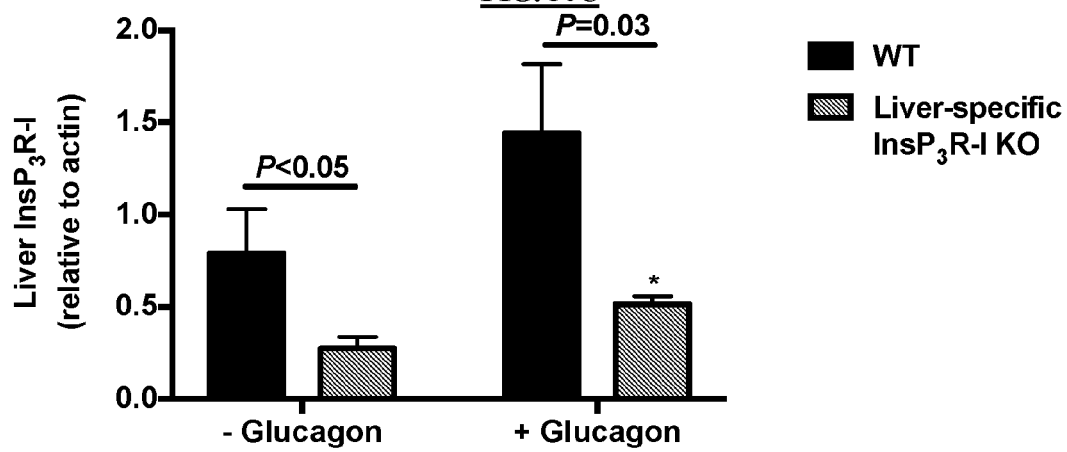
Figure 30D:
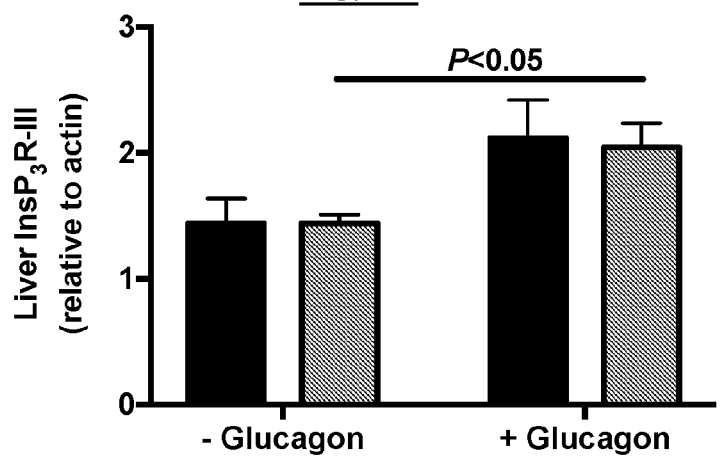
Figure 30G:
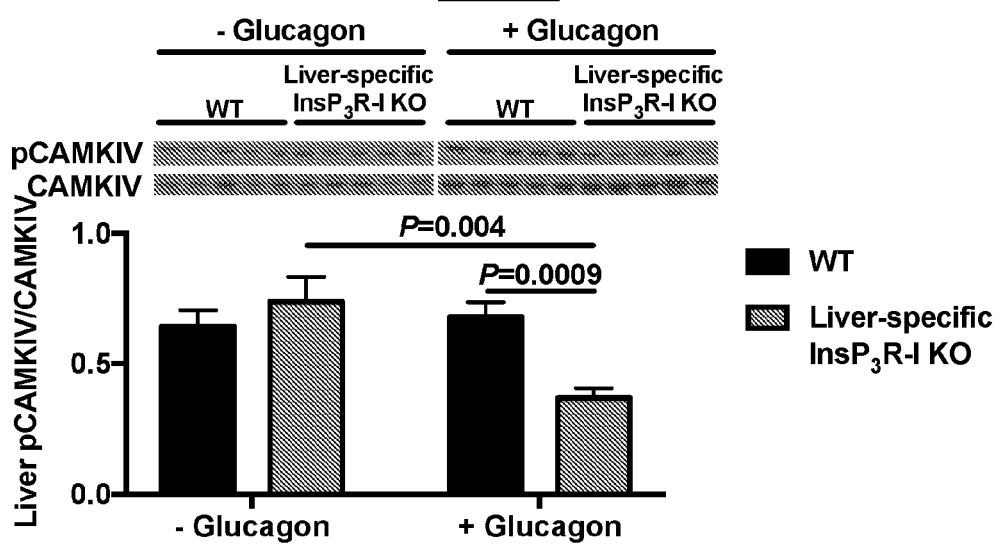
Figure 30H:
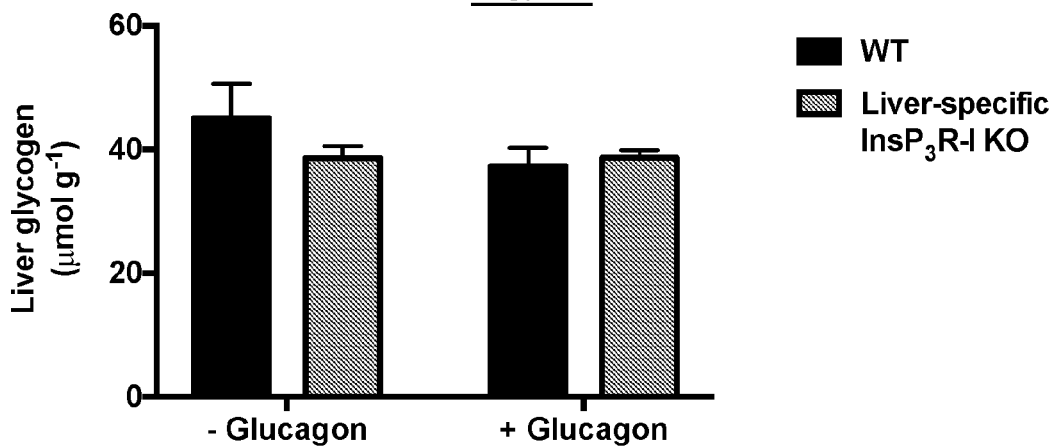
FIG. 30H is a graph showing liver glycogen content.
Figure 30I:
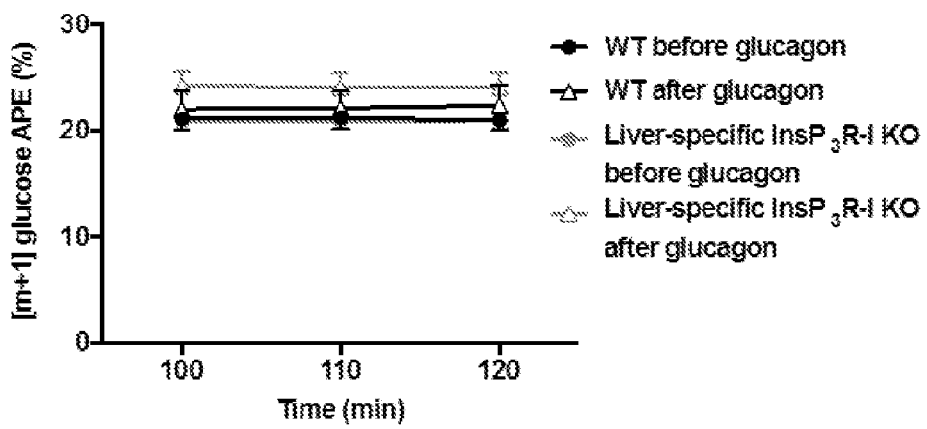
FIGS. 30I-30K are graphs showing plasma [m+1], [m+2], and [m+7] plasma glucose enrichment during a 120 min infusion of [3-$^{13}$C] lactate and [$^2$H$_7$] glucose.
Figure 30J:
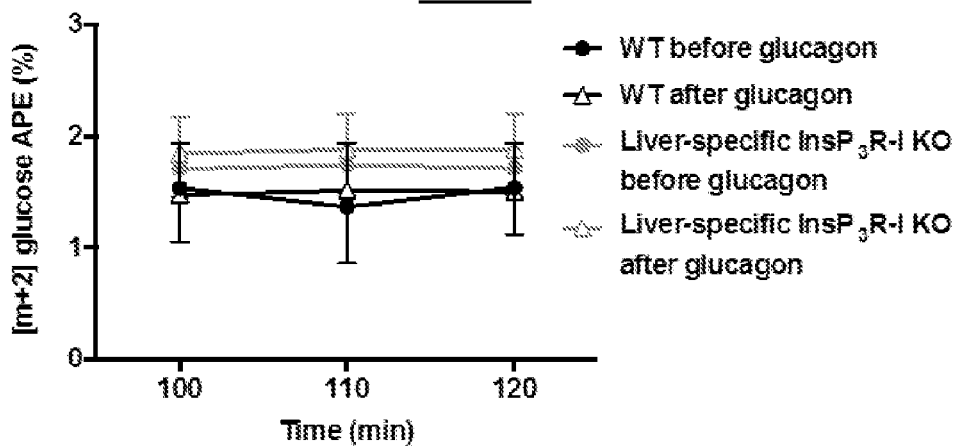
Figure 30K:
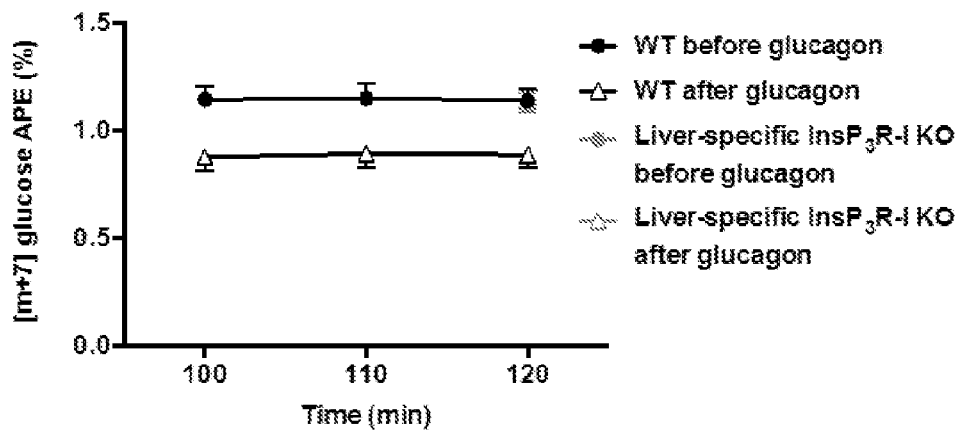
Figure 30L:
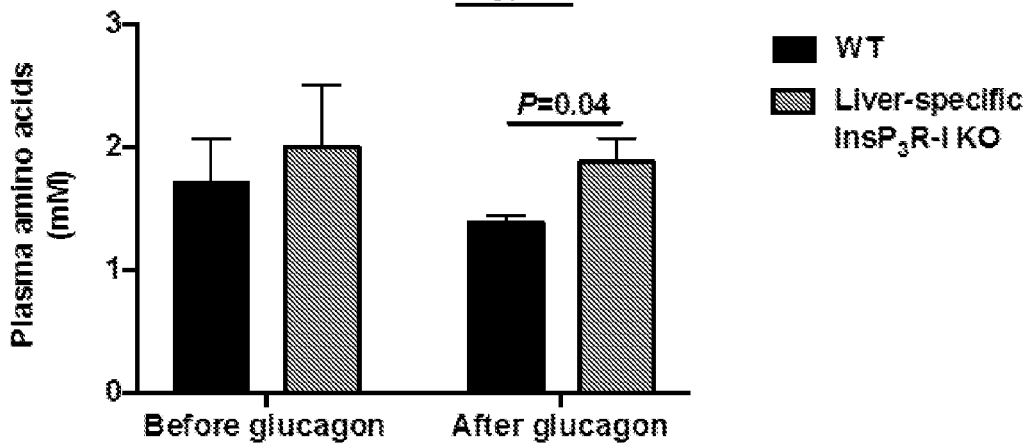
FIGS. 30L-30M are graphs showing plasma total amino acid and alanine concentrations. Groups were compared before and after glucagon by the 2-tailed paired Student's t-test.
Figure 30M:
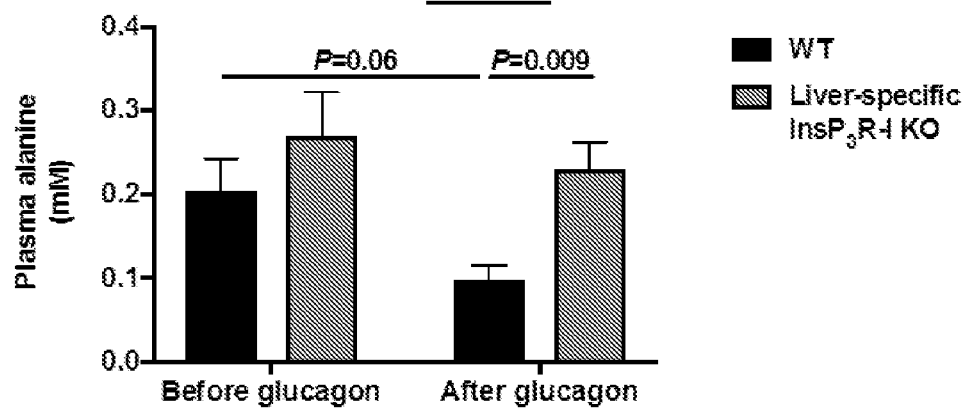
Figure 30N:
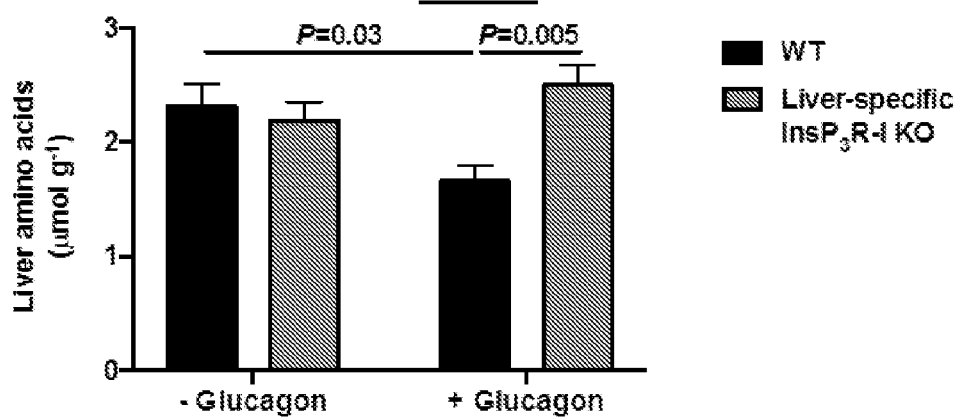
FIGS. 30N-30O are graphs showing liver total amino acid and alanine concentrations.
Figure 30O:
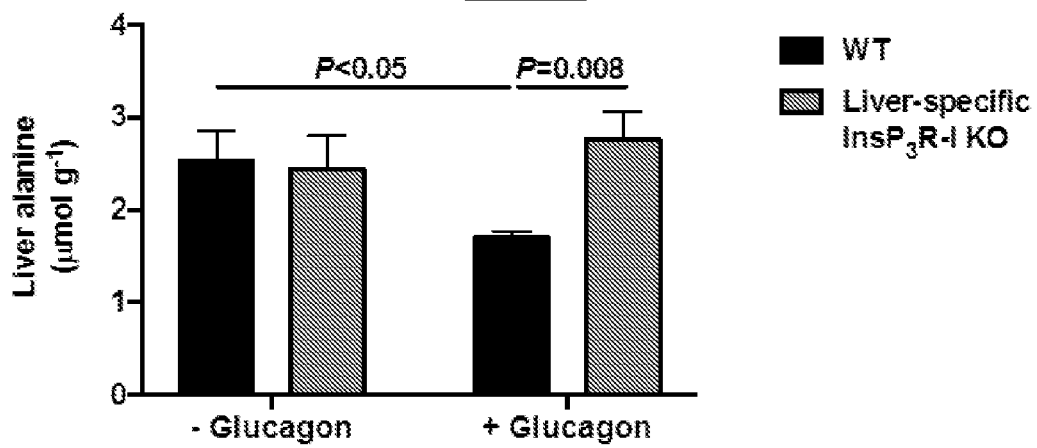
Figure 33A:
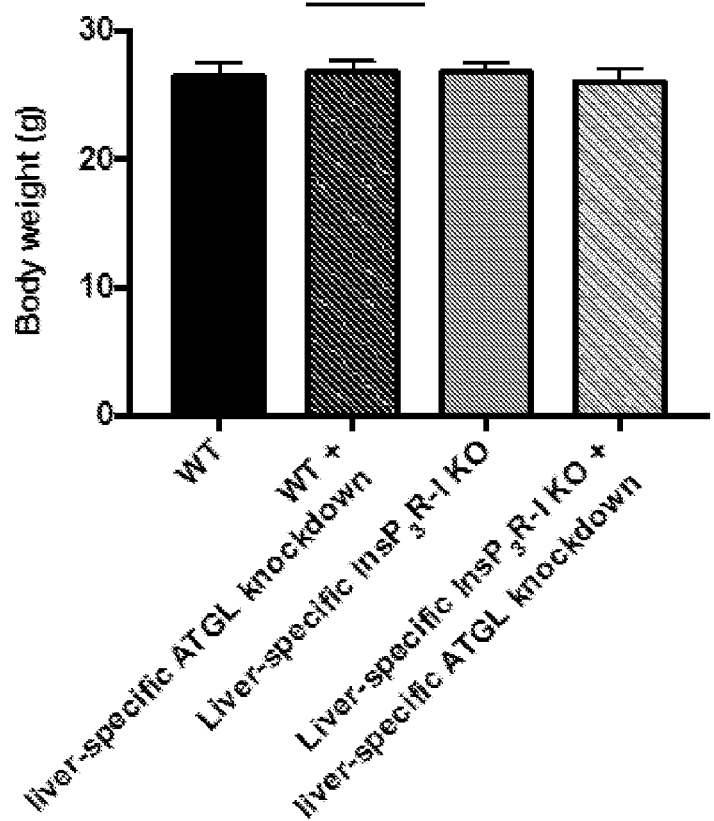
Figure 33B:
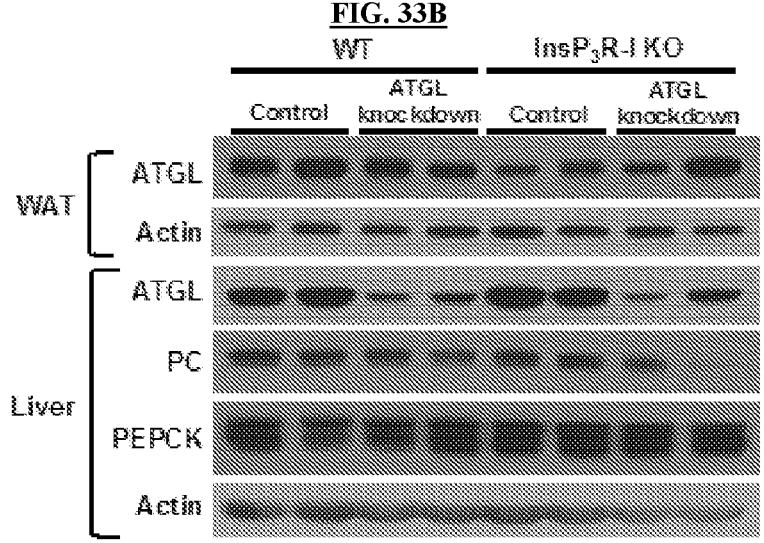
Figure 33C:
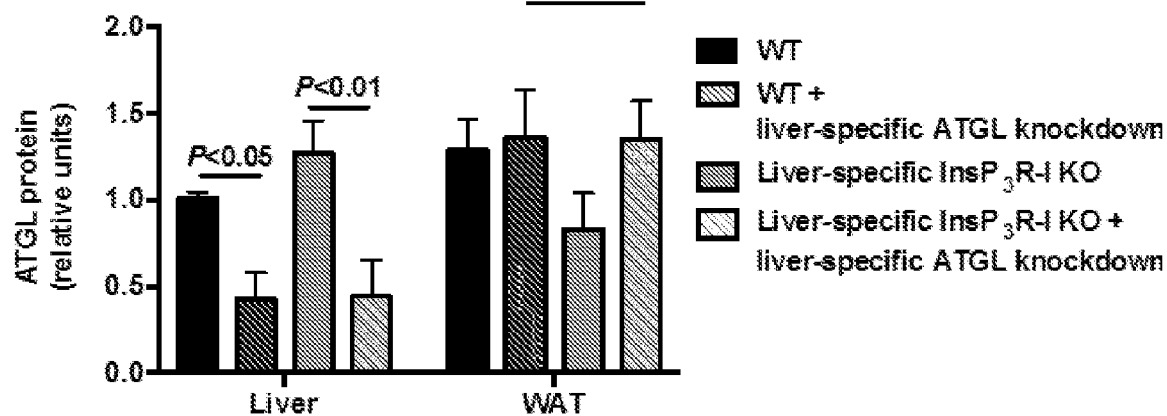
Figure 33D:
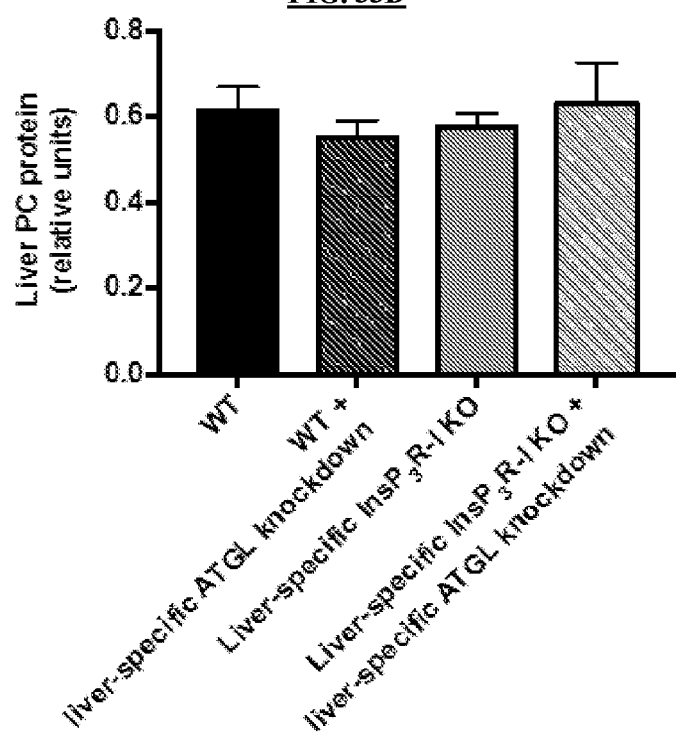
Figure 33E:
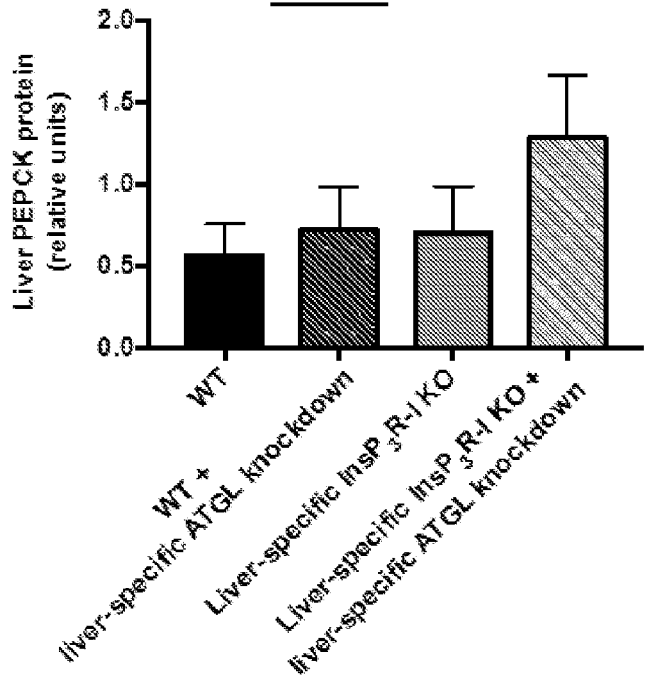
Figure 33F:
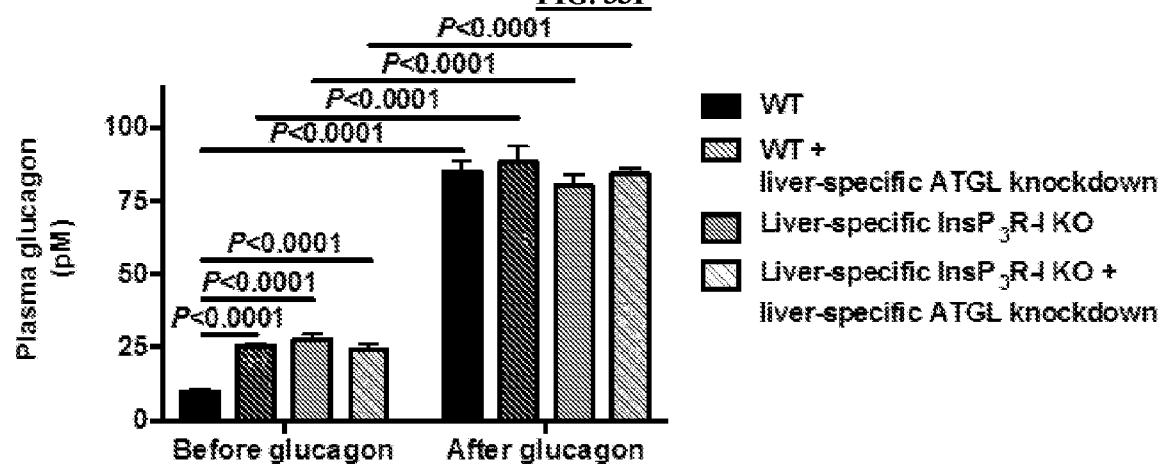
Figure 33I:
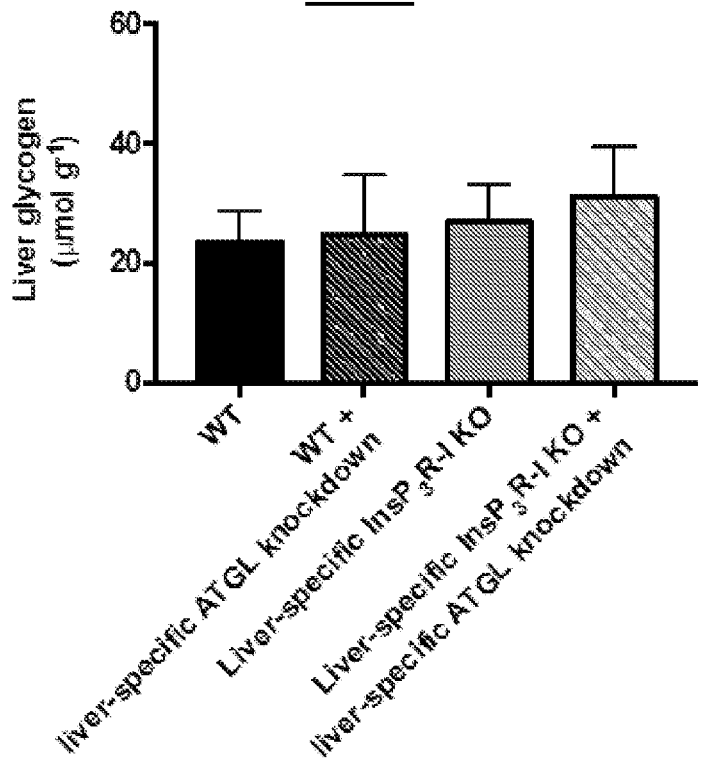

In mice, hepatic glycogenolysis was assumed to be negligible due to their prolonged (16 hr) fasted state and their low hepatic glycogen content (FIGS. 30H and 33I). Total glucose turnover (i.e. hepatic glucose production) was measured by determining the specific activity of [$^3$H] glucose in plasma using a scintillation counter, and the $V_{PC}/V_{HGP}$ ratio was calculated using the equation $$\frac{V_{PC}}{V_{HGP}} = \frac{G2}{XFE^2},$$

where G2 represents the [m+2] glucose enrichment corrected for any [m+2] glucose synthesized from $^{13}$C2-labeled trioses: Corrected m+2 glucose=G2=Measured [m+2] glucose−2·C4C5C6 [m+2]glucose, and XFE represents the fractional triose enrichment:

$$XFE = \frac{1}{1 + \frac{G1}{2*G2}},$$

where G1 represents the measured [m+1] glucose and G2 as described above. To calculate absolute $V_{PC}$ flux, we multiplied the measured HGP by the ratio $V_{PC}/V_{HGP}$. The ratio of hepatic $V_{PC}/V_{CS}$ flux was calculated as $$\frac{V_{PC}}{V_{CS}} = \frac{[5-^{13}C]\text{ glucose}}{2*[4-^{13}C]\text{ glucose}} - 1,$$

and calculated absolute $V_{CS}$ by dividing $V_{PC}$ by $V_{PC}/V_{CS}$. The derivations of each equation are described in detail in Example 1. The possible contribution of [$^{13}$C] bicarbonate to label the TCA cycle was corrected for as follows. Liver [$^{13}$C] bicarbonate enrichment was measured by GC-MS (HP-1 column: 12 m×0.2 mm×0.33 μm film, isothermal: 110° C.). Liver tissue (~25 μg) was placed in a GC-MS vial, purged with N$_2$ gas, and sealed. To each sample, a saturated aqueous solution of citric acid (50 μl) was injected into the vial through the cap. After ten minutes, CO$_2$ was sampled from the head-space and ions with m/z 44 and 45 daltons were monitored using electron impact ionization.

The fractional enrichment of glucose from $^{13}$CO$_2$ was increased from PC synthesis of [4-$^{13}$C]OAA from $^{13}$CO$_2$ and pyruvate. The labeling of glucose from 13-bicarbonate is dependent upon the relative flux of pyruvate to OAA with equilibration with fumarate and formation of PEP vs. flux of pyruvate to OAA to citrate (i.e. $V_{PC}/V_{CS}$). Only [1-$^{13}$C] OAA (from the equilibration of [4-$^{13}$C]OAA with fumarate) converted directly to PEP labels glucose (C3 and C4), since all $^{13}$CO$_2$ of [4-$^{13}$C]OAA is lost with flux through the TCA cycle. Hence, the correction of $^{13}$CO$_2$ follows from:
1. $^{13}$CO2 will label C4 of OAA to give [4-$^{13}$C]OAA.
2. [4-$^{13}$C]OAA randomizes to [1-$^{13}$C]OAA and [4-$^{13}$C]OAA. Enrichment in each position is ½ of the original [$^{13}$CO$_2$] enrichment.
3. [1-$^{13}$C]OAA→[1-13C]PEP: Label of [4-$^{13}$C]OAA is lost in OAA→PEP.
4. [1-$^{13}$C]PEP→[3-$^{13}$C] glucose and [4-$^{13}$C] glucose
5. $^{13}$C of [4-$^{13}$C]OAA and [1-$^{13}$C]OAA is lost as $^{13}$CO$_2$ with CS flux to $^{13}$C-citrate and first turn of the TCA cycle.
5. Therefore, the correction for [$^{13}$CO$_2$] is 2*[4-$^{13}$C] glucose-$^{13}$CO$_2$×½×CF, where [$^{13}$CO$_2$] is the liver $^{13}$C-bicarbonate enrichment, and CF=($V_{PC}$+$V_{CS}$)/$V_{PC}$
6. $V_{PC}/V_{CS}$ corrected for [$^{13}$CO$_2$] was determined iteratively.
The ratio $$\frac{V_{PDH}}{V_{CS}} = \frac{[4-^{13}C]\text{ glutamate}}{[3-^{13}C]\text{ alanine}}$$

was measured and absolute $V_{PK}$ was calculated by multiplying this ratio by the measured $V_{CS}$. Finally, the ratio of $V_{PK}$—assuming minimal malic enzyme flux—to ($V_{PC}$+$V_{PDH}$) was calculated as $$\frac{V_{PK}}{V_{PC}+V_{PDH}} = \frac{[2-^{13}C]\text{ alanine}}{[5-^{13}C]\text{ glucose}}.$$

Absolute $V_{PK}$ fluxes were then determined by multiplying $$\frac{V_{PK}}{V_{PC}+V_{PDH}}$$

by the sum of $V_{PC}$ and $V_{PDH}$. As discussed in Example 1, $$\frac{V_{PC}}{V_{CS}}$$

can be expanded to account for pyruvate recycling:

$$\frac{V_{PC}+\frac{1}{2}V_{PK}}{V_{CS}} = \frac{[5-^{13}C]\text{ glucose}}{2*[4-^{13}C]\text{ glucose}} - 1.$$

A maximum $$\frac{V_{PK}}{V_{PC}+V_{PDH}}$$

of 0.4 was measured, indicating that the maximal $$\frac{V_{PK}}{V_{PC}} \text{ is } 0.4. \text{ A}\frac{V_{PK}}{V_{PC}}$$

at this maximal value would generate a 17% underestimation of $$\frac{V_{PC}}{V_{CS}}.$$

Ex vivo NMR analysis was used to confirm PINTA measurements of flux ratios.

In rats, HGP was measured by measuring the plasma glucose [m+7] atom percent enrichment (APE) by gas chromatography/mass spectrometry (GC/MS) and using these data to calculate HGP according to the equation $$HGP = \left(\frac{\text{Tracer } APE}{\text{Plasma } APE} - 1\right) *\text{infusion rate}.$$

All other flux ratios and absolute fluxes were measured using the equations given above.

In the glucose tolerance tests, rodents were injected with 1 g kg$^{-1}$ 50% dextrose (rats) or 10% dextrose (mice) intraperitoneally. Blood samples were taken through the venous catheter (rats) or by tail bleeding (mice) for measurement of plasma glucose and insulin concentrations as described below (Biochemical analysis).

Biochemical Analysis

Plasma glucose concentrations were measured using a YSI Glucose Analyzer. Plasma insulin was measured by ELISA (Mercodia), while glucagon was measured in samples immediately spiked with aprotinin (0.5 mg μL$^{-1}$) whole blood by RIA by the Yale Diabetes Research Core. Plasma NEFA concentrations were measured using the Wako NEFA assay, while plasma glycerol and plasma and liver amino acid concentrations were measured by GC/MS. Liver acetyl- and malonyl-CoA (standard curve $R^2$=0.999 and 0.999), long-chain CoA, DAG, and ceramide concentrations were measured by LC-MS/MS, hepatic glycogen content following amyloglucosidase digestion, and TAG concentrations enzymatically. cAMP concentrations were measured using the Enzo Life Sciences Direct cAMP ELISA. Protein concentrations were measured by Western blot, using antibodies from Santa Cruz (PC, PEPCK, CAM-KII), Cell Signaling (ATGL, pCAMKIV, CAMKIV, pCRTC2, CRTC2, pACC, ACC, pAMPK, AMPK, pHSL, HSL, GAPDH, and β-actin), Novus Biologicals (pCAM-KII), Abcam (pATGL), LSBio (pInsP$_3$R-I), and BD Transduction Laboratories (InsP$_3$R-II, InsP$_3$R-III, PKCε). The antibody to pATGL was kindly provided by Dr. Hei Sook Sul, while the antibody to total InsP$_3$R-I was custom-made using an epitope against the last 18 amino acids of InsP$_3$R-I. Gluconeogenic gene mRNA expression was measured by qPCR[45] using primers sequences as follows:

TABLE 10

Primer Sequences

| Primer | SEQ ID | Sequence |
| --- | --- | --- |
| β-actin: F | SEQ ID NO: 1 | CCAGATCATGTTTGAGACCTTC |
| β-actin: R | SEQ ID NO: 2 | CATGAGGTAGTCTGTCAGGTCC |
| PEPCK: F | SEQ ID NO: 3 | CAGGAAGTGAGGAAGTTTGTGG |
| PEPCK: R | SEQ ID NO: 4 | ATGACACCCTCCTCCTGCAT |
| G6Pase: F | SEQ ID NO: 5 | GAAGGCCAAGAGATGGTGTGA |
| G6Pase: R | SEQ ID NO: 6 | TGCAGCTCTTGCGGTACATG |
| PC: F | SEQ ID NO: 7 | AGATGCACTTCCATCCCAAG |
| PC: R | SEQ ID NO: 8 | CCTTGGTCACGTGAACCTTT |

In Vitro Studies

Primary hepatocytes were isolated by the Yale Liver Center from wild-type and InsP$_3$R-I KO mice and plated on glass coverslips coated with Rat Collagen Type I. Cells were loaded with the ratiometric cytosolic Ca$^{2+}$ indicator dye, Fura-2 AM (Thermo Fisher Scientific), or the mitochondrial matrix-targeted Ca$^{2+}$ indicator, Rhod-2 AM (Thermo Fisher Scientific) according to manufacturer's instructions. Ca$^{2+}$ imaging experiments were performed in 4-(2-hydroxyethyl)-1-piperazine ethanesulfonic acid (HEPES)-buffered balanced salt solution (25 mM HEPES, 121 mM NaCl, 4.7 mM KCl, 1.2 mM MgSO$_4$, 1.2 mM KPO$_4$, 5 mM NaHCO$_3$, 2.0 mM CaCl$_2$, 10 mM Glucose, pH 7.4) with or without the PKA inhibitor H-89 (25 µM) two to five hr following initial plating. Coverslips were transferred to a custom-built perfusion chamber on the stage of an inverted microscope connected to a RedShirtImaging camera (Olympus Life Science, Waltham, Mass.). Cytosolic signals were monitored in Fura-2 AM-loaded cells using stimulation with 100 nM Glucagon (Sigma-Aldrich) or 50 nM Vasopressin (Sigma-Aldrich) on a 40× objective lens. For cytoplasmic calcium readings, changes in fluorescence (F, λ=340) were normalized by the initial fluorescence (F0, λ=380) and were expressed as F/F0. Mitochondrial signals were monitored in Rhod-2 AM-loaded cells using stimulation with 100 nM Glucagon or 50 nM Vasopressin on a 40× objective lens. Individual cell responses were normalized to their respective baseline Rhod-2 AM fluorescence values, and changes were expressed as Normalized Δ Fluorescence.

For in vitro glucose production and lipolysis studies, primary mouse hepatocytes were isolated by the Yale Liver Center. Following removal of cell debris by Percoll density gradient centrifugation, cells were plated on 6-well collagen-I coated dishes (4.0×10$^5$ cells/well) in 2 ml recovery media (DMEM High Glucose containing 10% FBS, 2% penicillin-streptomycin, 100 nM dexamethasone, 1 nM insulin, and 10 mM HEPES). After incubation for 6 hr at 37° C. and 5% CO$_2$, the attached cells were washed once in 1×PBS and then incubated overnight in 2 ml Low Glucose Culture Media (DMEM Low Glucose supplemented with 10% FBS, 2% penicillin-streptomycin and 10 mM HEPES for glucose production studies) or Serum Free Low Glucose Culture Media (DMEM Low Glucose supplemented with 0.5% fatty acid free BSA, 2% penicillin-streptomycin and 10 mM HEPES for lipolysis assays). The next morning, cells were washed twice in 1×PBS and culture media replaced with 2 mL glucose production media (DMEM Base Media supplemented with 0.5% fatty acid free BSA, 20 mM sodium lactate, 2 mM sodium pyruvate and 10 mM HEPES, pH 7.4) or Serum Free Low Glucose Culture Media (lipolysis assay) in the presence of 100 nM glucagon or vehicle control. After incubation for 8 hr at 37° C. and 5% CO$_2$, cell culture media was collected for analysis of glucose, NEFA, and glycerol concentrations as described above. $V_{PC}$ was determined by measuring $V_{PC}/V_{EGP}$ by PINTA as described above using 300 µL of the collected media, and multiplying this ratio by the measured glucose production rate. In a subset of studies, cells were incubated for 8 hr during the glucose production assay in media containing one of the following agents (all dissolved in 0.5% DMSO), or 0.5% DMSO vehicle: 20 µM ET-18-OCH$_3$ (Santa Cruz), 100 µM U-73122 (Sigma), 30 nM thapsigargin (Sigma), 100 nM vasopressin (Sigma) 50 µM 2-APB (R&D Systems), 70 µM caffeine (Sigma), 1 mM malic enzyme inhibitor hydroxymalonate (Sigma). To inhibit PKA, hepatocytes were incubated in H-89 dichloroacetate hydrate (Sigma, 25 µM) dissolved in media, or media lacking H-89 as a control. In the insulin treatment studies, hepatocytes were incubated in 1 nM insulin with 5% BSA and glucose production media for the duration of the glucose production assay. In the in vitro atglistatin study, hepatocytes were incubated in 10 µM atglistatin in 0.1% EtOH, or 0.1% EtOH vehicle. All values were normalized to total protein content determined from whole-cell lysates by a BCA protein assay (Thermo Fisher Scientific) according to the manufacturer's instructions and expressed as fold change verses vehicle-treated cells.

To assess oxygen consumption, primary mouse hepatocytes were isolated as described above and plated on collagen-I coated XF24 V7 cell culture plates (1.2×10$^4$ cells per well) in 2 mL recovery media as previously described (Camporez, J. P. et al. *Endocrinology* 154, 3099-3109). Following incubation for 6 hr at 37° C. and 5% CO$_2$, the cells were washed twice with 1 ml Low Glucose Culture Media and incubated overnight in 250 µl low glucose culture media at 37° C. and 5% CO$_2$. The following morning, cells were washed with XF24 assay media (DMEM Base containing 1.0 mM pyruvate, 2 mM glutamine and 5.5 mM glucose, pH 7.4). 500 µL of XF24 Assay Media was added to each well and plates were equilibrated at 37° C. for 1 h. Four measurements of basal oxygen consumption rates (picomoles per minute) were recorded on a Seahorse Bioscience XF$^e$ 24 Analyzer (Seahorse Biosciences) using an instrument protocol of 3-minute mix, 2-minute wait, and 3-minute measure. After baseline measurements, glucagon (or vehicle) was injected at a final concentration of 100 nM and oxygen consumption was recorded using the same instrument protocol. Ten measurements were taken following injection and the average of eight measurements were used for subsequent analyses. Oxygen consumption rates were normalized to total protein content and expressed as fold change compared to vehicle-treated cells. Experiments were repeated three times using 3-4 mice per genotype.

Statistical Analysis

Comparisons were performed using GraphPad Prism 7. The two-tailed paired or unpaired Student's t-test (as specified in the figure legends) was used to compare two groups, while two-way ANOVA with Bonferroni's multiple comparisons test was used to compare more than two groups. P-values less than 0.05 were considered significant. Data are presented as the mean±S.E.M. of the numbers given in the Brief Description of the Drawings section.

Selected Discussion

Figure 24D:
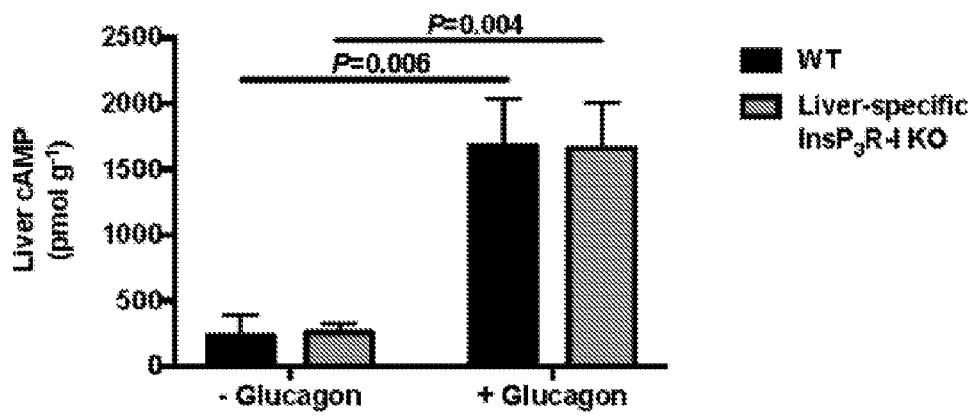
Figure 24E:
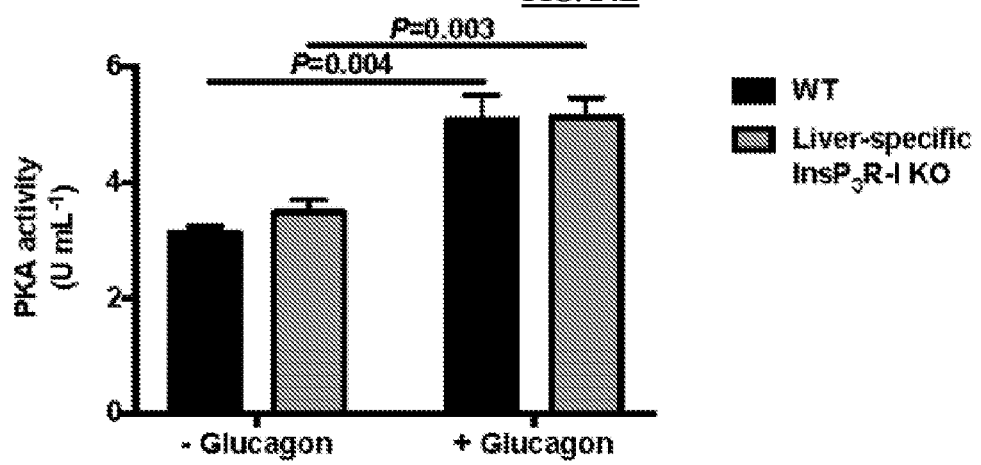
Figure 24F:
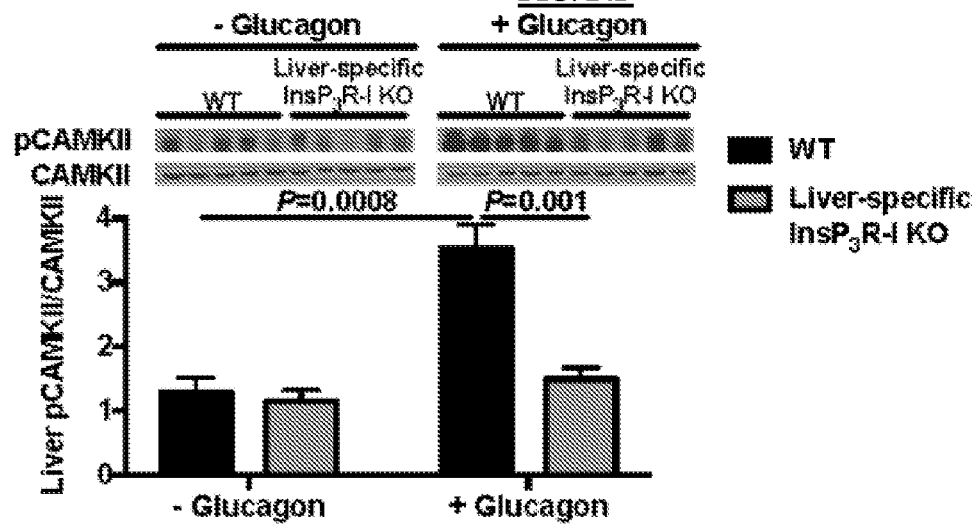
Figure 24G:
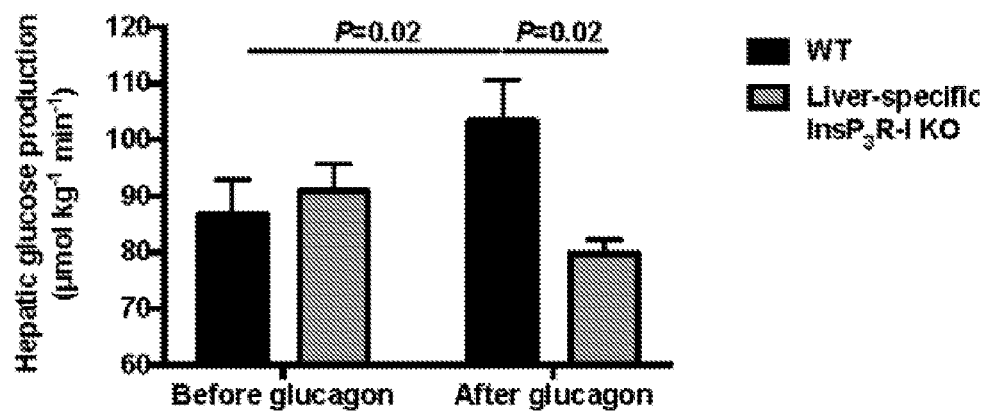
Figure 24H:
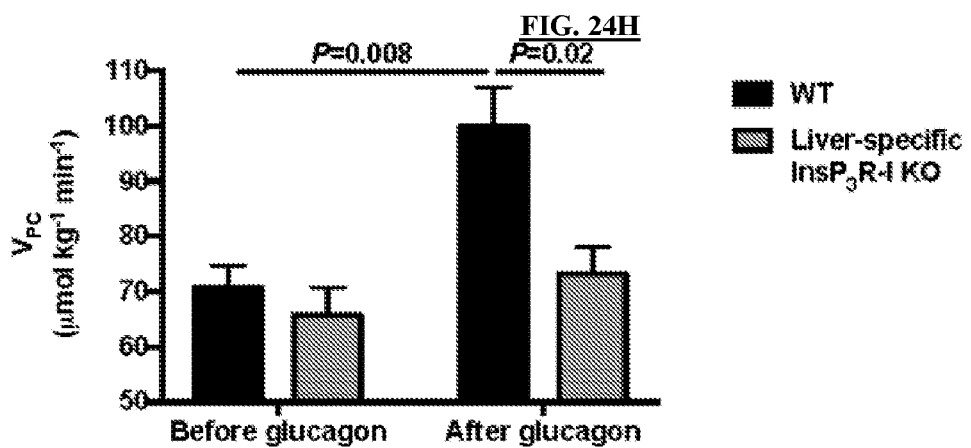
Figure 24I:
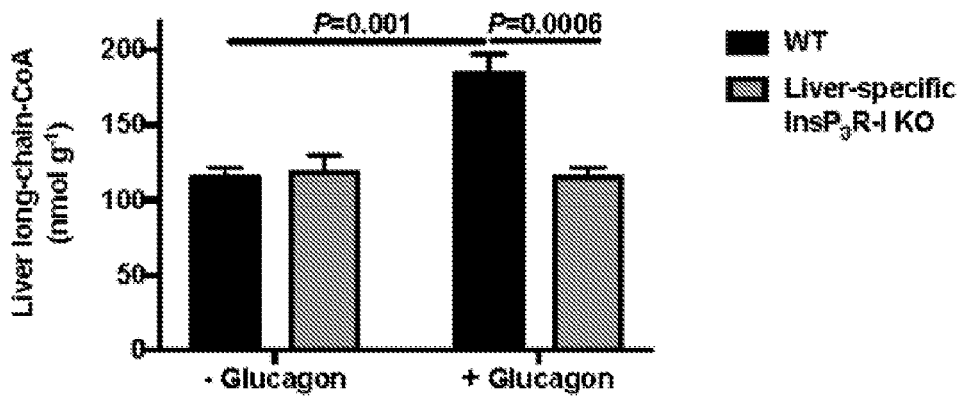
Figure 24J:
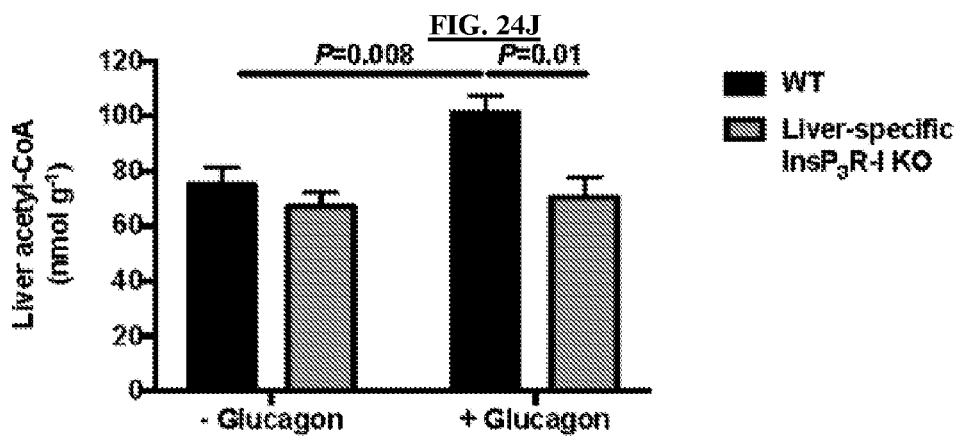
Figure 30P:
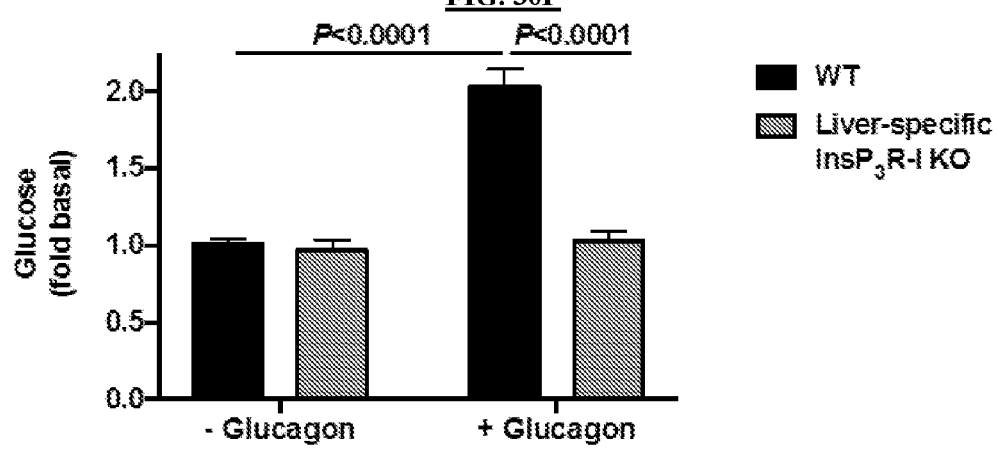
FIGS. 30P-30Q are graphs showing in vitro glucose production (n=9) and V$_{PC}$ flux (n=4) in isolated hepatocytes.
Figure 30Q:
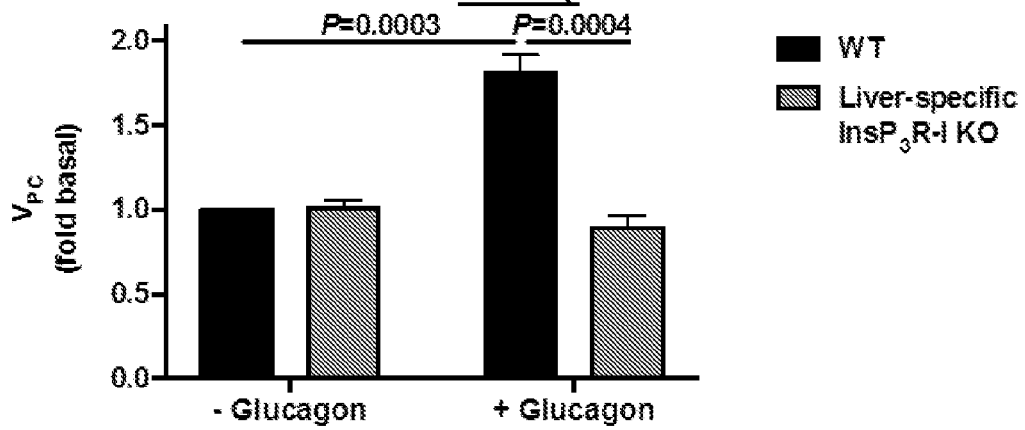

In order to examine the potential calcium dependence of the acute hepatic gluconeogenic response to glucagon, overnight-fasted, glycogen-depleted, liver-specific InsP$_3$R-I knockout (InsP$_3$R-I KO) mice and their age and weight-matched, wild-type (WT) littermates were studied (FIG. 30A). InsP$_3$R-I KO mice exhibited a marked reduction in hepatic InsP$_3$R-I protein expression with undetectable InsP$_3$R-II and unchanged InsP$_3$R-III protein expression (FIGS. 30B-30D). The mice were treated with an acute infusion of glucagon, which raised plasma glucagon concentrations approximately five-fold and led to a modest increase in plasma glucose and insulin concentrations in WT but not in liver-specific InsP$_3$R-I knockout mice (FIGS. 24A-24C). Concentrations of cAMP, activity of protein kinase A (PKA), and phosphorylation of CRTC2 were increased with glucagon in both genotypes, dissociating activity of each of these mediators from glucagon-induced changes in plasma glucose/insulin concentrations. However, glucagon infusion activated InsP$_3$R-I by increasing its phosphorylation two-fold only in WT livers (FIGS. 24D-24E and 30E-30F). Glucagon stimulated hepatic Ca$^{2+}$/calmodulin-dependent protein kinase (CAMK) isoform II but not CAMKIV phosphorylation in an InsP$_3$R-I-dependent manner (FIGS. 24F and 30G). Without intending to be limited to any particular theory, these data suggest that InsP$_3$R-I activation and resultant CAMKII activity are required for glucagon's acute effect to stimulate hepatic glucose production (HGP), which can be attributed almost entirely to gluconeogenesis in this hepatic glycogen-depleted state. To determine the mechanism by which glucagon acutely stimulates hepatic gluconeogenesis through InsP$_3$R-I activity, PINTA method was applied to quantify rates of hepatic glucose production and pyruvate carboxylase flux ($V_{PC}$). Using this approach ~25% increases in rates of HGP were measured. Without intending to be limited to any particular theory, this could be attributed to increased hepatic $V_{PC}$ flux associated with plasma and liver amino acid depletion without any alterations in hepatic glycogen content (FIGS. 24G-24H and 30H-30O, Tables 11-12). These reductions in amino acid concentrations were largely accounted for by reductions in alanine content, while glutamine/glutamate concentrations were not significantly altered by glucagon. The observed increase in the rate of in vivo HGP was mirrored by a two-fold increase in both glucose production and $V_{PC}$ flux in isolated hepatocytes from WT but not from InsP$_3$R-I KO hepatocytes incubated with glucagon (FIGS. 30P-30Q). The ability of insulin to suppress both glucose production and $V_{PC}$ flux was unaltered in InsP$_3$R-I KO mice (FIGS. 30R-30S). Malic enzyme activity was also dissociated from glucose production: incubation of hepatocytes with a small molecule inhibitor of malic enzyme activity had no impact on basal or glucagon-stimulated glucose production or $V_{PC}$ (FIGS. 30T-30U).

TABLE 11

Plasma amino acid concentrations. Data are the mean ± S.E.M. of n = 5 per group, with comparisons between genotypes by the 2-tailed unpaired Student's t-test, and comparisons within the same mice before and after glucagon infusion by the 2-tailed paired Student's t-test.
*Denotes comparisons to the same group before glucagon;
# denotes comparisons to WT mice after glucagon infusion.

| Plasma metabolite | WT before glucagon (mM) | InsP$_3$R1 KO before glucagon (mM) | WT after glucagon (mM) | InsP$_3$R1 KO after glucagon (mM) |
|---|---|---|---|---|
| Serine | 0.030 ± 0.005 | 0.032 ± 0.006 | 0.032 ± 0.003 | 0.037 ± 0.005 |
| Leucine | 0.54 ± 0.16 | 0.76 ± 0.23 | 0.48 ± 0.02 | 0.66 ± 0.08 |
| Isoleucine | 0.52 ± 0.17 | 0.62 ± 0.19 | 0.39 ± 0.02 | 0.54 ± 0.06# |
| Aspartate/asparagine | 0.034 ± 0.008 | 0.034 ± 0.015 | 0.013 ± 0.004* | 0.055 ± 0.023 |
| Phenylalanine | 0.091 ± 0.022 | 0.097 ± 0.023 | 0.065 ± 0.003 | 0.090 ± 0.007# |
| Glutamate/glutamine | 0.28 ± 0.07 | 0.19 ± 0.04 | 0.30 ± 0.01 | 0.27 ± 0.06 |
| Lactate | 1.21 ± 0.44 | 1.52 ± 0.35 | 1.59 ± 0.39 | 1.31 ± 0.10 |

TABLE 12

Liver amino acid concentrations. Data are the mean ± S.E.M. of n = 5 per group, with comparisons between genotypes and within the same genotype ,– vs. + glucagon treatment performed using the 2-tailed unpaired Student's t-test. + Denotes comparisons to KO mice without glucagon infusion; # denotes comparisons to WT mice after glucagon infusion.

| Liver metabolite | WT −glucagon (μmol/g) | InsP$_3$R1 KO −glucagon (μmol/g) | WT +glucagon (μmol/g) | InsP$_3$R1 KO +glucagon (μmol/g) |
|---|---|---|---|---|
| Glycine | 0.13 ± 0.04 | 0.11 ± 0.03 | 0.13 ± 0.03 | 0.22 ± 0.06+ |
| Serine | 0.006 ± 0.002 | 0.003 ± 0.002 | 0.007 ± 0.002 | 0.016 ± 0.005+ |
| Leucine | 0.25 ± 0.03 | 0.21 ± 0.03 | 0.22 ± 0.02 | 0.90 ± 0.42 |
| Isoleucine | 0.059 ± 0.015 | 0.038 ± 0.009 | 0.033 ± 0.004 | 0.062 ± 0.011# |
| Phenylalanine | 0.041 ± 0.005 | 0.036 ± 0.005 | 0.040 ± 0.004 | 0.091 ± 0.032 |
| Glutamate/glutamine | 1.05 ± 0.14 | 1.06 ± 0.07 | 0.74 ± 0.10 | 0.93 ± 0.10 |
| Lactate | 0.89 ± 0.24 | 1.10 ± 0.06 | 0.80 ± 0.28 | 0.94 ± 0.24 |

Figure 25A:
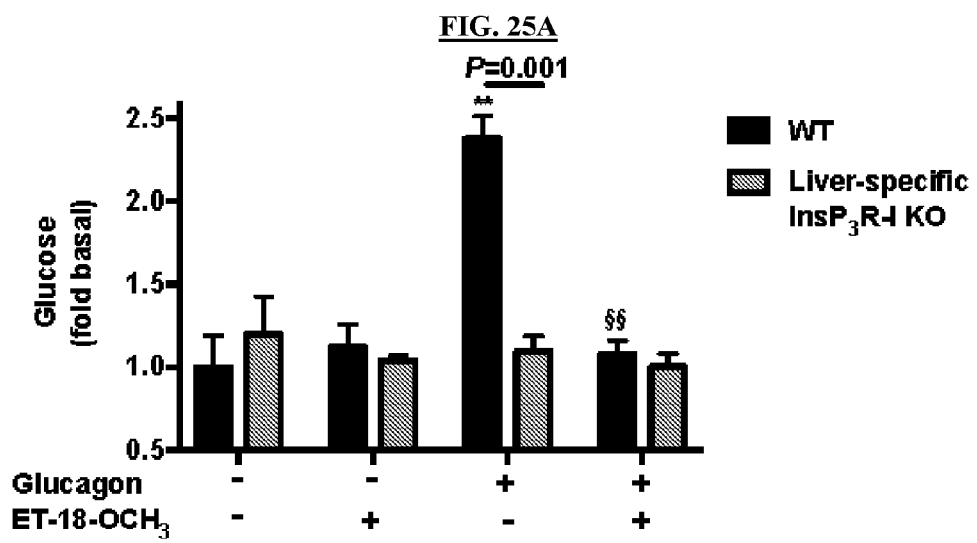
Figure 25B:
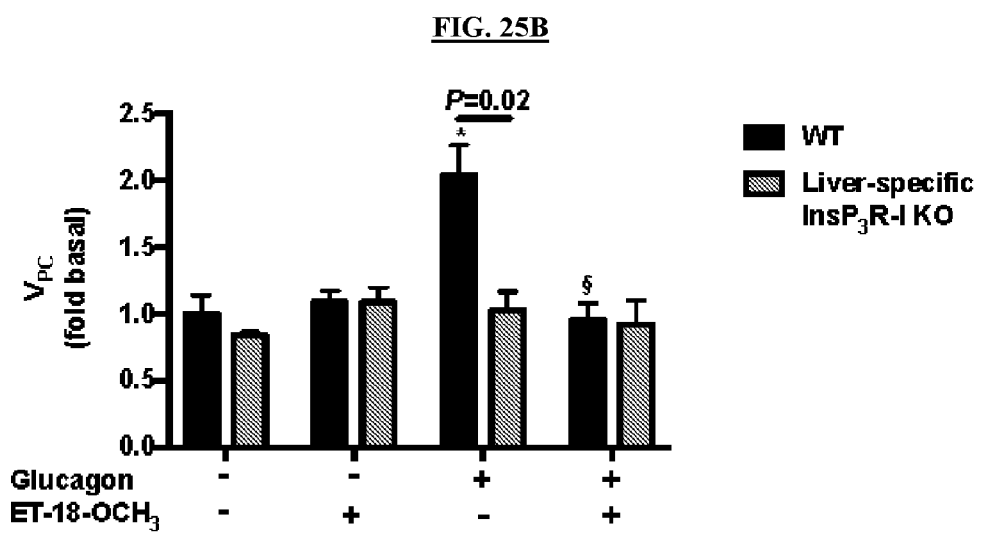
Figure 25F:
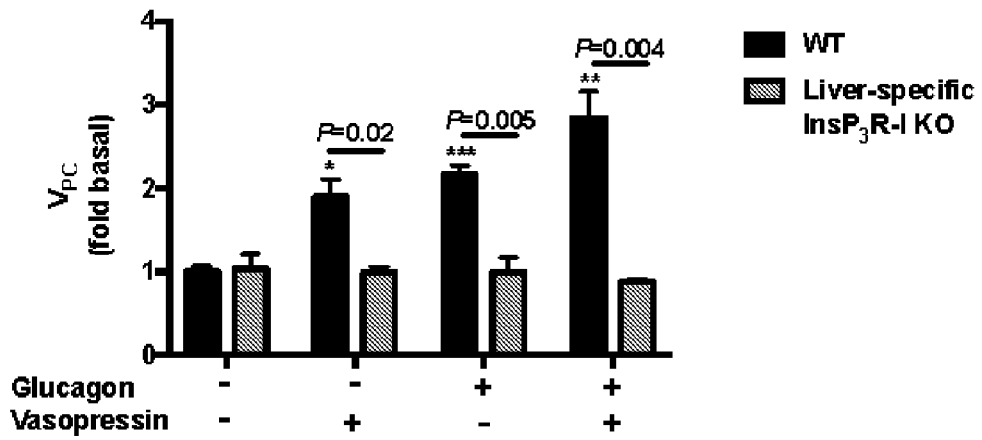
Figure 25G:
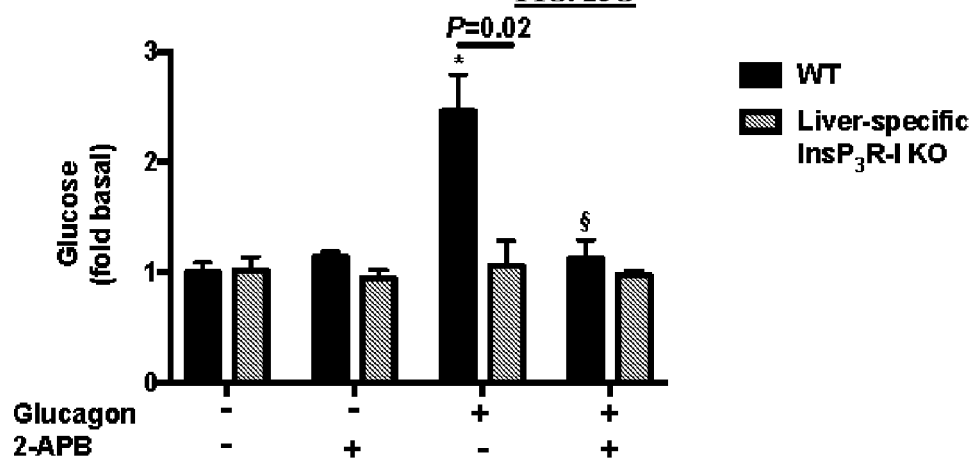
Figure 25H:
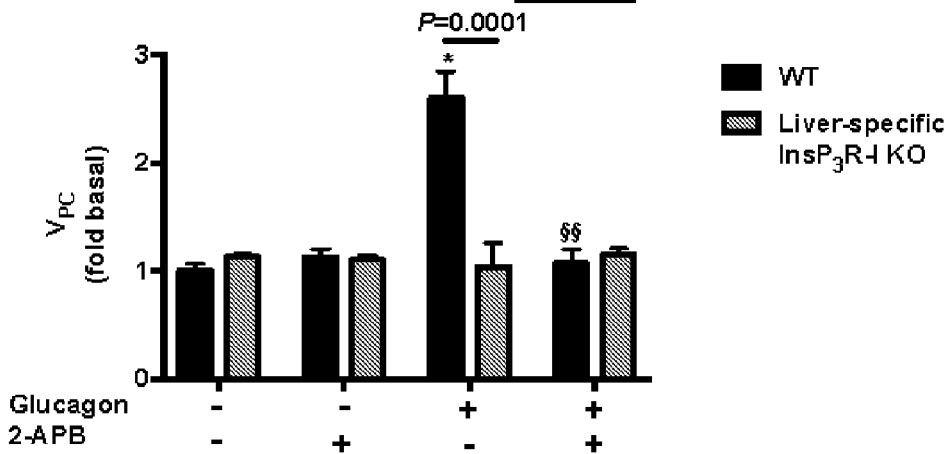
Figure 25I:
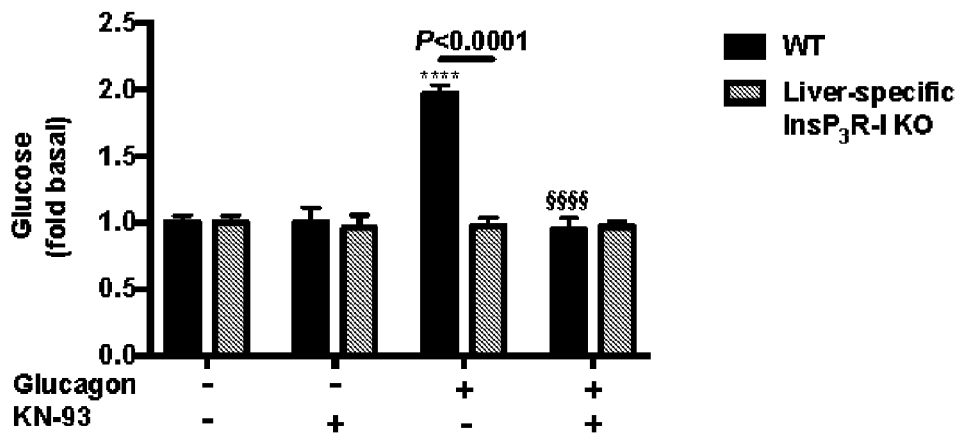
Figure 25J:
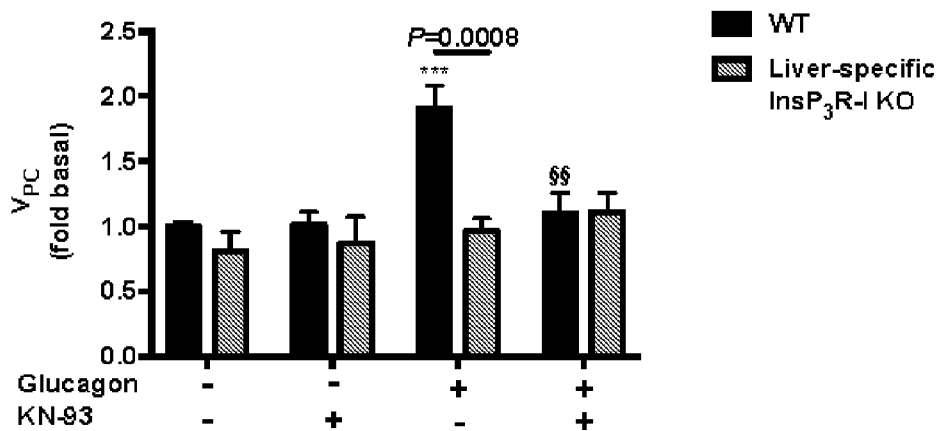
Figure 31C:
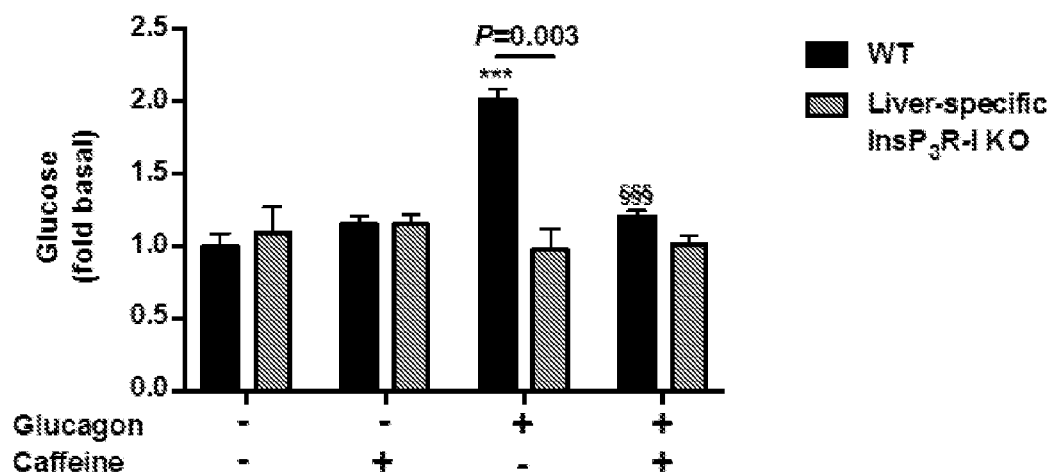
Figure 31D:
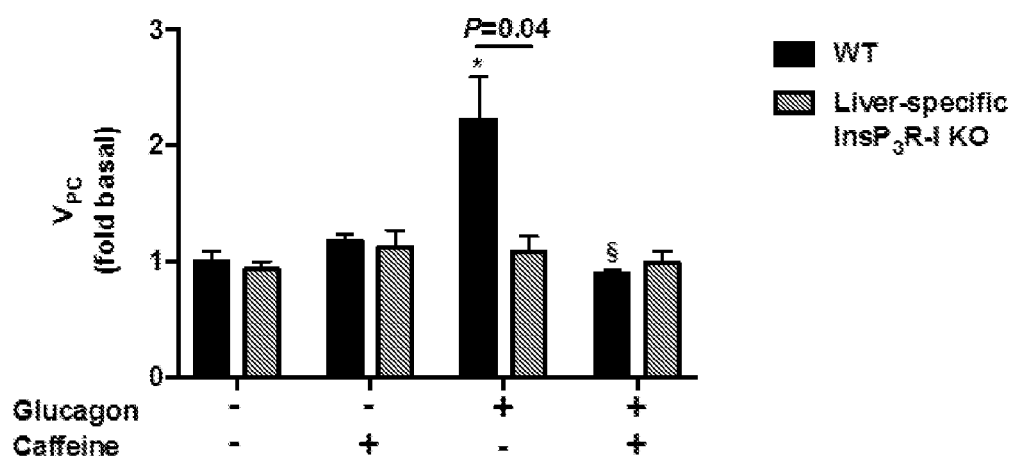
Figure 31E:
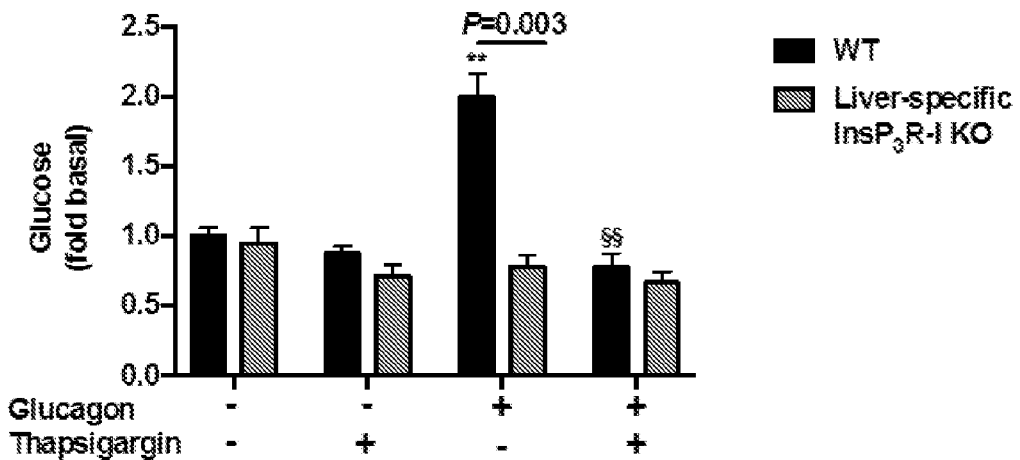
Figure 31I:
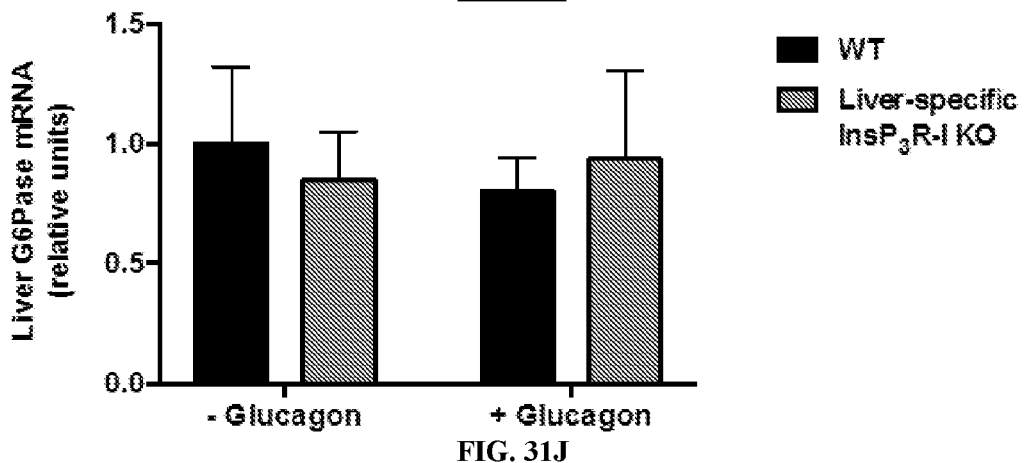
Figure 31J:
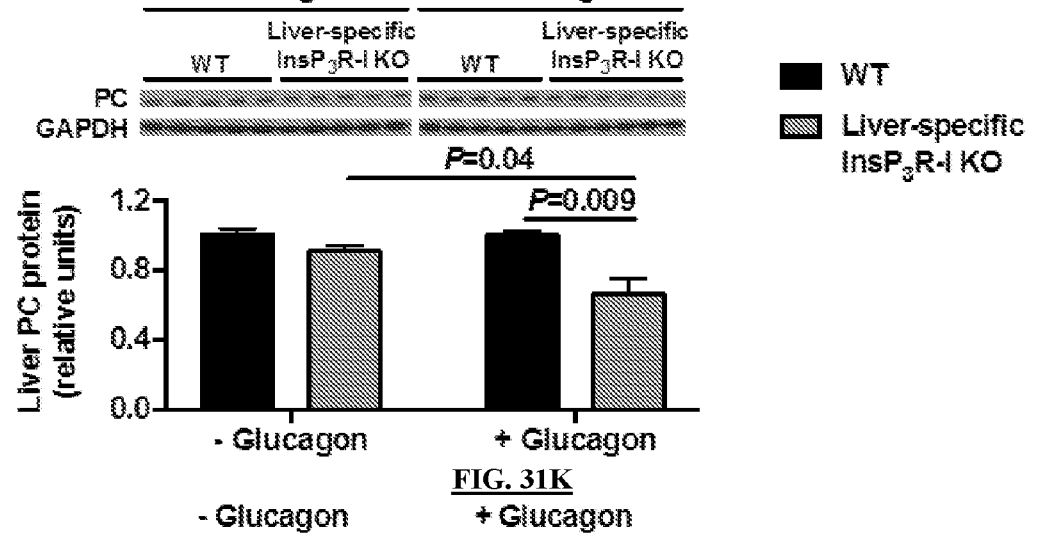
FIGS. 31J-31K are graphs showing liver PC and PEPCK protein. GAPDH blots, which were utilized for normalizing gluconeogenic protein expression, are duplicated between the two panels. These blots were stripped and re-probed for all three proteins of interest.
Figure 31K:
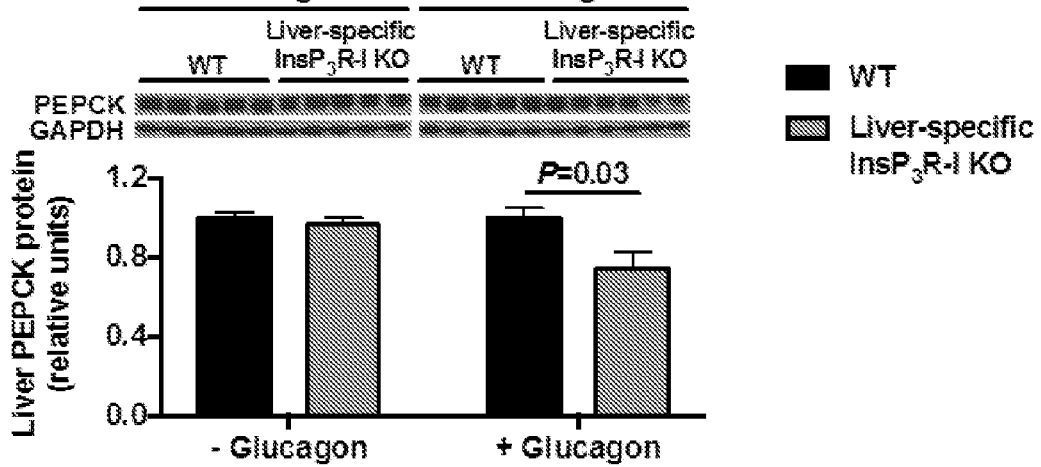

To further explore the mechanism by which glucagon stimulates hepatic glucose production and $V_{PC}$ flux and to examine the role of intrahepatic calcium signaling in these processes, isolated hepatocytes were treated with ET-18-OCH$_3$ or U-73122, two phospholipase C (PLC) antagonists. Both agents inhibited glucose production and $V_{PC}$ flux in WT but not InsP$_3$R-I KO hepatocytes, confirming that intact PLC signaling was required for glucagon to stimulate hepatic gluconeogenesis via InsP$_3$ receptor activation (FIGS. 25A-25B and 31A-31B). Similarly an inhibitor of PKA activity, H-89, abrogated glucagon's ability to stimulate glucose production and $V_{PC}$ only in WT hepatocytes, demonstrating that both the PLC and PKA pathways are required to activate gluconeogenesis in response to glucagon via InsP$_3$R-I signaling (FIGS. 25C-25D). Next to more specifically confirm the role of InsP$_3$R-I in mediating glucagon's in vitro effect to promote hepatic glucose production, hepatocytes were treated with vasopressin, an activator of the InsP$_3$ receptor. Vasopressin recapitulated the effect of glucagon to drive both glucose production and $V_{PC}$. Conversely two InsP$_3$ antagonists, 2-aminoethoxydiphenyl borate (2-ABP) and caffeine, inhibited glucagon-stimulated glucose production and $V_{PC}$ flux (FIGS. 25E-25H and 31C-31D). In addition incubation of hepatocytes in KN-93, a small molecule inhibitor of CAMKII/IV activity, abrogated glucagon's effect to stimulate gluconeogenesis in WT hepatocytes, consistent with a critical role for InsP$_3$R-I activation of CAMKII/IV in glucagon stimulation of gluconeogenesis (FIGS. 25I-25J). Thapsigargin, an inhibitor of the SERCA pump in both the sarcoplasmic and endoplasmic reticulum, also inhibited both glucose production and $V_{PC}$ stimulated by glucagon (FIGS. 31E-31F), suggesting that maintaining a normal balance of calcium throughout the cell is required for normal InsP$_3$R-I signaling. None of these agents had any effect in InsP$_3$R-I KO mice, indicating that InsP$_3$R-II and -III do not compensate for the absence of InsP$_3$R-I in liver (FIGS. 25A-25J and 31A-31F).

Figure 31N:
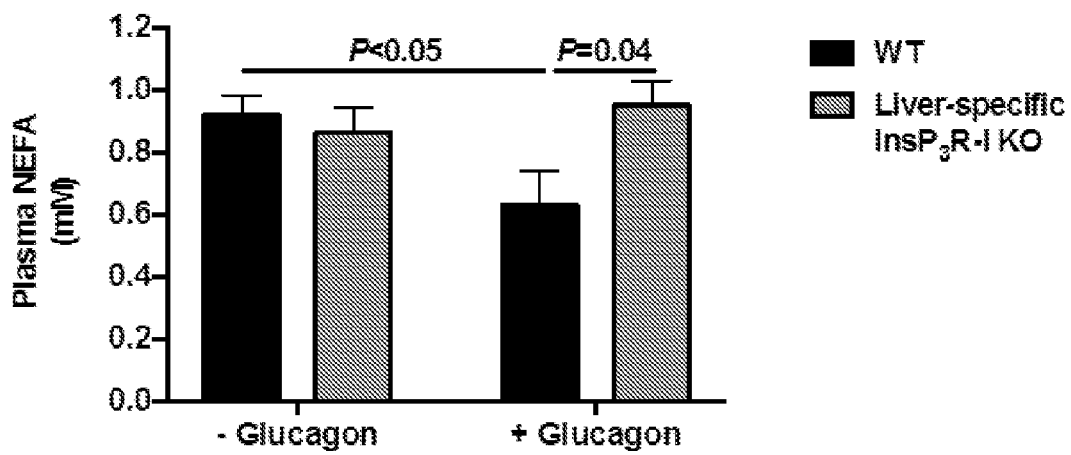
FIG. 31N is a graph showing plasma NEFA concentrations.
Figure 31O:
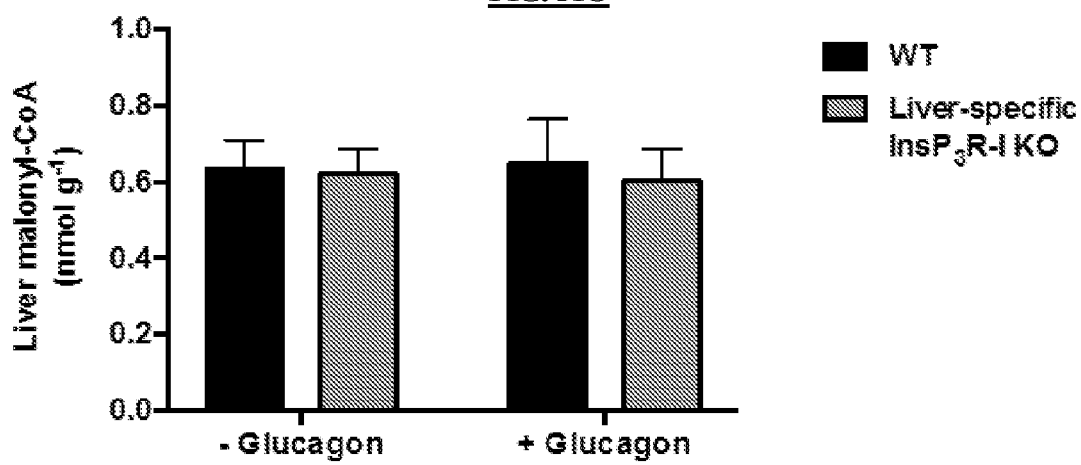
FIG. 31O is a graph showing liver malonyl-CoA concentrations.
Figure 31P:
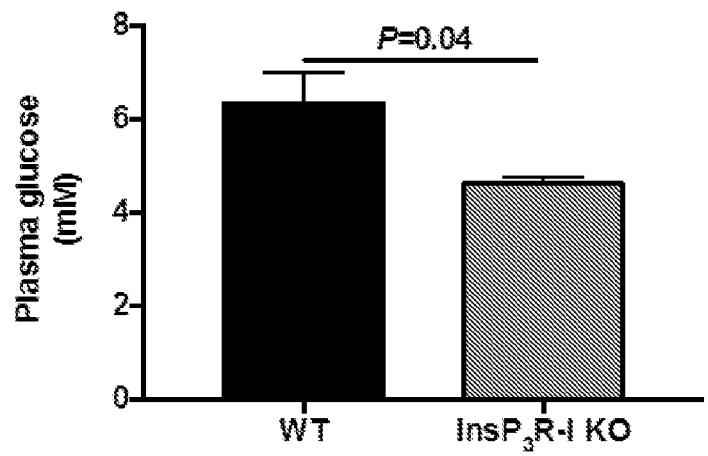
FIGS. 31P-31R are graphs showing plasma glucose, insulin, and glucagon concentrations in 48 hr fasted mice.
Figure 31Q:
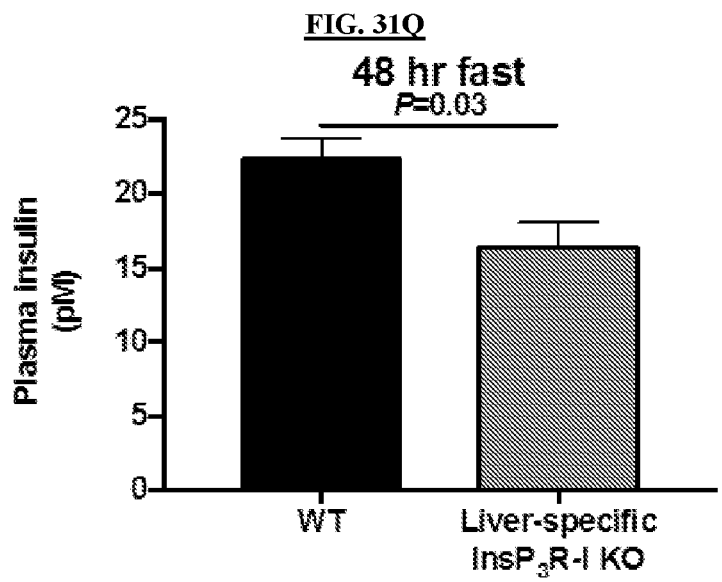
Figure 31R:
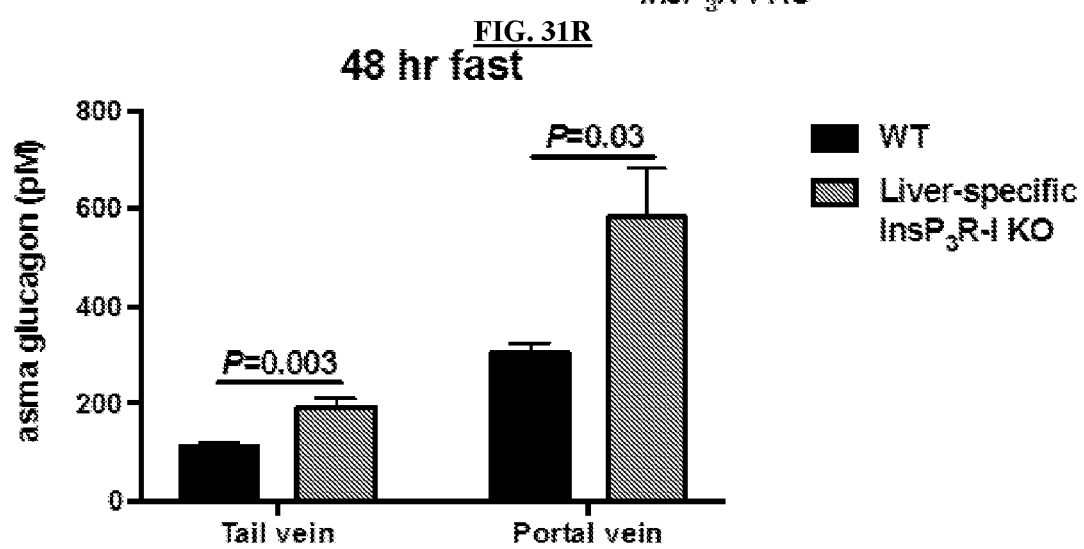
Figure 31S:
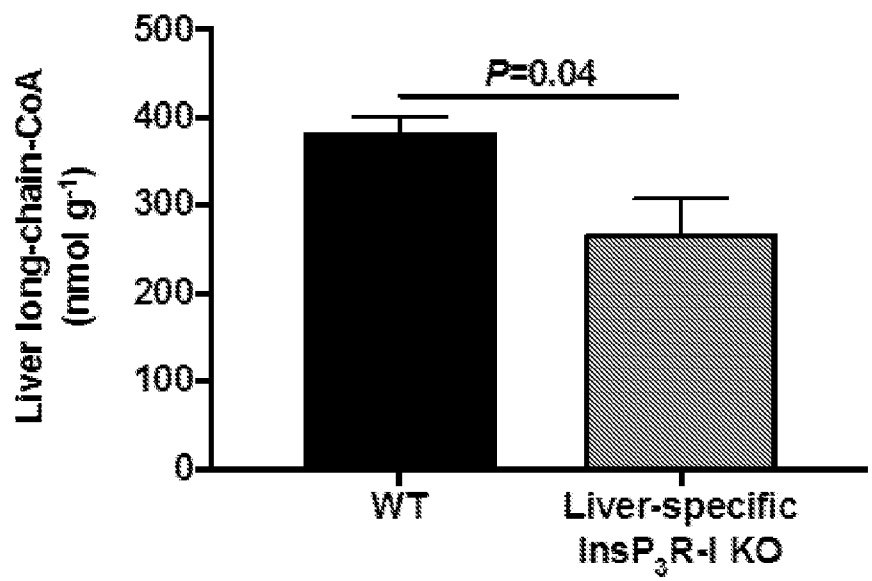
Figure 31T:
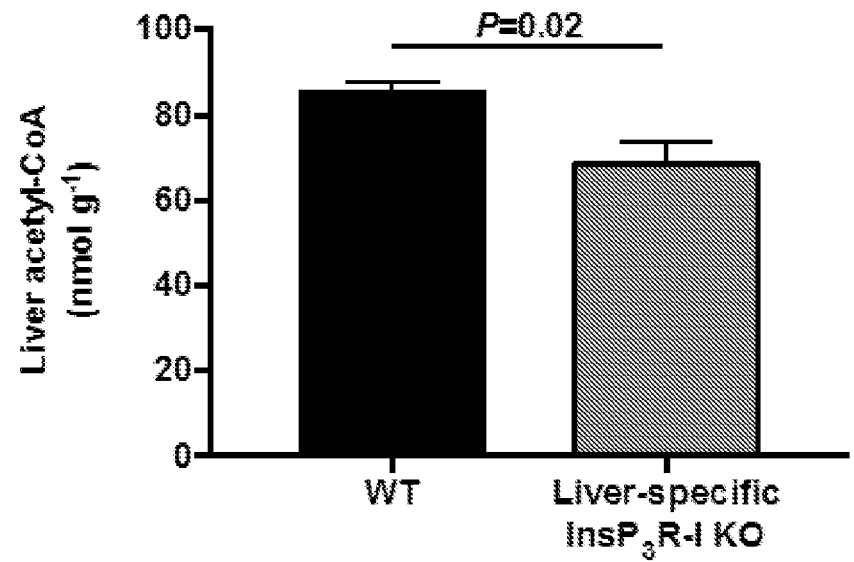

The observed increases in rates of hepatic glucose production occurred in the absence of any effect of glucagon to acutely increase hepatic gluconeogenic mRNA or protein expression in vivo or gluconeogenic protein expression in hepatocytes but were associated with 35-60% increases in hepatic long-chain acyl-CoA and acetyl-CoA content (FIGS. 24I-24J and 31G-31K). These increases in hepatic long-chain- and acetyl-CoA concentrations were dissociated from phosphorylation of both acetyl-CoA carboxylase and 5' AMP-activated protein kinase (AMPK), both of which were increased in InsP$_3$R-I KO mice but not in WT mice (FIGS. 31L-31M). Without intending to be limited to any particular theory, this likely reflects the interplay between glucagon's ability to promote the phosphorylation of both enzymes and the ability of hyperinusulinemia, which was observed only in WT mice infused with glucagon, to suppress it. Hepatic long-chain acyl-CoA and acetyl-CoA content increased in WT mice infused with glucagon despite reduced plasma non-esterified fatty acid (NEFA) concentrations in glucagon-treated WT mice (FIG. 31N), consistent with glucagon stimulation of intrahepatic but not white adipocyte tissue (WAT) lipolysis. As acetyl-CoA is a key allosteric activator of PC, the increase in hepatic acetyl-CoA content observed with glucagon infusion could explain the increases in $V_{PC}$ and HGP rates that occurred following glucagon treatment in WT mice. These changes occurred independently of any changes in hepatic malonyl-CoA content (FIG. 31O), indicating that malonyl-CoA suppression of carnitine palmitoyl transferase-I (CPT-I) was not responsible for glucagon stimulation of hepatic mitochondrial β-oxidation under these conditions. The measured malonyl-CoA concentrations in these overnight fasted mice were 80% lower than those measured in fed mice (WT 3.30±0.24 nmol g$^{-1}$, p<0.0001 vs. overnight fasted mice; KO 3.16±0.35 nmol g$^{-1}$, p=0.0001 vs. overnight fasted mice).

To further understand the physiologic function of glucagon-induced endogenous glucose production, we fasted WT and InsP$_3$R-I KO mice for 48 hr. In the starved state, despite 70-90% increases in plasma glucagon concentrations in the tail vein and portal vein, InsP$_3$R-I KO mice manifested relative reductions in plasma glucose and insulin concentrations associated with reductions in hepatic long-chain CoA and acetyl-CoA content without any changes in hepatic malonyl-CoA content (FIGS. 31P-31U). These data demonstrate that the hepatic gluconeogenic response to glucagon is of minimal importance in maintaining plasma glucose during a relatively short-term (overnight) fast, but becomes critical to maintain euglycemia in the starved state.

Figure 26A:
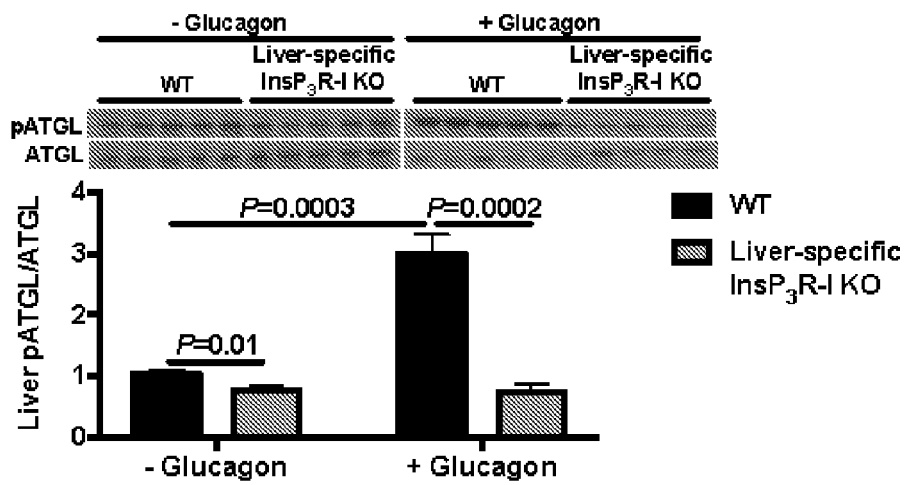
Figure 26F:
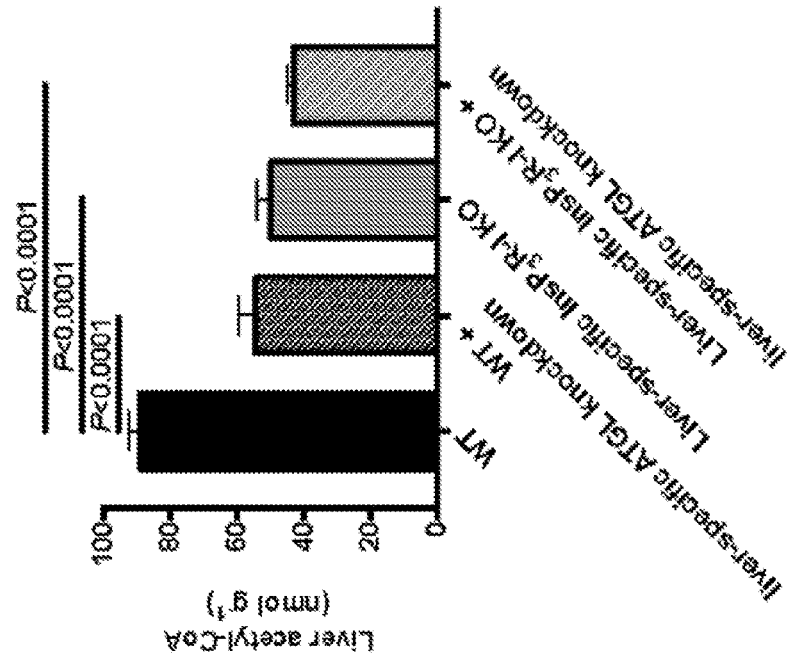
Figure 26E:
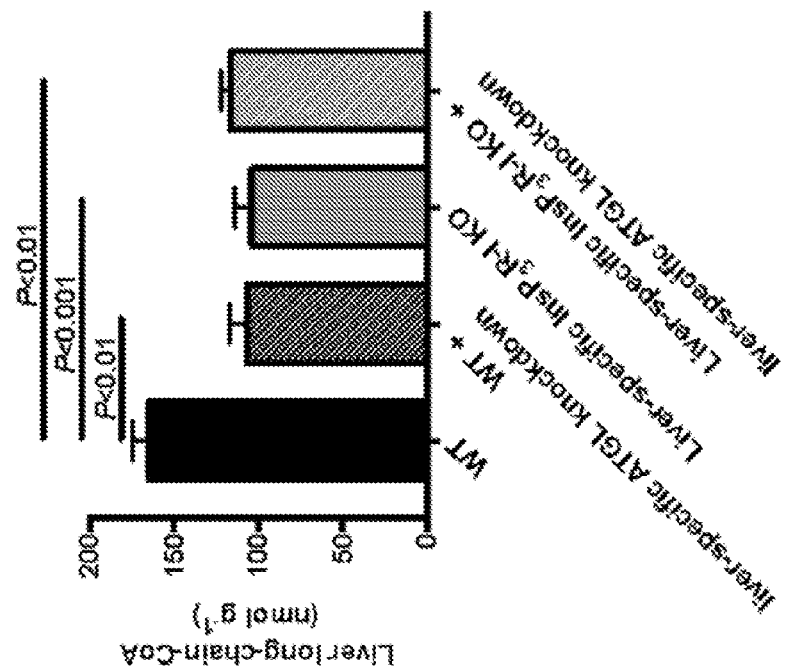
Figure 26G:
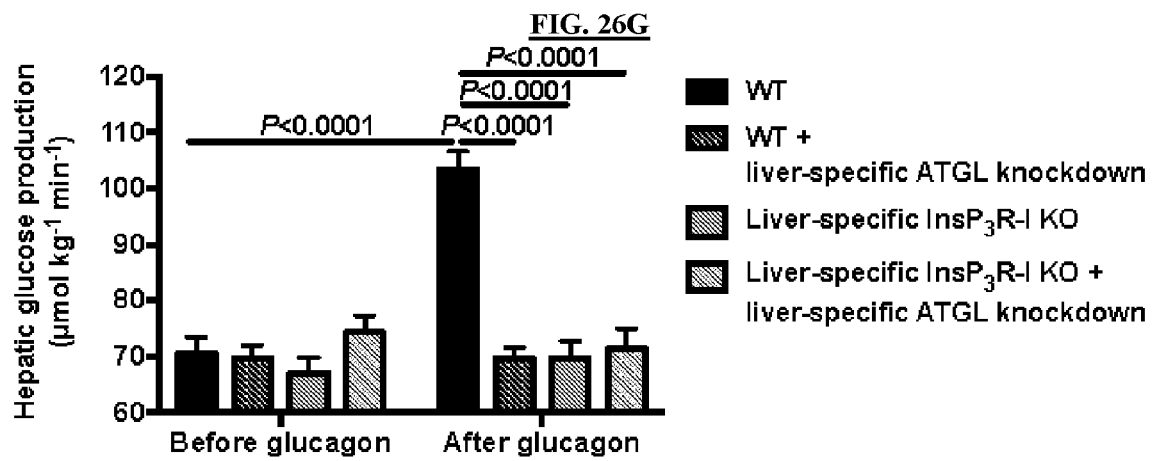
Figure 26H:
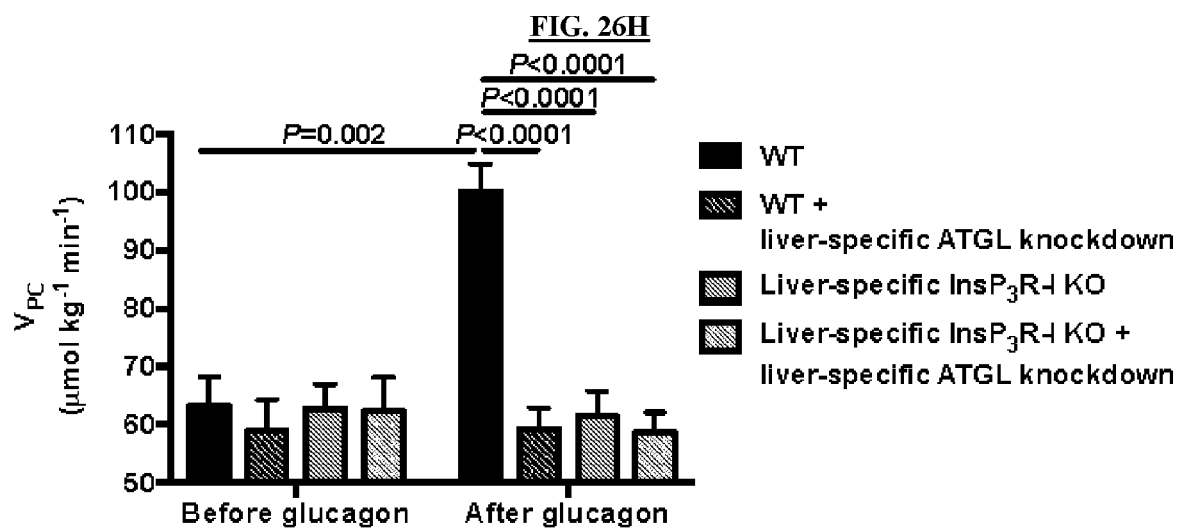
Figure 32B:
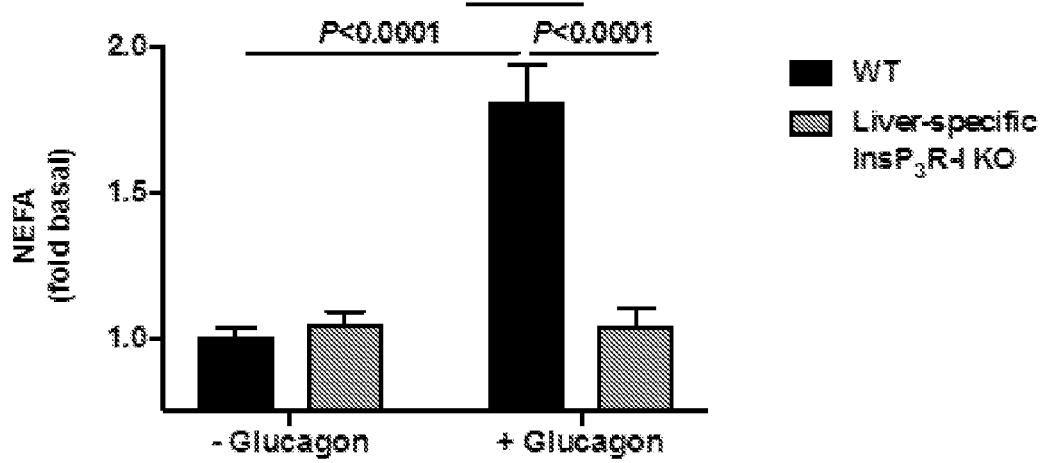
Figure 32C:
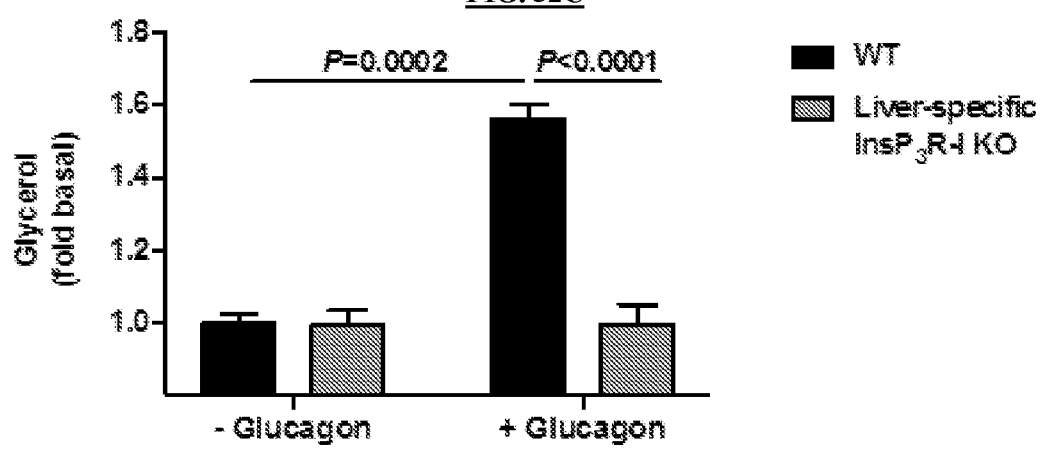
Figure 32D:
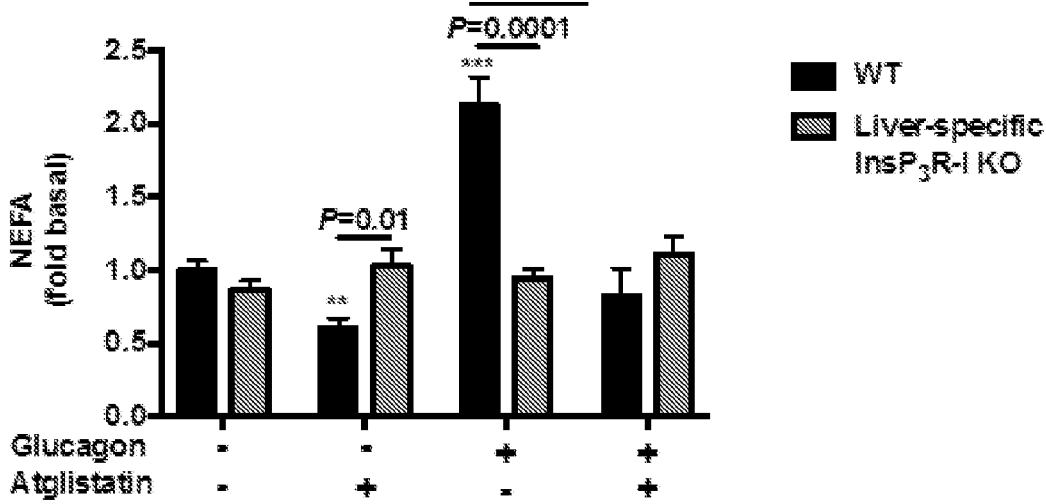
Figure 32G:
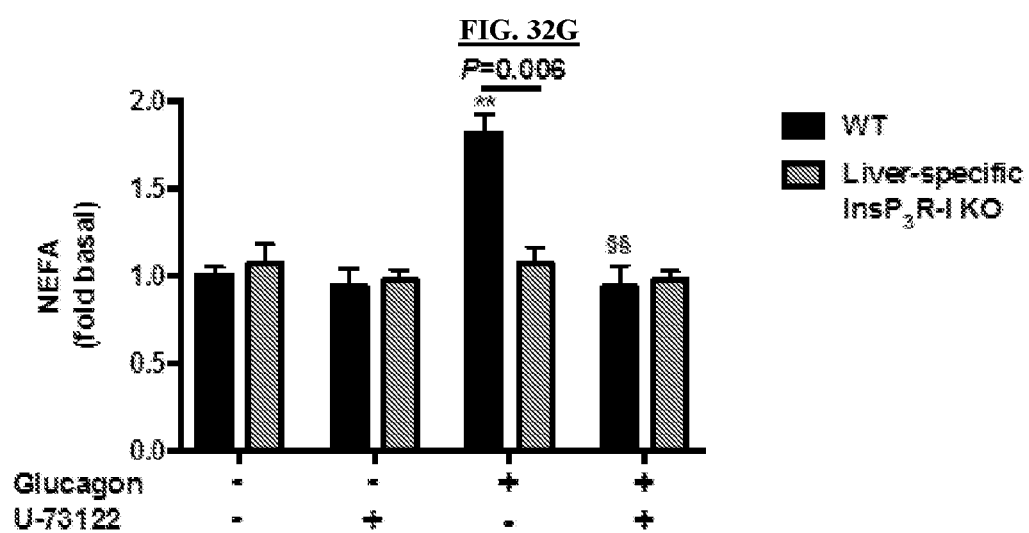
Figure 32H:
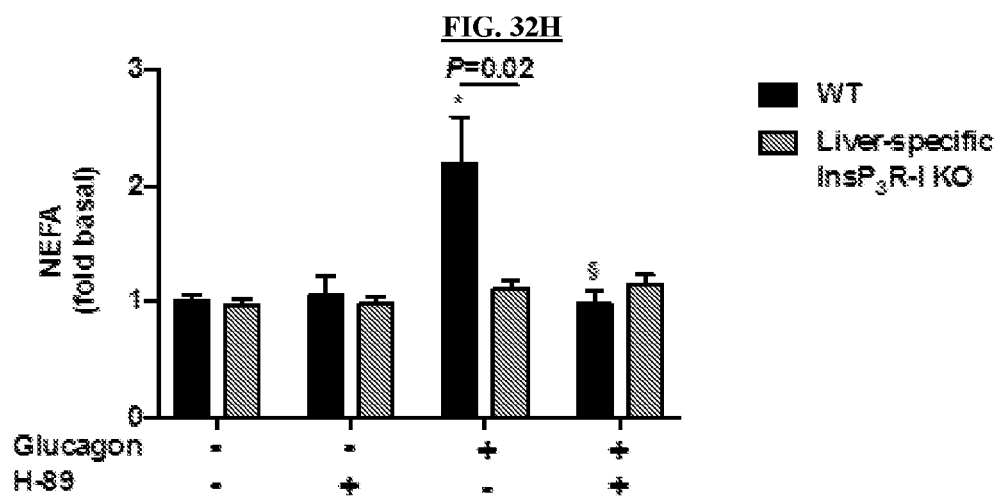
Figure 32I:
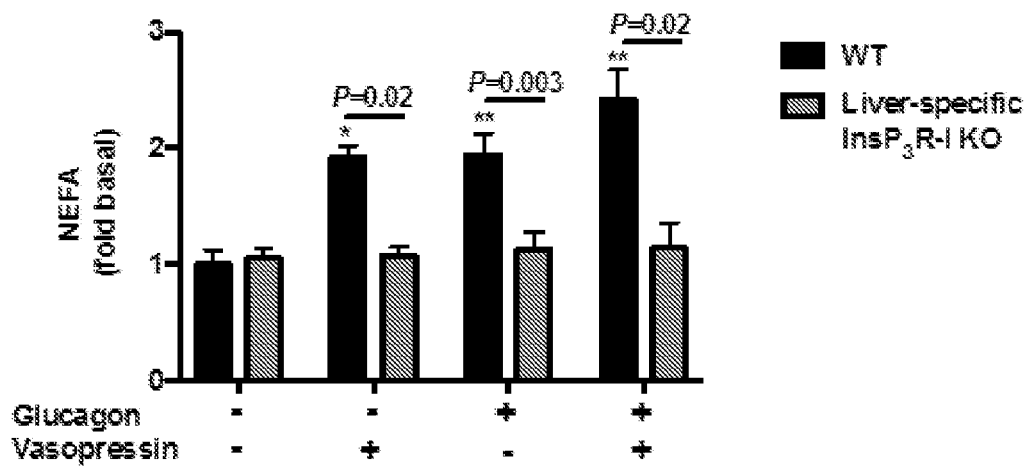
Figure 32J:
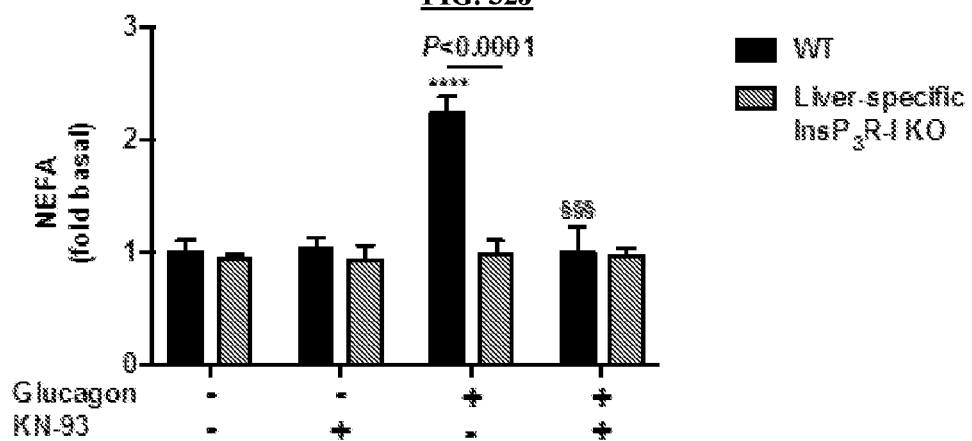
Figure 32K:
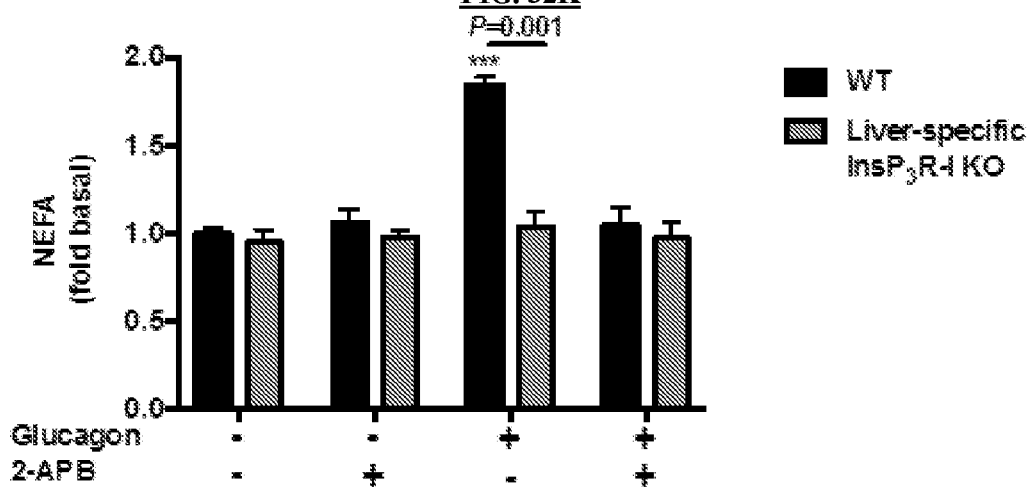
Figure 32L:
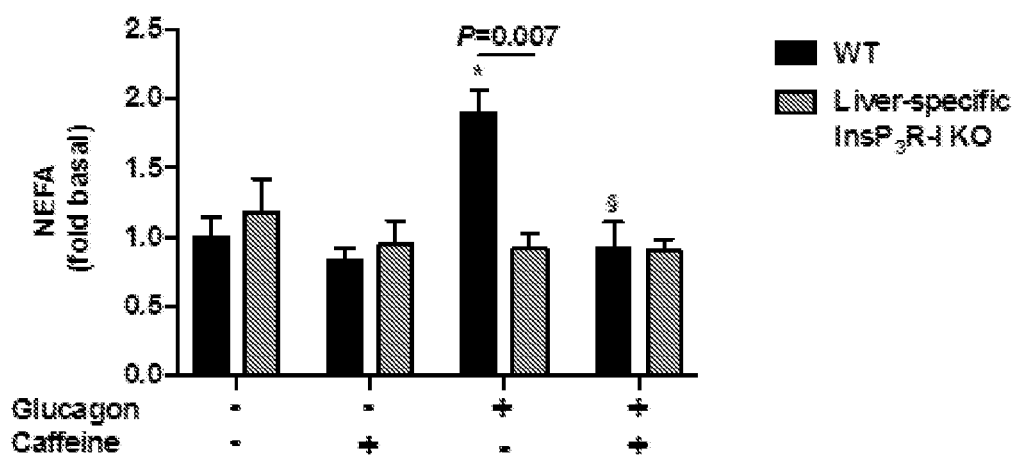
Figure 32M:
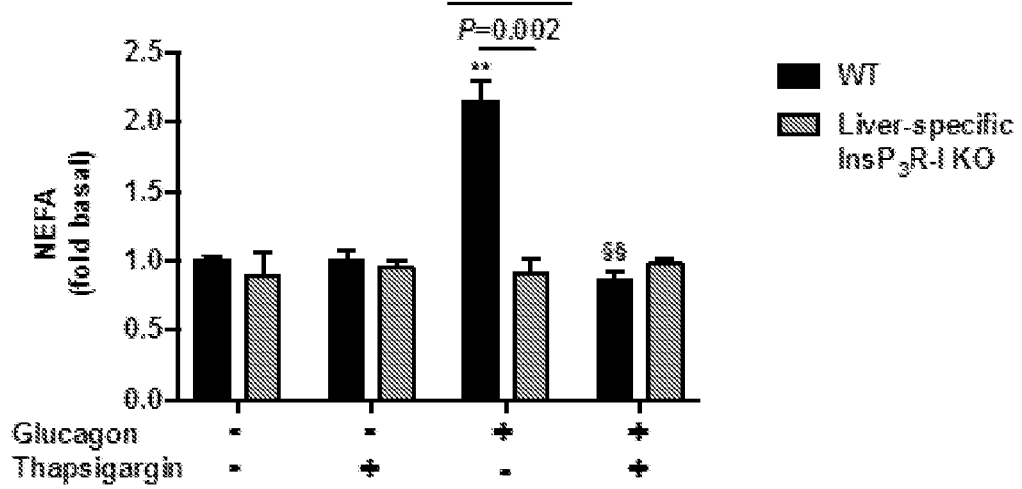

Hepatic adipose triglyceride lipase (ATGL) S406 phosphorylation, which has previously been shown to regulate ATGL activity, was increased three-fold by glucagon in vivo in WT but not InsP$_3$R-I KO mice (FIG. 26A). In contrast, hormone-sensitive lipase (HSL) phosphorylation was increased by glucagon in both genotypes, likely resulting from PKA activation but dissociating HSL activity from glucagon activation of glucose production and V$_{PC}$ (FIG. 32A). In vitro studies revealed 60-100% increases in NEFA and glycerol production with glucagon treatment in WT but not InsP$_3$R-I deficient hepatocytes, demonstrating glucagon stimulation of intrahepatic lipolysis (FIGS. 32B-32C). Confirming the critical role of glucagon-stimulated intrahepatic lipolysis to promote gluconeogenesis, glucagon had no effect to stimulate either glucose production or V$_{PC}$ in hepatocytes treated with atglistatin, a small molecule inhibitor of ATGL (FIGS. 26B and 32D-32E). Incubating hepatocytes with the InsP$_3$R agonist vasopressin recapitulated the effect of glucagon to stimulate intrahepatic lipolysis, whereas InsP$_3$R antagonists (2-APB and caffeine) or a CAMKII/IV inhibitor (KN-93) abrogated the effect of glucagon to stimulate intrahepatic lipolysis, thereby confirming that InsP$_3$R-mediated calcium signaling was required for glucagon stimulation of not only glucose production and V$_{PC}$ flux, but also intrahepatic lipolysis. Treatment with phospholipase C inhibitors (ET-18-OCH$_3$ and U-73122), a PKA inhibitor (H-89), or with a SERCA pump inhibitor (thapsigargin) also abrogated glucagon's effect to stimulate intrahepatic lipolysis, demonstrating that with each agent tested, intrahepatic lipolysis was correlated with both V$_{PC}$ flux and glucose production in isolated hepatocytes (FIGS. 32F-32M).

Figure 33J:
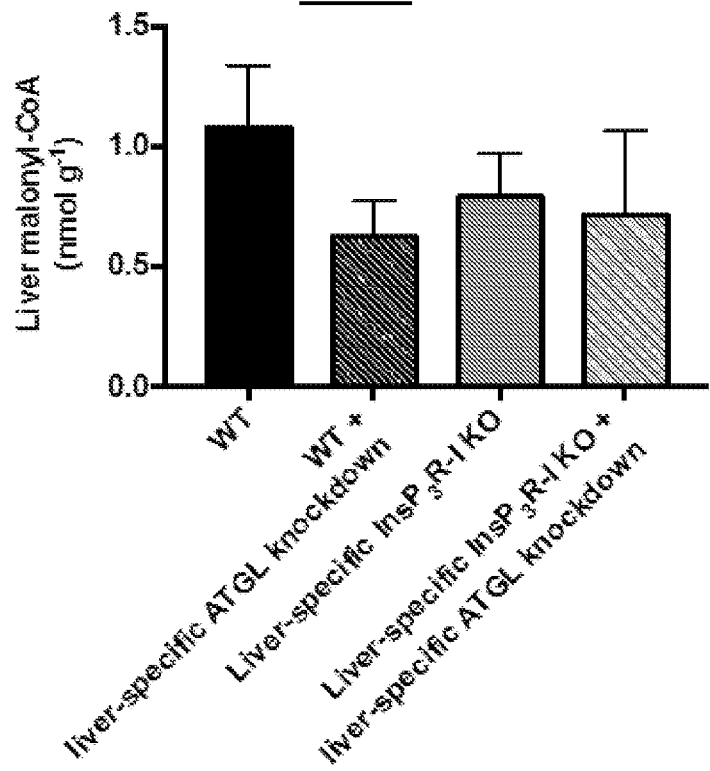
Figure 33D:
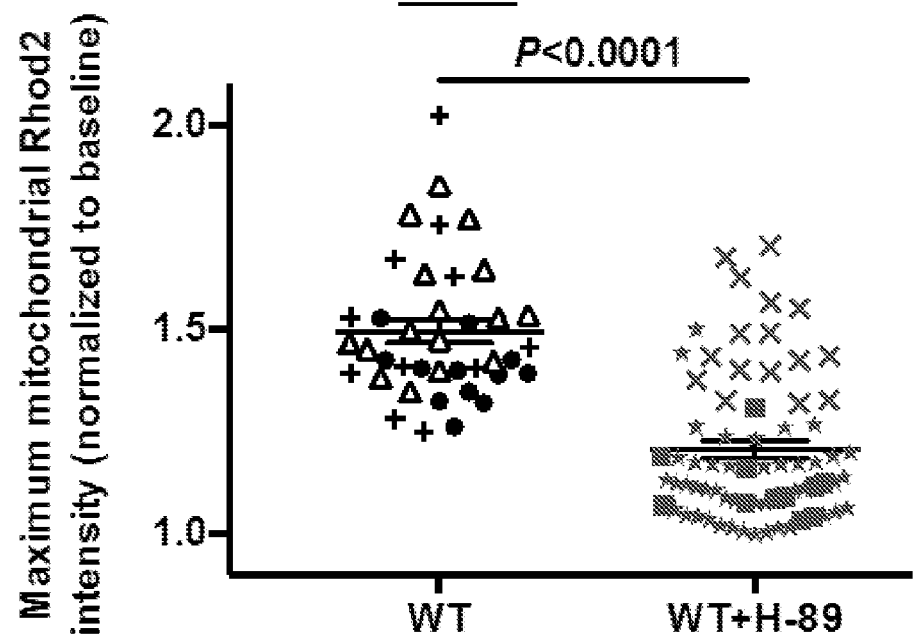

To examine the potential role of glucagon stimulation of intrahepatic lipolysis in vivo, ATGL was knocked down in a liver-specific manner in weight-matched WT and liver-specific InsP$_3$R-I knockout littermates (FIGS. 33A-33C). Liver-specific ATGL knockdown abrogated the effects of glucagon to stimulate HGP, V$_{PC}$ flux, and long-chain- and acetyl-CoA content in WT mice (FIG. 26C-26H), demonstrating a critical role for stimulation of intrahepatic lipolysis in mediating the increases in each parameter resulting from glucagon infusion. However, ATGL knockdown had no effect on these parameters in liver-specific InsP$_3$R-I knockout mice, indicating that glucagon acts in a calcium-dependent manner to stimulate intrahepatic lipolysis, increase hepatic acetyl-CoA content, increase V$_{PC}$ and hepatic glucose production. These alterations in hepatic gluconeogenesis were again dissociated from changes in hepatic glycogen content or hepatic gluconeogenic protein expression, with gluconeogenic protein expression if anything highest in liver-specific InsP$_3$R-I knockout mice with hepatic ATGL knockdown, a group in which glucagon failed to stimulate HGP or V$_{PC}$. In addition, the alterations in hepatic gluconeogenesis rates were dissociated from WAT lipolysis, with plasma NEFA and glycerol concentrations suppressed in WT control mice following glucagon treatment, which could be attributed to compensatory hyperinsulinemia (FIGS. 33B-33I). Malonyl-CoA was relatively low in all groups (FIG. 33J), again inconsistent with glucagon regulation of β-oxidation by modulation of hepatic malonyl-CoA content under these conditions. Taken together these data identify a novel mechanism by which glucagon stimulates hepatic gluconeogenesis by promoting intrahepatic lipolysis through stimulation of ATGL in a InsP$_3$R-I/Ca$^{2+}$/calcium-dependent manner, thereby increasing hepatic acetyl-CoA content and hepatic gluconeogenesis from allosteric stimulation of pyruvate carboxylase activity.

Figure 27A:
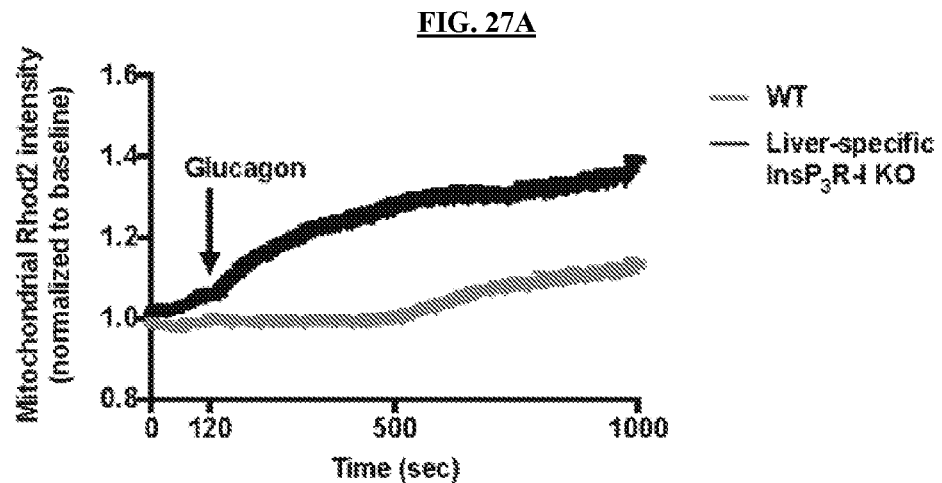
Figure 27B:
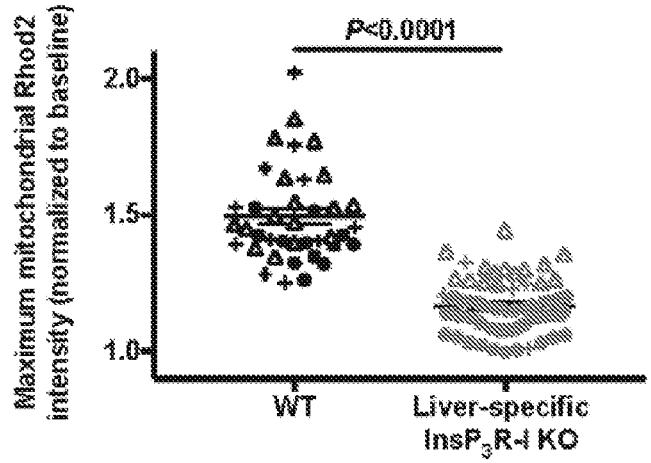
Figure 27C:
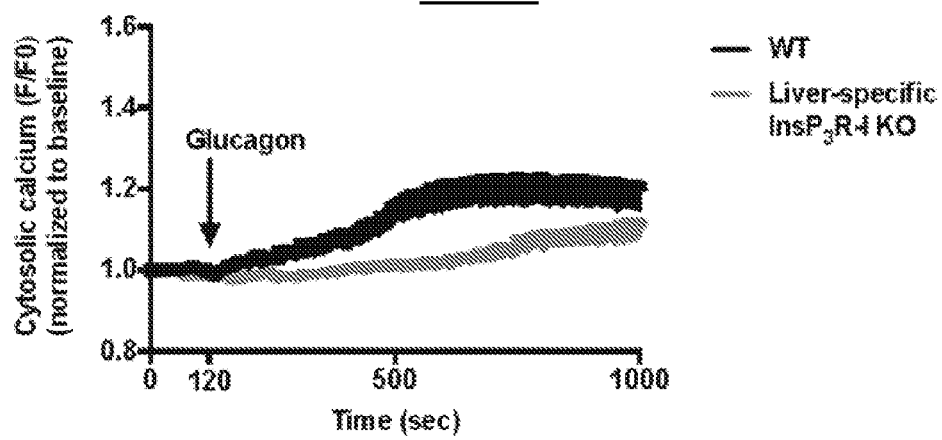
Figure 27D:
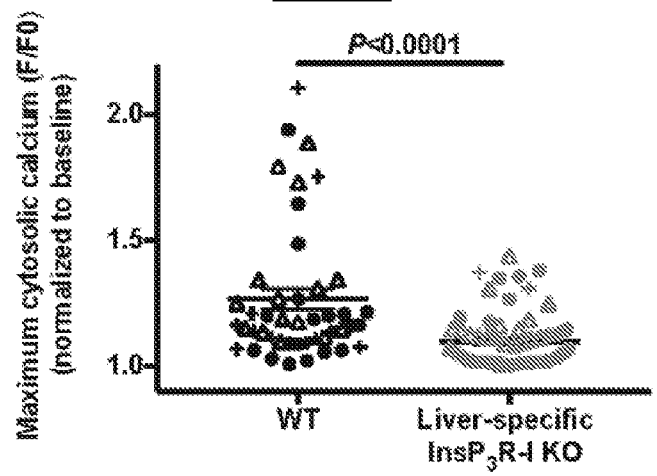
Figure 27H:
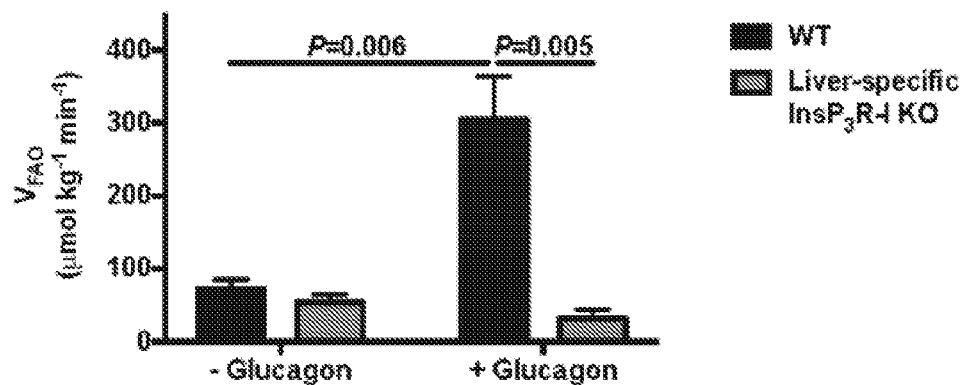
Figure 28A:
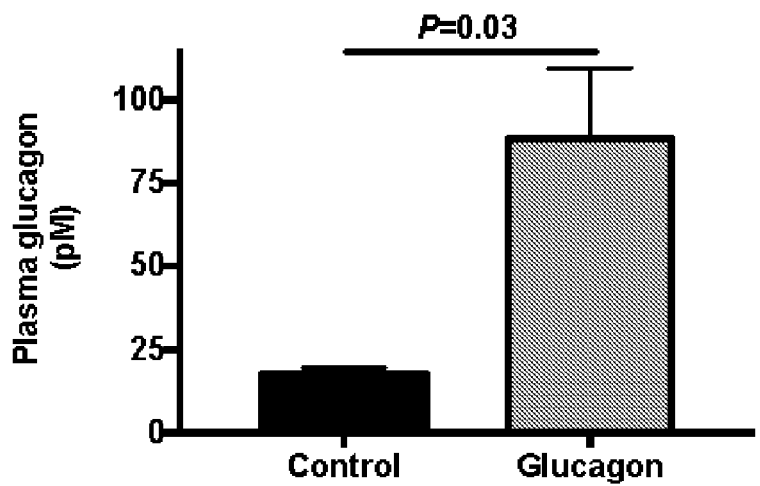
Figure 28B:
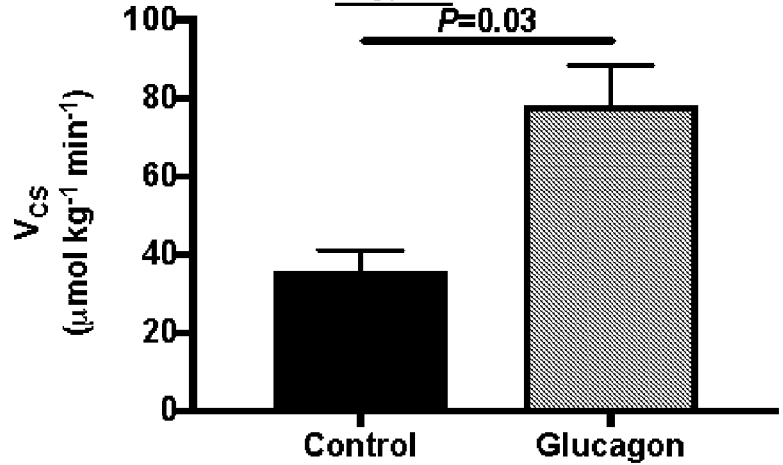
Figure 28F:
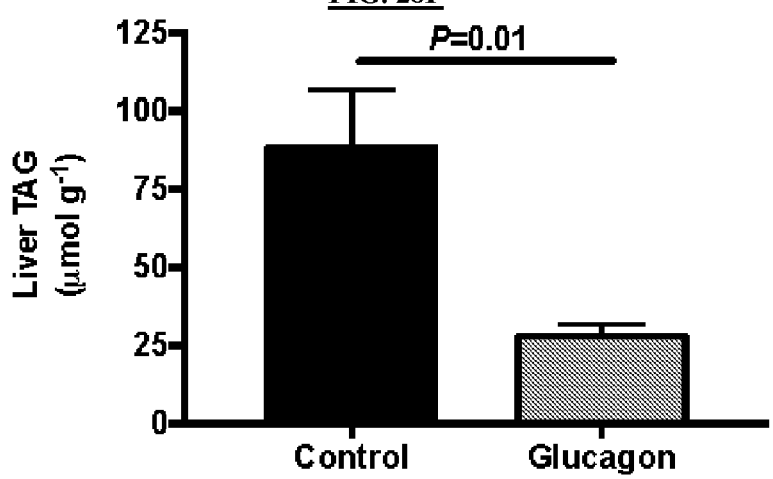
Figure 28G:
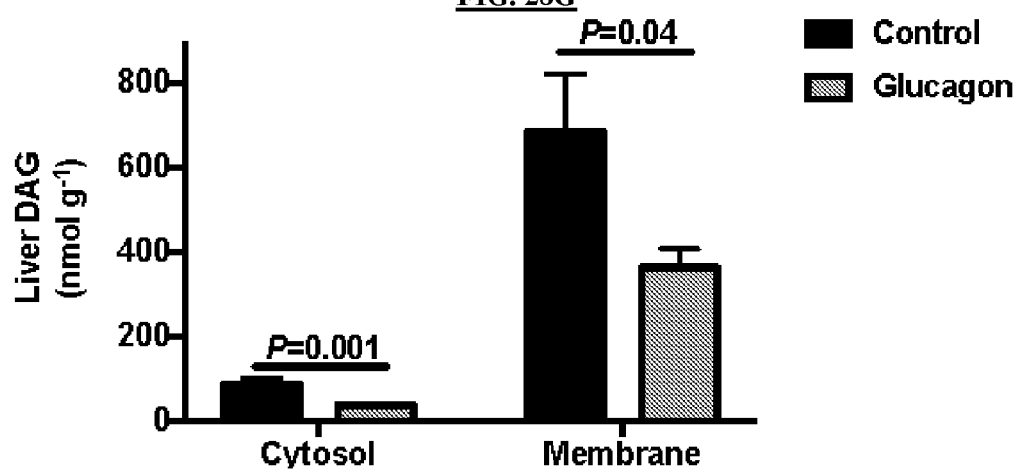
Figure 28H:
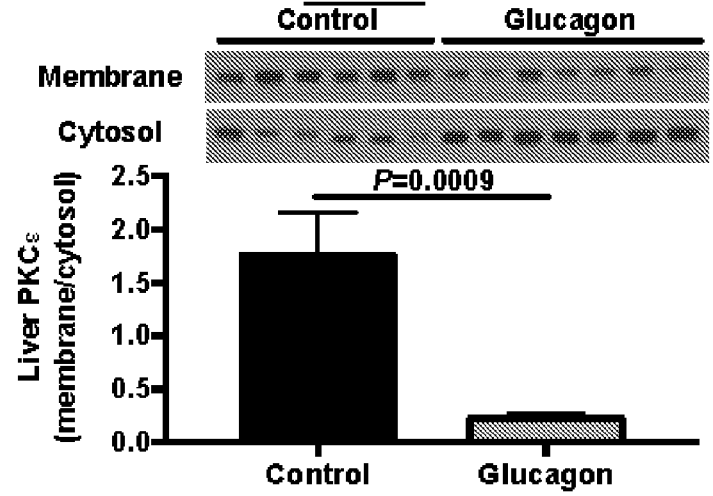
Figure 28I:
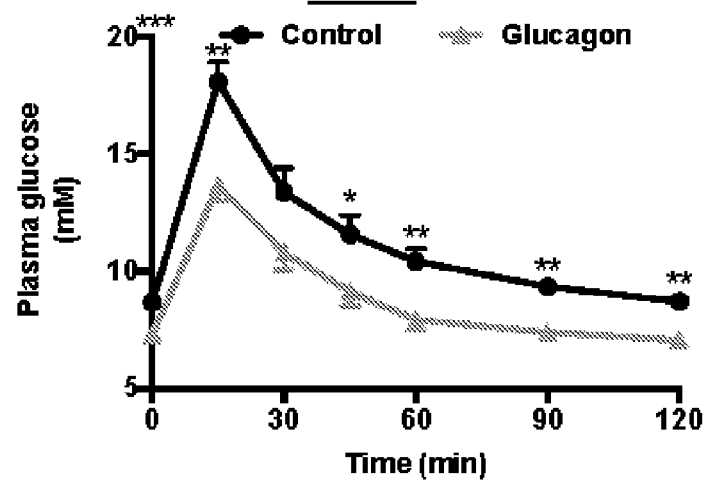
Figure 28J:
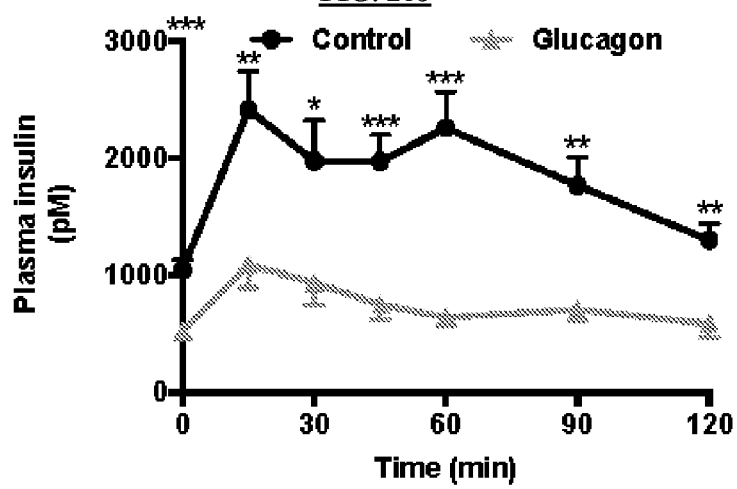
Figure 29A:
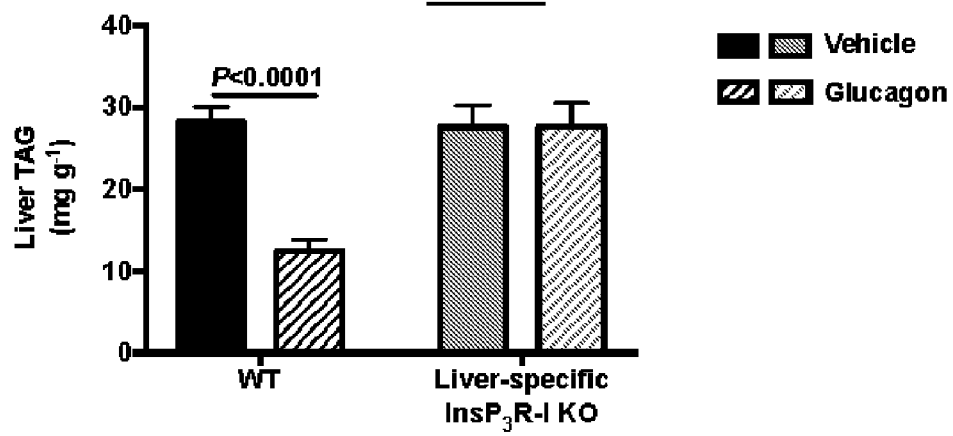
FIGS. 29A-29F are graphs showing that chronic increases in mitochondrial oxidation with a continuous 3.5 week glucagon infusion led to reversal of NAFLD and improvements in glucose tolerance in an InsP$_3$R-I dependent process.
Figure 29B:
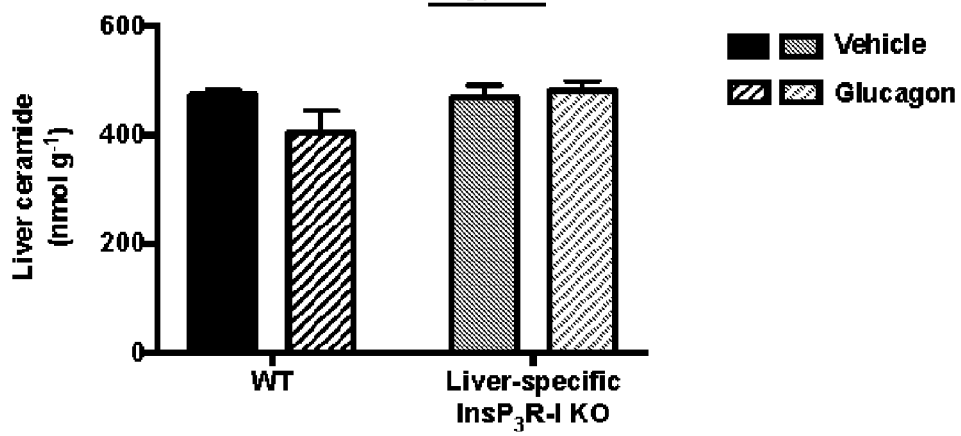
Figure 29C:
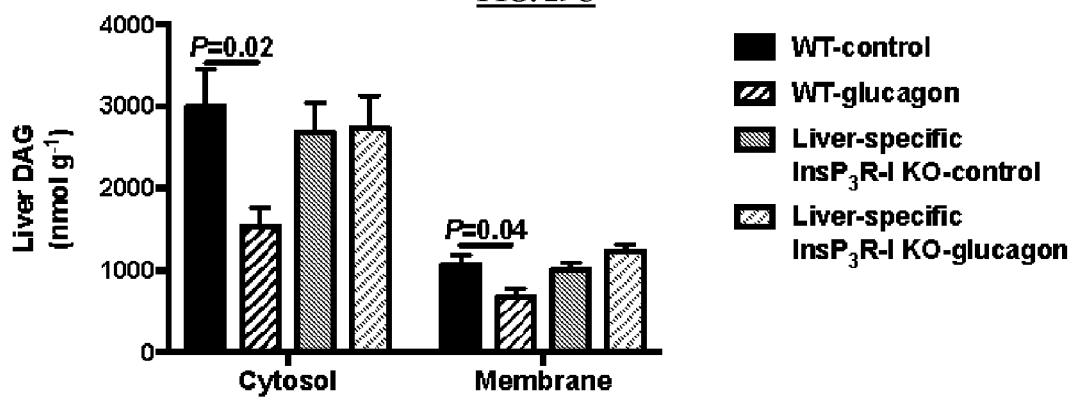
Figure 29D:
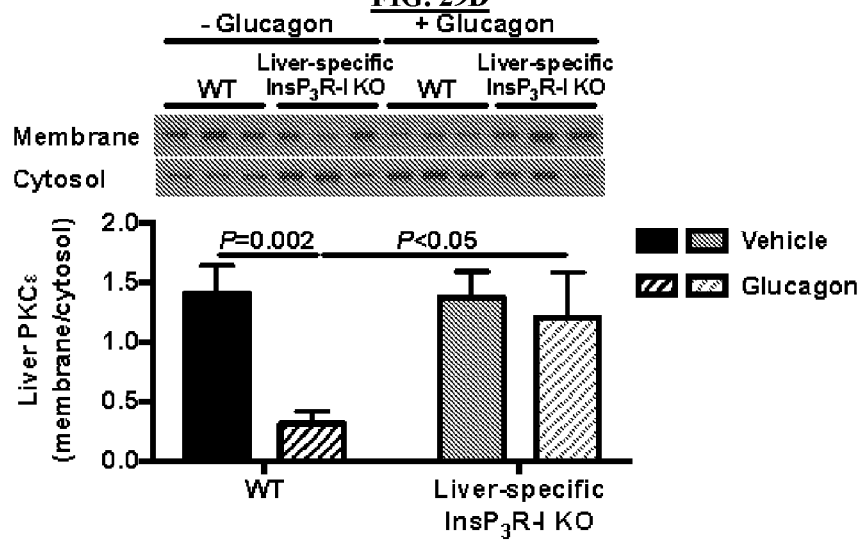
Figure 29E:
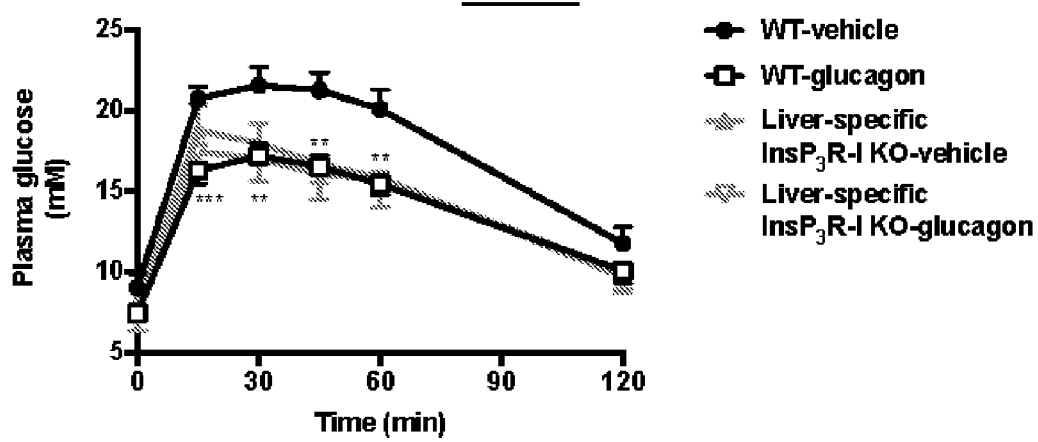
Figure 29F:
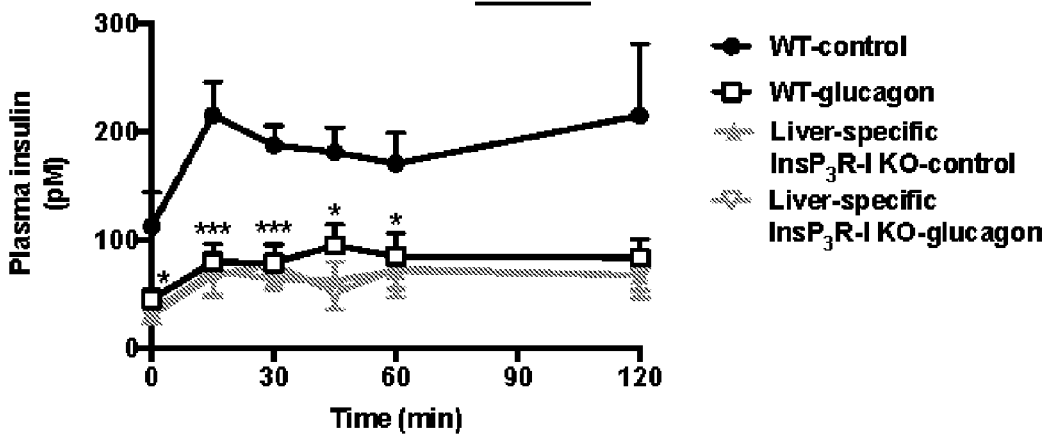
Figure 34C:
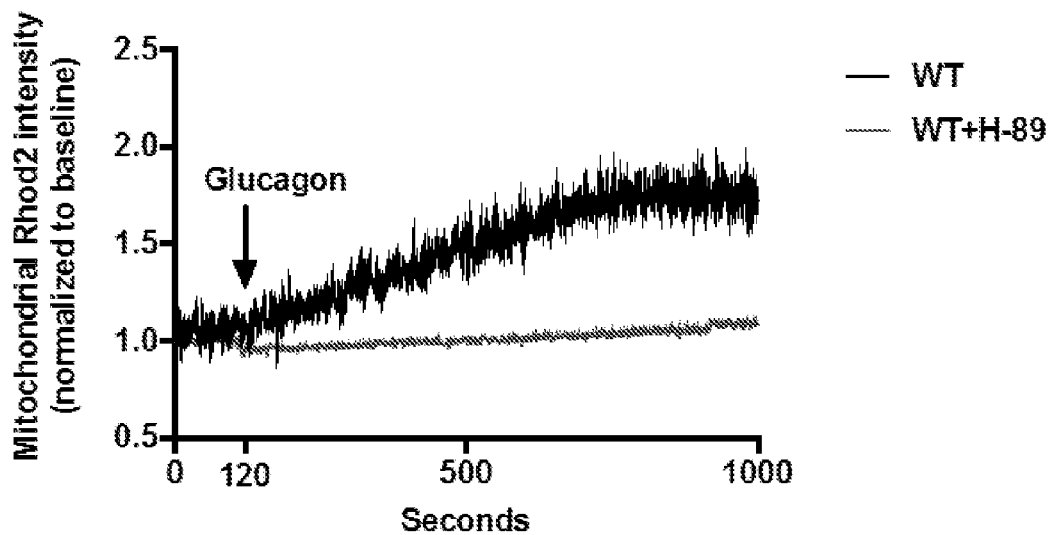
Figure 34E:
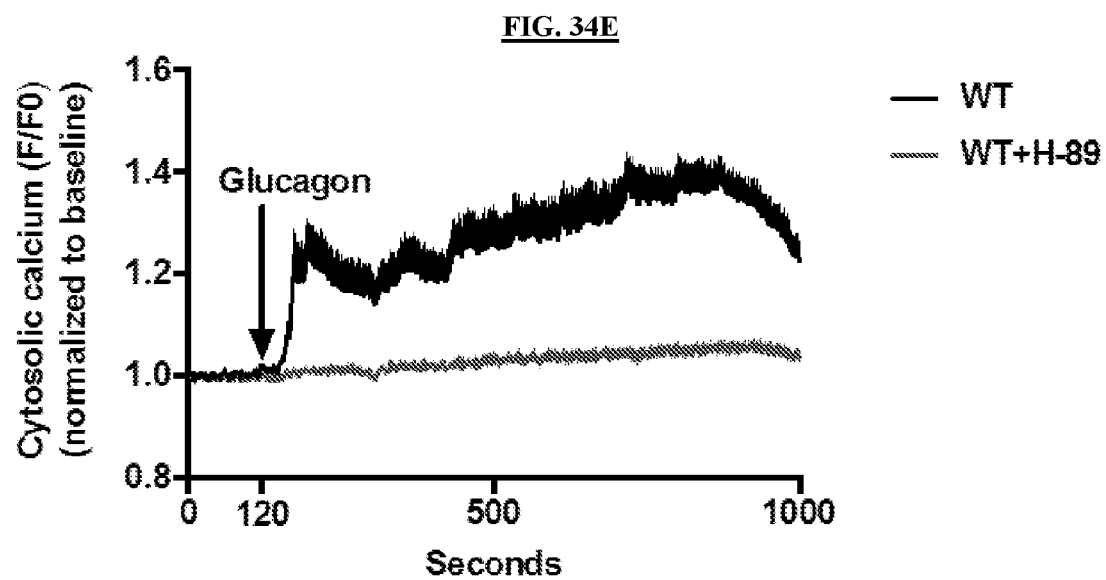
Figure 34F:
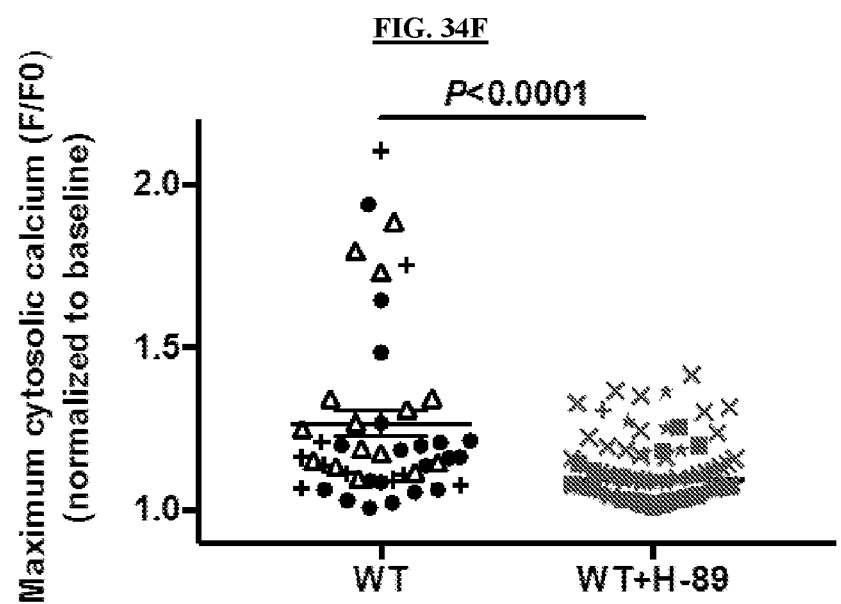
Figure 34G:
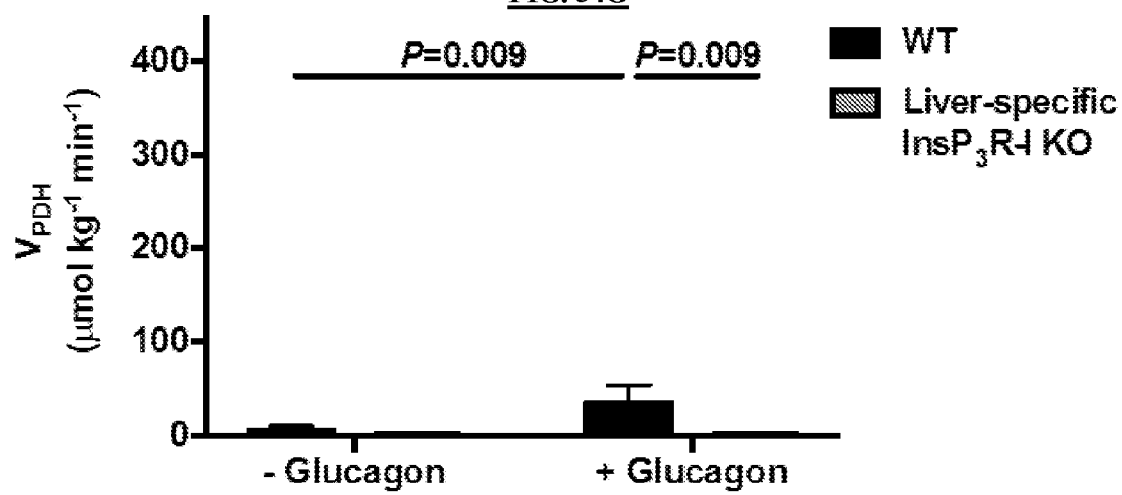
Figure 34H:
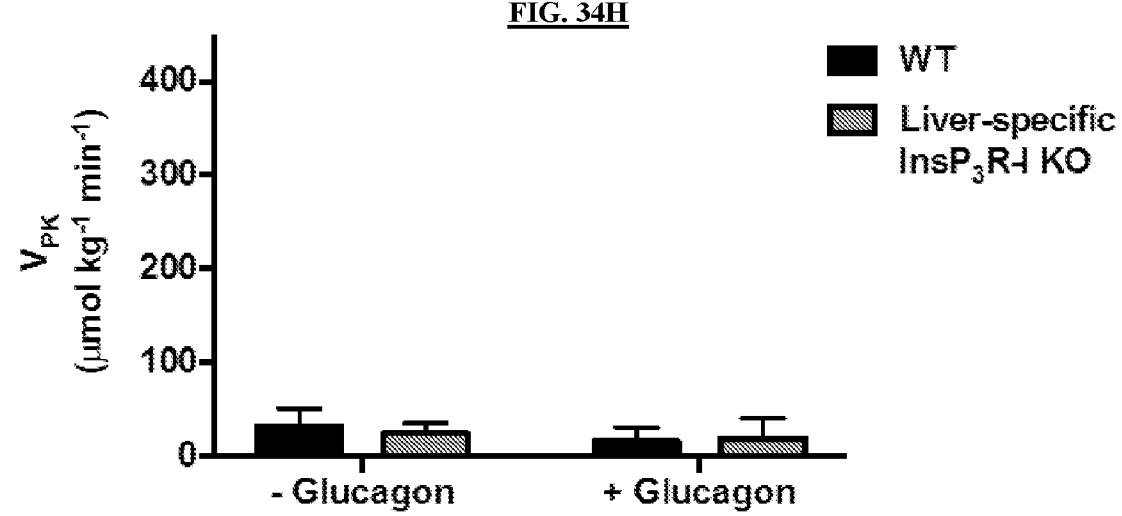
Figure 34I:
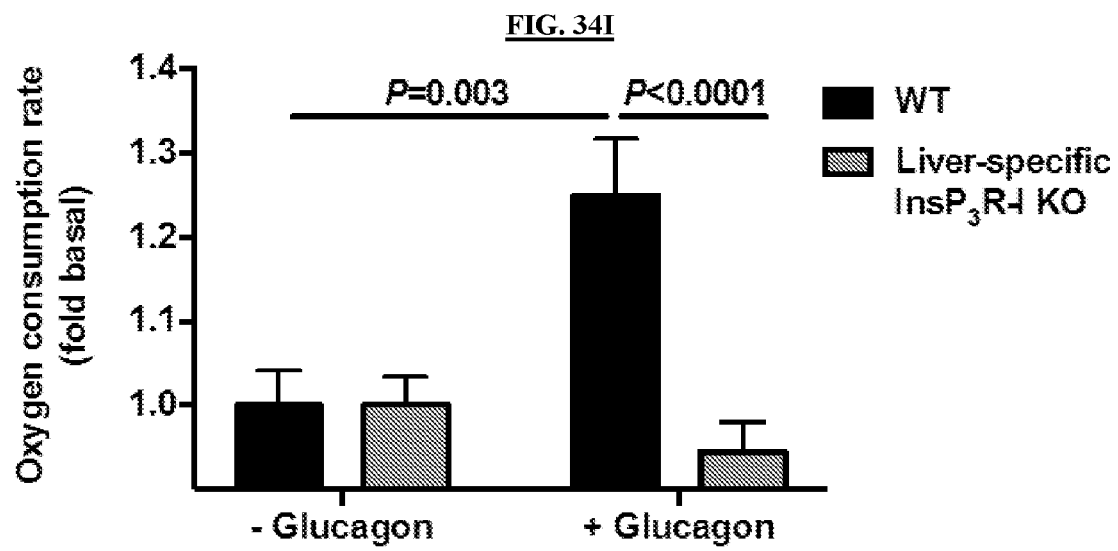

Glucagon promoted increases in both mitochondrial and cytosolic calcium signaling in isolated hepatocytes from female WT but not liver-specific InsP$_3$R-I knockout mice (FIGS. 27A-27D). The InsP$_3$R agonist vasopressin caused an almost identical increase in both cytosolic and mitochondrial calcium signaling in WT but not InsP$_3$R-I KO mice, consistent with glucagon stimulating InsP$_3$-mediated calcium signaling (FIGS. 27E-27F and 34A-34B). Incubation of WT hepatocytes in the PKA inhibitor H-89 abrogated the calcium response to glucagon (FIGS. 34C-34F), indicating, consistent with the glucose production/lipolysis data (FIGS. 25C-25D and 32H), that intact PKA function and resultant calcium signaling is required for glucagon's effects on the liver. Ex vivo PINTA analysis also revealed that glucagon treatment stimulated hepatic mitochondrial oxidation (V$_{CS}$) in vivo, increasing hepatic mitochondrial oxidation five-fold in WT mice, which could mostly be attributed to increased mitochondrial fat oxidation (FIGS. 27G-27H). However, liver-specific InsP$_3$R-I knockout mice failed to exhibit any increases in hepatic mitochondrial oxidation in response to glucagon treatment in vivo. Taken together these data suggest that glucagon stimulates hepatic mitochondrial oxidation through activation of InsP$_3$R-I resulting in increased intra-mitochondrial calcium, which in turn stimulates mitochondrial dehydrogenases. Consistent with this hypothesis, a 7-fold increase in hepatic pyruvate dehydrogenase flux (V$_{PDH}$) was observed in WT but not InsP$_3$R-I KO mice infused with glucagon, without any difference in pyruvate kinase flux (V$_{PK}$), with V$_{PK}$ representing a relatively small percentage (15-35%) of hepatic V$_{PC}$ flux (FIGS. 34G-34H) and consistent with relatively low hepatic pyruvate kinase flux under fasting conditions. In vitro studies confirmed an increase in oxygen consumption with glucagon stimulation in isolated hepatocytes from WT but not liver-specific InsP$_3$R-I knockout mice (FIG. 34I) demonstrating that glucagon mediates these effects in a cell autonomous manner and providing additional cross-validation for the PINTA approach to assess rates of hepatic mitochondrial oxidation in response to glucagon treatment in vivo. These data were replicated in hepatocytes from male mice, in which glucagon stimulated mitochondrial oxidation by ~60% in WT hepatocytes (p<0.0001 vs. WT hepatocytes without glucagon), but this effect was blunted (p<0.0001) in InsP$_3$R-I KO hepatocytes.

Figure 34J:
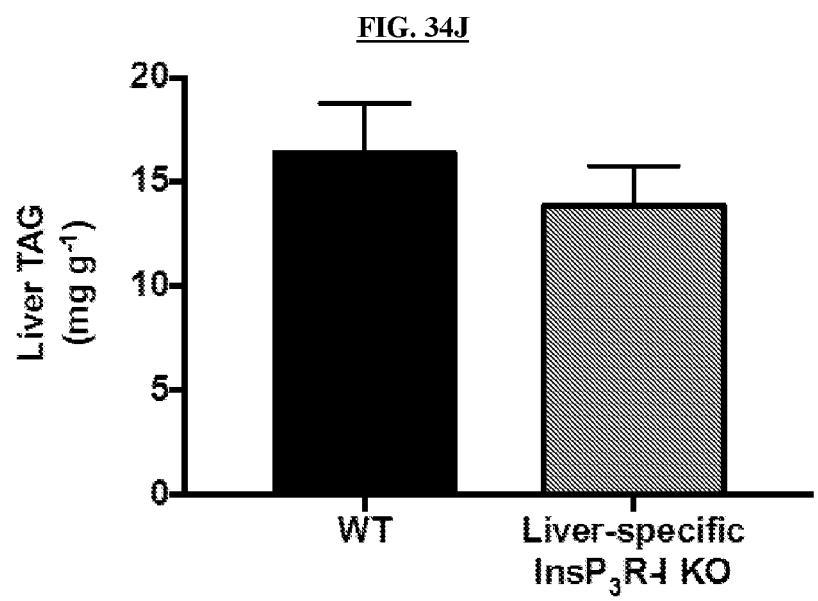
Figure 35A:
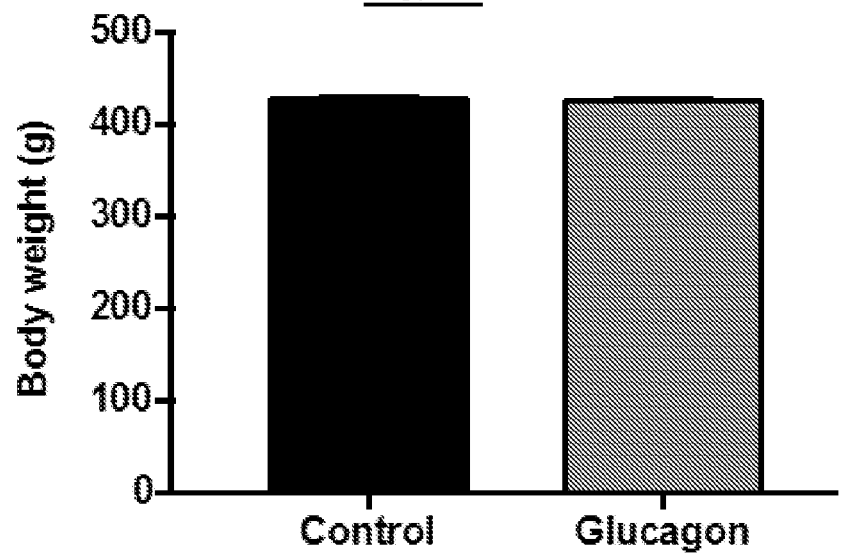
FIGS. 35A-35L are graphs showing that chronic increases in mitochondrial oxidation with a 10-day glucagon infusion led to reversal of NAFLD and improvements in glucose tolerance.
Figure 35B:
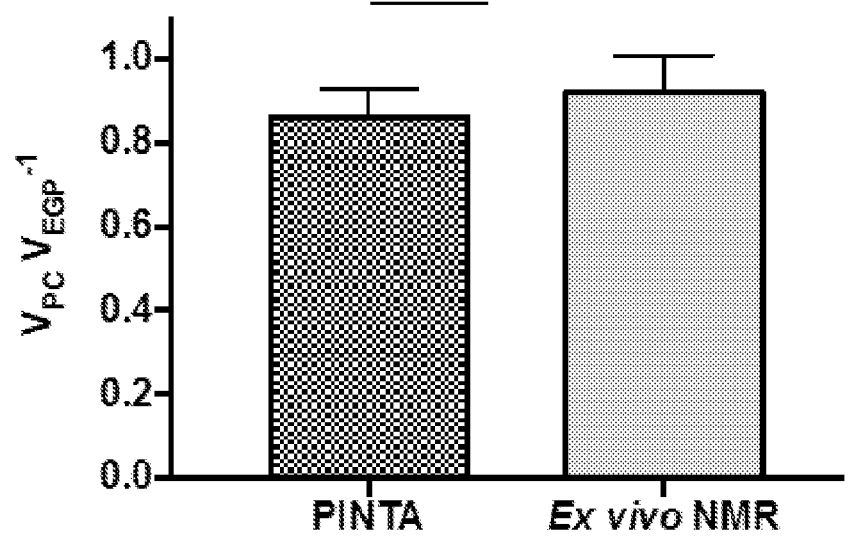
Figure 35C:
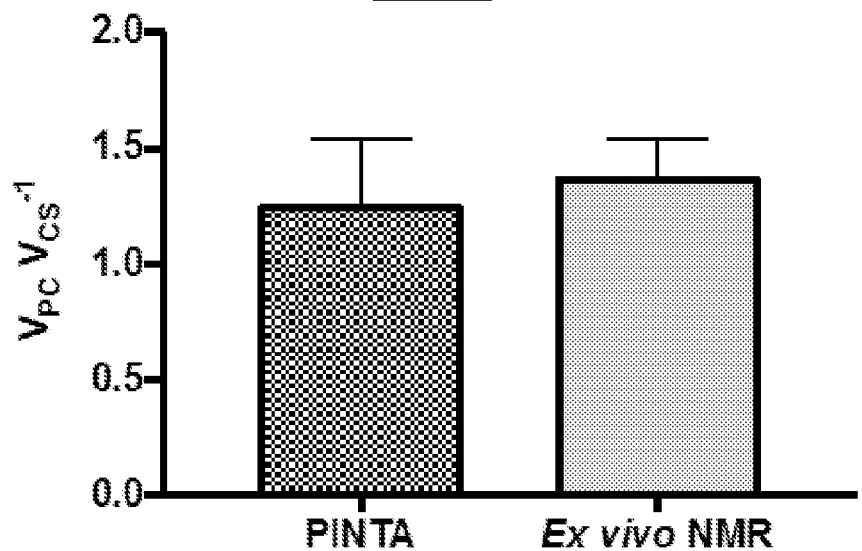
Figure 35D:
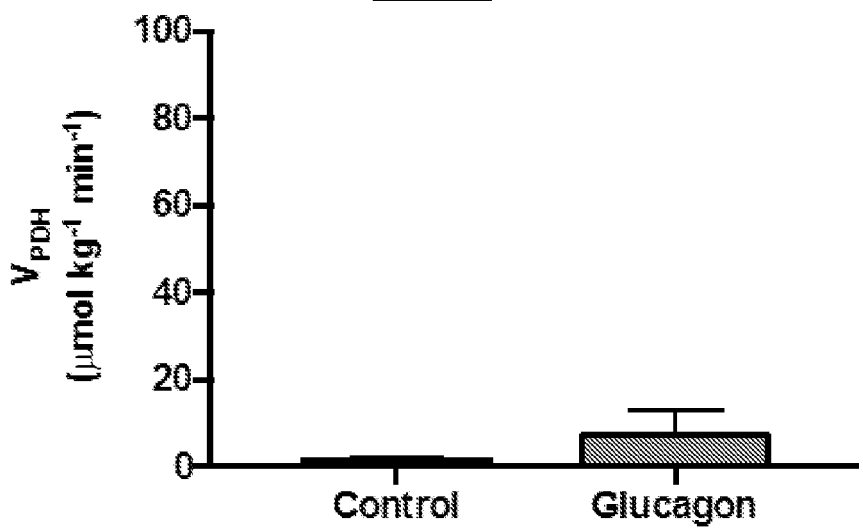
Figure 35E:
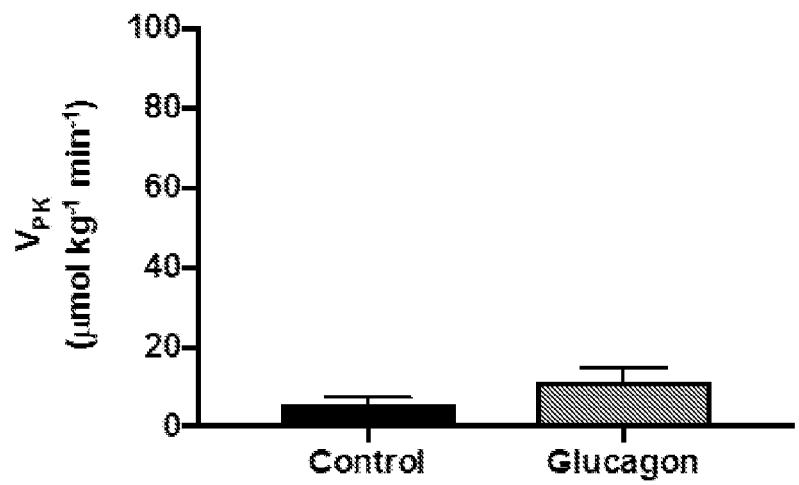
Figure 35F:
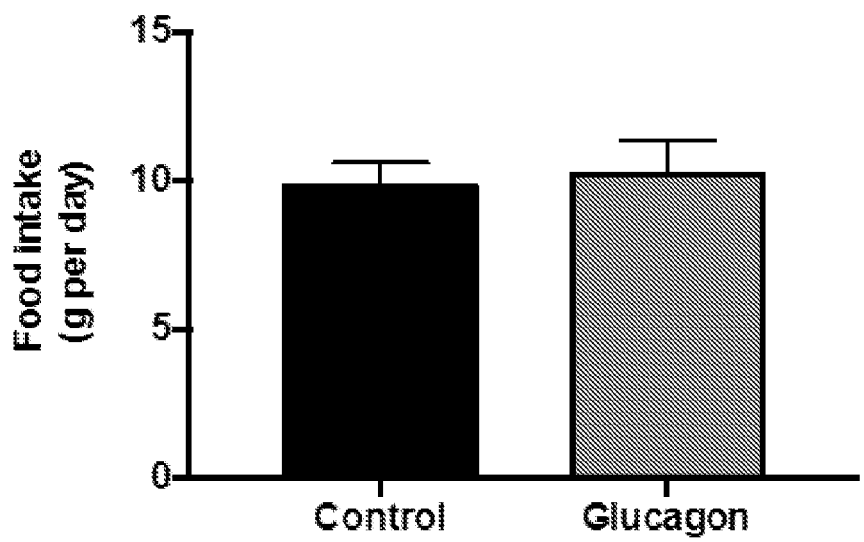
Figure 35G:
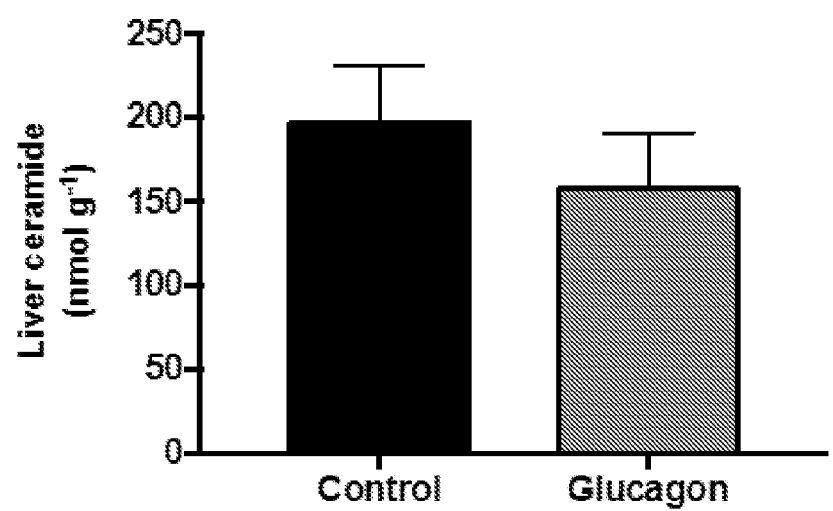
Figure 35H:
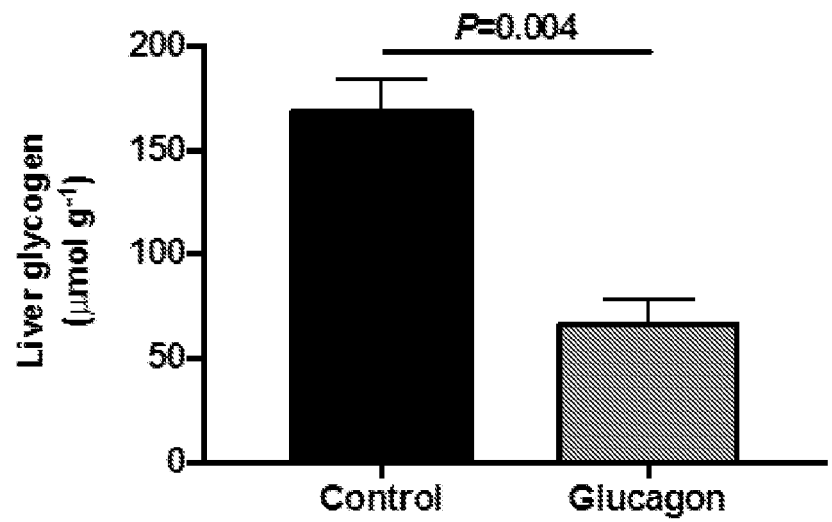
Figure 35I:
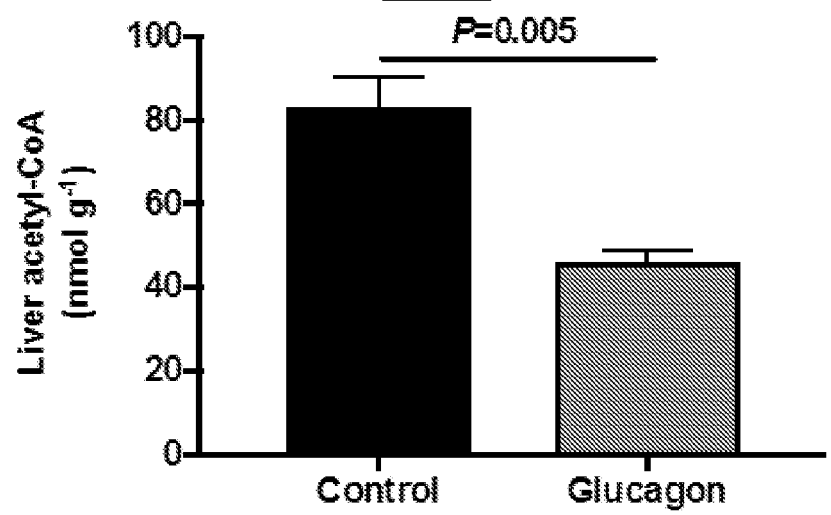
Figure 35J:
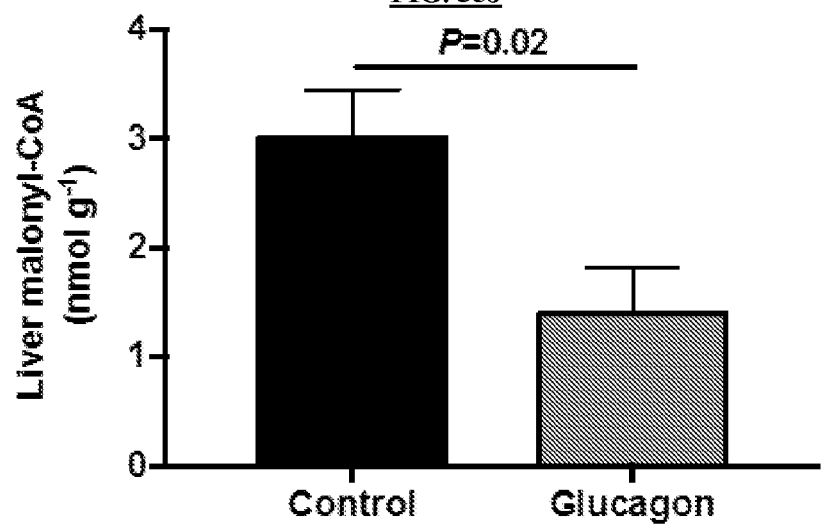
Figure 35K:
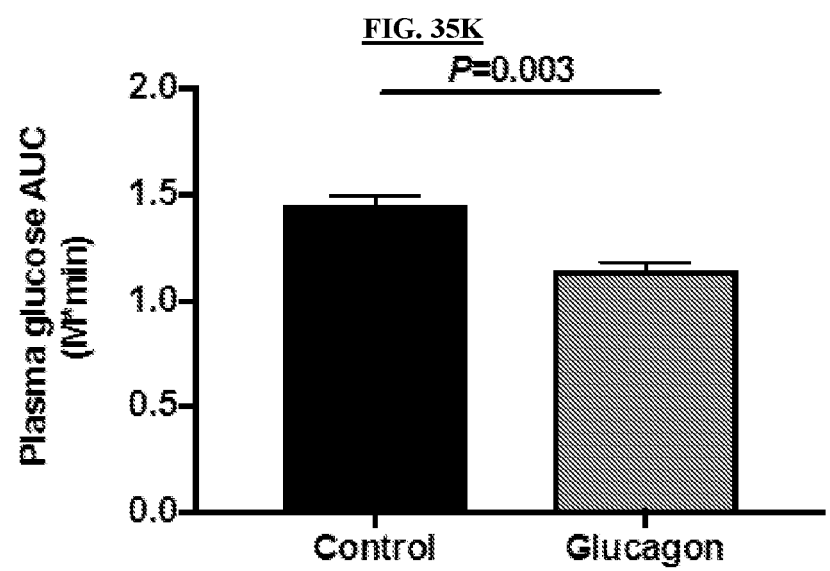
Figure 35L:
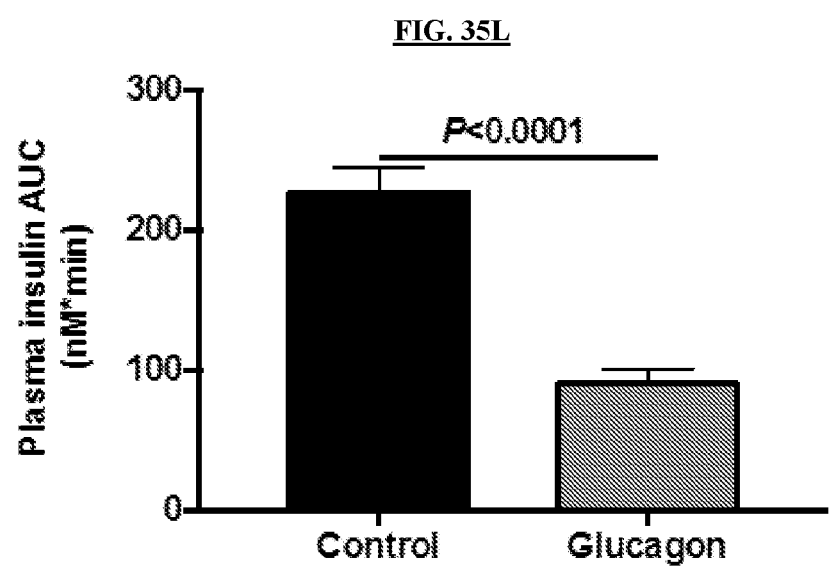
Figure 36A:
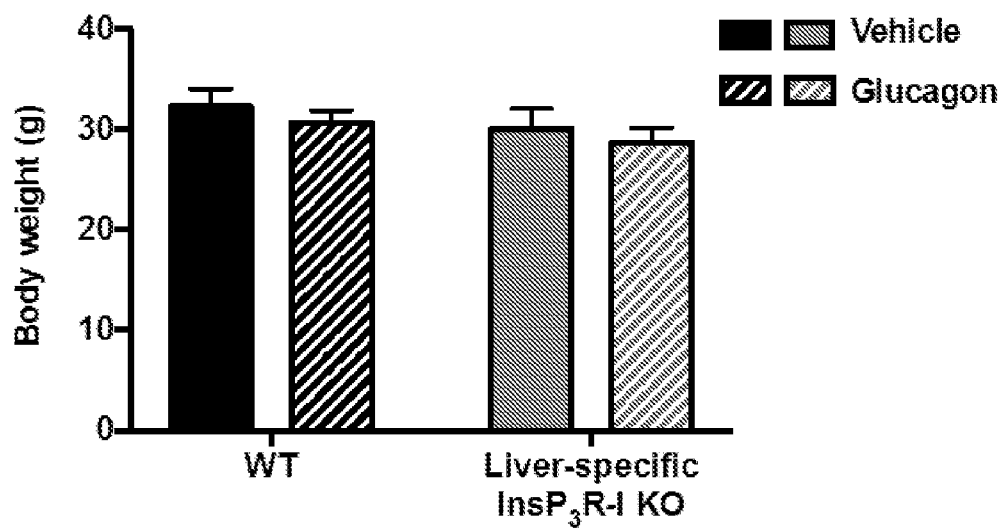
FIGS. 36A-36I are graphs showing that chronic glucagon treatment reversed NAFLD and glucose intolerance in WT but not InsP$_3$R-I KO mice.
Figure 36B:
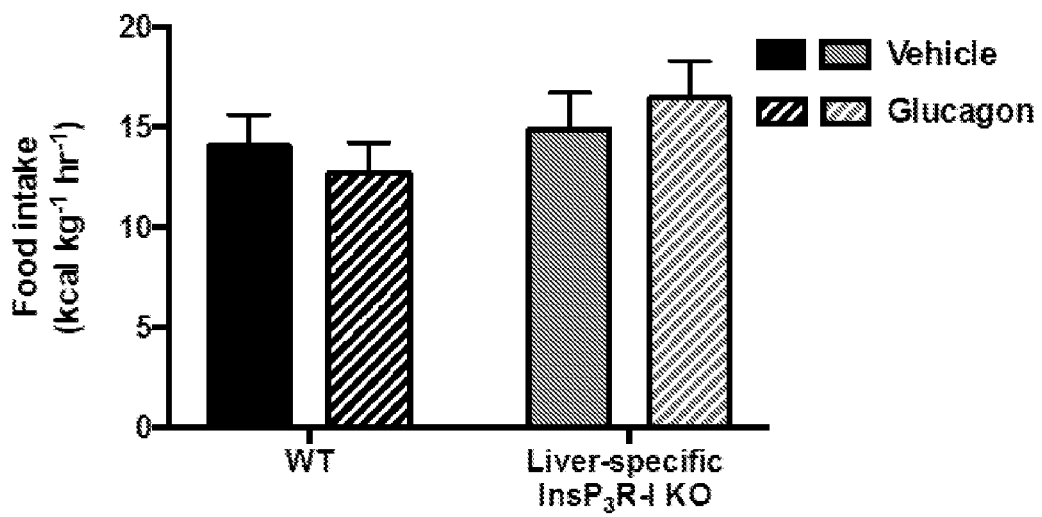
Figure 36C:
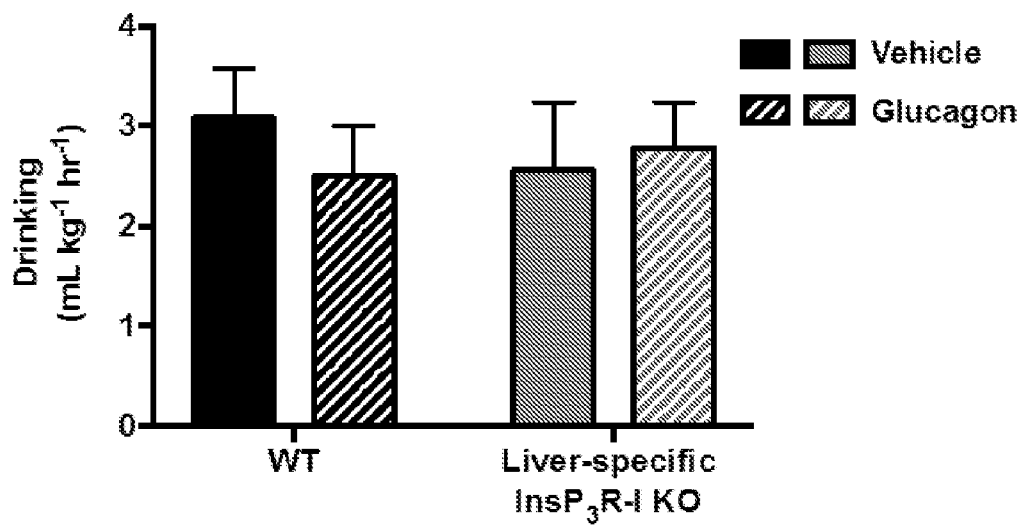
Figure 36D:
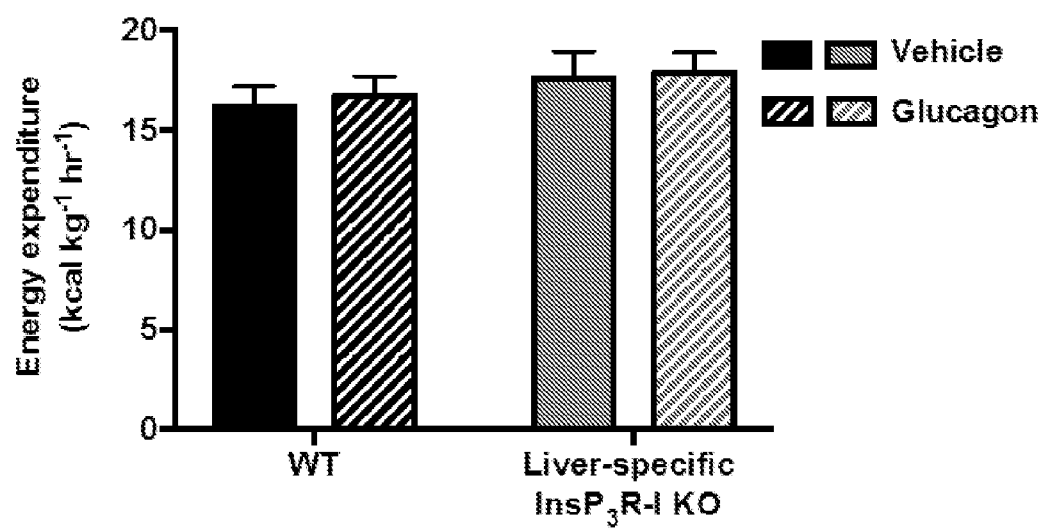
Figure 36E:
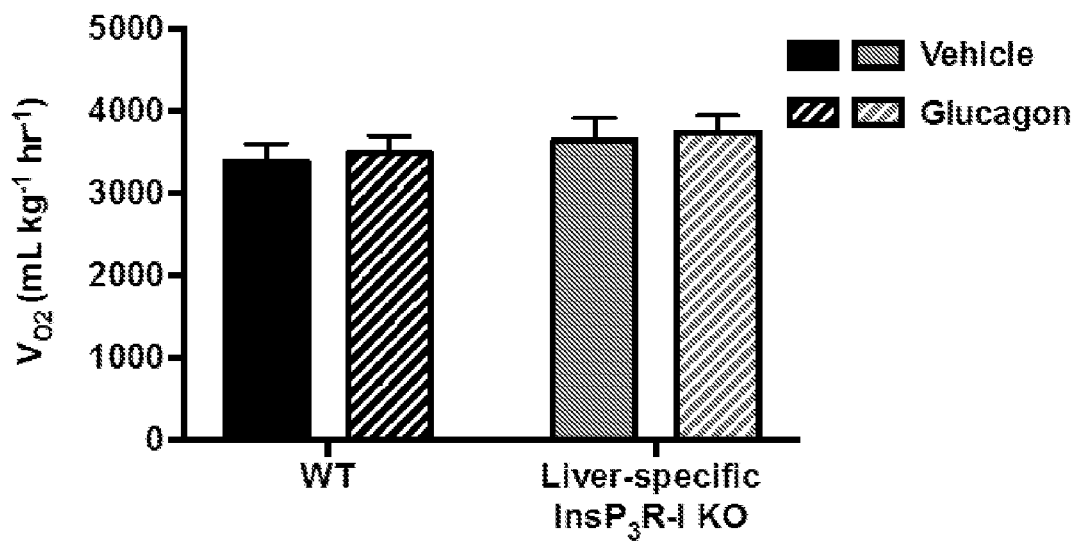
Figure 36F:
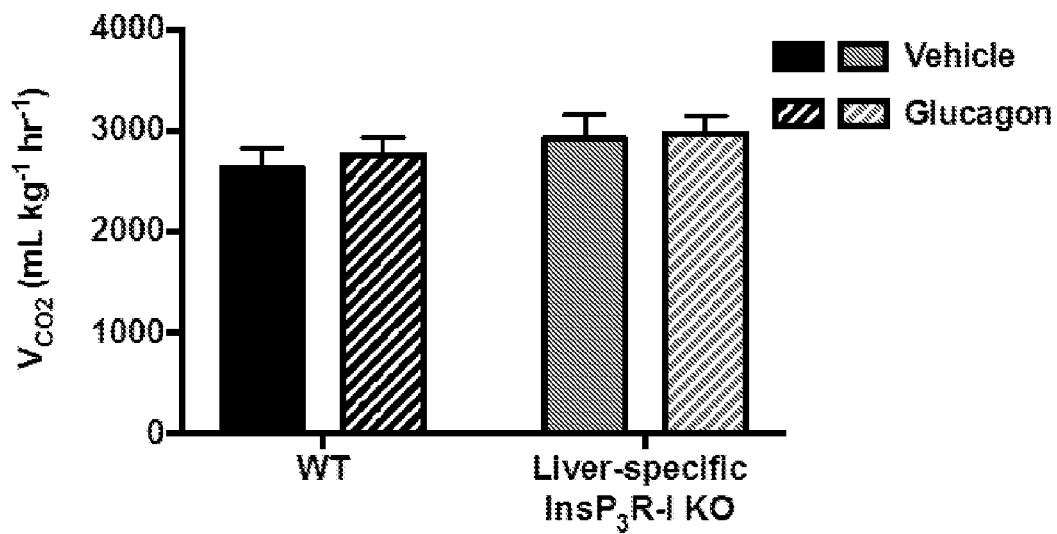
Figure 36G:
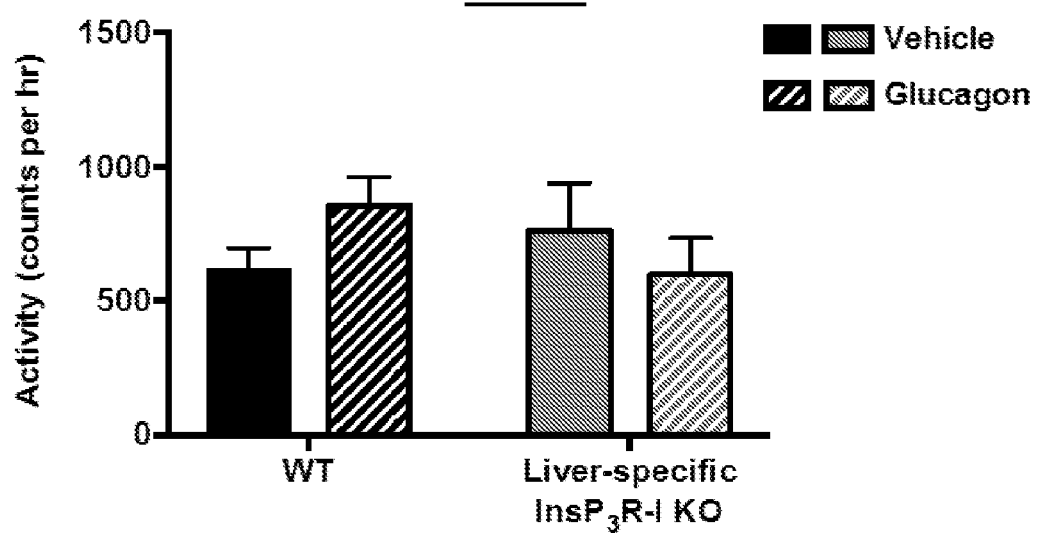
Figure 36H:
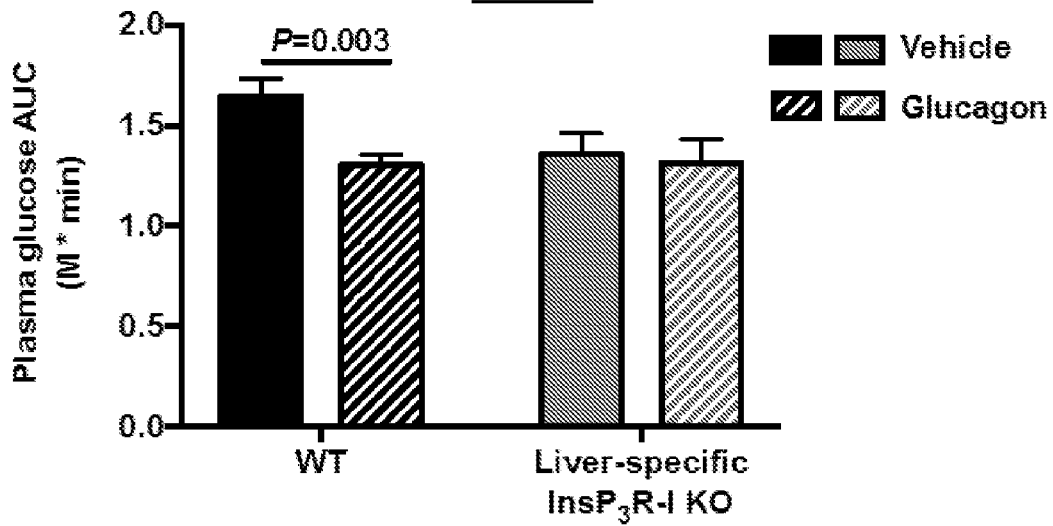
Figure 36I:
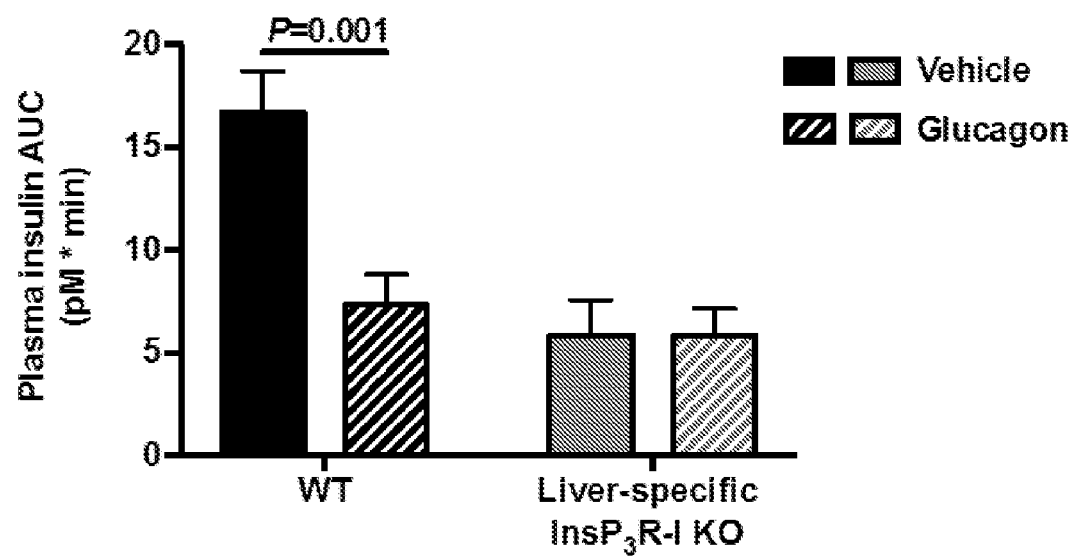

Surprisingly, liver triglyceride concentrations did not differ between chow fed WT and liver-specific InsP$_3$R-I KO mice (FIG. 34J), suggesting that physiologic glucagon concentrations may not promote sufficient mitochondrial fat oxidation in ad lib fed mice to alter hepatic triglyceride content. However, it was found that chronic increases in hepatic mitochondrial oxidation induced by chronic glucagon treatment would reverse NAFLD and improve whole body insulin sensitivity. Chronic glucagon infusion studies performed in awake high fat fed (HFD) rats with diet-induced obesity, and found that after ten days of treatment, chronic glucagon infusion caused a two-fold increase in rates of hepatic mitochondrial oxidation, which could entirely be attributed to increased rates of hepatic fat oxidation, with $V_{PC}/V_{EGP}$ and $V_{PC}/V_{CS}$ ratios identical between PINTA and ex vivo NMR analysis (FIGS. 28A-28C and 35A-35D). Consistent with the findings in the acute glucagon infusion studies, hepatic $V_{PK}$ flux did not change with chronic glucagon treatment, remaining a small proportion (~15-20%) of hepatic $V_{PC}$ flux (FIG. 35E). Two hours after withdrawal of the glucagon infusion, rats treated with glucagon exhibited 1.4 mM reductions in fasting plasma glucose and 50% reductions in fasting plasma insulin concentrations which were associated with 50-90% reductions in hepatic triglyceride and diacylglycerol concentrations and marked reductions in protein kinase C-epsilon (PKCε) translocation despite similar food intake, body weight, and hepatic ceramide content (FIGS. 28D-28H and 35F-35G, Tables 13-14). Consistent with chronic increases in hepatic glycogenolysis and/or reductions in glycogen synthesis due to lower plasma glucose and insulin concentrations, chronic glucagon infusion also resulted in reductions in liver glycogen content (FIG. 35H). In contrast to acute glucagon infusion, chronic glucagon infusion with withdrawal of glucagon treatment four hours before sacrifice resulted in suppression of both hepatic acetyl- and malonyl-CoA content (FIGS. 35I-35J). Consistent with the lower hepatic diacylglycerol/PKCε translocation and hepatic acetyl-CoA content and their respective roles to inhibit insulin receptor kinase activity and pyruvate carboxylase activity, HFD rats chronically infused with glucagon manifested improved glucose tolerance and insulin sensitivity as reflected by 20 and 60% reductions in glucose and insulin area under the curve, respectively, during an intraperitoneal glucose tolerance test (FIGS. 28I-28J and 35K-35L).

TABLE 13

DAG species following chronic glucagon infusion in rats. Data are the mean ± S.E.M. of n = 6 per group, with *P < 0.05, P < 0.01, *P < 0.001 by the 2-tailed unpaired Student's t-test.

| | Control (nmol g$^{-1}$) | Glucagon (nmol g$^{-1}$) |
|---|---|---|
| Cytosolic DAG | | |
| C18_1 C16 | 13.2 ± 1.9 | 5.3 ± 0.9** |
| C20_4 C20_5 | 1.1 ± 0.1 | 0.5 ± 0.1** |
| C16 C20_4 | 0.8 ± 0.1 | 0.5 ± 0.1* |
| C18 C20_4 | 20.0 ± 2.2 | 13.6 ± 1.1* |
| C18, C18 | 5.8 ± 0.6 | 5.6 ± 0.6 |
| C18_2, C18 | 1.6 ± 0.2 | 0.9 ± 0.1** |
| C18_1, C18 | 1.2 ± 0.1 | 0.6 ± 0.1** |
| C16, C16 | 3.6 ± 0.4 | 1.8 ± 0.2*** |
| C18, C16 | 2.3 ± 0.2 | 1.7 ± 0.1* |
| C18_1, C18_1 | 13.5 ± 2.4 | 4.2 ± 0.5 |
| C18_1, C18_2 | 12.6 ± 2.4 | 4.0 ± 0.5** |
| C18_2, C18_2 | 11.2 ± 2.2 | 3.6 ± 0.6** |
| C16, C18_2 | 20.5 ± 3.1 | 7.2 ± 1.0*** |
| Total DAG | 90.6 ± 12.7 | 38.3 ± 3.1** |
| Membrane DAG | | |
| C18_1 C16 | 96.4 ± 18.7 | 50.0 ± 9.0* |
| C20_4 C20_5 | 15.6 ± 1.3 | 11.3 ± 1.3* |
| C16 C20_4 | 5.8 ± 0.7 | 4.2 ± 0.7 |
| C18 C20_4 | 30.1 ± 2.6 | 21.5 ± 2.4* |
| C18, C18 | 6.9 ± 0.6 | 6.5 ± 0.5 |
| C18_2, C18 | 12.2 ± 2.2 | 7.8 ± 0.7 |
| C18_1, C18 | 6.2 ± 1.4 | 3.6 ± 0.4 |
| C16, C16 | 18.2 ± 3.1 | 10.2 ± 2.6 |
| C18, C16 | 7.4 ± 1.0 | 4.9 ± 0.5* |

TABLE 13-continued

DAG species following chronic glucagon infusion in rats. Data are the mean ± S.E.M. of n = 6 per group, with *P < 0.05, P < 0.01, *P < 0.001 by the 2-tailed unpaired Student's t-test.

| | Control (nmol g$^{-1}$) | Glucagon (nmol g$^{-1}$) |
|---|---|---|
| C18_1, C18_1 | 95.5 ± 27.7 | 44.1 ± 7.2 |
| C18_1, C18_2 | 113.0 ± 27.4 | 58.7 ± 7.8 |
| C18_2, C18_2 | 92.1 ± 23.5 | 44.0 ± 10.7 |
| C16, C18_2 | 186.5 ± 32.4 | 97.3 ± 13.4* |
| Total DAG | 685.7 ± 137.3 | 364.0 ± 44.7* |

TABLE 14

Ceramide species following chronic glucagon infusion in rats. Data are the mean ± S.E.M. of n = 8 per group. There were no significant differences by the 2-tailed unpaired Student's t-test.

| Ceramide | Control (nmol g$^{-1}$) | Glucagon (nmol g$^{-1}$) |
|---|---|---|
| C16 | 47.8 ± 9.7 | 40.1 ± 10.2 |
| C18 | 9.5 ± 1.8 | 7.1 ± 1.4 |
| C20 | 25.9 ± 8.7 | 15.9 ± 3.7 |
| C22 | 31.1 ± 4.7 | 26.9 ± 5.2 |
| C24 | 62.2 ± 7.4 | 52.8 ± 10.9 |
| C24:1 | 21.1 ± 3.9 | 15.2 ± 3.9 |
| Total ceramide | 197.6 ± 33.7 | 158.0 ± 33.4 |

Finally, to determine whether InsP$_3$R-I-dependent calcium signaling mediates the chronic effect of hyperglucagonemia to increase hepatic fat oxidation, reverse NAFLD, and improve glucose tolerance, a four-week continuous infusion of glucagon was performed in diet-induced obese WT and InsP$_3$R-I KO mice. Despite unchanged body weight, food and water intake, activity and energy expenditure, WT mice treated with glucagon exhibited 50-80% reductions in liver triglyceride and diacylglycerol content and PKCε translocation, resulting in a marked improvement in glucose tolerance, without any alterations in hepatic ceramide concentrations (FIGS. 29A-29F and 36A-36I). However, InsP$_3$R-I KO mice did not manifest any alterations in hepatic lipid content or glucose tolerance, demonstrating that the beneficial effect of glucagon to reverse NAFLD occurs through InsP$_3$R-I-mediated calcium signaling.

Collectively, these studies reveal that glucagon stimulates intrahepatic lipolysis through an InsP$_3$R-I/CAMKII-dependent process, leading to increases in hepatic acetyl-CoA content, which allosterically activates PC activity and $V_{PC}$ flux, and that this phenomenon explains its acute, transcription-independent effect to acutely stimulate hepatic gluconeogenesis in vivo. In addition, using PINTA analysis, it was found that glucagon stimulates hepatic mitochondrial oxidation ($V_{cs}$) through InsP$_3$R-I-mediated calcium signaling, and that this process can be exploited by short-term continuous glucagon treatment leading to two-fold increases in hepatic mitochondrial fat oxidation ($V_{FAO}$), which resulted in large reductions in hepatic steatosis and marked improvements in glucose tolerance through reversal of hepatic insulin resistance. Glucagon's effect on the liver required activity of both PKA and PLC, but activation of either PKA or PLC alone was not sufficient to increase hepatic gluconeogenesis or mitochondrial oxidation in the absence of InsP$_3$R-I-mediated calcium signaling. Thus these data provide a transcription-independent alternative mechanism that complements previous studies suggesting a PKA/CRTC2/ transcription-dependent mechanism (Wang, et al., *Nature* 485, 128-132, 2012) as well as a CD38/cADPR/transcription-dependent mechanism of action for glucagon (Rah, & Kim, *Sci Rep* 5, 10741, 2015).

Figure 37:
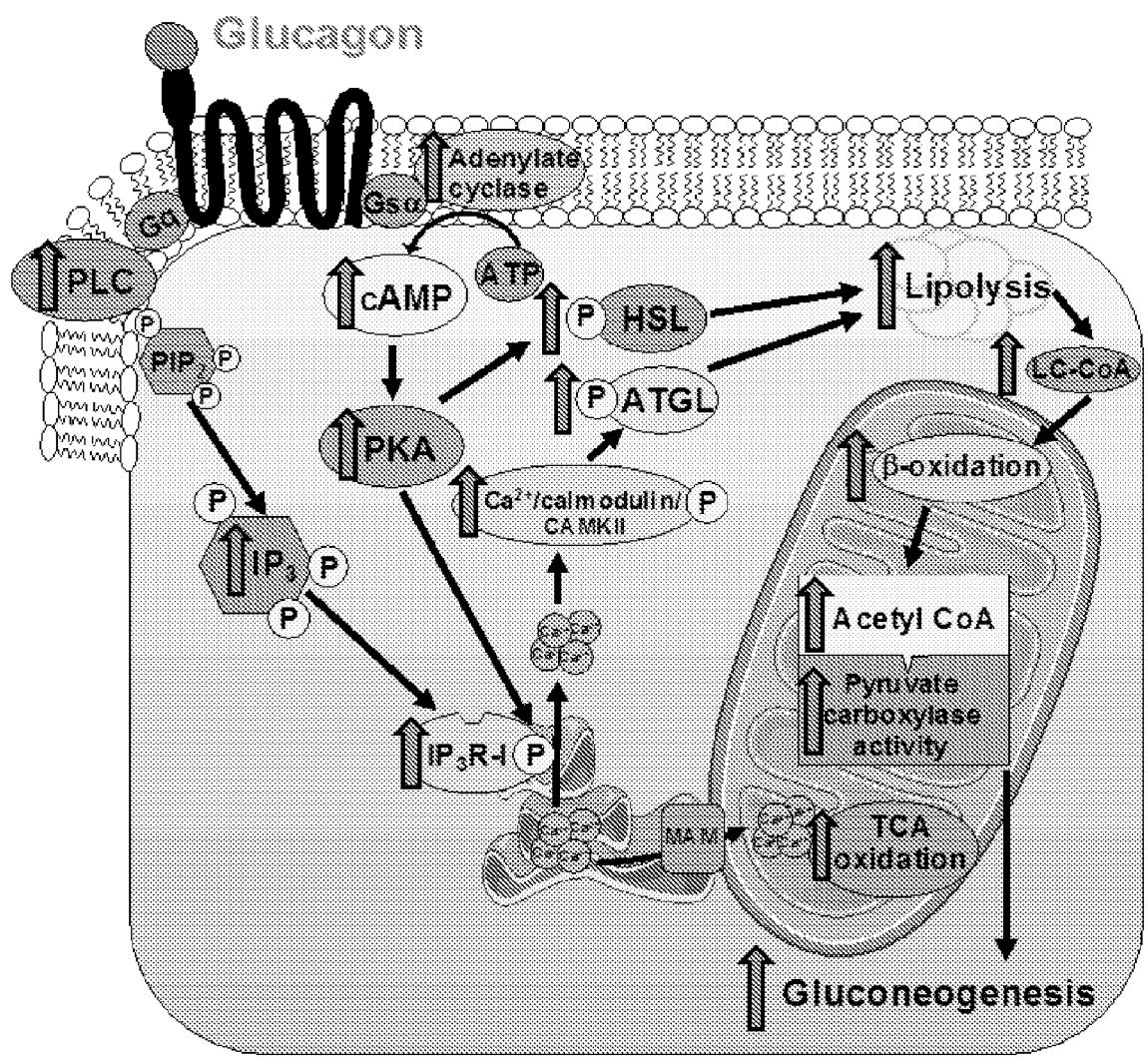
FIG. 37 is a scheme showing the mechanism by which glucagon acutely stimulates intrahepatic lipolysis, hepatic gluconeogenesis, and hepatic mitochondrial oxidation.

In summary, this study reveals several new aspects of glucagon biology and new mechanistic insights as to how glucagon stimulates hepatic gluconeogenesis and hepatic mitochondrial oxidation in vivo. Specifically, these results show (FIG. 37):

1) Physiological increases in plasma glucagon concentrations acutely stimulate hepatic gluconeogenesis in vivo through stimulation of intrahepatic lipolysis resulting in allosteric activation of pyruvate carboxylase flux ($V_{PC}$) and that this occurs independently of glucagon-mediated transcriptional/translational increases in hepatic gluconeogenic enzyme protein expression.

2) Glucagon stimulation of intrahepatic lipolysis and hepatic $V_{PC}$ flux is mediated through increased ATGL S406 phosphorylation and activity, in that hepatic knockdown of ATGL abrogated glucagon's effect to acutely increase hepatic acetyl-CoA content and stimulate hepatic pyruvate carboxylase flux and hepatic gluconeogenesis.

3) Physiological increases in plasma glucagon concentrations acutely stimulate rates of hepatic mitochondrial oxidation in vivo, which can mostly be attributed to increased rates of hepatic mitochondrial fat oxidation.

4) Glucagon stimulation of hepatic gluconeogenesis, intrahepatic lipolysis and mitochondrial oxidation are all dependent on intrahepatic calcium signaling mediated by InsP$_3$R-I as reflected by the abrogation of these effects in liver-specific InsP$_3$R-I knockout mice.

5) Chronic glucagon infusion leads to marked InsP$_3$R-I dependent reductions in hepatic steatosis, fasting hyperglycemia and reversal of hepatic insulin resistance in two high fat fed rodent models of NAFLD, which can be attributed to chronic stimulation of hepatic mitochondrial oxidation.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising
at least one isotopically labelled $C_3$ compound selected from the group consisting of $^{13}C$-labelled L-lactic acid, $^{13}C$-labelled pyruvic acid, and $^{13}C$-labelled alanine, or a salt or solvate thereof,
at least one isotopically labelled glucose selected from the group consisting of $^2H$-labelled glucose and $^3H$-labelled glucose, or a solvate thereof, and
$^{13}C$-labelled beta-hydroxybutyric acid, or a salt or solvate thereof wherein the $^{13}C$-labelled beta-hydroxybutyric acid comprises [1,2,3,4-$^{13}C_4$] beta-hydroxybutyric acid at a concentration of about 0.5 to about 5 mg/mL.

2. The composition of claim 1, wherein the at least one isotopically labelled glucose comprises at least one selected from the group consisting of [1,2,3,4,5,6,6-$^2H_7$] glucose, [1,2,3,4,5,6,6-$^3H_7$] glucose, and [3-$^3H$]glucose.

3. The composition of claim 1, wherein the at least one isotopically labelled $C_3$ compound comprises at least one selected from the group consisting of [3-$^{13}C$] L-lactic acid, [2-$^{13}C$] L-lactic acid, [2-$^{13}C$] pyruvate, [3-$^{13}C$] pyruvate, [2-$^{13}C$] alanine, and [3-$^{13}C$] alanine.

4. The composition of claim 1, wherein the at least one isotopically labelled $C_3$ compound is at a concentration of about 50 to about 500 mg/mL.

5. The composition of claim 1, wherein the at least one isotopically labelled glucose is at a concentration of about 10 to about 50 mg/mL.

6. The composition of claim 1, which is a pharmaceutically acceptable composition.

7. The composition of claim 6, which is formulated for intravenous infusion in a subject.

* * * * *

SEQUENCE LISTING

<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: B-actin: F

<400> SEQUENCE: 1
ccagatcatg tttgagacct tc         22

<210> SEQ ID NO 2
<211> LENGTH: 22
<212> TYPE: DNA
<213> ORGANISM: Artificial Sequence
<220> FEATURE:
<223> OTHER INFORMATION: B-actin: R

<400> SEQUENCE: 2
catgaggtag tctgtcaggt cc         22

<210> SEQ ID NO 3
<211> LENGTH: 22
<212> TYPE: DNA
<213> ORGANISM: Artificial Sequence
<220> FEATURE:
<223> OTHER INFORMATION: PEPCK: F

<400> SEQUENCE: 3
caggaagtga ggaagtttgt gg         22

<210> SEQ ID NO 4
<211> LENGTH: 20
<212> TYPE: DNA
<213> ORGANISM: Artificial Sequence
<220> FEATURE:
<223> OTHER INFORMATION: PEPCK: R

<400> SEQUENCE: 4
atgacaccct cctcctgcat             20

```
<210> SEQ ID NO 5
<211> LENGTH: 21
<212> TYPE: DNA
<213> ORGANISM: Artificial Sequence
<220> FEATURE:
<223> OTHER INFORMATION: G6Pase: F

<400> SEQUENCE: 5
gaaggccaag agatggtgtg a                                            21

<210> SEQ ID NO 6
<211> LENGTH: 20
<212> TYPE: DNA
<213> ORGANISM: Artificial Sequence
<220> FEATURE:
<223> OTHER INFORMATION: G6Pase: R

<400> SEQUENCE: 6
tgcagctctt gcggtacatg                                              20

<210> SEQ ID NO 7
<211> LENGTH: 20
<212> TYPE: DNA
<213> ORGANISM: Artificial Sequence
<220> FEATURE:
<223> OTHER INFORMATION: PC: F

<400> SEQUENCE: 7
agatgcactt ccatcccaag                                              20

<210> SEQ ID NO 8
<211> LENGTH: 20
<212> TYPE: DNA
<213> ORGANISM: Artificial Sequence
<220> FEATURE:
<223> OTHER INFORMATION: PC: R

<400> SEQUENCE: 8
ccttggtcac gtgaaccttt                                              20
```